(12) United States Patent
Cherukury et al.

(10) Patent No.: US 10,870,635 B2
(45) Date of Patent: Dec. 22, 2020

(54) COMPOUNDS AND THEIR USE AS BACE1 INHIBITORS

(71) Applicant: ALLGENESIS BIOTHERAPEUTICS, INC., Taipei (TW)

(72) Inventors: Madhu Cherukury, Taipei (TW); Hsiao-Wen Lin, Taipei (TW); Shu Chieh Yu, Taipei (TW); Riping Phang, Taipei (TW); Yesudoss Christu Rajan, Taipei (TW); Diane Dan-Shya Tang-Liu, Taipei (TW); Andrew D. White, Taipei (TW); Thomas Malone, Taipei (TW); Richard Beresis, Taipei (TW)

(73) Assignee: ALLGENESIS BIOTHERAPEUTICS, INC., Taipei (TW)

( * ) Notice: Subject to any disclaimer, the term of this patent is extended or adjusted under 35 U.S.C. 154(b) by 45 days.

(21) Appl. No.: 15/568,449

(22) PCT Filed: Apr. 20, 2016

(86) PCT No.: PCT/US2016/028502
§ 371 (c)(1),
(2) Date: Oct. 20, 2017

(87) PCT Pub. No.: WO2016/172255
PCT Pub. Date: Oct. 27, 2016

(65) Prior Publication Data
US 2018/0201604 A1   Jul. 19, 2018

Related U.S. Application Data

(60) Provisional application No. 62/150,715, filed on Apr. 21, 2015, provisional application No. 62/274,791, filed on Jan. 5, 2016.

(51) Int. Cl.
| | | |
|---|---|---|
| *C07D 239/22* | (2006.01) | |
| *C07D 405/04* | (2006.01) | |
| *C07D 409/04* | (2006.01) | |
| *C07D 413/04* | (2006.01) | |
| *C07D 417/04* | (2006.01) | |

(Continued)

(52) U.S. Cl.
CPC ............ *C07D 403/04* (2013.01); *A61P 25/28* (2018.01); *C07D 239/22* (2013.01); *C07D 401/04* (2013.01); *C07D 401/06* (2013.01); *C07D 401/12* (2013.01); *C07D 403/06* (2013.01); *C07D 403/10* (2013.01); *C07D 405/04* (2013.01); *C07D 405/14* (2013.01); *C07D 409/04* (2013.01); *C07D 409/14* (2013.01); *C07D 413/04* (2013.01); *C07D 413/08* (2013.01); *C07D 417/04* (2013.01); *C07D 417/08* (2013.01); *C07D 417/14* (2013.01); *C07D 471/04* (2013.01); *C07D 471/14* (2013.01); *C07D 491/048* (2013.01); *C07D 495/04* (2013.01); *C07D 498/04* (2013.01); *C07D 513/10* (2013.01)

(58) Field of Classification Search
CPC .. C07D 403/04; C07D 239/22; C07D 401/04; C07D 401/06; C07D 401/12; C07D 403/06; C07D 403/10; C07D 405/04; C07D 405/14; C07D 409/04; C07D 409/14; C07D 413/04; C07D 413/08; C07D 417/04; C07D 417/08; C07D 417/14; C07D 471/04; C07D 471/14; C07D 491/048; C07D 495/04; C07D 498/04; C07D 513/10
See application file for complete search history.

(56) References Cited

U.S. PATENT DOCUMENTS

| | | | |
|---|---|---|---|
| 7,763,609 B2 | 7/2010 | Zhu et al. | |
| 8,168,641 B2 | 5/2012 | Wu et al. | |
| 8,629,155 B2 | 1/2014 | Wu et al. | |
| 2009/0221579 A1 | 9/2009 | Albert et al. | |
| 2012/0035195 A1 | 2/2012 | Banner et al. | |
| 2012/0183563 A1* | 7/2012 | Scott ...................... | A61K 31/00 424/172.1 |

(Continued)

FOREIGN PATENT DOCUMENTS

| | | | | |
|---|---|---|---|---|
| WO | WO 2008/103351 A2 | 8/2008 | | |
| WO | WO2014/062553 | * | 4/2014 | ............. A61K 31/54 |

OTHER PUBLICATIONS

WIPO Application No. PCT/US2016/028502, International Search Report, dated Sep. 15, 2016.

(Continued)

*Primary Examiner* — Irina Neagu
(74) *Attorney, Agent, or Firm* — Ice Miller LLP

(57) ABSTRACT

The present invention relates to compounds of Formula (I) or a stereoisomer, tautomer, or pharmaceutically acceptable salt or solvate thereof, wherein X, Y, Z, Q, W, m, u, ring (A), $R^2$, $R^3$, $R^4$, $R^5$ and $R^6$, are as defined in the specification and claims. The present invention provides a pharmaceutical composition containing the compounds of Formula (I) and a therapeutic method of treating and/or preventing Downs syndrome, β-amyloid angiopathy, disorders associated with cognitive impairment, Alzheimer's disease, memory loss, attention deficit symptoms associated with Alzheimer's disease, neurodegenerative diseases, pre-senile dementia, senile dementia and dementia associated with Parkinson's disease, Alzheimer's disease and/or Down syndrome, age-related macular degeneration (AMD), glaucoma, olfactory function impairment, traumatic brain injury, progressive muscle diseases, Type II diabetes mellitus and cardiovascular diseases (stroke).

12 Claims, 7 Drawing Sheets

(51) Int. Cl.
*C07D 471/04* (2006.01)
*C07D 491/048* (2006.01)
*C07D 513/10* (2006.01)
*A61P 25/28* (2006.01)
*C07D 403/04* (2006.01)
*C07D 405/14* (2006.01)
*C07D 401/04* (2006.01)
*C07D 401/06* (2006.01)
*C07D 401/12* (2006.01)
*C07D 403/06* (2006.01)
*C07D 403/10* (2006.01)
*C07D 409/14* (2006.01)
*C07D 413/08* (2006.01)
*C07D 417/08* (2006.01)
*C07D 417/14* (2006.01)
*C07D 471/14* (2006.01)
*C07D 495/04* (2006.01)
*C07D 498/04* (2006.01)

(56) References Cited

U.S. PATENT DOCUMENTS

| | | |
|---|---|---|
| 2014/0023668 A1 | 1/2014 | Cumming et al. |
| 2014/0200213 A1 | 7/2014 | Wu et al. |
| 2015/0065567 A1 | 3/2015 | Imbimbo et al. |

OTHER PUBLICATIONS

WIPO Application No. PCT/US2016/028502, Written Opinion of the International Searching Authority, dated Sep. 15, 2016.

WIPO Application No. PCT/US2016/028502, Invitation to Pay Additional Fees and, Where Applicable, Protest Fee, dated Jul. 12, 2016.

* cited by examiner

COMPOUNDS AND THEIR USE AS BACE1 INHIBITORS

CROSS REFERENCE TO RELATED APPLICATIONS

This application is a U.S. national stage entry of PCT/US2016/028502 filed Apr. 20, 2016, which claims priority to U.S. Provisional Application No. 62/274,791 filed Jan. 5, 2016 and U.S. Provisional Application No. 62/150,715 filed Apr. 21, 2015, all of which are incorporated herein by reference.

BACKGROUND OF THE INVENTION

The present invention relates to novel compounds used for inhibiting beta-secretase 1 (BACE1). BACE1 enzymes are involved in cleaving amyloid precursor protein to form amyloid beta (Aβ) peptides. The accumulation and deposition of Aβ may lead to pathologies, including but not limited to, neurodegeneration, dementia, and Alzheimer's disease. BACE1 inhibitors would block the formation of Aβ, reducing the formation of aggregates that may lead to disease.

Alzheimer's disease (AD) is characterized by the generation, aggregation, and deposition of amyloid-β peptide (Aβ) in the brain (May et al., J. Neuroscience (2011), 31(46): 16507-16516). According to the amyloid cascade hypothesis, Aβ initiates a neurodegenerative cascade as either a soluble oligomer or a major constituent of cerebral amyloid plaques (Hardy and Selkoe, 2002). Aβ is generated from the membrane-spanning β-amyloid precursor protein (APP) by sequential endoproteolytic cleavages. Three proteases (α-secretase, β-secretase and γ-secretase) that are involved in the processing of amyloid precursor protein. First, β-secretase cleaves APP at the NH2 terminus of Aβ to release sAPP and C99, a COOH-terminal fragment that remains membrane bound. Then C99 is further processed by γ-secretase to release various isoforms of Aβ, of which Aβ$_{42}$ appears most pathogenic (Younkin, 1995).

The currently available AD treatments are palliative. While these drugs ameliorate the cognitive and behavioral disorders of AD patients, they do not prevent disease progression (Farlow, M R et al. 2010). The drugs for treating AD currently on the market include acetyl cholinesterase inhibitors (AChE inhibitors) (Birks, J., 2006) and N-methyl-D-aspartate receptor (NMDA) receptor antagonists (McShane, R. et al., 2006). The approved drugs include, for example, NMDA receptor antagonists such as memantine (Namenda®, Forrest Pharmaceuticals, Inc.), AChE inhibitors such as donepezil (Aricept®, Pfizer), rivastigmine (Exelon®, Novartis), galantamine (Razadyne®, Reminyl®), and tacrine (Cognex®) (EP2694521 A1). Given the progressive and degenerative nature of the disease and a desirable treatment outcome of slower deterioration, although no further deterioration or even a showing of slow deterioration are the desirable outcomes, less than half of the patients receiving AChE inhibitors achieve a clinically significant response and the efficacy is short in duration, usually 6-12 months (Francis et al., *J Neurol Neurosurq Psychiatry* 1999, 137-147). Therefore, there is an unmet medical need for AD treatments that halt disease progression (Kastenholz et al., Amyloid-Journal of Protein Folding Disorders, 2009, 16 (2): 81-3; WO 2015135474 A1).

Several BACE1 inhibitors have been investigated in clinical studies as potential treatments for AD. For example, the compound MK-8931 has been reported by Merck to reduce CSF Aβ40, Aβ42 and soluble APPβ in AD patients (Forman et al, 11th International Conference on Alzheimer's & Parkinson's Diseases, Florence, Italy, 7 Mar. 2013). Other examples include LY2811376 (May et al., J. Neurosci (2011), 31(46): 16507-16516) and LY2886721 (May et al., 11th International Conference on Alzheimer's & Parkinson's Diseases, Florence, Italy, 7 Mar. 2013). The preclinical research on LY-2886721 by Eli Lily scientists aided the compound to enter a Phase II clinical trial. LY-2811376, however, was discontinued due to retinal toxicity in animal toxicology study (May et al., J. of Neuroscience (2011) 31(46):16507-16516) and LY-2886721 was terminated due to liver toxicity in humans (May et al., J. of Neuroscience (2015) 35(3):1199-1210).

Three proteases α-secretase, β-secretase and γ-secretase- are of particular interest as they are central to the generation and modulation of amyloid-β peptide and can be targeted by small compounds in vitro and in vivo (Strooper et al., Nat. Rev Neurol. (2010) 6(2): 99-107.). Alpha-secretase agonists may increase soluble APP production (e.g., the West Victoria Merrill Lynch). β-secretase inhibitors may indirectly reduce Aβ production (e.g., AZD-3293, VTP-37948 and HPP-854, etc.). γ-secretase inhibitors can also directly reduce Aβ production (e.g., Avagacestat, Elnd-007, Semagacestat, MK-0752, and PF-3084014, etc.). By adjusting the γ-secretase enzyme, γ-secretase modulators (e.g., EVP-0962, CHF-5074) produce a shear mode, thereby reducing Aβ$_{42}$. However, the shearing action of γ-secretase on other substrates (e.g., the transmembrane receptor Notch) is not significantly inhibited by the γ-secretase modulator, thus the impact on other γ-secretase substrates related signaling pathways is minimized.

A β-secretase inhibitor is a compound that impedes the activity of β-secretase (see Cole S. L. and Vassar R., Mol. Neurodegener., (2007) 2:22; Ghosh A. K. et al., Neurotherapeutics (2008) 5: 399-408; Querfurth H. W. and LaFerla F. M., N. Engl. J. Med. (2010) 362: 329-344; Vassar R. et al., J. Neurochem., 2014, Accepted Article, doi: dx.doi.org/10.1111/jnc.12715). This includes β-secretase inhibitors either in or having been in clinical trials (e.g. AZD3293, AZD3839, CTS-21166, E2609, HPP854, LY-2886721, LY-2811376, MK-8931, PF-05297909, B11181181, CNP520, JNJ54861911, RG7129, SCH 1359113, TAK-070) and/or, preclinical trials (e.g., GRL-8234, MBI-3); and/or generic equivalents, and/or any other compounds or molecules in which inhibition of β-secretase activity has been determined and demonstrated by methodology known in the art. A "β-secretase inhibitor" as used in the specification and claims can include both one β-secretase inhibitor and more than one β-secretase inhibitors.

SUMMARY OF THE INVENTION

The present invention relates to novel organic molecules capable of modulating, regulating and inhibiting BACE1 enzyme. In particular, the present invention relates to novel BACE1 inhibitors which can be used for the treatment of Aβ-related pathologies.

The compounds of the present invention possess several characteristics as described below in more detail: they are effective in inhibiting beta secretase activity; they are non-pgp substrates; they exhibit a low risk to cardiotoxicity; they present a good selectivity for BACE over other BACE1 related enzymes (such as cathepsin D and pepsin); and they are also effective in reducing the neurodegenerative biomarkers in mammals.

In one aspect, the invention provides a compound represented by Formula (I) or a pharmaceutically acceptable salt thereof or stereoisomeric forms thereof or the enantiomers, diastereomers, tautomers, zwitterions, and pharmaceutically acceptable salts thereof:

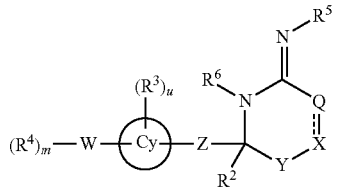

wherein

X is absent or present and when present is selected from the group consisting of C(O), C(S), S(O)$_2$, (CR$^7$R$^8$)$_n$, O, N, NR$^1$, S, and S(O);

Y is absent or present and when present is (CR$^7$R$^8$)$_n$;

Z is absent or present and when present is selected from the group consisting of alkyl, haloalkyl, heteroalkyl, alkenyl, alkynyl, (CR$^{10}$R$^{11}$)$_o$NR$^9$(CR$^{12}$R$^{13}$)$_p$, (CR$^{10}$R$^{11}$)$_o$NR$^9$C(O)(CR$^{12}$R$^{13}$)$_p$, (CR$^{10}$R$^{11}$)$_o$C(O)NR$^9$(CR$^{12}$R$^{13}$)$_p$, (CR$^{10}$R$^{11}$)$_o$C(O)(CR$^{12}$R$^{13}$)$_p$, (CR$^{10}$R$^{11}$)$_o$C(O)O(CR$^{12}$R$^{13}$)$_p$, (CR$^{10}$R$^{11}$)$_o$OC(O)(CR$^{12}$R$^{13}$)$_p$, (CR$^{10}$R$^{11}$)$_o$OC(O)NR$^9$(CR$^{12}$R$^{13}$)$_p$, (CR$^{10}$R$^{11}$)$_o$NR$^9$C(O)O(CR$^{12}$R$^{13}$)$_p$, (CR$^{10}$R$^{11}$)$_o$NR$^9$C(O)NR$^9$(CR$^{12}$R$^{13}$)$_p$, (CR$^{10}$R$^{11}$)$_o$O(CR$^{12}$R$^{13}$)$_p$, (CR$^{10}$R$^{11}$)$_o$S(O)$''$(CR$^{12}$R$^{13}$)$_p$, and cycloalkyl;

W is absent or present and when present is selected from the group consisting of alkyl, haloalkyl, heteroalkyl, alkenyl, alkynyl, OR$^9$, O, NR$^9$R$^{10}$, NR$^9$, C(O)R$^9$, C(O)NR$^9$, NR$^9$C(O), C(O)OR$^9$, OC(O)R$^9$, COR$^9$R$^{10}$, and heterocycloalkyl;

Q is absent or present and when present is selected from O, S, NR$^1$, CR$^1$, (CR$^{14}$R$^{15}$)$_t$, C(O), cycloalkyl, or heterocyclic;

ring

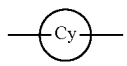

is selected from the group consisting of monocyclic aryl, multicyclic aryl, monocyclic heteroaryl, multicyclic heteroaryl, monocyclic carbocyclic, multicyclic carbocyclic, monocyclic heterocyclic, and multicyclic heterocyclic ring systems;

the bond between Q and X may be a single or double bond;

R$^1$ is selected from hydrogen, alkyl, cycloalkyl, haloalkyl, heteroalkyl, heterohaloalkyl, or heteroalkynyl;

R$^2$ is selected from hydrogen, deuterium, halogen, CN, alkyl, cycloalkyl, haloalkyl, heteroalkyl, aryl, heteroaryl, heterohaloalkyl, or heteroalkynyl;

R$^3$ is independently selected from the group consisting of: hydrogen, deuterium, halogen, CN, C(O), alkyl, haloalkyl, heteroalkyl, alkenyl, alkynyl, aryl, arylalkyl, cycloalkyl, heteroaryl, heteroarylalkyl, and heterocycloalkyl;

R$^4$ is independently selected from the group consisting of: hydrogen, deuterium, halogen, hydroxyl, CN, alkyl, haloalkyl, heteroalkyl, alkenyl, alkynyl, aryl, arylalkyl, arylalkenyl, arylalkynyl, cycloalkyl, heteroaryl, heteroarylalkyl, heteroarylalkenyl, heteroarylalkynyl, and heterocycloalkyl;

R$^5$ is selected from hydrogen, simple alkyl or a prodrug moiety. Said prodrug moiety may include but not be limited to C(O)R$^{14}$ and CR$^{15}$R$^{16}$OC(O)R$^{14}$;

R$^6$ is selected from hydrogen, simple alkyl or a prodrug moiety. Said prodrug moiety may include but not be limited to C(O)R$^{17}$ and CR$^{18}$R$^{19}$OC(O)R$^{17}$;

R$^7$ is independently selected from hydrogen, deuterium, halogen, simple alkyl, or haloalkyl;

R$^8$ is independently selected from hydrogen, deuterium, halogen, simple alkyl, or haloalkyl;

R$^9$ is independently selected from hydrogen, deuterium, halogen, simple alkyl, or alkynyl, R$^{10}$ is independently selected from hydrogen, deuterium, halogen, or simple alkyl;

R$^{11}$ is independently selected from hydrogen, deuterium, halogen, or simple alkyl;

R$^{12}$ is independently selected from hydrogen, deuterium, or simple alkyl;

R$^{13}$ is independently selected from hydrogen, deuterium, or simple alkyl;

R$^{14}$ is a straight chain or branched alkyl group of 3 to 28 carbons, monocyclic aryl, multicyclic aryl, monocyclic heteroaryl, multicyclic heteroaryl, simple alkyl, haloalkyl, or heteroalkyl;

R$^{15}$ is independently selected from hydrogen, deuterium, halogen, or simple alkyl;

R$^{16}$ is independently selected from hydrogen, deuterium, halogen, or simple alkyl;

R$^{17}$ is a straight chain or branched alkyl group of 3 to 28 carbons, monocyclic aryl, multicyclic aryl, monocyclic heteroaryl, or multicyclic heteroaryl;

R$^{18}$ is independently selected from hydrogen, deuterium, halogen, or simple alkyl;

R$^{19}$ is independently selected from hydrogen, deuterium, halogen, or simple alkyl;

n is 0 or more;
m is 0 or more;
o is 0, 1, 2, or 3;
p is 0, 1, 2, or 3;
t is 0, 1, or 2;
u is 0, 1, or 2;

The present invention also provides a pharmaceutical composition comprising the compounds of Formula (I) in a therapeutically effective amount in association with a pharmaceutically acceptable excipient, carrier or diluent.

The compounds of Formula (I) are useful as BACE1 inhibitors and may be administered to treat diseases related to aberrant activity of the BACE1 enzyme, for example Down's syndrome; β-amyloid angiopathy; disorders associated with cognitive impairment; Alzheimer's disease; memory loss; attention deficit symptoms associated with Alzheimer's disease; neurodegenerative diseases; pre-senile dementia; senile dementia; dementia associated with Alzheimer's disease, Parkinson's disease and/or Down's Syndrome; age-related macular degeneration (AMD); glaucoma; olfactory function impairment; traumatic brain injury; progressive muscle diseases; Type II diabetes mellitus and cardiovascular diseases (e.g., stroke).

DEFINITIONS

Figure 1:
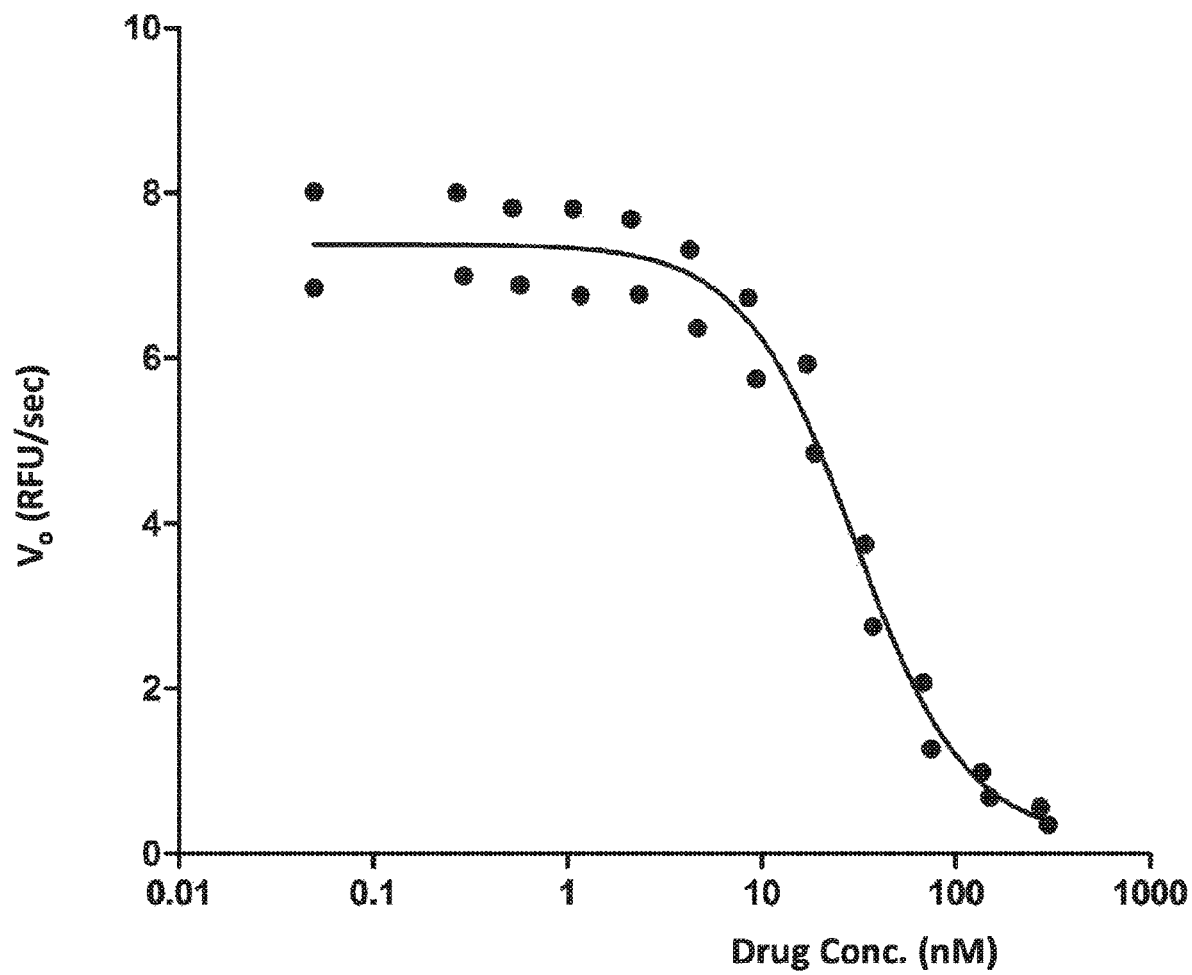
FIG. 1 shows an exemplary dose response curve evaluating the inhibition of amyloid β peptide secretion by the treatment of a selected BACE1 inhibitor using the AnaSpec BACE1 fluorescent assay.

The term "alkyl", as used herein, refers to saturated, monovalent or divalent hydrocarbon moieties having linear or branched moieties or combinations thereof and containing 1 to about 20 carbon atoms. Branched means that one or more alkyl groups such as methyl, ethyl, or propyl are attached to a linear alkyl chain. One methylene ($CH_2$) group, of the alkyl group can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can have one or more chiral centers. Alkyl groups may be unsubstituted or optionally substituted by one or more substituents which may be the same or different, each substituent being as described herein or independently selected from the group consisting of halogen atoms, cyano groups, hydroxyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups, ester groups, ketone groups.

The term "simple alkyl" refers to an alkyl moiety as defined above having linear or branched moieties or combinations thereof and containing about 1 to 5 carbon atoms. Non-limiting examples of simple alkyl groups include methyl, ethyl, isopropyl, and t-butyl.

The term "carbocyclic" or "cycloalkyl", as used herein, refers to a monovalent or divalent group of 3 to 15 carbon atoms derived from a saturated cyclic hydrocarbon. Carbocyclic groups can be monocyclic or multicyclic. Carbocyclic groups can be independently substituted by halogen atoms, sulfonyl $C_{1-8}$ alkyl groups, sulfoxide $C_{1-8}$ alkyl groups, sulfonamide groups, nitro groups, cyano groups, $OC_{1-8}$ alkyl groups, $SC_{1-8}$ alkyl groups, $C_{1-8}$ alkyl groups, $C_{2-6}$ alkenyl groups, $C_{2-6}$ alkynyl groups, ketone groups, alkylamino groups, amide groups, amino groups, aryl groups, $C_{3-8}$ cycloalkyl groups or hydroxyl groups. Non-limiting examples of suitable monocyclic carbocyclic groups include cyclopropyl, cyclopentyl, cyclohexyl, and the like. Non-limiting examples of suitable multicyclic carbocyclic groups include I-decalin, norbornyl, adamantyl and the like.

The term "cycloalkenyl", as used herein, refers to a monovalent or divalent group of 3 to 8 carbon atoms derived from a saturated cycloalkyl, and having at least one double bond. Cycloalkenyl groups can be monocyclic or multicyclic. Cycloalkenyl groups can be independently substituted by halogen atoms, sulfonyl groups, sulfoxide groups, nitro groups, cyano groups, $OC_{1-6}$ alkyl groups, $SC_{1-6}$ alkyl groups, $C_{1-6}$ alkyl groups, $C_{2-6}$ alkenyl groups, $C_{2-6}$ alkynyl groups, ketone groups, alkylamino groups, amide groups, amino groups, aryl groups, $C_{3-8}$ cycloalkyl groups or hydroxyl groups. Non-limiting examples of suitable monocyclic cycloalkenyls include cyclopentenyl, cyclohexenyl, cycloheptenyl, and the like. N Non-limiting example of a suitable multicyclic cycloalkenyl is 2,3,3a,4,5,6-hexahydro-1H-indene, 1,2,3,4,4a,5,6,8a-octahydronaphthalene and the like.

The term "halogen", as used herein, refers to an atom of chlorine, bromine, fluorine, iodine.

The term "haloalkyl" means an alkyl as defined above wherein one or more hydrogen atoms on the alkyl is replaced by a halo group as defined above.

The term "heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable heteroatoms include O, S, S(O), $S(O)_2$, and —NH—, and —N(alkyl)-.

The term "heterohaloalkyl" means an alkyl as defined above wherein one methylene ($CH_2$) group of the alkyl group is replaced by a heteroatom and one or more hydrogen atoms on the alkyl is replaced by a halo group as defined above.

The term "alkenyl", as used herein, refers to a monovalent or divalent hydrocarbon moiety having 2 to 10 carbon atoms, derived from a saturated alkyl, and having at least one double bond. One methylene ($CH_2$) group, of the alkenyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. $C_{2-10}$ alkenyl can be in the E or Z configuration. Alkenyl groups may be unsubstituted or optionally substituted by one or more substituents which may be the same or different, each substituent being as described herein or independently selected from the group consisting of halogen atoms, hydroxyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups, ester groups, ketone groups. Non-limiting examples of suitable alkenyl groups include ethenyl, propenyl, n-butenyl, 3-methylbut-2-enyl, n-pentenyl, octenyl and decenyl.

The term "alkynyl", as used herein, refers to a monovalent or divalent hydrocarbon moiety having 2 to 10 carbon atoms, derived from a saturated alkyl, and having at least one triple bond. One methylene ($CH_2$) group, of the alkynyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkynyl groups may be unsubstituted or optionally substituted by one or more substituents which may be the same or different, each substituent being as described herein or independently selected from the group consisting of halogen atoms, hydroxyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups, ester groups, ketone groups. Non-limiting examples of suitable alkynyl groups include ethynyl, propynyl, 2-butynyl, and decynyl.

The term "heteroalkynyl" means an alkynyl moiety as defined above, having one or more carbon atoms, for example one, two or three carbon atoms, replaced with one or more heteroatoms, which may be the same or different, where the point of attachment to the remainder of the molecule is through a carbon atom of the heteroalkynyl radical. Suitable heteroatoms include O, S, S(O), S(O)$_2$, and —NH—, —N(alkyl)-.

The term "aryl" as used herein, refers to an organic moiety derived from an aromatic hydrocarbon consisting of a ring containing 6 to 10 carbon atoms, and by removal of one hydrogen atom. Aryl groups can be substituted by halogen atoms, sulfonyl $C_{1-6}$ alkyl groups, sulfoxide $C_{1-6}$ alkyl groups, sulfonamide groups, carboxcyclic acid groups, $C_{1-6}$ alkyl carboxylates (ester) groups, amide groups, nitro groups, cyano groups, $OC_{1-6}$ alkyl groups, $SC_{1-6}$ alkyl groups, $C_{1-6}$ alkyl groups, $C_{2-6}$ alkenyl groups, $C_{2-6}$ alkynyl groups, ketone groups, aldehydes, alkylamino groups, amino groups, aryl groups, $C_{3-8}$ cycloalkyl groups or hydroxyl groups. Aryls can be monocyclic or multicyclic. Non-limiting examples of suitable aryl groups include phenyl and naphthyl.

The term "arylalkenyl" as used herein refers to a group derived from aryl and alkenyl groups as defined herein.

The term "arylalkynyl" as used herein refers to a group derived from aryl and alkynyl groups as defined herein.

The term "heteroaryl" as used herein, refers to a 5 to 14 membered ring, which is aromatic containing at least one heteroatom selected from oxygen, nitrogen, sulfur, or combinations of at least two thereof, interrupting the carbocyclic ring structure. Heteroaryl groups can be monocyclic or multicyclic. "Heteroaryl" may also include a heteroaryl fused to an aryl as described above. A nitrogen atom of a heteroaryl can be optionally oxidized to the corresponding N-oxide. Heteroaryl ring moieties can be unsubstituted or optionally substituted by one or more halogen atoms, sulfonyl groups, sulfoxide groups, nitro groups, cyano groups, $OC_{1-6}$ alkyl groups, $SC_{1-6}$ alkyl groups, $C_{1-8}$ alkyl groups, $C_{2-6}$ alkenyl groups, $C_{2-6}$ alkynyl groups, amide groups, ketone groups, alkylamino groups, amino groups, aryl groups, ester groups, ketone groups, carboxylic acid groups, $C_{3-8}$ cycloalkyl groups or hydroxyl groups. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, triazolyl, benzothienyl, quinolinyl, imidazolyl, thienopyridyl, quinazolinyl, thienopyrimidyl, pyrrolopyridyl, imidazopyridyl, isoquinolinyl, 1H-indolyl, benzoazaindolyl, dibenzo[b,d]thiophenyl, benzo[4,5]thieno[2,3-b]pyridinyl, benzothiazolyl, pyrido[2,3-b]indolizinyl, thieno[2,3-d]oxazolyl, 1H-pyrrolo[3,2-b]pyridinyl, 1H-pyrrolo[2,3-b]pyridinyl, dibenzo[b,d]thiophenyl, benzo[4,5]imidazo[1,2-a]pyridinyl, 9H-pyrido[2,3-b]indolyl, benzo[4,5]thieno[2,3-b]pyridinyl, benzofuro[2,3-b]pyridinyl and the like.

The term "heteroarylalkyl" as used herein refers to a group derived from heteroaryl and alkyl groups as defined herein.

The term "heteroarylalkenyl" as used herein refers to a group derived from heteroaryl and alkenyl groups as defined herein.

The term "heteroarylalkynyl" as used herein refers to a group derived from heteroaryl and alkynyl groups as defined herein.

The term "heterocyclic" as used herein, refers to a non-aromatic 3 to 10 membered ring, which can be saturated or unsaturated, containing at least one heteroatom selected form oxygen, nitrogen, sulfur, or combinations of at least two thereof, interrupting the carbocyclic ring structure. The heterocyclic ring can be interrupted by a C(O); the S and N heteroatoms can be oxidized. Heterocyclic groups can be monocyclic or multicyclic. Heterocyclic ring moieties may be fused to one or more aryl or heteroaryl ring groups. Heterocyclic ring moieties can be substituted by halogen atoms, sulfonyl groups, sulfoxide groups, nitro groups, cyano groups, $OC_{1-6}$ alkyl groups, $SC_{1-6}$ alkyl groups, $C_{1-8}$ alkyl groups, $C_{2-6}$ alkenyl groups, $C_{2-6}$ alkynyl groups, amide groups, ketone groups, alkylamino groups, amino groups, aryl groups, ester groups, ketone groups, carboxylic acid groups, $C_{3-8}$ cycloalkyl groups or hydroxyl groups. Non-limiting examples of suitable monocyclic heterocyclic rings include piperidyl, pyrrolidinyl, morpholinyl, thiomorpholinyll, 4-dioxanyl, tetrahydrofuranyl, and the like. Non-limiting examples of heterocyclic ring moieties fused to one or more aryl or heteroaryl groups include isoindoline, 1,2,3,4-tetrahydroquinoline, 9,10-dihydroacridine, 5,10-dihydrobenzo[b][1,6]naphthyridine, chromane, 9H-xanthene, thiochromane, 9H-thioxanthene, 10H-chromeno[3,2-c]pyridine, 2,3,4,5-tetrahydro-1H-benzo[b]azepine, 10,11-dihydro-5H-dibenzo[b,f]azepine, 3-methyl-10,11-dihydro-5H-dibenzo[b,f]azepine, 2,3,4,5-tetrahydro-1H-benzo[e][1,4]diazepine, 2,3,4,5-tetrahydro-1H-benzo[b][1,4]diazepine, 10,11-dihydro-5H-dibenzo[b, e][1,4]diazepine, 1,2,3,5-tetrahydrobenzo[e][1,4]oxazepine, 2,3,4,5-tetrahydrobenzo[b][1,4]oxazepine, 7-methyl-5,11-dihydrodibenzo[b, e][1,4]oxazepine, 1,2,3,5-tetrahydrobenzo[e][1,4]thiazepine, 2,3,4,5-tetrahydrobenzo[b][1,4]thiazepine, 5,11-dihydrodibenzo[b,e][1,4]thiazepine, 1,2,3,5-tetrahydrobenzo[e][1,4]thiazepine 4,4-dioxide, 2,3,4,5-tetrahydrobenzo[b][1,4]thiazepine 1,1-dioxide, 5,11-dihydrodibenzo[b,e][1,4]thiazepine 10,10-dioxide, 3-methyl-5,11-dihydrodibenzo[b, e][1,4]thiazepine 10,10-dioxide, (1aS,10bR)-1,1a,6,10b-tetrahydrobenzo[b]cyclopropa[d]pyrido[3,2-f]azepine, (1aS,10bR)-4-fluoro-1,1a,6,10b-tetrahydrobenzo[b]cyclopropa[d]pyrido[3,2-f]azepine, 6,11-dihydro-5H-benzo[b]pyrido[3,2-f]azepine, 10,11-dihydro-5H-benzo[b]pyrido[3,4-f]azepine, 6,7,8,9-tetrahydro-5H-pyrido[2,3-b]azepine, 6,11-dihydro-5H-benzo[b]pyrido[3,2-f]azepine, 2-methyl-6,11-dihydro-5H-benzo[b]pyrido[3,2-f]azepine, 2,3,4,5-tetrahydropyrido[3,2-b][1,4]oxazepine, 6,11-dihydrobenzo[e]pyrido[3,2-b][1,4]oxazepine, 5,11-dihydrobenzo[b]pyrido[2,3-e][1,4]oxazepine, 2,3,4,5-tetrahydropyrido[3,2-b][1,4]thiazepine, 6,11-dihydrobenzo[e]pyrido[3,2-b][1,4]thiazepine, 5,11-dihydrobenzo[b]pyrido[2,3-e][1,4]thiazepine, 2,3,4,5-tetrahydropyrido[3,2-b][1,4]thiazepine 1,1-dioxide, 6,11-dihydrobenzo[e]pyrido[3,2-b][1,4]thiazepine 5,5-dioxide, 5,11-dihydrobenzo[b]pyrido[2,3-e][1,4]thiazepine 6,6-dioxide and the like.

The term "heterocycloalkyl" as used herein refers to a group derived from heterocyclic and alkyl groups as defined herein.

The term "hydroxyl" as used herein, represents a group of formula "OH".

The term "carbonyl" as used herein, represents a group of formula "C(O)".

The term "ketone" as used herein, represents an organic compound having a carbonyl group linked to a carbon atom such as $C(O)R^x$, wherein $R^x$ can be alkyl, aryl, cycloalkyl, cycloalkenyl, heterocycle as defined above.

The term "ester" as used herein, represents an organic compound having a carbonyl group linked to a carbon atom such as $C(O)OR^x$, wherein $R^x$ can be alkyl, aryl, cycloalkyl, cycloalkenyl, heterocycle as defined above.

The term "amine" as used herein, represents a group of formula "$NR^xR^y$", wherein $R^x$ and $R^y$ can be the same or independently H, alkyl, aryl, cycloalkyl, cycloalkenyl, heterocycle as defined above.

The term "carboxyl" as used herein, represents a group of formula "C(O)O".

The term "sulfonyl" as used herein, represents a group of formula "$SO_2$".

The term "sulfate" as used herein, represents a group of formula "$O-S(O)_2-O$".

The term "sulfonate" as used herein, represents a group of the formula "$S(O)_2-O$".

The term "carboxylic acid" as used herein, represents a group of formula "$C(O)OH$".

The term "nitro" as used herein, represents a group of formula "$NO_2$".

The term "cyano" as used herein, represents a group of formula "CN".

The term "amide" as used herein, represents a group of formula "$C(O)NR^xR^y$," or "$NR^xR^yC(O)$" wherein $R^x$ and $R^y$ can be the same or independently H, alkyl, aryl, cycloalkyl, cycloalkenyl, heterocycle as defined above.

The term "sulfonamide" as used herein, represents a group of formula "$S(O)_2NR^xR^y$" wherein $R^x$ and $R^y$ can be the same or independently H, alkyl, aryl, cycloalkyl, cycloalkenyl, heterocycle as defined above.

The term "sulfoxide" as used herein, represents a group of formula "$S(O)$".

The term "phosphonic acid" as used herein, represents a group of formula "$P(O)(OH)_2$".

The term "phosphoric acid" as used herein, represents a group of formula "$OP(O)(OH)_2$".

The term "sulphonic acid" as used herein, represents a group of formula "$S(O)_2OH$".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

DETAILED DESCRIPTION OF THE INVENTION

The present invention relates to novel organic molecules capable of modulating, regulating and inhibiting BACE1. In particular, the present invention relates to novel BACE1 inhibitors which can be used for the treatment of Aβ-related pathologies.

In one aspect, the invention provides compounds represented by Formula (I) or a pharmaceutically acceptable salt thereof or stereoisomeric forms thereof or the enantiomers, diastereomers, tautomers, zwitterions, and pharmaceutically acceptable salts thereof:

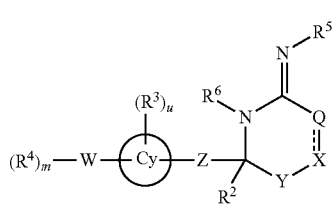

Formula (I)

wherein

X is absent or present and when present selected from the group consisting of $C(O)$, $C(S)$, $S(O)_2$, $(CR^7R^8)_n$, O, N, $NR^1$, S and $S(O)$;

Y is absent or present and when present is $(CR^7R^8)_n$, X and Y together may also include

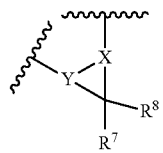

according to some embodiments;

Z is absent or present and when present is selected from the group consisting of alkyl, haloalkyl, heteroalkyl, alkenyl, alkynyl, $(CR^{10}R^{11})_oNR^9(CR^{12}R^{13})_p$, $(CR^{10}R^{11})_oNR^9C(O)(CR^{12}R^{13})$, $(CR^{10}R^{11})_oC(O)NR^9(CR^{12}R^{13})_p$, $(CR^{10}R^{11})_oC(O)(CR^{12}R^{13})_p$, $(CR^{10}R^{11})_oC(O)O(CR^{12}R^{13})_p$, $(CR^{10}R^{11})_oOC(O)(CR^{12}R^{13})_p$, $(CR^{10}R^{11})_oOC(O)NR^9(CR^{12}R^{13})_p$, $(CR^{10}R^{11})_oNR^9C(O)O(CR^{12}R^{13})_p$, $(CR^{10}R^{11})_oNR^9C(O)NR^9(CR^{12}R^{13})_p$, $(CR^{10}R^{11})_oO(CR^{12}R^{13})_p$, $(CR^{10}R^{11})_oS(O)_n(CR^{12}R^{13})_p$ and cycloalkyl;

W is absent or present and when present is selected from the group consisting of alkyl, haloalkyl, heteroalkyl, alkenyl, alkynyl, $OR^9$, O, $NR^9R^{10}$, $NR^9$, $C(O)R^9$, $C(O)NR^9$, $NR^9C(O)$, $C(O)OR^9$, $OC(O)R^9$, $COR^9R^{10}$ and heterocycloalkyl;

Q is absent or present and when present is selected from O, S, $NR^1$, $CR^1$, $(CR^{14}R^{15})_r$, $C(O)$ or cycloalkyl;

ring

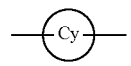

is selected from the group consisting of monocyclic aryl, multicyclic aryl, monocyclic heteroaryl, multicyclic heteroaryl, monocyclic carbocyclic, multicyclic carbocyclic, monocyclic heterocyclic, and multicyclic heterocyclic ring systems;

the bond between Q and X is a single or double bond;

$R^1$ is selected from hydrogen, alkyl, cycloalkyl, haloalkyl, heteroalkyl, heterohaloalkyl or heteroalkynyl;

$R^2$ is selected from hydrogen, deuterium, halogen, CN, alkyl, cycloalkyl, haloalkyl, heteroalkyl, aryl, heteroaryl, heterohaloalkyl or heteroalkynyl;

$R^3$ is independently selected from the group consisting of: hydrogen, deuterium, halogen, CN, alkyl, haloalkyl, heteroalkyl, alkenyl, alkynyl, aryl, arylalkyl, cycloalkyl, heteroaryl, heteroarylalkyl, heterocycloalkyl and C(O);

$R^4$ is independently selected from the group consisting of: hydrogen, deuterium, halogen, hydroxyl, CN, alkyl, haloalkyl, heteroalkyl, alkenyl, alkynyl, aryl, arylalkyl, arylalkenyl, arylalkynyl, cycloalkyl, heteroaryl, heteroarylalkyl, heteroarylalkenyl, heteroarylalkynyl and heterocycloalkyl;

$R^5$ is selected from hydrogen, simple alkyl or a prodrug moiety. Said prodrug moiety may be selected from but not limited to $C(O)R^{14}$ and $CR^{15}R^{16}OC(O)R^{14}$;

$R^6$ is selected from hydrogen, simple alkyl or a prodrug moiety. Said prodrug moiety may be selected from but not limited to $C(O)R^{17}$ and $CR^{18}R^{19}OC(O)R^{17}$;

$R^7$ is absent or present and when present is independently selected from hydrogen, deuterium, halogen, simple alkyl or haloalkyl;

$R^8$ is absent or present and when present is independently selected from hydrogen, deuterium, halogen, simple alkyl or haloalkyl;

$R^9$ is independently selected from hydrogen, deuterium, halogen, simple alkyl or alkynyl, $R^{10}$ is independently selected from hydrogen, deuterium, halogen or simple alkyl;

$R^{11}$ is independently selected from hydrogen, deuterium, halogen or simple alkyl;

$R^{12}$ is independently selected from hydrogen, deuterium or simple alkyl;

$R^{13}$ is independently selected from hydrogen, deuterium or simple alkyl;

$R^{14}$ is a straight chain or branched alkyl group of 3 to 28 carbons, cycloalkyl, heterocycloalkyl, monocyclic aryl, multicyclic aryl, monocyclic heteroaryl, multicyclic heteroaryl, simple alkyl, haloalkyl or heteroalkyl;

$R^{15}$ is independently selected from hydrogen, deuterium, halogen, simple alkyl;

$R^{16}$ is independently selected from hydrogen, deuterium, halogen, simple alkyl;

$R^{17}$ is a straight chain or branched alkyl group of 3 to 28 carbons, cycloalkyl, heterocycloalkyl, monocyclic aryl, multicyclic aryl, monocyclic heteroaryl or multicyclic heteroaryl;

$R^{18}$ is independently selected from hydrogen, deuterium, halogen, simple alkyl;

$R^{19}$ is independently selected from hydrogen, deuterium, halogen, simple alkyl;

n is 0 or more;
m is 0 or more;
o is 0, 1, 2, or 3
p is 0, 1, 2, or 3
t is 0, 1, or 2; and
u is 0, 1, or 2.

Those skilled in the art will recognize that the compounds of Formula (I) may exist as tautomeric and/or stereoisomeric forms, and all such tautomeric and stereoisomeric forms are contemplated herein as part of the present invention. Said compound can be represented by any of the following structures:

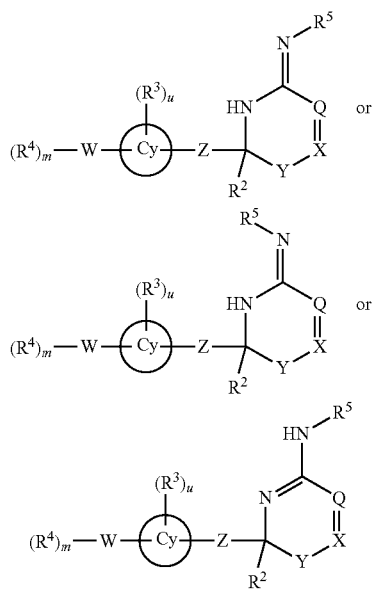

Preferred compounds of Formula (I) include but are not limited to the following structures:

| Example | Structure | Compound name |
|---|---|---|
| 1 | 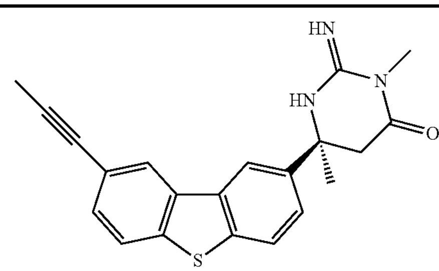 | (S)-2-Imino-3,6-dimethyl-6-(8-(prop-1-yn-1-yl)dibenzo[b,d]thiophen-2-yl)tetrahydropyrimidin-4(1H)-one |
| 2 | 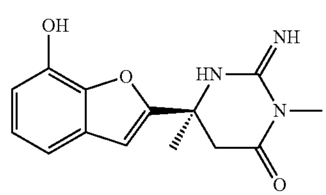 [SMILES: CN1C(=N)N[C@](C)(c2cc3cccc(O)c3o2)CC1=O] | (S)-6-(7-Hydroxybenzofuran-2-yl)-2-imino-3,6-dimethyltetrahydropyrimidin-4(1H)-one |
| 3 | 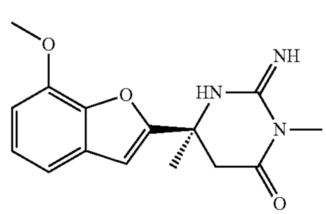 [SMILES: COc1cccc2cc([C@]3(C)CC(=O)N(C)C(=N)N3)oc12] | (S)-2-Imino-6-(7-methoxybenzofuran-2-yl)-3,6-dimethyltetrahydropyrimidin-4(1H)-one |

| Example | Structure | Compound name |
|---|---|---|
| 4 | 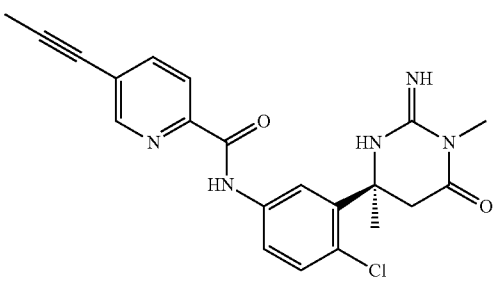 | (S)-N-(4-Chloro-3-(2-imino-1,4-dimethyl-6-oxohexa-hydropyrimidin-4-yl)phenyl)-5-(prop-1-yn-1-yl)picolinamide |
| 5 | 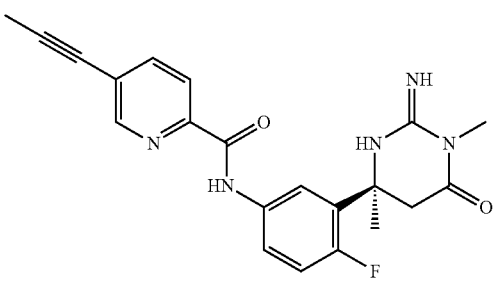 | (S)-N-(4-Fluoro-3-(2-imino-1,4-dimethyl-6-oxohexahydropyrimidin-4-yl)phenyl)-5-(prop-1-yn-1-yl)picolinamide |
| 6 | 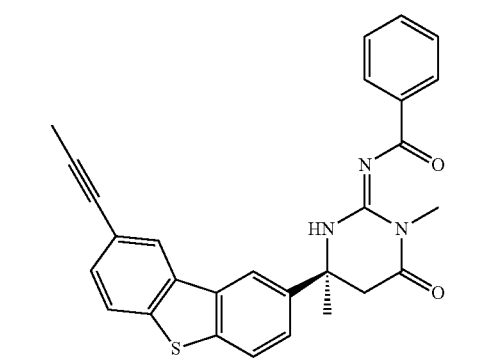 [SMILES: CC#Cc1ccc2sc3ccc([C@]4(C)CC(=O)N(C)/C(=N\C(=O)c5ccccc5)N4)cc3c2c1] | (S,Z)-N-(1,4-Dimethyl-6-oxo-4-(8-(prop-1-yn-1-yl)dibenzo[b,d]thiophen-2-yl)tetrahydropyrimidin-2(1H)-ylidene)benzamide |
| 7 | 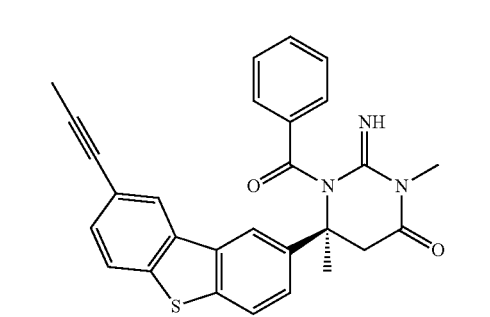 [SMILES: CC#Cc1ccc2sc3ccc([C@]4(C)CC(=O)N(C)C(=N)N4C(=O)c4ccccc4)cc3c2c1] | (S)-1-Benzoyl-2-imino-3,6-dimethyl-6-(8-(prop-1-yn-1-yl)dibenzo[b,d]thiophen-2-yl)tetrahydropyrimidin-4(1H)-one |
| 8 | 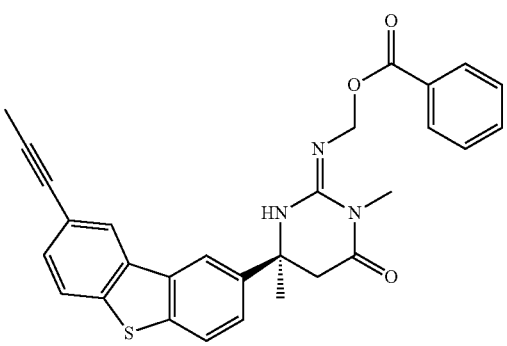 [SMILES: CC#Cc1ccc2sc3ccc([C@]4(C)CC(=O)N(C)/C(=N\COC(=O)c5ccccc5)N4)cc3c2c1] | (S,Z)-((1,4-Dimethyl-6-oxo-4-(8-(prop-1-yn-1-yl)dibenzo[b,d]thiophen-2-yl)tetrahydropyrimidin-2(1H)-ylidene)amino)methyl benzoate |

-continued

| Example | Structure | Compound name |
|---|---|---|
| 9 | 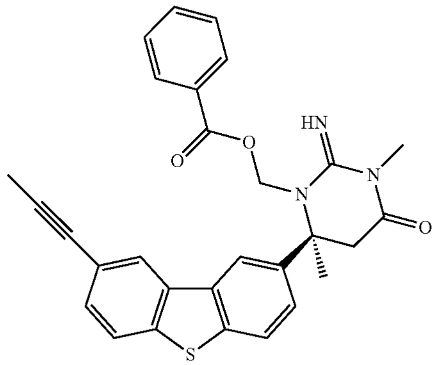 [SMILES: CC#Cc1ccc2sc3ccc([C@]4(C)CC(=O)N(C)C(=N)N4COC(=O)c4ccccc4)cc3c2c1] | (S)-(2-Imino-3,6-dimethyl-4-oxo-6-(8-(prop-1-yn-1-yl)dibenzo[b,d]thiophen-2-yl)tetrahydropyrimidin-1(2H)-yl)methyl benzoate |
| 10 | 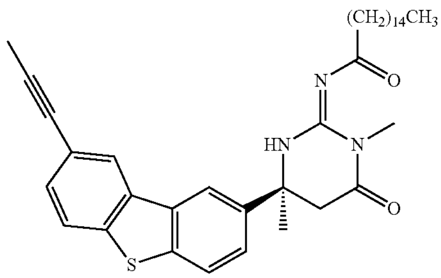 | (S,Z)-N-(1,4-Dmethyl-6-oxo-4-(8-(prop-1-yn-1-yl)dibenzo[b,d]thiophen-2-yl)tetrahydropyrimidin-2(1H)-ylidene)palmitamide |
| 11 | 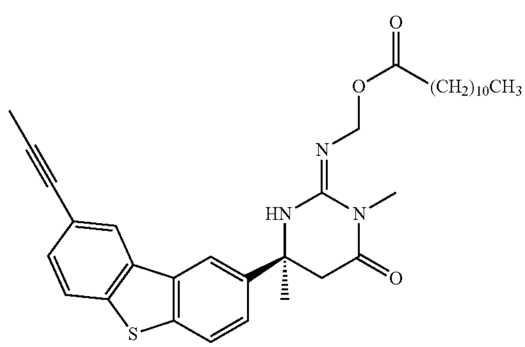 | (S,Z)-((1,4-Dimethyl-6-oxo-4-(8-(prop-1-yn-1-yl)dibenzo[b,d]thiophen-2-yl)tetrahydropyrimidin-2(1H)-ylidene)amino)methyl dodecanoate |
| 12 | 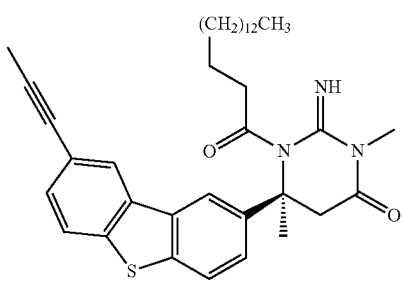 | (S)-2-Imino-3,6-dimethyl-1-palmitoyl-6-(8-(prop-1-yn-1-yl)dibenzo[b,d]thiophen-2-yl)tetrahydropyrimidin-4(1H)-one |
| 13 | 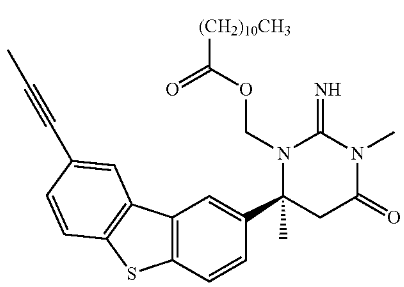 | (S)-(2-Imino-3,6-dimethyl-4-oxo-6-(8-(prop-1-yn-1-yl)dibenzo[b,d]thiophen-2-yl)tetrahydropyrimidin-1(2H)-yl)methyldodecanoate |

-continued

| Example | Structure | Compound name |
|---|---|---|
| 14 | 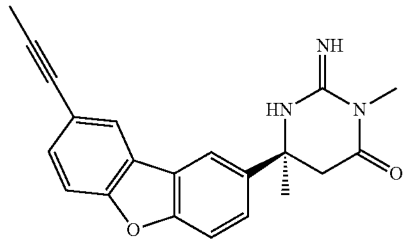 [SMILES: CC#Cc1ccc2oc3ccc([C@]4(C)CC(=O)N(C)C(=N)N4)cc3c2c1] | (S)-2-Imino-3,6-dimethyl-6-(8-(prop-1-yn-1-yl)dibenzo[b,d]furan-2-yl)tetrahydropyrimidin-4(1H)-one |
| 15 | 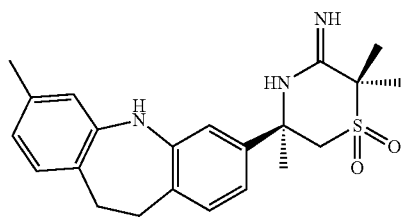 | (R)-3Imino-2,2,5-trimethyl-5-(7-methyl-10,11-dihydro-5H-dibenzo[b,f]azepin-3-yl)thiomorpholine 1,1-dioxide |
| 16 | 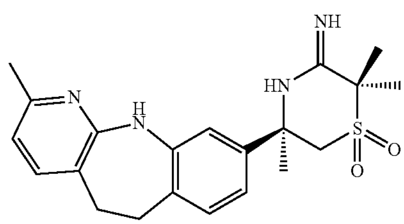 | (R)-3-Imino-2,2,5-trimethyl-5-(2-methyl-6,11-dihydro-5H-benzo[b]pyrido[3,2-f]azepin-9-yl)thiomorpholine 1,1-dioxide |
| 17 | 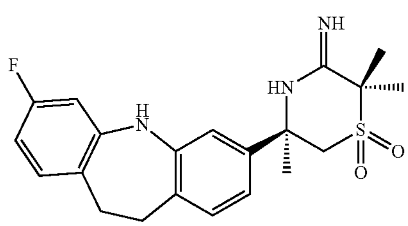 | (R)-5-(7Fluoro-10,11-dihydro-5H-dibenzo[b,f]azepin-3-yl)-3-imino-2,2,5-trimethylthiomorpholine 1,1-dioxide |
| 18 | 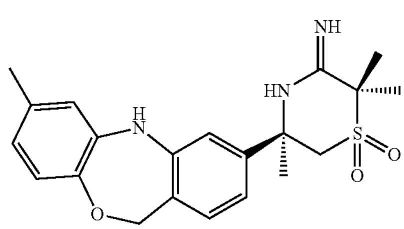 | (R)-3-Imino-2,2,5-trimethyl-5-(7-methyl-5,11-dihydrodibenzo[b,e][1,4]oxazepin-3-yl)thiomorpholine 1,1-dioxide |
| 19 | 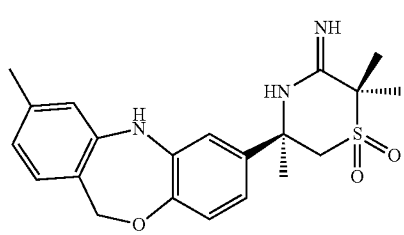 | (R)-3-Imino-2,2,5-trimethyl-5-(3-methyl-5,11-dihydrodibenzo[b,e][1,4]oxazepin-7-yl)thiomorpholine 1,1-dioxide |

| Example | Structure | Compound name |
|---|---|---|
| 20 | 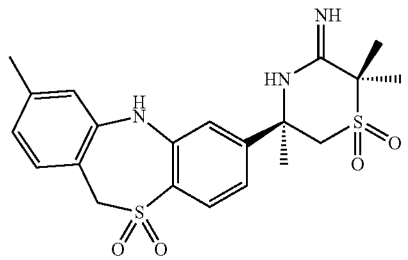 | (R)-7-(5-Imino-3,6,6-trimethyl-1,1-dioxidothiomorpholin-3-yl)-3-methyl-5,11-dihydrodibenzo[b,e][1,4]thiazepine 10,10-dioxide |
| 21 | 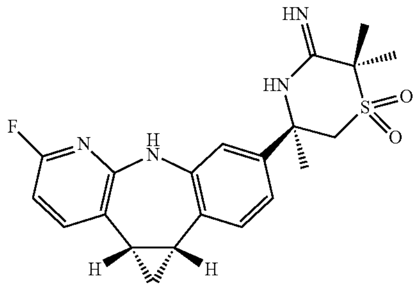 | (R)-5-((1aS,10bR)-4-Fluoro-1,1a,6,10b-tetrahydrobenzo[b]cyclopropa[d]pyrido[3,2-f]azepin-8-yl)-3-imino-2,2,5-trimethylthiomorpholine 1,1-dioxide |
| 22 | 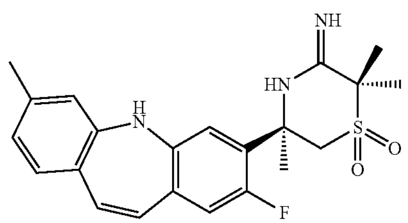 | (R)-5-(2-Fluoro-7-methyl-5H-dibenzo[b,f]azepin-3-yl)-3-imino-2,2,5-trimethylthiomorpholine 1,1-dioxide |
| 23 | 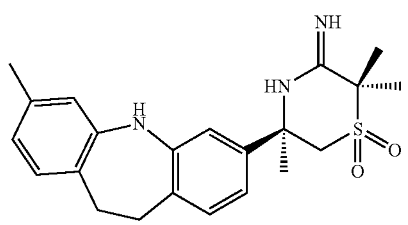 | (R)-3Imino-2,2,5-trimethyl-5-(7-methyl-10,11-dihydro-5H-dibenzo[b,f]azepin-3-yl)thiomorpholine 1,1-dioxide |

Preferred compounds of formula (I) also include the structures of the following Formula:

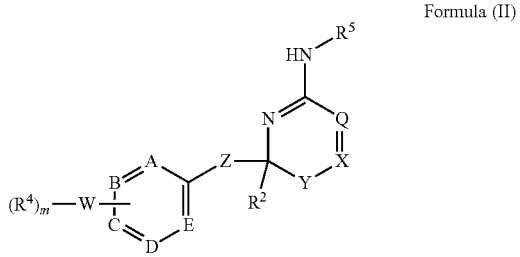

Formula (II)

wherein

A is selected from a substituted or unsubstituted carbon or nitrogen; B is selected from a substituted or unsubstituted carbon, or nitrogen;

C is selected from a substituted or unsubstituted carbon or nitrogen;

D is selected from a substituted or unsubstituted carbon or nitrogen; and

E is selected from a substituted or unsubstituted carbon or nitrogen.

Preferred compounds of Formula (II) include but are not limited to the following structures:

| Example | Structure | IUPAC name |
|---|---|---|
| 24 | 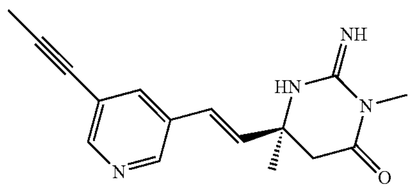 [SMILES: CC#Cc1cncc(/C=C/[C@]2(C)CC(=O)N(C)C(=N)N2)c1] | (S,E)-2-Imino-3,6-dimethyl-6-(2-(5-(prop-1-yn-1-yl)pyridin-3-yl)vinyl)tetrahydropyrimidin-4(1H)-one |

Preferred compounds of formula (I) also include the structures of the following Formulas:

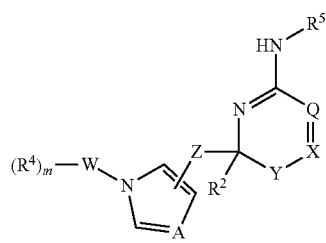

Formula (IIIa)

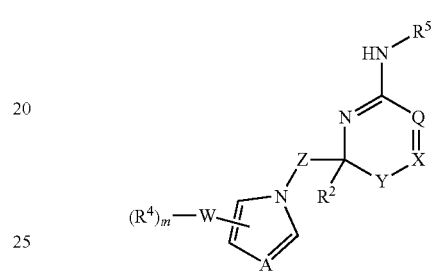

Formula (IIIb)

wherein
A is selected from a substituted or unsubstituted carbon or nitrogen.

Preferred compounds of Formula (III) include but are not limited to the following structures:

| Example | Structure | Compound name |
|---|---|---|
| 25 | 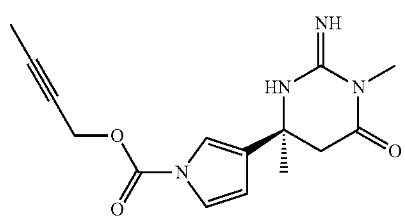 [SMILES: CC#CCOC(=O)n1ccc([C@]2(C)CC(=O)N(C)C(=N)N2)c1] | (S)-But-2-yn-1-yl 3-(2-imino-1,4-dimethyl-6-oxohexahydropyrimidin-4-yl)-1H-pyrrole-1-carboxylate |
| 26 | 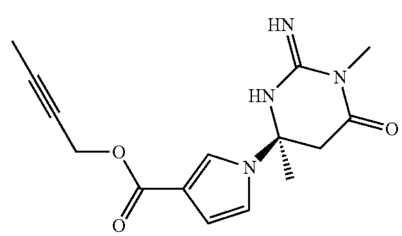 [SMILES: CC#CCOC(=O)c1ccn([C@]2(C)CC(=O)N(C)C(=N)N2)c1] | (R)-But-2-yn-1-yl 1-(2-imino-1,4-dimethyl-6-oxohexahydropyrimidin-4-yl)-1H-pyrrole-3-carboxylate |
| 27 | 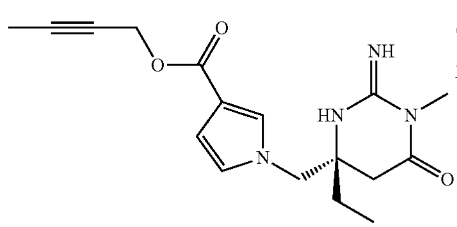 | (R)-But-2-yn-1-yl 1-((4-ethyl-2-imino-1-methyl-6-oxohexahydropyrimidin-4-yl)methyl)-1H-pyrrole-3-carboxylate |

-continued
| Example | Structure | Compound name |
|---|---|---|
| 28 | 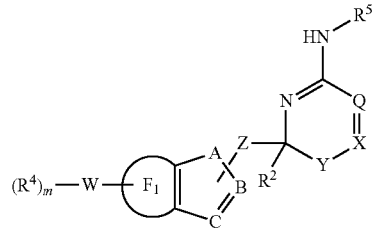 | (S)-But-2-yn-1-yl 1-((4-ethyl-2-imino-1-methyl-6-oxo-hexahydropyrimidin-4-yl)methyl)-1H-pyrrole-3-carboxylate |
Preferred compounds of formula (I) also include the structures of the following Formula:
Formula (IV)
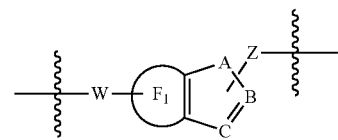
wherein
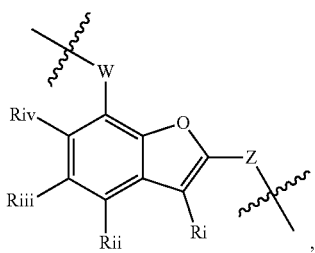
is selected from
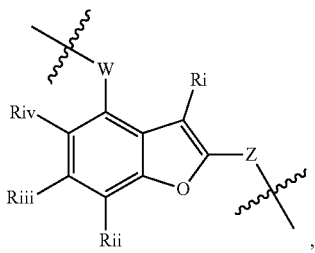,
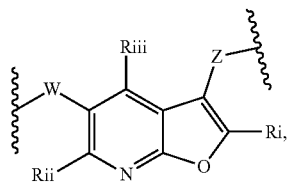
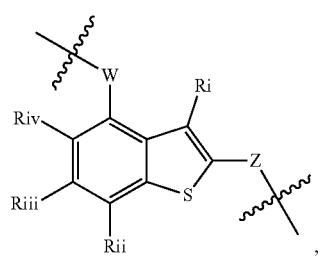,
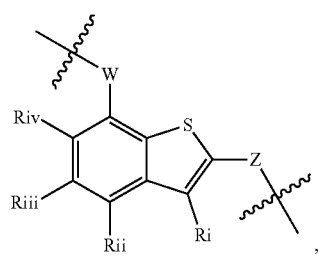,
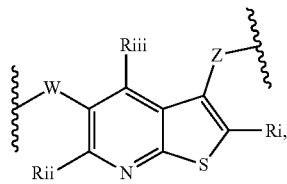,
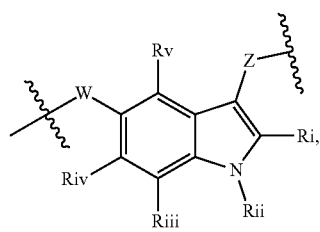

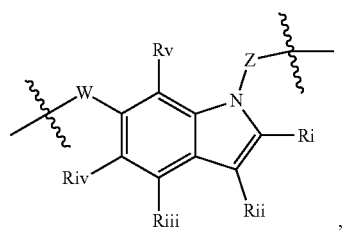

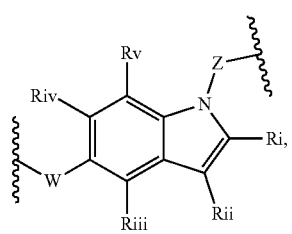

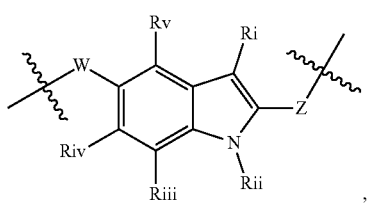

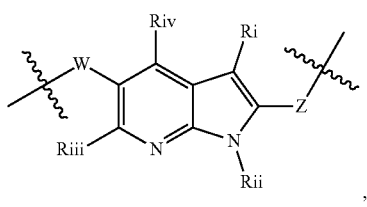

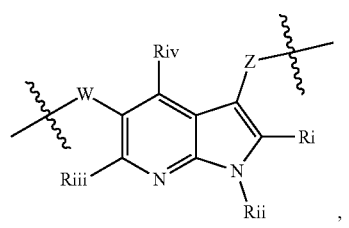

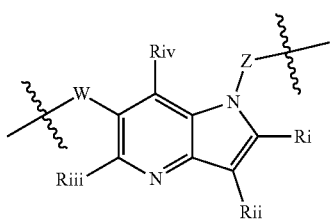

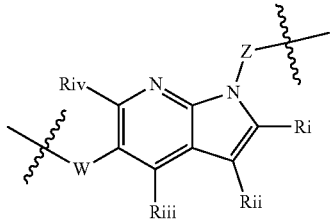

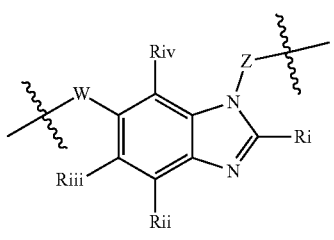

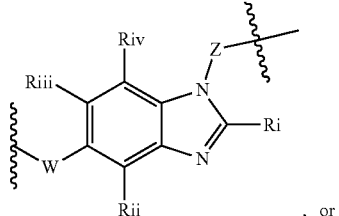

, or

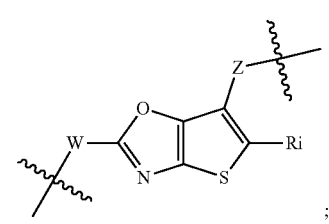

;

wherein

A is selected from a substituted or unsubstituted carbon, oxygen, sulfur or nitrogen;

B is selected from a substituted or unsubstituted carbon or nitrogen;

C is selected from a substituted or unsubstituted carbon or nitrogen; and each of Ri, Rii, Riii, Riv, and Rv, independently, is hydrogen, halogen, cyano group, amino group, amido group, $C_{1-6}$ alkyl, $C_{1-6}$ alkoxyl, $C_{2-6}$ alkenyl, or $C_{2-6}$ alkynyl, or is a moiety selected from $C_{3-10}$ cycloalkyl, $C_{1-10}$ heterocycloalkyl, aryl, and heteroaryl, each of which is optionally mono-, di-, or tri-substituted with halogen, nitro group, cyano group, amino group, amido group, $C_{1-6}$ alkyl, $C_{1-6}$ alkoxyl, $C_{2-6}$ alkenyl, $C_{2-6}$ alkynyl, aryl, or heteroaryl, or optionally fused with $C_{3-10}$ cycloalkyl, $C_{1-10}$ heterocycloalkyl, aryl, or heteroaryl.

Preferred compounds of Formula (IV) include but are not limited to the following structures:

| Example | Structure | Compound name |
|---|---|---|
| 2 | 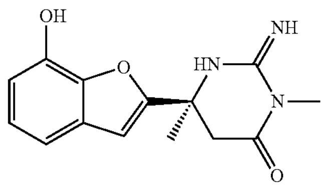 [SMILES: CN1C(=N)N[C@](C)(c2cc3cccc(O)c3o2)CC1=O] | (S)-6-(7-Hydroxybenzofuran-2-yl)-2-imino-3,6-dimethyltetrahydropyrimidin-4(1H)-one |
| 3 | 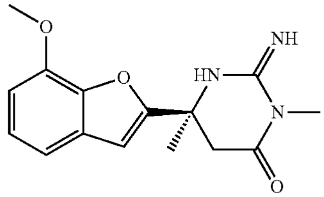 [SMILES: COc1cccc2cc([C@]3(C)CC(=O)N(C)C(=N)N3)oc12] | (S)-2-Imino-6-(7-methoxybenzofuran-2-yl)-3,6-dimethyltetrahydropyrimidin-4(1H)-one |
| 29 | 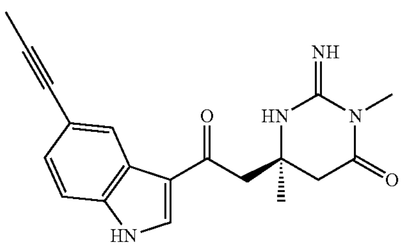 [SMILES: CC#Cc1ccc2[nH]cc(C(=O)C[C@]3(C)CC(=O)N(C)C(=N)N3)c2c1] | (R)-2-Imino-3,6-dimethyl-6-(2-oxo-2-(5-(prop-1-yn-1-yl)-1H-indol-3-yl)ethyl)tetrahydropyrimidin-4(1H)-one |
| 30 | 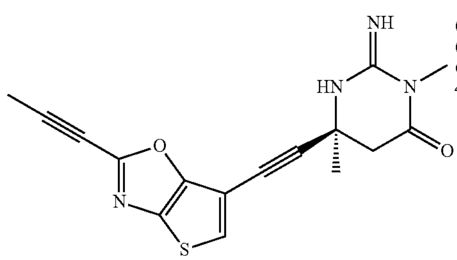 | (S)-2-Imino-3,6-dimethyl-6-((2-(prop-1-yn-1-yl)thieno[2,3-d]oxazol-6-yl)ethynyl)tetrahydropyrimidin-4(1H)-one |
| 31 | 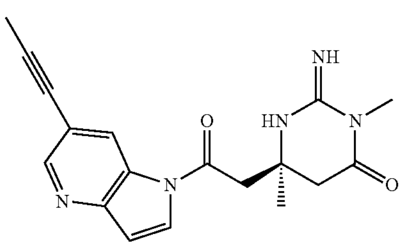 [SMILES: CC#Cc1cnc2ccn(C(=O)C[C@]3(C)CC(=O)N(C)C(=N)N3)c2c1] | (R)-2-Imino-3,6-dimethyl-6-(2-oxo-2-(6-(prop-1-yn-1-yl)-1H-pyrrolo[3,2-b]pyridin-1-yl)ethyl)tetrahydropyrimidin-4(1H)-one |
| 32 | 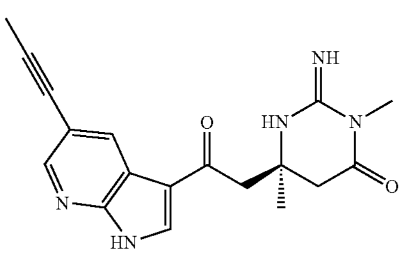 [SMILES: CC#Cc1cnc2[nH]cc(C(=O)C[C@]3(C)CC(=O)N(C)C(=N)N3)c2c1] | (R)-2-Imino-3,6-dimethyl-6-(2-oxo-2-(5-(prop-1-yn-1-yl)-1H-pyrrolo[2,3-b]pyridin-3-yl)ethyl)tetrahydropyrimidin-4(1H)-one |

-continued

| Example | Structure | Compound name |
|---|---|---|
| 33 | 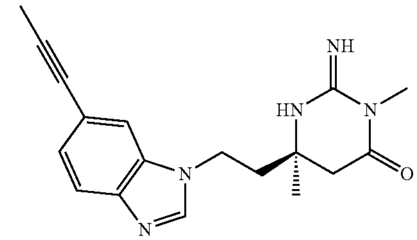 [SMILES: CC#Cc1ccc2ncn(CC[C@]3(C)CC(=O)N(C)C(=N)N3)c2c1] | (R)-2-Imino-3,6-dimethyl-6-(2-(6-(prop-1-yn-1-yl)-1H-benzo[d]imidazol-1-yl)ethyl)tetrahydropyrimidin-4(1H)-one |
| 34 | 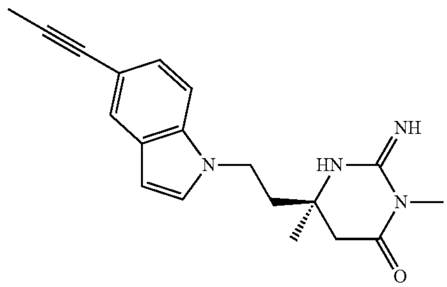 | (R)-2-Imino-3,6-dimethyl-6-(2-(5-(prop-1-yn-1-yl)-1H-indol-1-yl)ethyl)tetrahydropyrimidin-4(1H)-one |
| 35 | 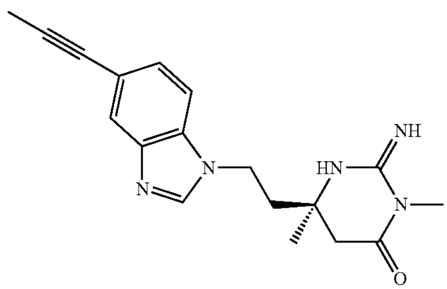 [SMILES: CC#Cc1ccc2c(c1)ncn2CC[C@]1(C)CC(=O)N(C)C(=N)N1] | (R)-2-Imino-3,6-dimethyl-6-(2-(5-(prop-1-yn-1-yl)-1H-benzo[d]imidazol-1-yl)ethyl)tetrahydropyrimidin-4(1H)-one |
| 36 | 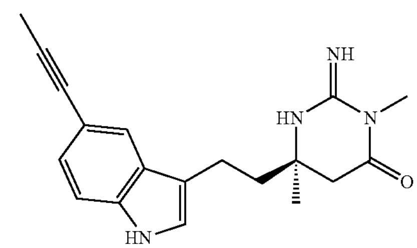 [SMILES: CC#Cc1ccc2[nH]cc(CC[C@]3(C)CC(=O)N(C)C(=N)N3)c2c1] | (R)-2-Imino-3,6-dimethyl-6-(2-(5-(prop-1-yn-1-yl)-1H-indol-3-yl)ethyl)tetrahydropyrimidin-4(1H)-one |
| 37 | 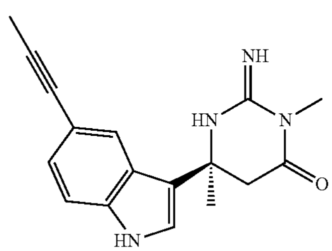 [SMILES: CC#Cc1ccc2[nH]cc([C@]3(C)CC(=O)N(C)C(=N)N3)c2c1] | (S)-2-Imino-3,6-dimethyl-6-(5-(prop-1-yn-1-yl)-1H-indol-3-yl)tetrahydropyrimidin-4(1H)-one |
| 38 | 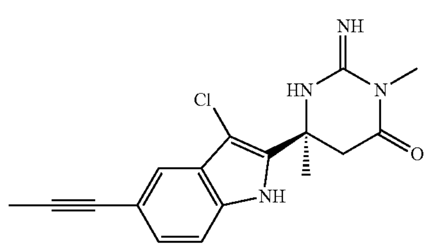 [SMILES: CC#Cc1ccc2[nH]c([C@]3(C)CC(=O)N(C)C(=N)N3)c(Cl)c2c1] | (S)-6-(3-Chloro-5-(prop-1-yn-1-yl)-1H-indol-2-yl)-2-imino-3,6-dimethyltetrahydropyrimidin-4(1H)-one |

-continued

| Example | Structure | Compound name |
|---------|-----------|---------------|
| 39 | 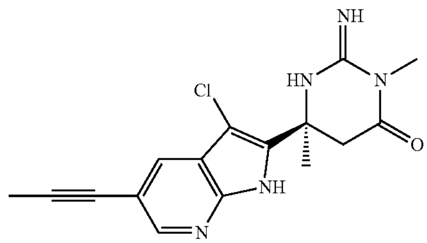 [SMILES: CC#Cc1cnc2[nH]c([C@]3(C)CC(=O)N(C)C(=N)N3)c(Cl)c2c1] | (S)-6-(3-Chloro-5-(prop-1-yn-1-yl)-1H-pyrrolo[2,3-b]pyridin-2-yl)-2-imino-3,6-dimethyltetrahydro-pyrimidin-4(1H)-one |
| 40 | 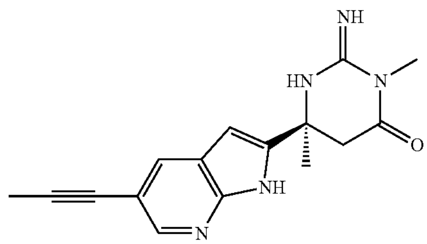 [SMILES: CC#Cc1cnc2[nH]c([C@]3(C)CC(=O)N(C)C(=N)N3)cc2c1] | (S)-2-Imino-3,6-dimethyl-6-(5-(prop-1-yn-1-yl)-1H-pyrrolo[2,3-b]pyridin-2-yl)tetrahydropyrimidin-4(1H)-one |
| 41 | 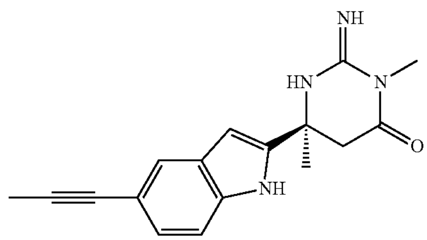 [SMILES: CC#Cc1ccc2[nH]c([C@]3(C)CC(=O)N(C)C(=N)N3)cc2c1] | (S)-2-Imino-3,6-dimethyl-6-(5-(prop-1-yn-1-yl)-1H-indol-2-yl)tetrahydro-pyrimidin-4(1H)-one |
| 42 | 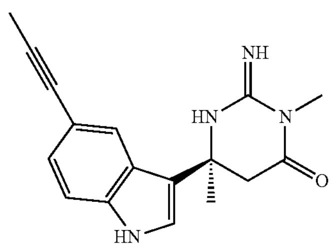 [SMILES: CC#Cc1ccc2[nH]cc([C@]3(C)CC(=O)N(C)C(=N)N3)c2c1] | S)-2-Imino-3,6-dimethyl-6-(5-(prop-1-yn-1-yl)-1H-indol-3-yl)tetrahydro-pyrimidin-4(1H)-one |
| 43 | 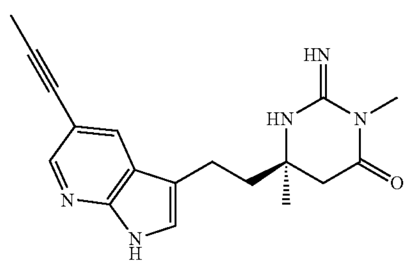 [SMILES: CC#Cc1cnc2[nH]cc(CC[C@]3(C)CC(=O)N(C)C(=N)N3)c2c1] | (R)-2-Imino-3,6-dimethyl-6-(2-(5-(prop-1-yn-1-yl)-1H-pyrrolo[2,3-b]pyridin-3-yl)ethyl)tetrahydropyrimidin-4(1H)-one |
| 44 | 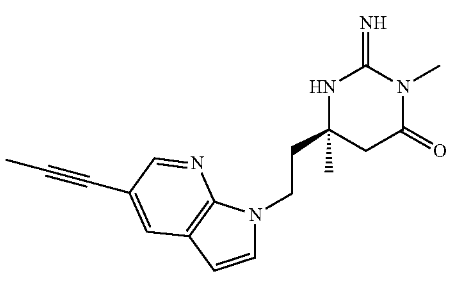 [SMILES: CC#Cc1cnc2c(ccn2CC[C@]2(C)CC(=O)N(C)C(=N)N2)c1] | (R)-2-Imino-3,6-dimethyl-6-(2-(5-(prop-1-yn-1-yl)-1H-pyrrolo[2,3-b]pyridin-1-yl)ethyl)tetrahydropyrimidin-4(1H)-one |

-continued

| Example | Structure | Compound name |
|---|---|---|
| 45 | 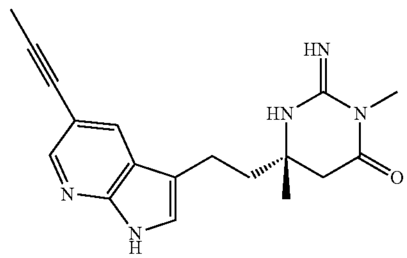 [SMILES: CC#Cc1cnc2[nH]cc(CC[C@@]3(C)CC(=O)N(C)C(=N)N3)c2c1] | (S)-2-Imino-3,6-dimethyl-6-(2-(5-(prop-1-yn-1-yl)-1H-pyrrolo[2,3-b]pyridin-3-yl)ethyl)tetrahydropyrimidin-4(1H)-one |
| 46 | 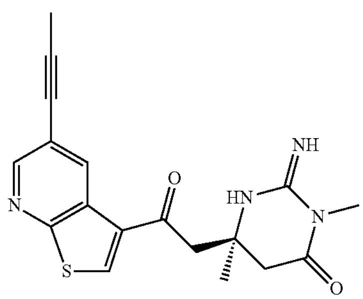 [SMILES: CC#Cc1cnc2scc(C(=O)C[C@]3(C)CC(=O)N(C)C(=N)N3)c2c1] | (R)-2-Imino-3,6-dimethyl-6-(2-oxo-2-(5-(prop-1-yn-1-yl)thieno[2,3-b]pyridin-3-yl)ethyl)tetrahydropyrimidin-4(1H)-one |
| 47 | 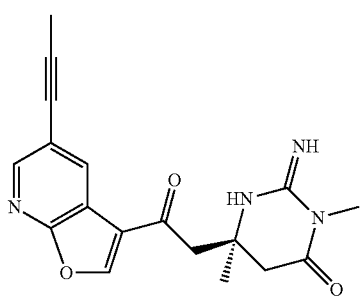 [SMILES: CC#Cc1cnc2occ(C(=O)C[C@]3(C)CC(=O)N(C)C(=N)N3)c2c1] | (R)-2-Imino-3,6-dimethyl-6-(2-oxo-2-(5-(prop-1-yn-1-yl)furo[2,3-b]pyridin-3-yl)ethyl)tetrahydropyrimidin-4(1H)-one |
| 48 | 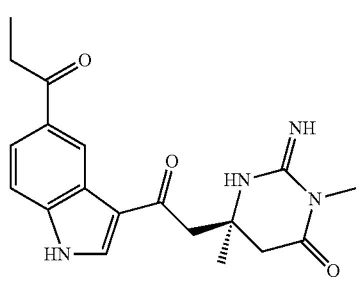 [SMILES: CCC(=O)c1ccc2[nH]cc(C(=O)C[C@]3(C)CC(=O)N(C)C(=N)N3)c2c1] | (R)-2-Imino-3,6-dimethyl-6-(2-oxo-2-(5-propionyl-1H-indol-3-yl)ethyl)tetrahydropyrimidin-4(1H)-one |
| 49 | 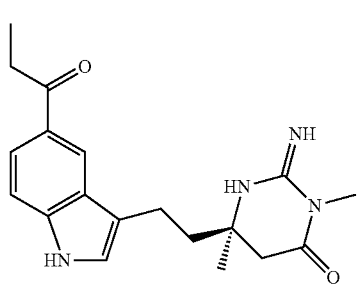 [SMILES: CCC(=O)c1ccc2[nH]cc(CC[C@]3(C)CC(=O)N(C)C(=N)N3)c2c1] | (R)-2-Imino-3,6-dimethyl-6-(2-(5-propionyl-1H-indol-3-yl)ethyl)tetrahydropyrimidin-4(1H)-one |

-continued

| Example | Structure | Compound name |
|---|---|---|
| 50 | 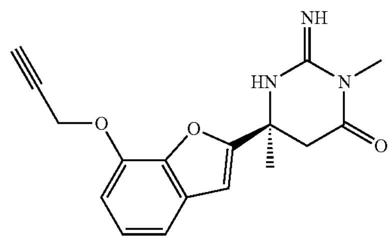 [SMILES: C#CCOc1cccc2cc([C@]3(C)CC(=O)N(C)C(=N)N3)oc12] | (S)-6-(7-(But-2-yn-1-yloxy)benzofuran-2-yl)-2-imino-3,6-dimethyltetrahydropyrimidin-4(1H)-one |
| 51 | 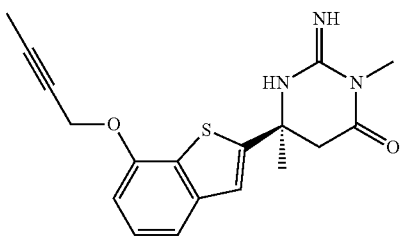 [SMILES: CC#CCOc1cccc2cc([C@]3(C)CC(=O)N(C)C(=N)N3)sc12] | (S)-6-(7-(But-2-yn-1-yloxy)benzo[b]thiophen-2-yl)-2-imino-3,6-dimethyltetrahydropyrimidin-4(1H)-one |
| 52 | 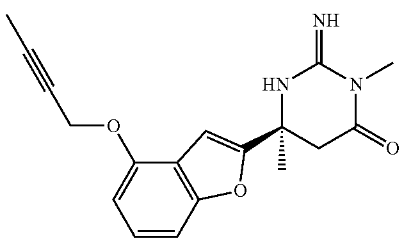 | (S)-6-(4-(But-2-yn-1-yloxy)benzofuran-2-yl)-2-imino-3,6-dimethyltetrahydropyrimidin-4(1H)-one |
| 53 | 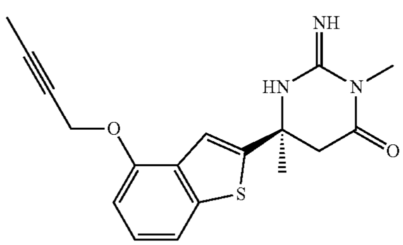 [SMILES: CC#CCOc1cccc2oc([C@]3(C)CC(=O)N(C)C(=N)N3)cc12] | (S)-6-(4-(But-2-yn-1-yloxy)benzo[b]thiophen-2-yl)-2-imino-3,6-dimethyl-tetrahydropyrimidin-4(1H)-one |
| 54 | 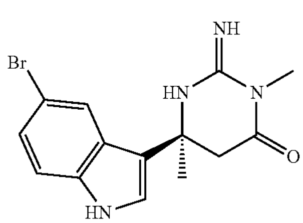 [SMILES: CN1C(=N)N[C@](C)(c2c[nH]c3ccc(Br)cc23)CC1=O] | (S)-6-(5-Bromo-1H-indol-3-yl)-2-imino-3,6-dimethyltetrahydropyrimidin-4(1H)-one |

Preferred compounds of formula (I) also include the structures of the following Formula:

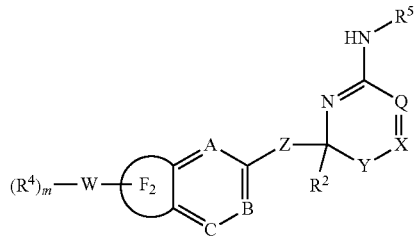

Formula (V)

wherein

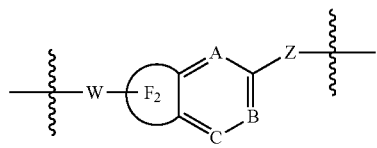

is selected from

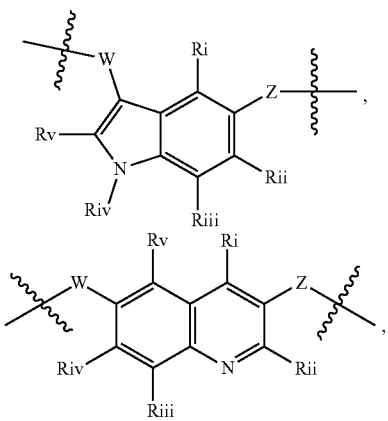

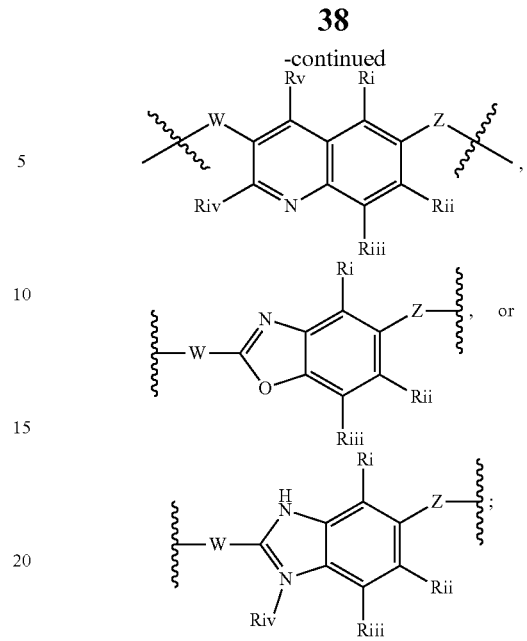

Wherein

A is selected from a substituted or unsubstituted carbon or nitrogen;

B is selected from a substituted or unsubstituted carbon or nitrogen;

C is selected from a substituted or unsubstituted carbon or nitrogen; and each of Ri, Rii, Riii, Riv, and Rv, independently, is hydrogen, halogen, cyano group, amino group, amido group, $C_{1-6}$ alkyl, $C_{1-6}$ alkoxyl, $C_{2-6}$ alkenyl, or $C_{2-6}$ alkynyl, or is a moiety selected from $C_{3-10}$ cycloalkyl, $C_{1-10}$ heterocycloalkyl, aryl, and heteroaryl, each of which is optionally mono-, di-, or tri-substituted with halogen, nitro group, cyano group, amino group, amido group, $C_{1-6}$ alkyl, $C_{1-6}$ alkoxyl, $C_{2-6}$ alkenyl, $C_{2-6}$ alkynyl, aryl, or heteroaryl, or optionally fused with $C_{3-10}$ cycloalkyl, $C_{1-10}$ heterocycloalkyl, aryl, or heteroaryl.

Preferred compounds of Formula (V) include but are not limited to the following structures:

| Example | Structure | Compound name |
|---------|-----------|---------------|
| 55 | 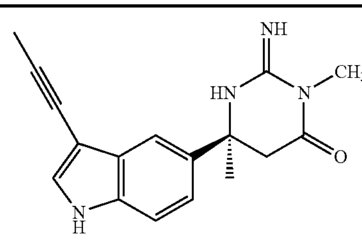 | (S)-2-Imino-3,6-dimethyl-6-(3-(prop-1-yn-1-yl)-1H-indol-5-yl)tetrahydropyrimidin-4(1H)-one |
| 56 | 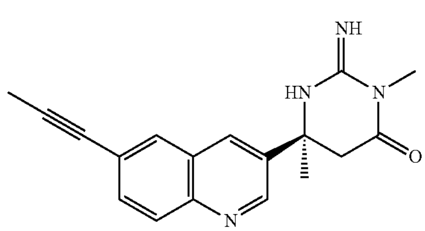 [SMILES: CC#Cc1ccc2ncc([C@]3(C)CC(=O)N(C)C(=N)N3)cc2c1] | (S)-2-Imino-3,6-dimethyl-6-(6-(prop-1-yn-1-yl)quinolin-3-yl)tetrahydropyrimidin-4(1H)-one |

-continued

| Example | Structure | Compound name |
|---|---|---|
| 57 | 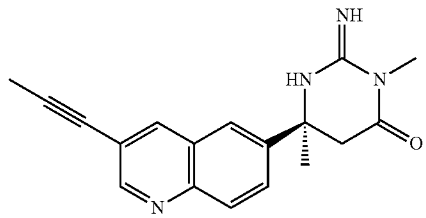 [SMILES: CC#Cc1cnc2ccc([C@]3(C)CC(=O)N(C)C(=N)N3)cc2c1] | (S)-2-Imino-3,6-dimethyl-6-(3-(prop-1-yn-1-yl)quinolin-6-yl)tetrahydropyrimidin-4(1H)-one |
| 58 | 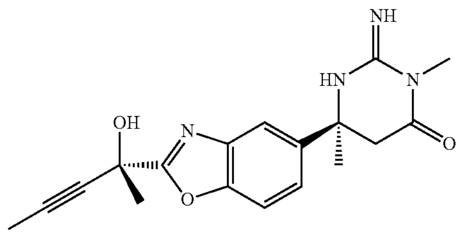 [SMILES: CC#C[C@](C)(O)c1nc2cc([C@]3(C)CC(=O)N(C)C(=N)N3)ccc2o1] | (S)-6-(2-((S)-2-Hydroxypent-3-yn-2-yl)benzo[d]oxazol-5-yl)-2-imino-3,6-dimethyltetrahydropyrimidin-4(1H)-one |
| 69 | 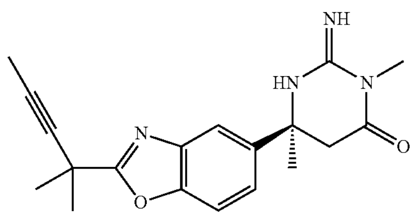 [SMILES: CC#CC(C)(C)c1nc2cc([C@]3(C)CC(=O)N(C)C(=N)N3)ccc2o1] | (S)-2-Imino-3,6-dimethyl-6-(2-(2-methylpent-3-yn-2-yl)benzo[d]oxazol-5-yl)tetrahydropyrimidin-4(1H)-one |
| 60 | 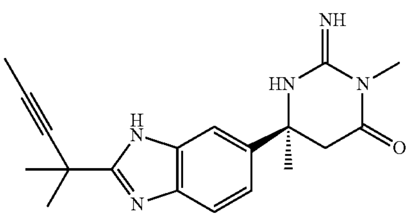 [SMILES: CC#CC(C)(C)c1nc2ccc([C@]3(C)CC(=O)N(C)C(=N)N3)cc2[nH]1] | (S)-2-Amino-3,6-dimethyl-6-(2-(2-methylpent-3-yn-2-yl)-1H-benzo[d]imidazol-6-yl)-5,6-dihydropyrimidin-4(3H)-one |

Preferred compounds of formula (I) also include the structures of the following Formula:

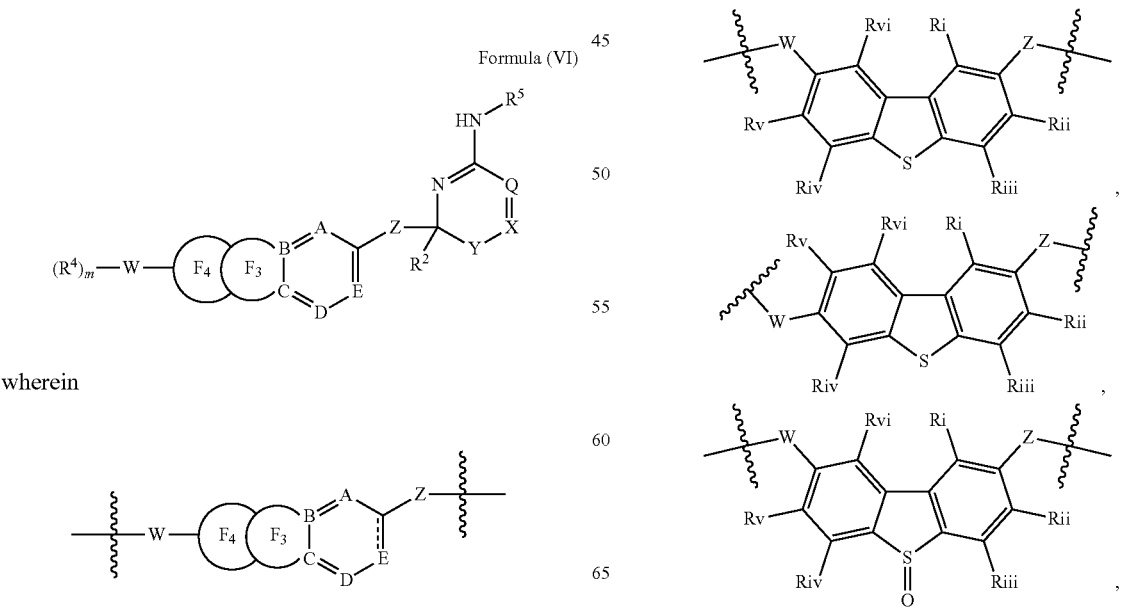

wherein is selected from

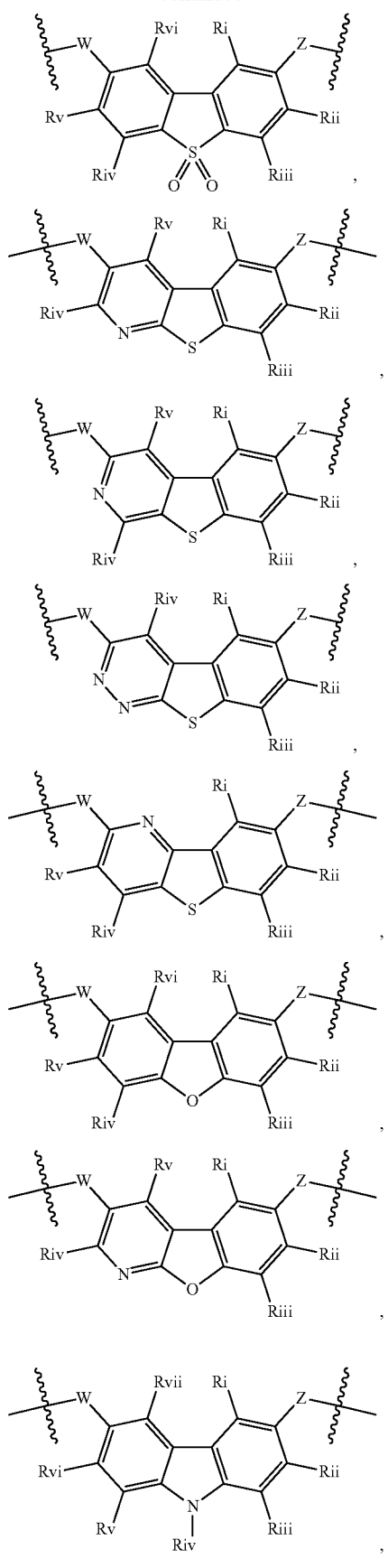
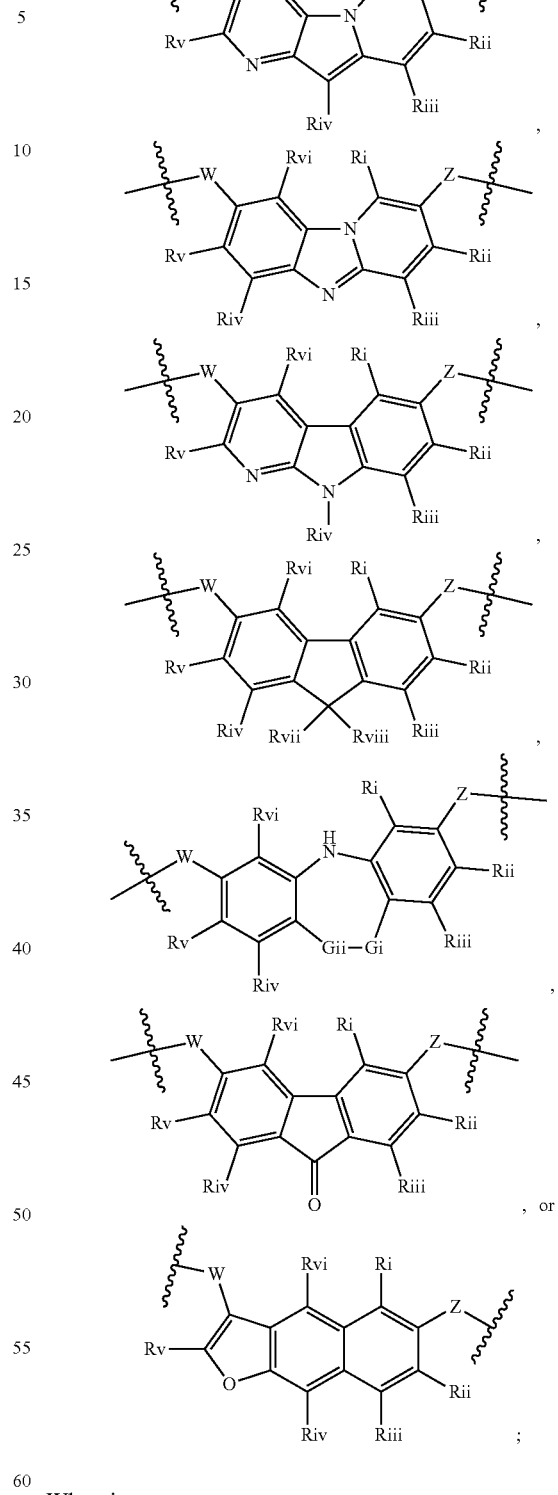
Wherein
A is selected from a substituted or unsubstituted carbon or nitrogen;
B is selected from a substituted or unsubstituted carbon or nitrogen;
C is selected from a substituted or unsubstituted carbon or nitrogen;

D is selected from a substituted or unsubstituted carbon or nitrogen;

E is selected from a substituted or unsubstituted carbon or nitrogen;

Gi is selected from $CH_2$, O, or $SO_2$;

Gii is selected from $CH_2$ or O;

the bond between Gi and Gii is a single or double bond; and each of Ri, Rii, Riii, Riv, Rv, Rvi, Rvii and Rviii, independently, is hydrogen, halogen, cyano group, amino group, amido group, hydroxyl, $C_{1-6}$ alkyl, $C_{1-6}$ alkoxyl, $C_{2-6}$ alkenyl, or $C_{2-6}$ alkynyl, or is a moiety selected from $C_{3-10}$ cycloalkyl, $C_{1-10}$ heterocycloalkyl, aryl, and heteroaryl, each of which is optionally mono-, di-, or tri-substituted with halogen, nitro group, cyano group, amino group, amido group, $C_{1-6}$ alkyl, $C_{1-6}$ alkoxyl, $C_{2-6}$ alkenyl, $C_{2-6}$ alkynyl, aryl, or heteroaryl, or optionally fused with $C_{3-10}$ cycloalkyl, $C_{1-10}$ heterocycloalkyl, aryl, or heteroaryl. In accordance with some examples, Rvii and Rviii may be taken together with their attached carbon atom to form a carbonyl group.

Preferred compounds of Formula (VI) include but are not limited the following structures:

| Example | Structure | Compound name |
|---|---|---|
| 1 | 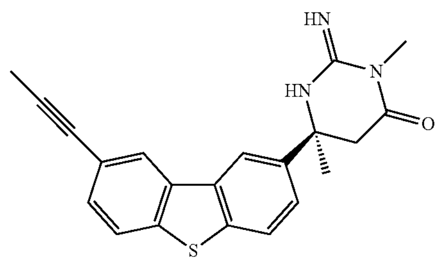 [SMILES: CC#Cc1ccc2sc3ccc([C@]4(C)CC(=O)N(C)C(=N)N4)cc3c2c1] | (S)-2-Imino-3,6-dimethyl-6-(8-(prop-1-yn-1-yl)dibenzo[b,d]thiophen-2-yl)tetrahydropyrimidin-4(1H)-one |
| 6 | 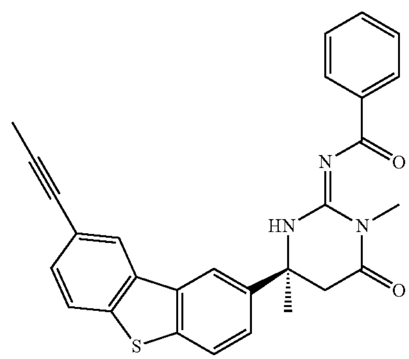 [SMILES: CC#Cc1ccc2sc3ccc([C@]4(C)CC(=O)N(C)/C(=N\C(=O)c5ccccc5)N4)cc3c2c1] | (S,Z)-N-(1,4-Dimethyl-6-oxo-4-(8-(prop-1-yn-1-yl)dibenzo[b,d]thiophen-2-yl)tetrahydropyrimidin-2(1H)-ylidene)benzamide |
| 7 | 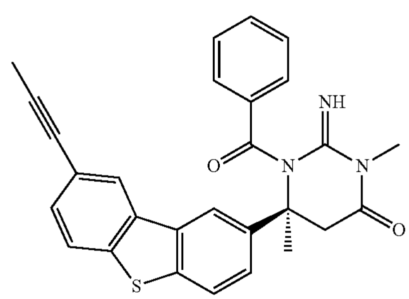 [SMILES: CC#Cc1ccc2sc3ccc([C@]4(C)CC(=O)N(C)C(=N)N4C(=O)c4ccccc4)cc3c2c1] | (S)-1-Benzoyl-2-imino-3,6-dimethyl-6-(8-(prop-1-yn-1-yl)dibenzo[b,d]thiophen-2-yl)tetrahydropyrimidin-4(1H)-one |
| 8 | 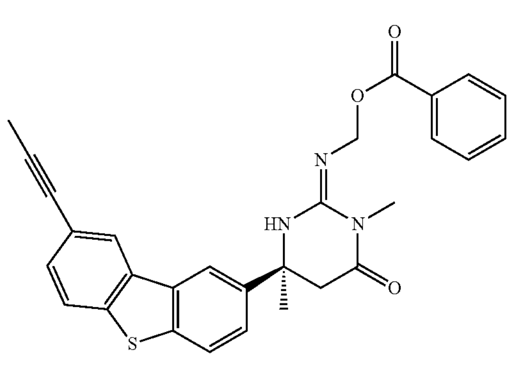 [SMILES: CC#Cc1ccc2sc3ccc([C@]4(C)CC(=O)N(C)/C(=N\COC(=O)c5ccccc5)N4)cc3c2c1] | (S,Z)-((1,4-Dimethyl-6-oxo-4-(8-(prop-1-yn-1-yl)dibenzo[b,d]thiophen-2-yl)tetrahydropyrimidin-2(1H)-ylidene)amino)methylbenzoate |

| Example | Structure | Compound name |
|---|---|---|
| 9 | 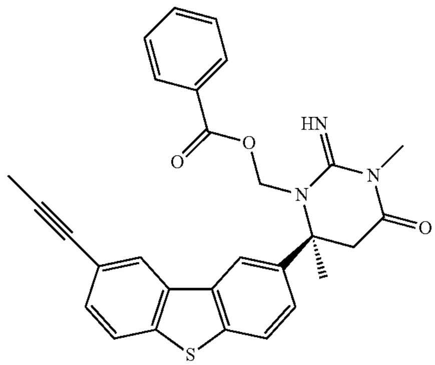 [SMILES: CC#Cc1ccc2sc3ccc([C@]4(C)CC(=O)N(C)C(=N)N4COC(=O)c4ccccc4)cc3c2c1] | (S)-(2-Imino-3,6-dimethyl-4-oxo-6-(8-(prop-1-yn-1-yl)dibenzo[b,d]thiophen-2-yl)tetrahydropyrimidin-1(2H)-yl) methylbenzoate |
| 10 | 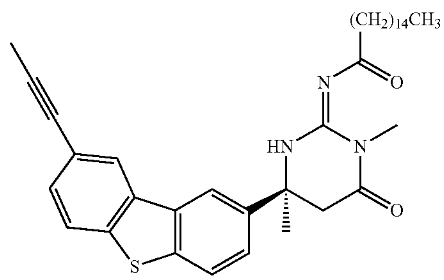 | (S,Z)-N-(1,4-Dmethyl-6-oxo-4-(8-(prop-1-yn-1-yl)dibenzo[b,d]thiophen-2-yl)tetrahydropyrimidin-2(1H)-ylidene) palmitamide |
| 11 | 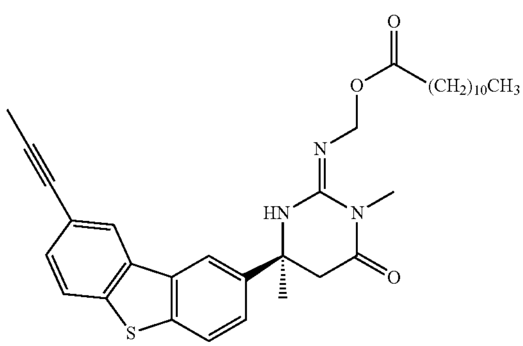 | (S,Z)-((1,4-Dimethyl-6-oxo-4-(8-(prop-1-yn-1-yl)dibenzo[b,d]thiophen-2-yl)tetrahydropyrimidin-2(1H)-ylidene) amino)methyl dodecanoate |
| 12 | 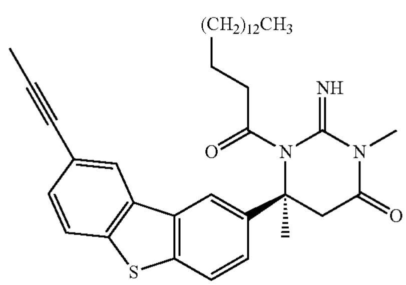 | (S)-2-Imino-3,6-dimethyl-1-palmitoyl-6-(8-(prop-1-yn-1-yl)dibenzo[b,d]thiophen-2-yl)tetrahydropyrimidin-4(1H)-one |
| 13 | 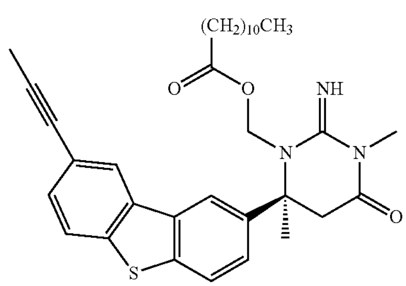 | (S)-(2-Imino-3,6-dimethyl-4-oxo-6-(8-(prop-1-yn-1-yl)dibenzo[b,d]thiophen-2-yl)tetrahydropyrimidin-1(2H)-yl) methyl dodecanoate |

-continued

| Example | Structure | Compound name |
|---|---|---|
| 14 | 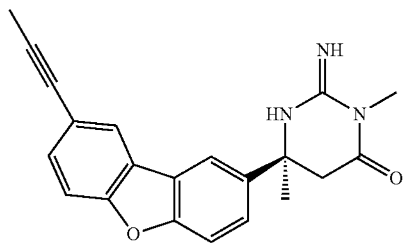 [SMILES: CC#Cc1ccc2oc3ccc([C@]4(C)CC(=O)N(C)C(=N)N4)cc3c2c1] | (S)-2-Imino-3,6-dimethyl-6-(8-(prop-1-yn-1-yl)dibenzo[b,d]furan-2-yl)tetrahydropyrimidin-4(1H)-one |
| 15 | 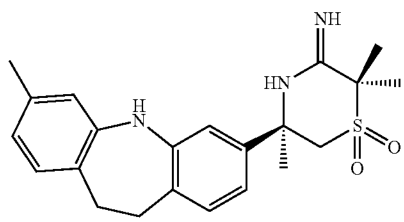 | (R)-3Imino-2,2,5-trimethyl-5-(7-methyl-10,11-dihydro-5H-dibenzo[b,f]azepin-3-yl)thiomorpholine 1,1-dioxide |
| 16 | 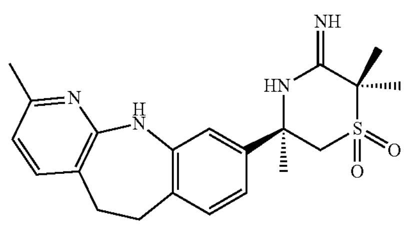 | (R)-3-Imino-2,2,5-trimethyl-5-(2-methyl-6,11-dihydro-5H-benzo[b]pyrido[3,2-f]azepin-9-yl)thiomorpholine 1,1-dioxide |
| 17 | 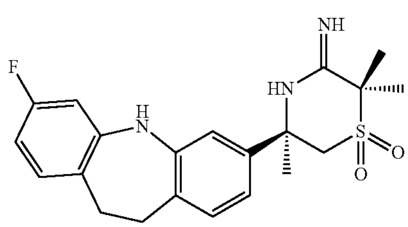 | (R)-5-(7Fluoro-10,11-dihydro-5H-dibenzo[b,f]azepin-3-yl)-3-imino-2,2,5-trimethylthiomorpholine 1,1-dioxide |
| 18 | 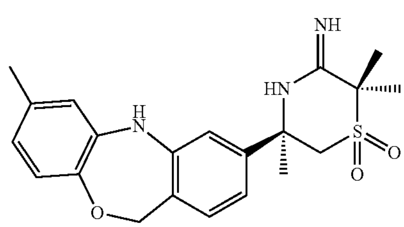 | (R)-3-Imino-2,2,5-trimethyl-5-(7-methyl-5,11-dihydrodibenzo[b,e][1,4]oxazepin-3-yl)thiomorpholine 1,1-dioxide |
| 19 | 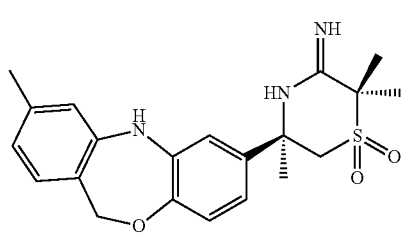 | (R)-3-Imino-2,2,5-trimethyl-5-(3-methyl-5,11-dihydrodibenzo[b,e][1,4]oxazepin-7-yl)thiomorpholine 1,1-dioxide |

| Example | Structure | Compound name |
|---|---|---|
| 20 | 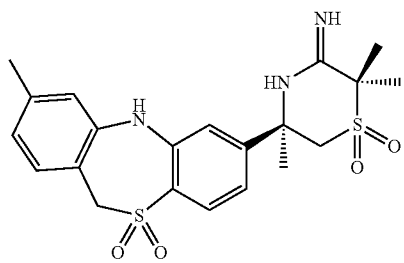 | (R)-7-(5-Imino-3,6,6-trimethyl-1,1-dioxidothiomorpholin-3-yl)-3-methyl-5,11-dihydrodibenzo[b,e][1,4]thiazepine 10,10-dioxide |
| 21 | 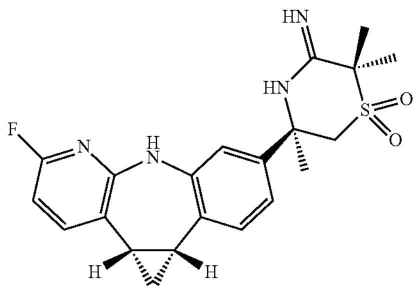 | (R)-5-((1aS,10bR)-4-Fluoro-1,1a,6,10b-tetrahydrobenzo[b]cyclopropa[d]pyrido[3,2-f]azepin-8-yl)-3-imino-2,2,5-trimethylthiomorpholine 1,1-dioxide |
| 22 | 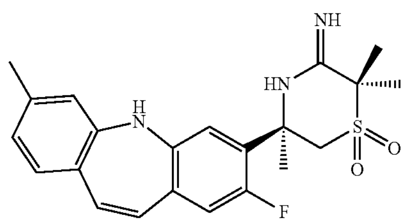 | (R)-5-(2-Fluoro-7-methyl-5H-dibenzo[b,f]azepin-3-yl)-3-imino-2,2,5-trimethylthiomorpholine 1,1-dioxide |
| 23 | 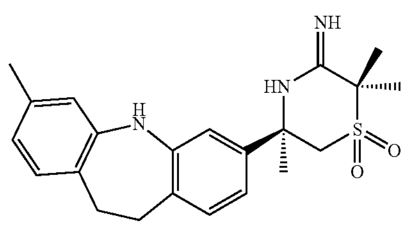 | (R)-3Imino-2,2,5-trimethyl-5-(7-methyl-10,11-dihydro-5H-dibenzo[b,f]azepin-3-yl)thiomorpholine 1,1-dioxide |
| 61 | 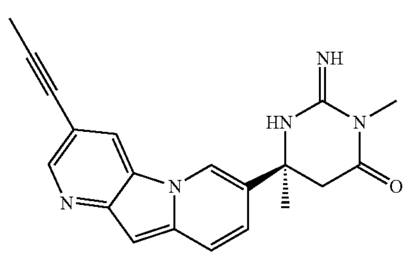 [SMILES: CC#Cc1cnc2cc3ccc([C@]4(C)CC(=O)N(C)C(=N)N4)cn3c2c1] | (S)-2-Imino-3,6-dimethyl-6-(3-(prop-1-yn-1-yl)pyrido[2,3-b]indolizin-7-yl)tetrahydropyrimidin-4(1H)-one |
| 62 | 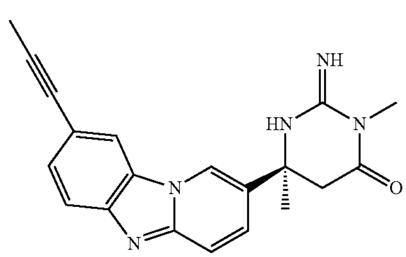 [SMILES: CC#Cc1ccc2nc3ccc([C@]4(C)CC(=O)N(C)C(=N)N4)cn3c2c1] | (S)-2-Imino-3,6-dimethyl-6-(8-(prop-1-yn-1-yl)benzo[4,5]imidazo[1,2-a]pyridin-2-yl)tetrahydropyrimidin-4(1H)-one |

-continued

| Example | Structure | Compound name |
|---|---|---|
| 63 | 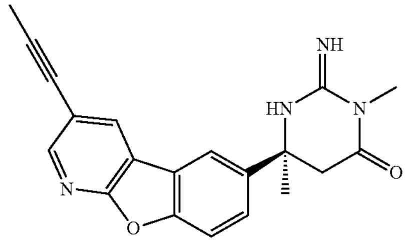 | (S)-2-Imino-3,6-dimethyl-6-(3-(prop-1-yn-1-yl)benzofuro[2,3-b]pyridin-6-yl)tetrahydropyrimidin-4(1H)-one |
| 64 | 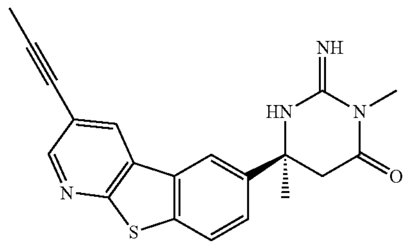 [SMILES: CC#Cc1cnc2oc3ccc([C@]4(C)CC(=O)N(C)C(=N)N4)cc3c2c1] | (S)-2-Imino-3,6-dimethyl-6-(3-(prop-1-yn-1-yl)benzo[4,5]thieno[2,3-b]pyridin-6-yl)tetrahydropyrimidin-4(1H)-one |
| 65 | 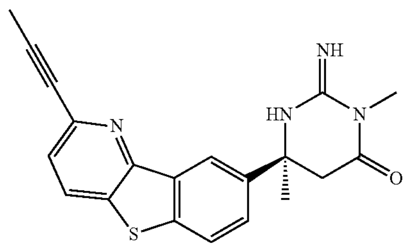 [SMILES: CC#Cc1ccc2sc3ccc([C@]4(C)CC(=O)N(C)C(=N)N4)cc3c2n1] | (S)-2-Imino-3,6-dimethyl-6-(2-(prop-1-yn-1-yl)benzo[4,5]thieno[3,2-b]pyridin-8-yl)tetrahydropyrimidin-4(1H)-one |
| 66 | 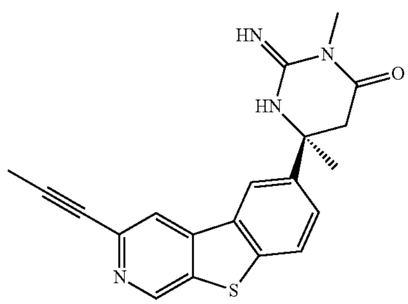 [SMILES: CC#Cc1cc2c(cn1)sc1ccc([C@]3(C)CC(=O)N(C)C(=N)N3)cc12] | (S)-2-Imino-3,6-dimethyl-6-(3-(prop-1-yn-1-yl)benzo[4,5]thieno[2,3-c]pyridin-6-yl)tetrahydropyrimidin-4(1H)-one |
| 67 | 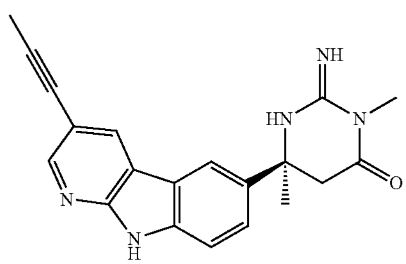 [SMILES: CC#Cc1cnc2[nH]c3ccc([C@]4(C)CC(=O)N(C)C(=N)N4)cc3c2c1] | (S)-2-Imino-3,6-dimethyl-6-(3-(prop-1-yn-1-yl)-9H-pyrido[2,3-b]indol-6-yl)tetrahydropyrimidin-4(1H)-one |
| 68 | 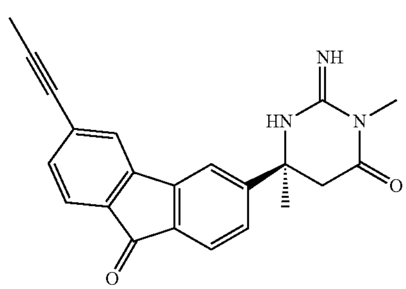 [SMILES: CC#Cc1ccc2c(c1)-c1cc([C@]3(C)CC(=O)N(C)C(=N)N3)ccc1C2=O] | (S)-2-Imino-3,6-dimethyl-6-(9-oxo-6-(prop-1-yn-1-yl)-9H-fluoren-3-yl)tetrahydropyrimidin-4(1H)-one |

-continued

| Example | Structure | Compound name |
|---|---|---|
| 69 | 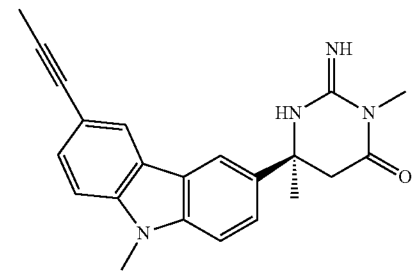 [SMILES: CC#Cc1ccc2c(c1)c1cc([C@]3(C)CC(=O)N(C)C(=N)N3)ccc1n2C] | (S)-2-Imino-3,6-dimethyl-6-(9-methyl-6-(prop-1-yn-1-yl)-9H-carbazol-3-yl)tetrahydropyrimidin-4(1H)-one |
| 70 | 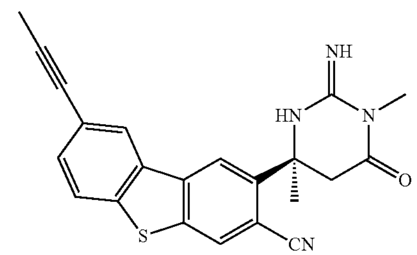 [SMILES: CC#Cc1ccc2sc3cc(C#N)c([C@]4(C)CC(=O)N(C)C(=N)N4)cc3c2c1] | (S)-2-(2-Imino-1,4-dimethyl-6-oxohexahydropyrimidin-4-yl)-8-(prop-1-yn-1-yl)dibenzo[b,d]thiophene-3-carbonitrile |
| 71 | 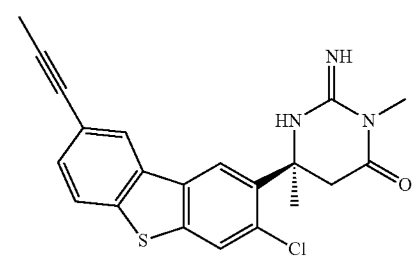 [SMILES: CC#Cc1ccc2sc3cc(Cl)c([C@]4(C)CC(=O)N(C)C(=N)N4)cc3c2c1] | (S)-6-(3-Chloro-8-(prop-1-yn-1-yl)dibenzo[b,d]thiophen-2-yl)-2-imino-3,6-dimethyltetrahydropyrimidin-4(1H)-one |
| 72 | 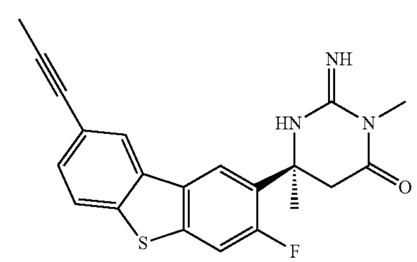 [SMILES: CC#Cc1ccc2sc3cc(F)c([C@]4(C)CC(=O)N(C)C(=N)N4)cc3c2c1] | (S)-6-(3-Fluoro-8-(prop-1-yn-1-yl)dibenzo[b,d]thiophen-2-yl)-2-imino-3,6-dimethyltetrahydropyrimidin-4(1H)-one |
| 73 | 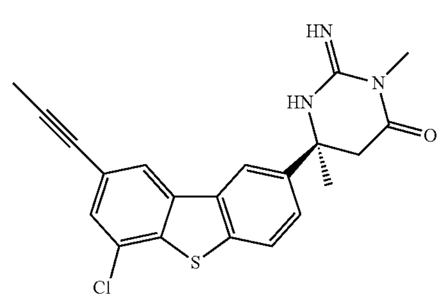 [SMILES: CC#Cc1cc(Cl)c2sc3ccc([C@]4(C)CC(=O)N(C)C(=N)N4)cc3c2c1] | (S)-6-(6-Chloro-8-(prop-1-yn-1-yl)dibenzo[b,d]thiophen-2-yl)-2-imino-3,6-dimethyltetrahydropyrimidin-4(1H)-one |

| Example | Structure | Compound name |
|---|---|---|
| 74 | 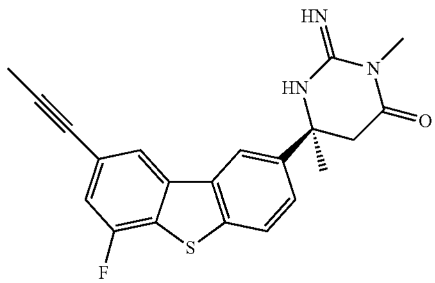 [SMILES: CC#Cc1cc(F)c2sc3ccc([C@]4(C)CC(=O)N(C)C(=N)N4)cc3c2c1] | (S)-6-(6-Fluoro-8-(prop-1-yn-1-yl) dibenzo[b,d]thiophen-2-yl)-2-imino-3,6-dimethyltetrahydropyrimidin-4(1H)-one |
| 75 | 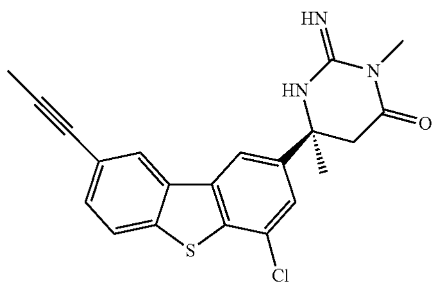 | (S)-6-(4-Chloro-8-(prop-1-yn-1-yl) dibenzo[b,d]thiophen-2-yl)-2-imino-3,6-dimethyltetrahydropyrimidin-4(1H)-one |
| 76 | 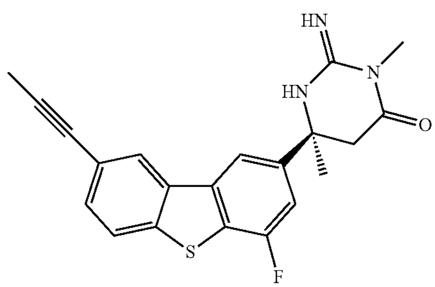 [SMILES: CC#Cc1ccc2sc3c(F)cc([C@]4(C)CC(=O)N(C)C(=N)N4)cc3c2c1] | (S)-6-(4-Fluoro-8-(prop-1-yn-1-yl) dibenzo[b,d]thiophen-2-yl)-2-imino-3,6-dimethyltetrahydropyrimidin-4(1H)-one |
| 77 | 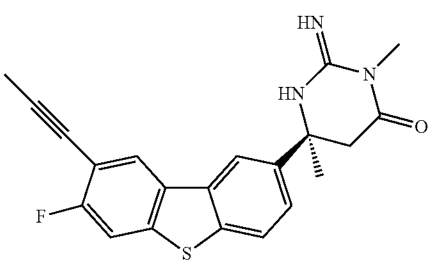 [SMILES: CC#Cc1cc2c(cc1F)sc1ccc([C@]3(C)CC(=O)N(C)C(=N)N3)cc12] | (S)-6-(7-Fluoro-8-(prop-1-yn-1-yl) dibenzo[b,d]thiophen-2-yl)-2-imino-3,6-dimethyltetrahydropyrimidin-4(1H)-one |
| 78 | 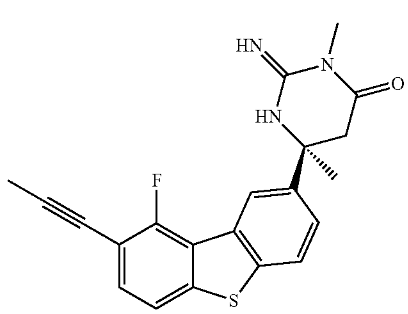 | (S)-6-(9-Fluoro-8-(prop-1-yn-1-yl) dibenzo[b,d]thiophen-2-yl)-2-imino-3,6-dimethyltetrahydropyrimidin-4(1H)-one |

-continued

| Example | Structure | Compound name |
|---|---|---|
| 79 | 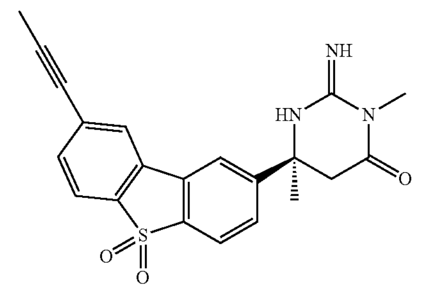 [SMILES: CC#Cc1ccc2c(c1)-c1cc([C@]3(C)CC(=O)N(C)C(=N)N3)ccc1S2(=O)=O] | (S)-6-(5,5-Dioxido-8-(prop-1-yn-1-yl)dibenzo[b,d]thiophen-2-yl)-2-imino-3,6-dimethyltetrahydropyrimidin-4(1H)-one |
| 80 | 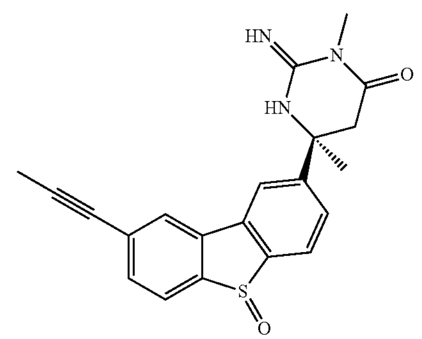 [SMILES: CC#Cc1ccc2c(c1)-c1cc([C@]3(C)CC(=O)N(C)C(=N)N3)ccc1S2=O] | (6S)-2-Imino-3,6-dimethyl-6-(5-oxido-8-(prop-1-yn-1-yl)dibenzo[b,d]thiophen-2-yl)tetrahydropyrimidin-4(1H)-one |
| 81 | 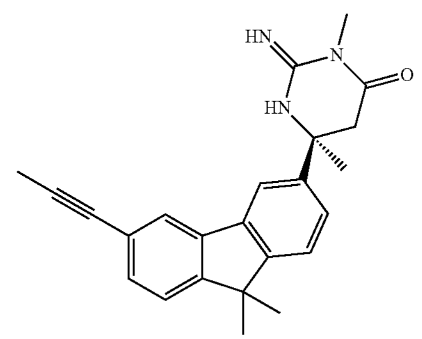 [SMILES: CC#Cc1ccc2c(c1)-c1cc([C@]3(C)CC(=O)N(C)C(=N)N3)ccc1C2(C)C] | (S)-6-(9,9-Dimethyl-6-(prop-1-yn-1-yl)-9H-fluoren-3-yl)-2-imino-3,6-dimethyl-tetrahydropyrimidin-4(1H)-one |
| 82 | 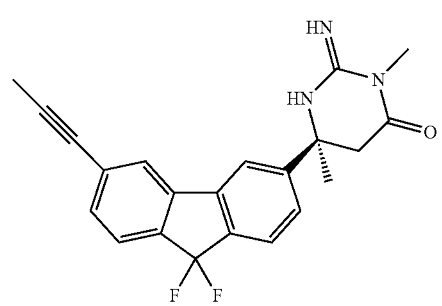 [SMILES: CC#Cc1ccc2c(c1)-c1cc([C@]3(C)CC(=O)N(C)C(=N)N3)ccc1C2(F)F] | (S)-6-(9,9-Difluoro-6-(prop-1-yn-1-yl)-9H-fluoren-3-yl)-2-imino-3,6-dimethyltetrahydropyrimidin-4(1H)-one |
| 83 | 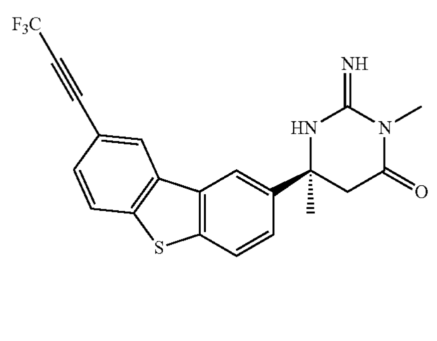 [SMILES: CN1C(=N)N[C@](C)(c2ccc3sc4ccc(C#CC(F)(F)F)cc4c3c2)CC1=O] | (S)-2-Imino-3,6-dimethyl-6-(8-(3,3,3-trifluoroprop-1-yn-1-yl)dibenzo[b,d]thiophen-2-yl)tetrahydropyrimidin-4(1H)-one |

-continued

| Example | Structure | Compound name |
|---|---|---|
| 84 | 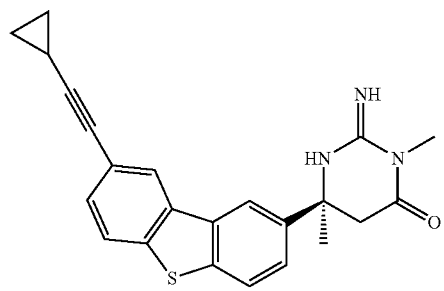 [SMILES: CN1C(=N)N[C@](C)(c2ccc3sc4ccc(C#CC5CC5)cc4c3c2)CC1=O] | (S)-6-(8-(Cyclopropylethynyl)dibenzo[b,d]thiophen-2-yl)-2-imino-3,6-dimethyltetrahydropyrimidin-4(1H)-one |
| 85 | 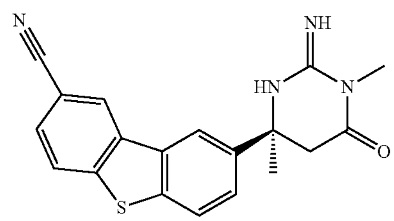 [SMILES: CN1C(=N)N[C@](C)(c2ccc3sc4ccc(C#N)cc4c3c2)CC1=O] | (S)-8-(2-Imino-1,4-dimethyl-6-oxohexahydropyrimidin-4-yl)dibenzo[b,d]thiophene-2-carbonitrile |
| 86 | 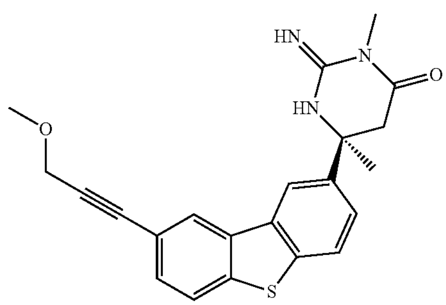 [SMILES: COCC#Cc1ccc2sc3ccc([C@]4(C)CC(=O)N(C)C(=N)N4)cc3c2c1] | (S)-2-Imino-6-(8-(3-methoxyprop-1-yn-1-yl)dibenzo[b,d]thiophen-2-yl)-3,6-dimethyltetrahydropyrimidin-4(1H)-one |
| 87 | 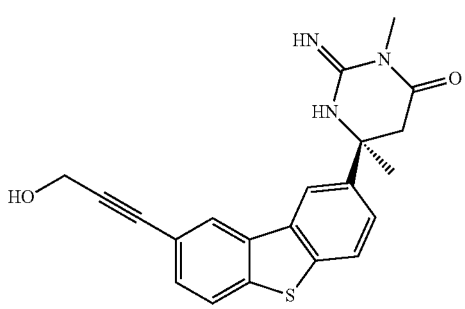 [SMILES: CN1C(=N)N[C@](C)(c2ccc3sc4ccc(C#CCO)cc4c3c2)CC1=O] | (S)-6-(8-(3-Hydroxyprop-1-yn-1-yl)dibenzo[b,d]thiophen-2-yl)-2-imino-3,6-dimethyltetrahydropyrimidin-4(1H)-one |
| 88 | 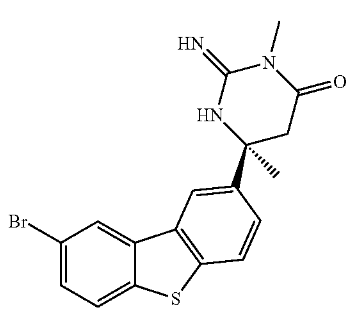 [SMILES: CN1C(=N)N[C@](C)(c2ccc3sc4ccc(Br)cc4c3c2)CC1=O] | (S)-6-(8-Bromodibenzo[b,d]thiophen-2-yl)-2-imino-3,6-dimethyltetrahydropyrimidin-4(1H)-one |

-continued

| Example | Structure | Compound name |
|---|---|---|
| 89 | 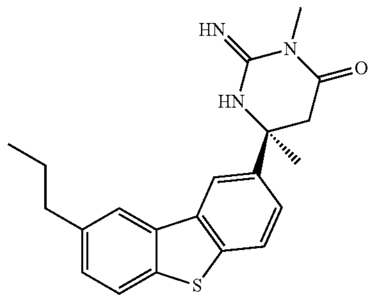 [SMILES: CCCc1ccc2sc3ccc([C@]4(C)CC(=O)N(C)C(=N)N4)cc3c2c1] | (S)-2-Imino-3,6-dimethyl-6-(8-propyl-dibenzo[b,d]thiophen-2-yl)tetrahydro-pyrimidin-4(1H)-one |
| 90 | 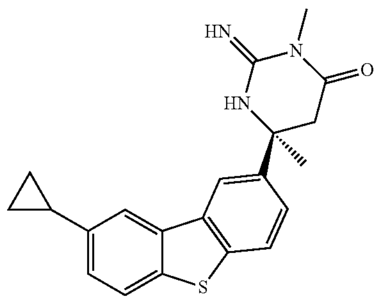 [SMILES: CN1C(=N)N[C@](C)(c2ccc3sc4ccc(C5CC5)cc4c3c2)CC1=O] | (S)-6-(8-Cyclopropyldibenzo[b,d]thiophen-2-yl)-2-imino-3,6-dimethyl-tetrahydropyrimidin-4(1H)-one |
| 91 | 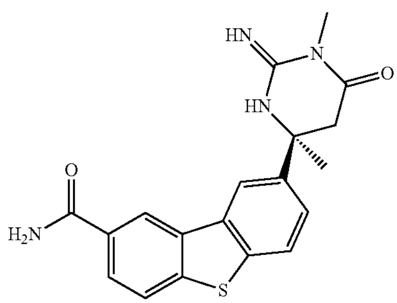 [SMILES: CN1C(=N)N[C@](C)(c2ccc3sc4ccc(C(N)=O)cc4c3c2)CC1=O] | (S)-8-(2-Imino-1,4-dimethyl-6-oxohexahydropyrimidin-4-yl)dibenzo[b,d]thiophene-2-carboxamide |
| 92 | 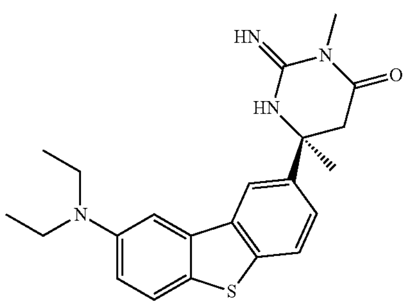 [SMILES: CCN(CC)c1ccc2sc3ccc([C@]4(C)CC(=O)N(C)C(=N)N4)cc3c2c1] | (S)-6-(8-(Diethylamino)dibenzo[b,d]thiophen-2-yl)-2-imino-3,6-dimethyl-tetrahydropyrimidin-4(1H)-one |
| 93 | 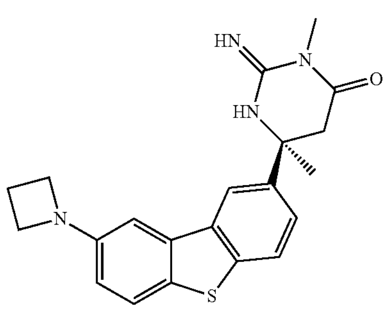 [SMILES: CN1C(=N)N[C@](C)(c2ccc3sc4ccc(N5CCC5)cc4c3c2)CC1=O] | (S)-6-(8-(Azetidin-1-yl)dibenzo[b,d]thiophen-2-yl)-2-imino-3,6-dimethyl-tetrahydropyrimidin-4(1H)-one |

| Example | Structure | Compound name |
|---|---|---|
| 94 | 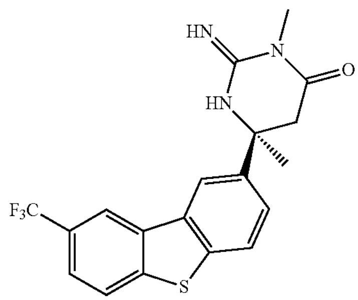 [SMILES: CN1C(=N)N[C@](C)(c2ccc3sc4ccc(C(F)(F)F)cc4c3c2)CC1=O] | (S)-2-Imino-3,6-dimethyl-6-(8-(trifluoromethyl)dibenzo[b,d]thiophen-2-yl)tetrahydropyrimidin-4(1H)-one |
| 95 | 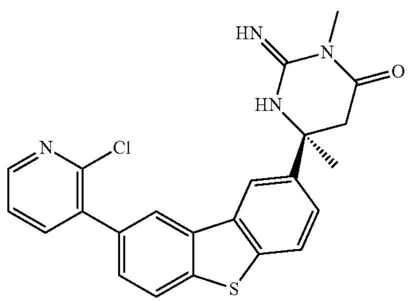 [SMILES: CN1C(=N)N[C@](C)(c2ccc3sc4ccc(-c5cccnc5Cl)cc4c3c2)CC1=O] | (S)-6-(8-(2-Chloropyridin-3-yl)dibenzo[b,d]thiophen-2-yl)-2-imino-3,6-dimethyltetrahydropyrimidin-4(1H)-one |
| 96 | 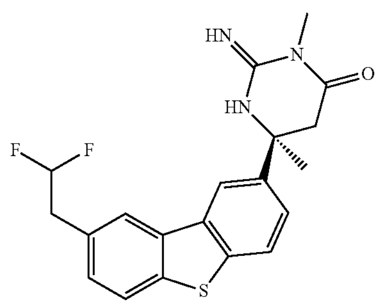 [SMILES: CN1C(=N)N[C@](C)(c2ccc3sc4ccc(CC(F)F)cc4c3c2)CC1=O] | (S)-6-(8-(2,2-Difluoroethyl)dibenzo[b,d]thiophen-2-yl)-2-imino-3,6-dimethyltetrahydropyrimidin-4(1H)-one |
| 97 | 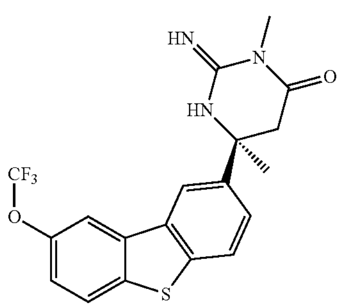 [SMILES: CN1C(=N)N[C@](C)(c2ccc3sc4ccc(OC(F)(F)F)cc4c3c2)CC1=O] | (S)-2-Imino-3,6-dimethyl-6-(8-(trifluoromethoxy)dibenzo[b,d]thiophen-2-yl)tetrahydropyrimidin-4(1H)-one |
| 98 | 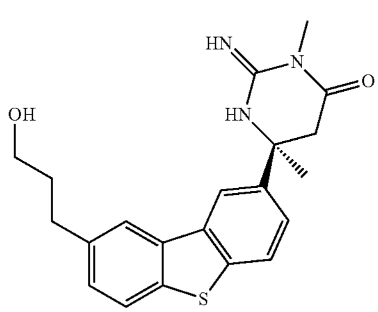 [SMILES: CN1C(=N)N[C@](C)(c2ccc3sc4ccc(CCCO)cc4c3c2)CC1=O] | (S)-6-(8-(3-Hydroxypropyl)dibenzo[b,d]thiophen-2-yl)-2-imino-3,6-dimethyltetrahydropyrimidin-4(1H)-one |

| Example | Structure | Compound name |
|---|---|---|
| 99 | 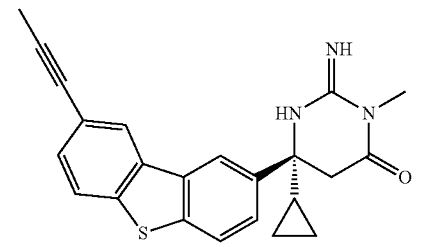 [SMILES: CC#Cc1ccc2sc3ccc([C@]4(C5CC5)CC(=O)N(C)C(=N)N4)cc3c2c1] | (R)-6-Cyclopropyl-2-imino-3-methyl-6-(8-(prop-1-yn-1-yl)dibenzo[b,d]thiophen-2-yl)tetrahydropyrimidin-4(1H)-one |
| 100 | 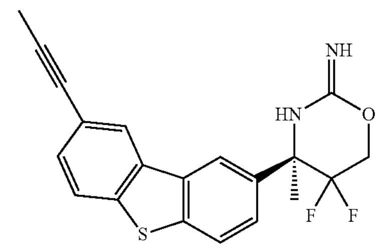 [SMILES: CC#Cc1ccc2sc3ccc([C@@]4(C)NC(=N)OCC4(F)F)cc3c2c1] | (R)-5,5-Difluoro-4-methyl-4-(8-(prop-1-yn-1-yl)dibenzo[b,d]thiophen-2-yl)-1,3-oxazinan-2-imine |
| 101 | 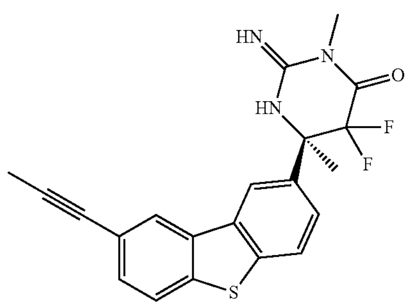 [SMILES: CC#Cc1ccc2sc3ccc([C@@]4(C)NC(=N)N(C)C(=O)C4(F)F)cc3c2c1] | (R)-5,5-Difluoro-2-imino-3,6-dimethyl-6-(8-(prop-1-yn-1-yl)dibenzo[b,d]thiophen-2-yl)tetrahydropyrimidin-4(1H)-one |
| 102 | 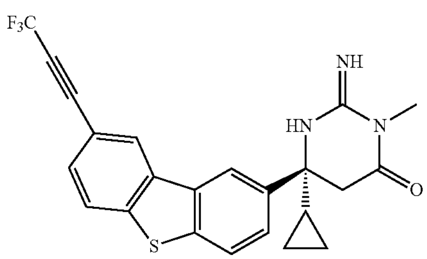 [SMILES: CN1C(=N)N[C@@](c2ccc3sc4ccc(C#CC(F)(F)F)cc4c3c2)(C2CC2)CC1=O] | (R)-6-Cyclopropyl-2-imino-3-methyl-6-(8-(3,3,3-trifluoroprop-1-yn-1-yl)dibenzo[b,d]thiophen-2-yl)tetrahydropyrimidin-4(1H)-one |
| 103 | 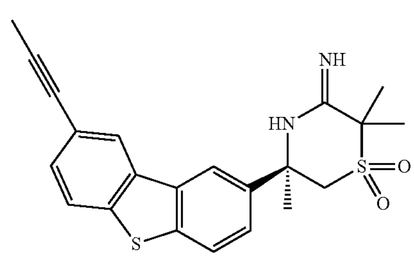 [SMILES: CC#Cc1ccc2sc3ccc([C@]4(C)CS(=O)(=O)C(C)(C)C(=N)N4)cc3c2c1] | (R)-3-Imino-2,2,5-trimethyl-5-(8-(prop-1-yn-1-yl)dibenzo[b,d]thiophen-2-yl)thiomorpholine 1,1-dioxide |
| 104 | 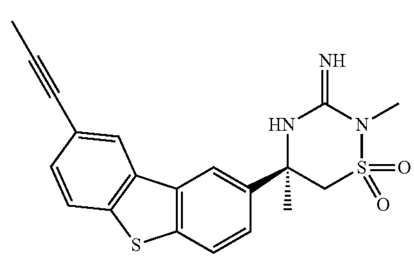 [SMILES: CC#Cc1ccc2sc3ccc([C@]4(C)CS(=O)(=O)N(C)C(=N)N4)cc3c2c1] | (R)-3-Imino-2,5-dimethyl-5-(8-(prop-1-yn-1-yl)dibenzo[b,d]thiophen-2-yl)-1,2,4-thiadiazinane 1,1-dioxide |

-continued

| Example | Structure | Compound name |
|---|---|---|
| 105 | 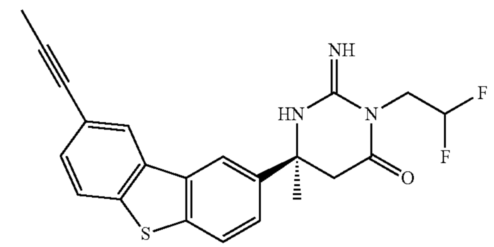 [SMILES: CC#Cc1ccc2sc3ccc([C@]4(C)CC(=O)N(CC(F)F)C(=N)N4)cc3c2c1] | (S)-3-(2,2-Difluoroethyl)-2-imino-6-methyl-6-(8-(prop-1-yn-1-yl)dibenzo[b,d]thiophen-2-yl)tetrahydropyrimidin-4(1H)-one |
| 106 | 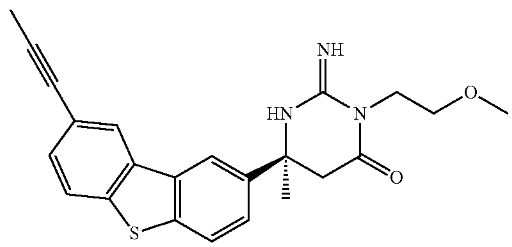 [SMILES: CC#Cc1ccc2sc3ccc([C@]4(C)CC(=O)N(CCOC)C(=N)N4)cc3c2c1] | (S)-2-Imino-3-(2-methoxyethyl)-6-methyl-6-(8-(prop-1-yn-1-yl)dibenzo[b,d]thiophen-2-yl)tetrahydropyrimidin-4(1H)-one |
| 107 | 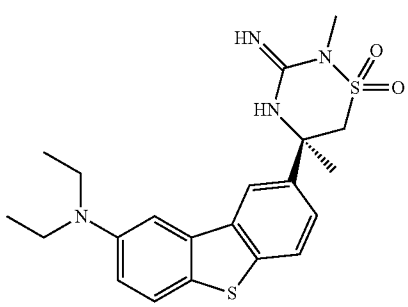 [SMILES: CCN(CC)c1ccc2sc3ccc([C@]4(C)CS(=O)(=O)N(C)C(=N)N4)cc3c2c1] | (R)-5-(8-(Diethylamino)dibenzo[b,d]thiophen-2-yl)-3-imino-2,5-dimethyl-1,2,4-thiadiazinane 1,1-dioxide |
| 108 | 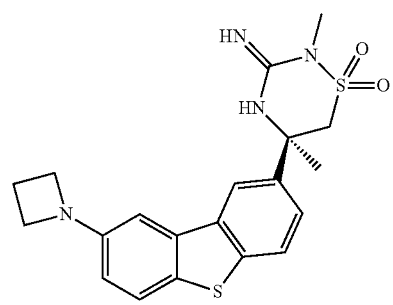 [SMILES: CN1C(=N)N[C@](C)(c2ccc3sc4ccc(N5CCC5)cc4c3c2)CS1(=O)=O] | (R)-5-(8-(Azetidin-1-yl)dibenzo[b,d]thiophen-2-yl)-3-imino-2,5-dimethyl-1,2,4-thiadiazinane 1,1-dioxide |
| 109 | 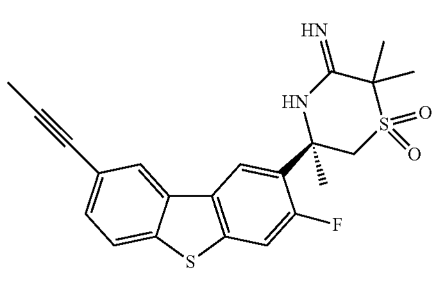 [SMILES: CC#Cc1ccc2sc3cc(F)c([C@]4(C)CS(=O)(=O)C(C)(C)C(=N)N4)cc3c2c1] | (R)-5-(3-Fluoro-8-(prop-1-yn-1-yl)dibenzo[b,d]thiophen-2-yl)-3-imino-2,2,5-trimethylthiomorpholine 1,1-dioxide |

| Example | Structure | Compound name |
|---|---|---|
| 110 | 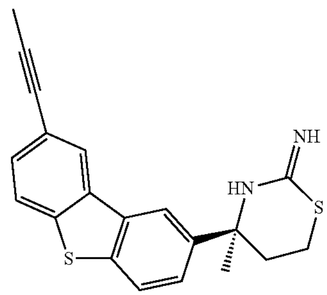 [SMILES: CC#Cc1ccc2sc3ccc([C@]4(C)CCSC(=N)N4)cc3c2c1] | (S)-4-Methyl-4-(8-(prop-1-yn-1-yl) dibenzo[b,d]thiophen-2-yl)-1,3-thiazinan-2-imine |
| 111 | 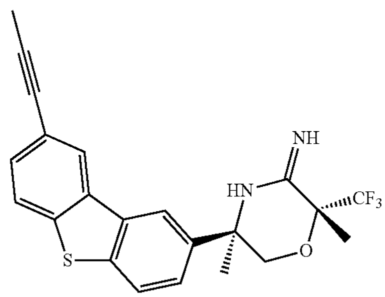 [SMILES: CC#Cc1ccc2sc3ccc([C@]4(C)CO[C@@](C)(C(F)(F)F)C(=N)N4)cc3c2c1] | (2R,5R)-2,5-Dimethyl-5-(8-(prop-1-yn-1-yl)dibenzo[b,d]thiophen-2-yl)-2-(trifluoromethyl)morpholin-3-imine |
| 112 | 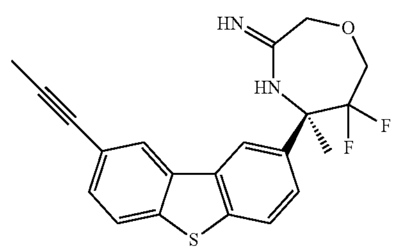 [SMILES: CC#Cc1ccc2sc3ccc([C@@]4(C)NC(=N)COCC4(F)F)cc3c2c1] | (R)-6,6-Difluoro-5-methyl-5-(8-(prop-1-yn-1-yl)dibenzo[b,d]thiophen-2-yl)-1,4-oxazepan-3-imine |
| 113 | 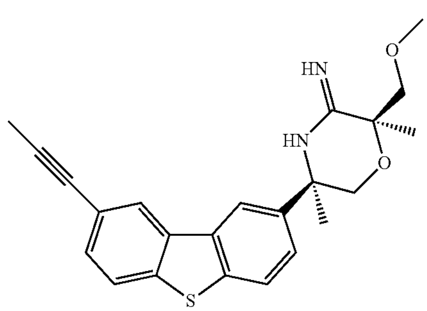 [SMILES: CC#Cc1ccc2sc3ccc([C@]4(C)CO[C@](C)(COC)C(=N)N4)cc3c2c1] | (2S,5R)-2-(Methoxymethyl)-2,5-dimethyl-5-(8-(prop-1-yn-1-yl)dibenzo[b,d]thiophen-2-yl)morpholin-3-imine |
| 114 | 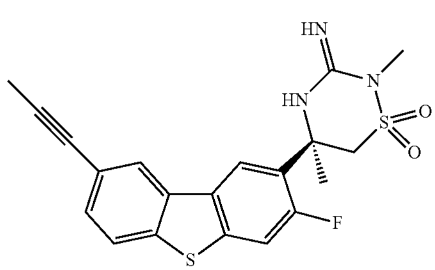 [SMILES: CC#Cc1ccc2sc3cc(F)c([C@]4(C)CS(=O)(=O)N(C)C(=N)N4)cc3c2c1] | (R)-5-(3-Fluoro-8-(prop-1-yn-1-yl) dibenzo[b,d]thiophen-2-yl)-3-imino-2,5-dimethyl-1,2,4-thiadiazinane 1,1-dioxide |

| Example | Structure | Compound name |
|---|---|---|
| 115 | 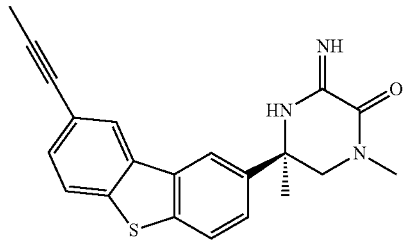 [SMILES: CC#Cc1ccc2sc3ccc([C@]4(C)CN(C)C(=O)C(=N)N4)cc3c2c1] | (R)-3-Imino-1,5-dimethyl-5-(8-(prop-1-yn-1-yl)dibenzo[b,d]thiophen-2-yl)piperazin-2-one |
| 116 | 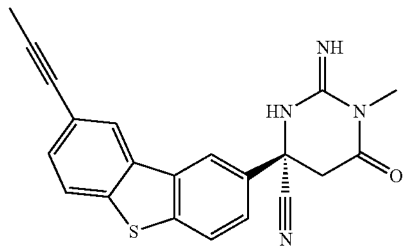 [SMILES: CC#Cc1ccc2sc3ccc([C@]4(C#N)CC(=O)N(C)C(=N)N4)cc3c2c1] | (S)-2-Imino-1-methyl-6-oxo-4-(8-(prop-1-yn-1-yl)dibenzo[b,d]thiophen-2-yl)hexahydropyrimidine-4-carbonitrile |
| 117 | 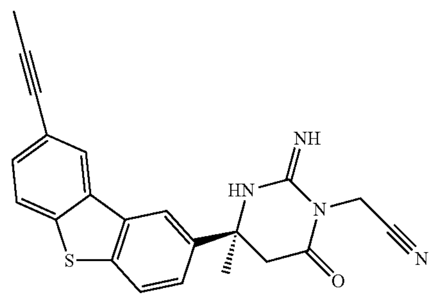 [SMILES: CC#Cc1ccc2sc3ccc([C@]4(C)CC(=O)N(CC#N)C(=N)N4)cc3c2c1] | (S)-2-(2-Imino-4-methyl-6-oxo-4-(8-(prop-1-yn-1-yl)dibenzo[b,d]thiophen-2-yl)tetrahydropyrimidin-1(2H)-yl)acetonitrile |
| 118 | 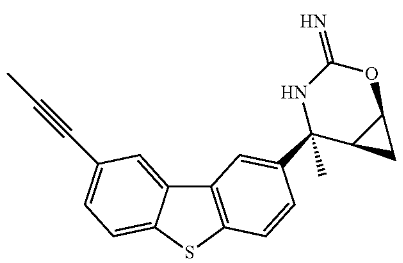 [SMILES: CC#Cc1ccc2sc3ccc([C@@]4(C)NC(=N)O[C@H]5C[C@H]54)cc3c2c1] | (1S,5R,6S)-5-Methyl-5-(8-(prop-1-yn-1-yl)dibenzo[b,d]thiophen-2-yl)-2-oxa-4-azabicyclo[4.1.0]heptan-3-imine |
| 119 | 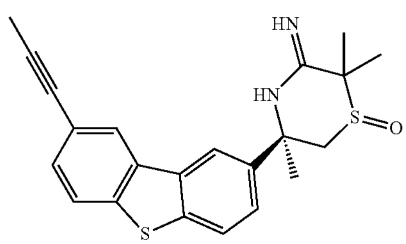 [SMILES: CC#Cc1ccc2sc3ccc([C@]4(C)CS(=O)C(C)(C)C(=N)N4)cc3c2c1] | (5R)-3-Imino-2,2,5-trimethyl-5-(8-(prop-1-yn-1-yl)dibenzo[b,d]thiophen-2-yl)thiomorpholine 1-oxide |
| 120 | 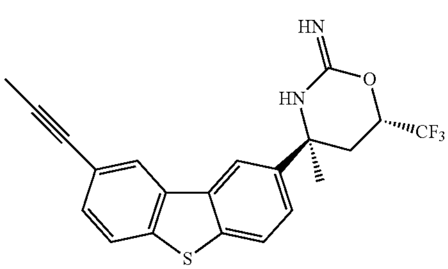 [SMILES: CC#Cc1ccc2sc3ccc([C@]4(C)C[C@@H](C(F)(F)F)OC(=N)N4)cc3c2c1] | (4S,6S)-4-Methyl-4-(8-(prop-1-yn-1-yl)dibenzo[b,d]thiophen-2-yl)-6-(trifluoromethyl)-1,3-oxazinan-2-imine |

| Example | Structure | Compound name |
|---|---|---|
| 121 | 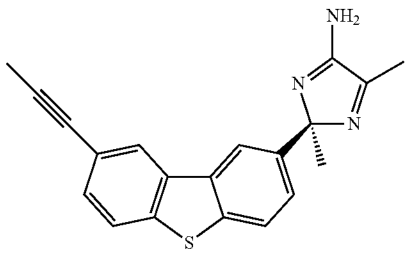 [SMILES: CC#Cc1ccc2sc3ccc([C@]4(C)N=C(C)C(N)=N4)cc3c2c1] | (R)-2,5-Dimethyl-2-(8-(prop-1-yn-1-yl)dibenzo[b,d]thiophen-2-yl)-2H-imidazol-4-amine |
| 122 | 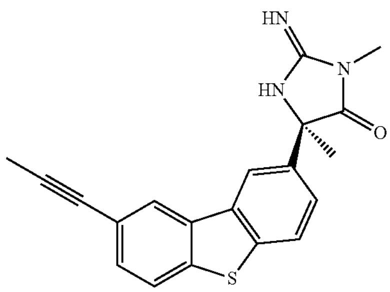 [SMILES: CC#Cc1ccc2sc3ccc([C@@]4(C)NC(=N)N(C)C4=O)cc3c2c1] | (R)-2-Imino-3,5-dimethyl-5-(8-(prop-1-yn-1-yl)dibenzo[b,d]thiophen-2-yl)imidazolidin-4-one |
| 123 | 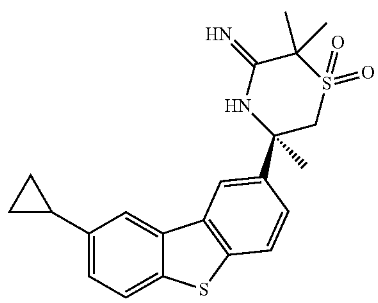 [SMILES: CC1(C)C(=N)N[C@](C)(c2ccc3sc4ccc(C5CC5)cc4c3c2)CS1(=O)=O] | (R)-5-(8-Cyclopropyldibenzo[b,d]thiophen-2-yl)-3-imino-2,2,5-trimethylthiomorpholine 1,1-dioxide |
| 124 | 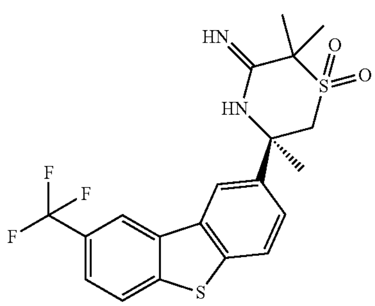 [SMILES: CC1(C)C(=N)N[C@](C)(c2ccc3sc4ccc(C(F)(F)F)cc4c3c2)CS1(=O)=O] | (R)-3-Imino-2,2,5-trimethyl-5-(8-(trifluoromethyl)dibenzo[b,d]thiophen-2-yl)thiomorpholine 1,1-dioxide |
| 125 | 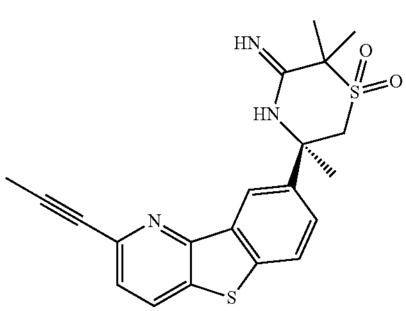 [SMILES: CC#Cc1ccc2sc3ccc([C@]4(C)CS(=O)(=O)C(C)(C)C(=N)N4)cc3c2n1] | (R)-3-Imino-2,2,5-trimethyl-5-(2-(prop-1-yn-1-yl)benzo[4,5]thieno[3,2-b]pyridin-8-yl)thiomorpholine 1,1-dioxide |

-continued

| Example | Structure | Compound name |
|---|---|---|
| 126 | 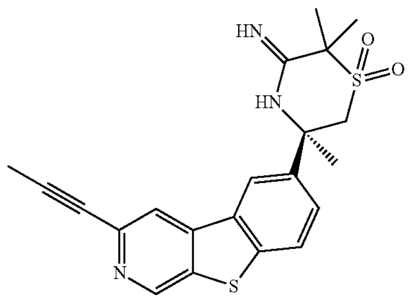 [SMILES: CC#Cc1cc2c(cn1)sc1ccc([C@]3(C)CS(=O)(=O)C(C)(C)C(=N)N3)cc12] | (R)-3-Imino-2,2,5-trimethyl-5-(3-(prop-1-yn-1-yl)benzo[4,5]thieno[2,3-c]pyridin-6-yl)thiomorpholine 1,1-dioxide |
| 127 | 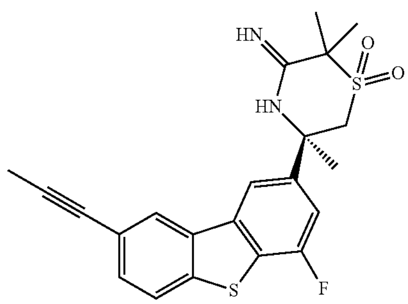 [SMILES: CC#Cc1ccc2sc3c(F)cc([C@]4(C)CS(=O)(=O)C(C)(C)C(=N)N4)cc3c2c1] | (R)-5-(4-Fluoro-8-(prop-1-yn-1-yl)dibenzo[b,d]thiophen-2-yl)-3-imino-2,2,5-trimethylthiomorpholine 1,1-dioxide |
| 128 | 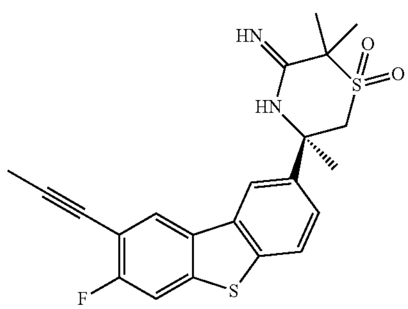 [SMILES: CC#Cc1cc2c(cc1F)sc1ccc([C@]3(C)CS(=O)(=O)C(C)(C)C(=N)N3)cc12] | (R)-5-(7-Fluoro-8-(prop-1-yn-1-yl)dibenzo[b,d]thiophen-2-yl)-3-imino-2,2,5-trimethylthiomorpholine 1,1-dioxide |
| 129 | 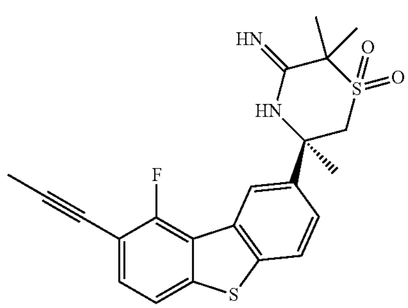 [SMILES: CC#Cc1ccc2sc3ccc([C@]4(C)CS(=O)(=O)C(C)(C)C(=N)N4)cc3c2c1F] | (R)-5-(9-Fluoro-8-(prop-1-yn-1-yl)dibenzo[b,d]thiophen-2-yl)-3-imino-2,2,5-trimethylthiomorpholine 1,1-dioxide |
| 130 | 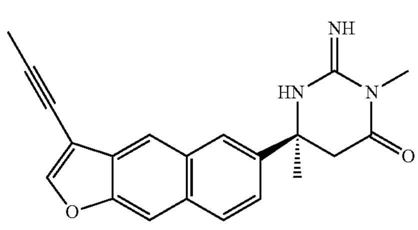 [SMILES: CC#Cc1coc2cc3ccc([C@]4(C)CC(=O)N(C)C(=N)N4)cc3cc12] | (S)-2-Imino-3,6-dimethyl-6-(3-(prop-1-yn-1-yl)naphtho[2,3-b]furan-6-yl)tetrahydropyrimidin-4(1H)-one |

-continued

| Example | Structure | Compound name |
|---|---|---|
| 131 | 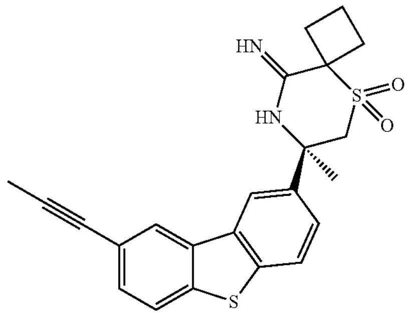 [SMILES: CC#Cc1ccc2sc3ccc([C@]4(C)CS(=O)(=O)C5(CCC5)C(=N)N4)cc3c2c1] | (R)-9-Imino-7-methyl-7-(8-(prop-1-yn-1-yl)dibenzo[b,d]thiophen-2-yl)-5-thia-8-azaspiro[3.5]nonane 5,5-dioxide |
| 132 | 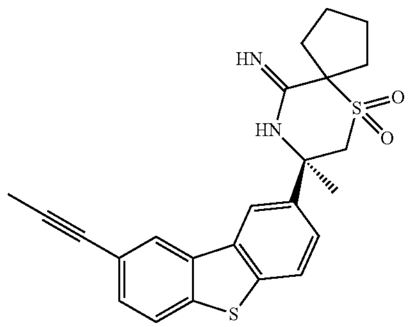 [SMILES: CC#Cc1ccc2sc3ccc([C@]4(C)CS(=O)(=O)C5(CCCC5)C(=N)N4)cc3c2c1] | (R)-10-Imino-8-methyl-8-(8-(prop-1-yn-1-yl)dibenzo[b,d]thiophen-2-yl)-6-thia-9-azaspiro[4.5]decane 6,6-dioxide |
| 133 | 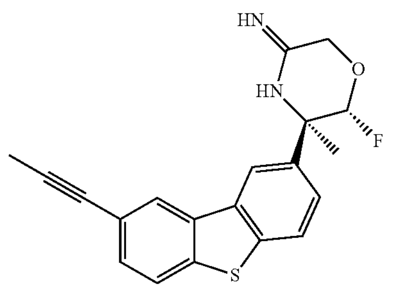 [SMILES: CC#Cc1ccc2sc3ccc([C@@]4(C)NC(=N)CO[C@@H]4F)cc3c2c1] | (5R,6R)-6-Fluoro-5-methyl-5-(8-(prop-1-yn-1-yl)dibenzo[b,d]thiophen-2-yl)morpholin-3-imine |
| 134 | 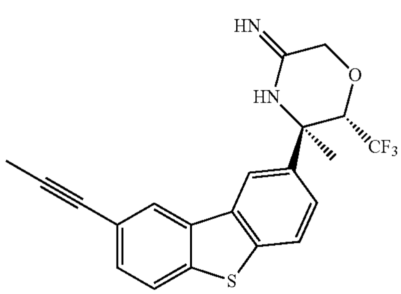 [SMILES: CC#Cc1ccc2sc3ccc([C@@]4(C)NC(=N)CO[C@@H]4C(F)(F)F)cc3c2c1] | (5R,6S)-5-Methyl-5-(8-(prop-1-yn-1-yl)dibenzo[b,d]thiophen-2-yl)-6-(trifluoromethyl)morpholin-3-imine |
| 135 | 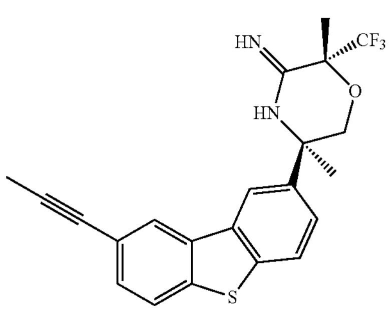 [SMILES: CC#Cc1ccc2sc3ccc([C@]4(C)CO[C@@](C)(C(F)(F)F)C(=N)N4)cc3c2c1] | (2R,5R)-2,5-Dimethyl-5-(8-(prop-1-yn-1-yl)dibenzo[b,d]thiophen-2-yl)-2-(trifluoromethyl)morpholin-3-imine |

-continued

| Example | Structure | Compound name |
|---|---|---|
| 136 | 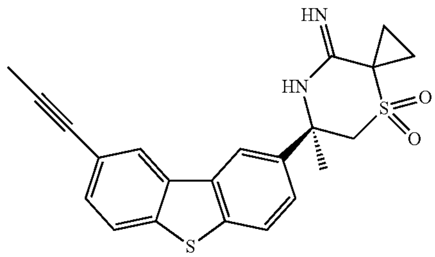 [SMILES: CC#Cc1ccc2sc3ccc([C@]4(C)CS(=O)(=O)C5(CC5)C(=N)N4)cc3c2c1] | (R)-8-Imino-6-methyl-6-(8-(prop-1-yn-1-yl)dibenzo[b,d]thiophen-2-yl)-4-thia-7-azaspiro[2.5]octane 4,4-dioxide |
| 137 | 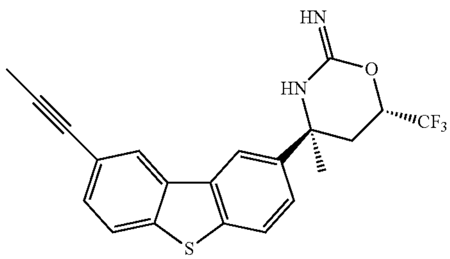 [SMILES: CC#Cc1ccc2sc3ccc([C@]4(C)C[C@@H](C(F)(F)F)OC(=N)N4)cc3c2c1] | (4S,6S)-4-Methyl-4-(8-(prop-1-yn-1-yl)dibenzo[b,d]thiophen-2-yl)-6-(trifluoromethyl)-1,3-oxazinan-2-imine |
| 138 | 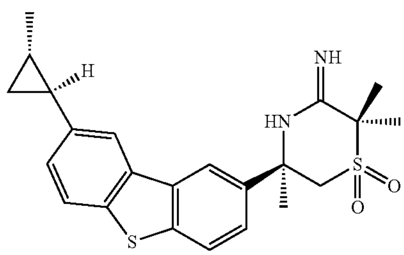 | (R)-3-Imino-2,2,5-trimethyl-5-(8-((1S,2S)-2-methylcyclopropyl)dibenzo[b,d]thiophen-2-yl)thiomorpholine 1,1-dioxide |
| 139 | 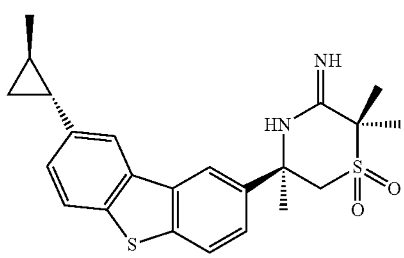 | (R)-3-Imino-2,2,5-trimethyl-5-(8-((1R,2R)-2-methylcyclopropyl)dibenzo[b,d]thiophen-2-yl)thiomorpholine 1,1-dioxide |
| 140 | 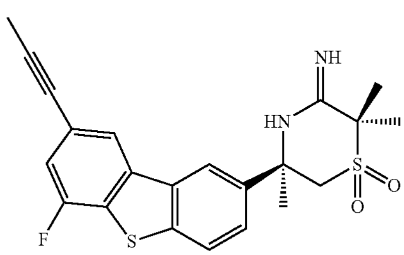 | (R)-5-(6-Fluoro-8-(prop-1-yn-1-yl)dibenzo[b,d]thiophen-2-yl)-3-imino-2,2,5-trimethylthiomorpholine 1,1-dioxide |
| 141 | 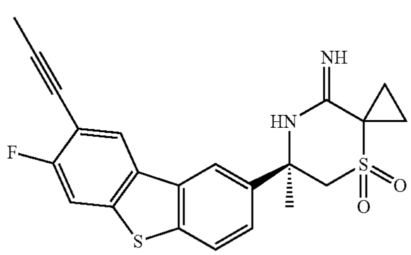 [SMILES: CC#Cc1cc2c(cc1F)sc1ccc([C@]3(C)CS(=O)(=O)C4(CC4)C(=N)N3)cc12] | (R)-6-(7-Fluoro-8-(prop-1-yn-1-yl)dibenzo[b,d]thiophen-2-yl)-8-imino-6-methyl-4-thia-7-azaspiro[2.5]octane 4,4-dioxide |

| Example | Structure | Compound name |
| --- | --- | --- |
| 142 | 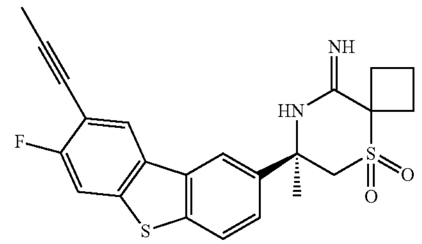 [SMILES: CC#Cc1cc2c(cc1F)sc1ccc([C@]3(C)CS(=O)(=O)C4(CCC4)C(=N)N3)cc12] | (R)-7-(7-Fluoro-8-(prop-1-yn-1-yl) dibenzo[b,d]thiophen-2-yl)-9-imino-7-methyl-5-thia-8-azaspiro[3.5]nonane 5,5-dioxide |
| 143 | 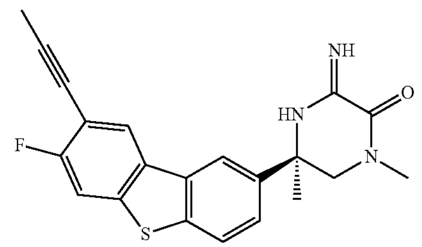 [SMILES: CC#Cc1cc2c(cc1F)sc1ccc([C@]3(C)CN(C)C(=O)C(=N)N3)cc12] | (R)-5-(7-Fluoro-8-(prop-1-yn-1-yl) dibenzo[b,d]thiophen-2-yl)-3-imino-1,5-dimethylpiperazin-2-one |
| 144 | 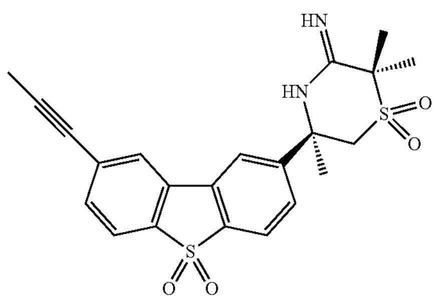 | (R)-5-(5,5-Dioxido-8-(prop-1-yn-1-yl) dibenzo[b,d]thiophen-2-yl)-3-imino-2,2,5-trimethylthiomorpholine 1,1-dioxide |
| 145 | 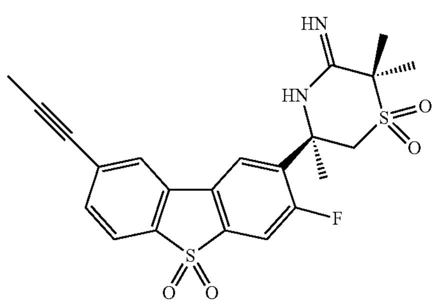 | (R)-5-(3-Fluoro-5,5-dioxido-8-(prop-1-yn-1-yl)dibenzo[b,d]thiophen-2-yl)-3-imino-2,2,5-trimethylthiomorpholine 1,1-dioxide |
| 146 | 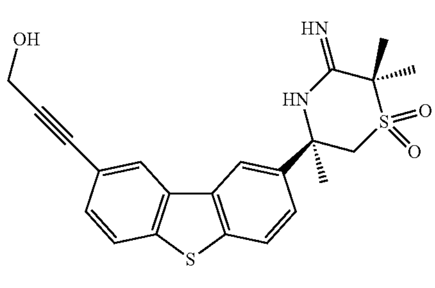 | (R)-5-(8-(3-Hydroxyprop-1-yn-1-yl) dibenzo[b,d]thiophen-2-yl)-3-imino-2,2,5-trimethylthiomorpholine 1,1-dioxide |

| Example | Structure | Compound name |
|---|---|---|
| 147 | 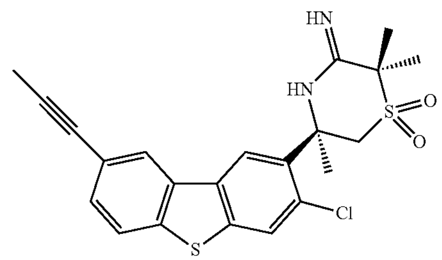 | (R)-5-(3-Chloro-8-(prop-1-yn-1-yl) dibenzo[b,d]thiophen-2-yl)-3-imino-2,2,5-trimethylthiomorpholine 1,1-dioxide |
| 148 | 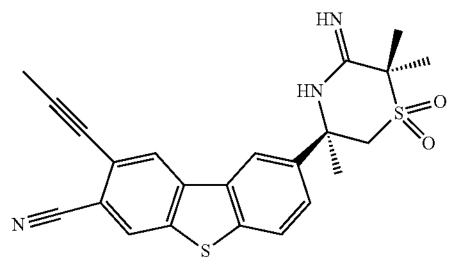 | (R)-8-(5-Imino-3,6,6-trimethyl-1,1-dioxidothiomorpholin-3-yl)-2-(prop-1-yn-1-yl)dibenzo[b,d]thiophene-3-carbonitrile |
| 149 | 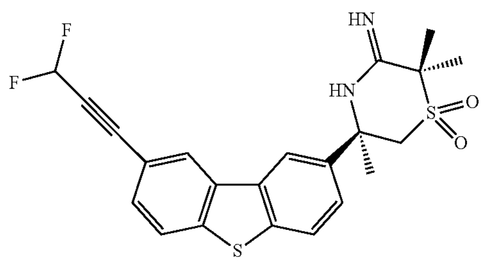 | (R)-5-(8-(3,3-Difluoroprop-1-yn-1-yl) dibenzo[b,d]thiophen-2-yl)-3-imino-2,2,5-trimethylthiomorpholine 1,1-dioxide |
| 150 | 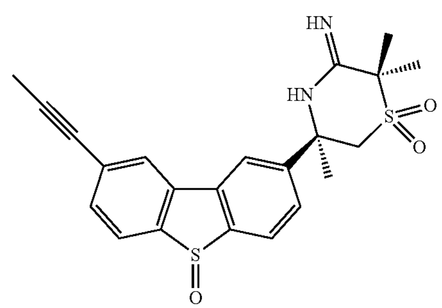 | (5R)-3-Imino-2,2,5-trimethyl-5-(5-oxido-8-(prop-1-yn-1-yl)dibenzo[b,d]thiophen-2-yl)thiomorpholine 1,1-dioxide |
| 151 | 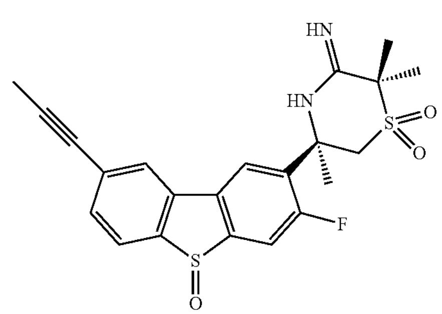 | (5R)-5-(3-Fluoro-5-oxido-8-(prop-1-yn-1-yl)dibenzo[b,d]thiophen-2-yl)-3-imino-2,2,5-trimethylthiomorpholine 1,1-dioxide |

| Example | Structure | Compound name |
|---|---|---|
| 152 | 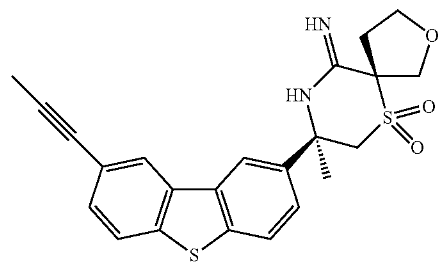 [SMILES: CC#Cc1ccc2sc3ccc([C@]4(C)CS(=O)(=O)[C@]5(CCOC5)C(=N)N4)cc3c2c1] | (5R,8R)-10-Imino-8-methyl-8-(8-(prop-1-yn-1-yl)dibenzo[b,d]thiophen-2-yl)-2-oxa-6-thia-9-azaspiro[4.5]decane 6,6-dioxide |
| 153 | 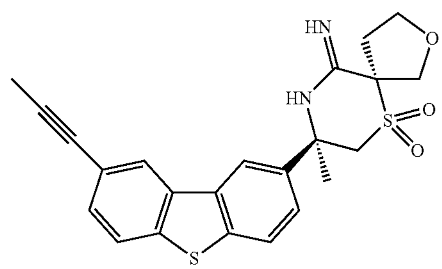 [SMILES: CC#Cc1ccc2sc3ccc([C@]4(C)CS(=O)(=O)[C@@]5(CCOC5)C(=N)N4)cc3c2c1] | (5S,8R)-10-Imino-8-methyl-8-(8-(prop-1-yn-1-yl)dibenzo[b,d]thiophen-2-yl)-2-oxa-6-thia-9-azaspiro[4.5]decane 6,6-dioxide |
| 154 | 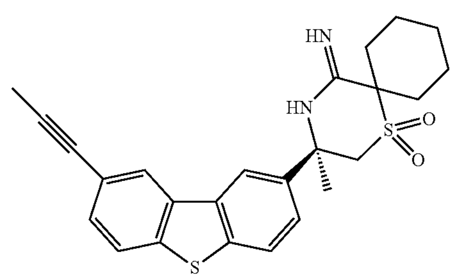 [SMILES: CC#Cc1ccc2sc3ccc([C@]4(C)CS(=O)(=O)C5(CCCCC5)C(=N)N4)cc3c2c1] | (R)-5-Imino-3-methyl-3-(8-(prop-1-yn-1-yl)dibenzo[b,d]thiophen-2-yl)-1-thia-4-azaspiro[5.5]undecane 1,1-dioxide |
| 155 | 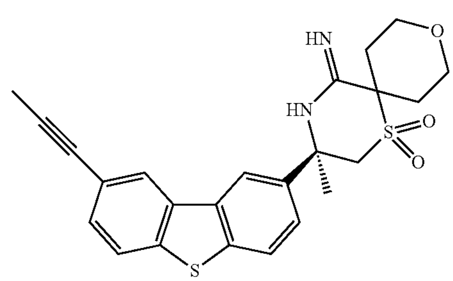 | (R)-5-imino-3-methyl-3-(8-(prop-1-yn-1-yl)Dibenzo[b,d]thiophen-2-yl)-9-oxa-1-thia-4-azaspiro[5.5]undecane 1,1-dioxide |
| 156 | 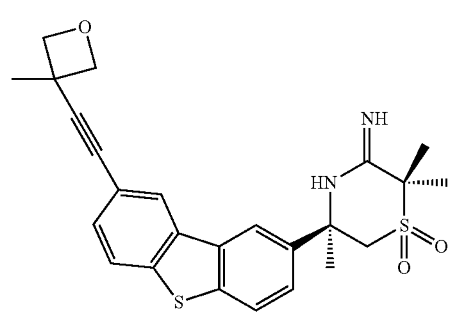 | (R)-5-Amino-3,6,6-trimethyl-3-(8-((3-methyloxetan-3-yl)ethynyl)dibenzo[b,d]thiophen-2-yl)-3,6-dihydro-2H-1,4-thiazine 1,1-dioxide |

| Example | Structure | Compound name |
|---|---|---|
| 157 | 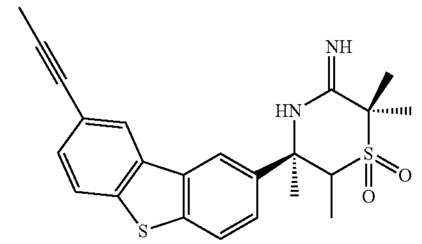 | (3R)-5-Amino-2,3,6,6-tetramethyl-3-(8-(prop-1-yn-1-yl)dibenzo[b,d]thiophen-2-yl)-3,6-dihydro-2H-1,4-thiazine 1,1-dioxide |
| 158 | 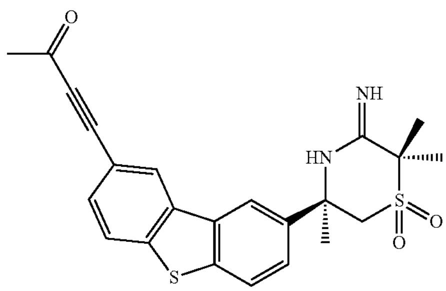 | (R)-4-(8-(5-Imino-3,6,6-trimethyl-1,1-dioxidothiomorpholin-3-yl)dibenzo[b,d]thiophen-2-yl)but-3-yn-2-one |
| 159 | 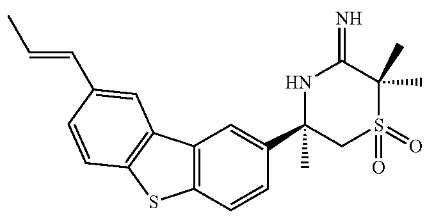 | ((R,E)-3-Imino-2,2,5-trimethyl-5-(8-(prop-1-en-1-yl)dibenzo[b,d]thiophen-2-yl)thiomorpholine 1,1-dioxide |
| 160 | 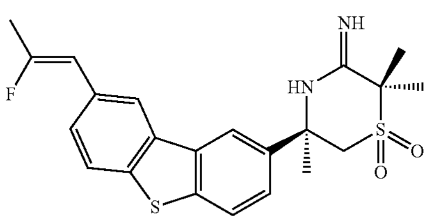 | (R,Z)-5-(8-(2-Fluoroprop-1-en-1-yl)dibenzo[b,d]thiophen-2-yl)-3-imino-2,2,5-trimethylthiomorpholine 1,1-dioxide |
| 161 | 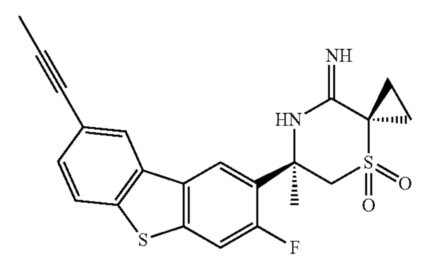 | (R)-6-(3-Fluoro-8-(prop-1-yn-1-yl)dibenzo[b,d]thiophen-2-yl)-8-imino-6-methyl-4-thia-7-azaspiro[2.5]octane 4,4-dioxide |
| 162 | 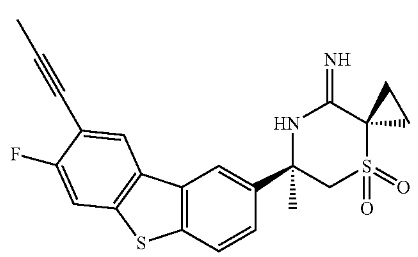 | (R)-6-(7-Fluoro-8-(prop-1-yn-1-yl)dibenzo[b,d]thiophen-2-yl)-8-imino-6-methyl-4-thia-7-azaspiro[2.5]octane 4,4-dioxide |

-continued

| Example | Structure | Compound name |
|---|---|---|
| 163 | 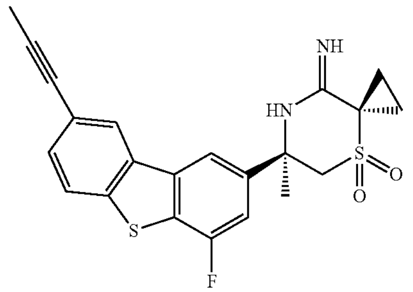 | (R)-6-(4-Fluoro-8-(prop-1-yn-1-yl)dibenzo[b,d]thiophen-2-yl)-8-imino-6-methyl-4-thia-7-azaspiro[2.5]octane 4,4-dioxide |
| 164 | 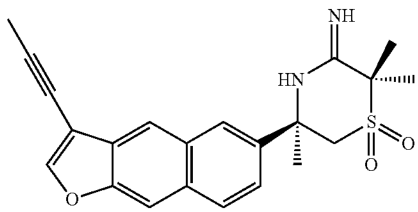 | (R)-3-Imino-2,2,5-trimethyl-5-(3-(prop-1-yn-1-yl)naphtho[2,3-b]furan-6-yl)thiomorpholine 1,1-dioxide |
| 165 | 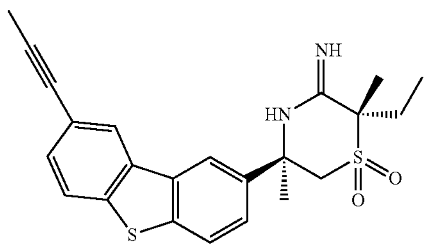 [SMILES: CC#Cc1ccc2sc3ccc([C@]4(C)CS(=O)(=O)[C@@](C)(CC)C(=N)N4)cc3c2c1] | (2S,5R)-2-Ethyl-3-imino-2,5-dimethyl-5-(8-(prop-1-yn-1-yl)dibenzo[b,d]thiophen-2-yl)thiomorpholine 1,1-dioxide |
| 166 | 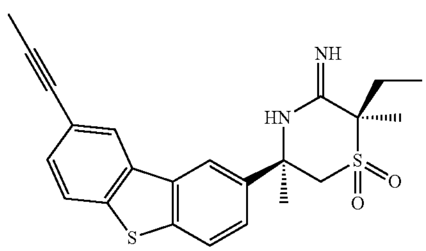 [SMILES: CC#Cc1ccc2sc3ccc([C@]4(C)CS(=O)(=O)[C@](C)(CC)C(=N)N4)cc3c2c1] | (2R,5R)-2-Ethyl-3-imino-2,5-dimethyl-5-(8-(prop-1-yn-1-yl)dibenzo[b,d]thiophen-2-yl)thiomorpholine 1,1-dioxide |
| 167 | 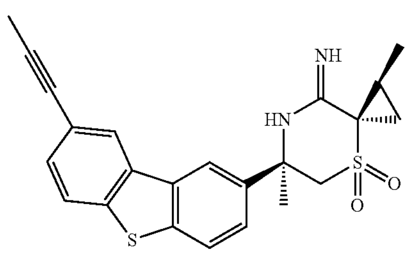 [SMILES: CC#Cc1ccc2sc3ccc([C@]4(C)CS(=O)(=O)[C@@]5(C[C@@H]5C)C(=N)N4)cc3c2c1] | (1S,3R,6R)-8-Imino-1,6-dimethyl-6-(8-(prop-1-yn-1-yl)dibenzo[b,d]thiophen-2-yl)-4-thia-7-azaspiro[2.5]octane 4,4-dioxide |
| 168 | 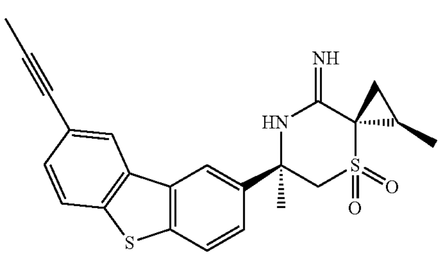 [SMILES: CC#Cc1ccc2sc3ccc([C@]4(C)CS(=O)(=O)[C@]5(C[C@H]5C)C(=N)N4)cc3c2c1] | (1R,3S,6R)-8-Imino-1,6-dimethyl-6-(8-(prop-1-yn-1-yl)dibenzo[b,d]thiophen-2-yl)-4-thia-7-azaspiro[2.5]octane 4,4-dioxide |

| Example | Structure | Compound name |
|---|---|---|
| 169 | 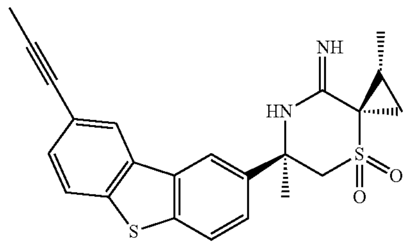 [SMILES: CC#Cc1ccc2sc3ccc([C@]4(C)CS(=O)(=O)[C@@]5(C[C@H]5C)C(=N)N4)cc3c2c1] | (1R,3R,6R)-8-Imino-1,6-dimethyl-6-(8-(prop-1-yn-1-yl)dibenzo[b,d]thiophen-2-yl)-4-thia-7-azaspiro[2.5]octane 4,4-dioxide |
| 170 | 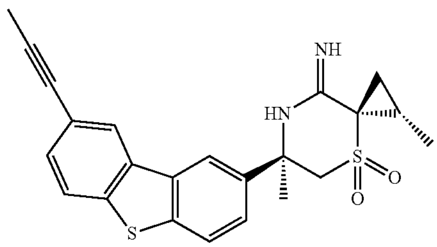 [SMILES: CC#Cc1ccc2sc3ccc([C@]4(C)CS(=O)(=O)[C@]5(C[C@@H]5C)C(=N)N4)cc3c2c1] | (1S,3S,6R)-8-Imino-1,6-dimethyl-6-(8-(prop-1-yn-1-yl)dibenzo[b,d]thiophen-2-yl)-4-thia-7-azaspiro[2.5]octane 4,4-dioxide |
| 171 | 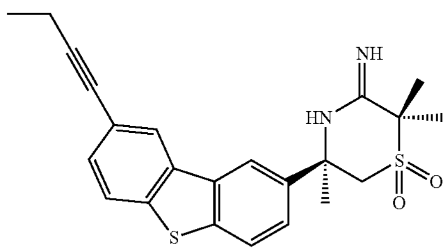 | (R)-5-(8-(But-1-yn-1-yl)dibenzo[b,d]thiophen-2-yl)-3-imino-2,2,5-trimethyl-thiomorpholine 1,1-dioxide |
| 172 | 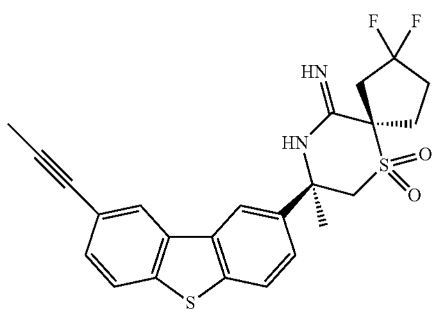 [SMILES: CC#Cc1ccc2sc3ccc([C@]4(C)CS(=O)(=O)[C@@]5(CCC(F)(F)C5)C(=N)N4)cc3c2c1] | (5R,8R)-2,2-Difluoro-10-imino-8-methyl-8-(8-(prop-1-yn-1-yl)dibenzo[b,d]thiophen-2-yl)-6-thia-9-azaspiro[4.5]decane 6,6-dioxide |
| 173 | 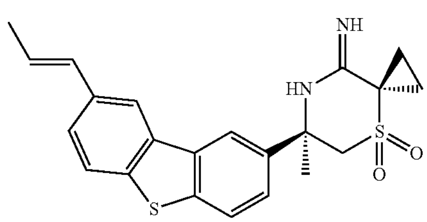 | (R,E)-8-Imino-6-methyl-6-(8-(prop-1-en-1-yl)dibenzo[b,d]thiophen-2-yl)-4-thia-7-azaspiro[2.5]octane 4,4-dioxide |
| 174 | 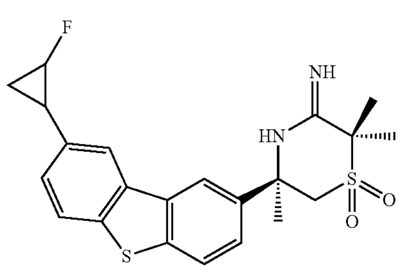 | (5R)-5-(8-(2-Fluorocyclopropyl)dibenzo[b,d]thiophen-2-yl)-3-imino-2,2,5-trimethylthiomorpholine 1,1-dioxide |

-continued

| Example | Structure | Compound name |
|---|---|---|
| 175 | 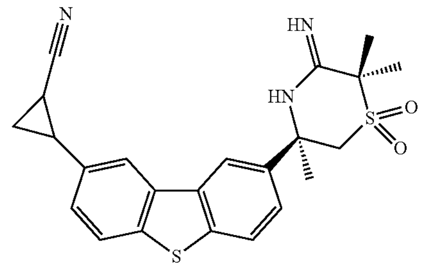 | 2-(8-((R)-5-Imino-3,6,6-trimethyl-1,1-dioxidothiomorpholin-3-yl)dibenzo[b,d]thiophen-2-yl)cyclopropane-carbonitrile |
| 176 | 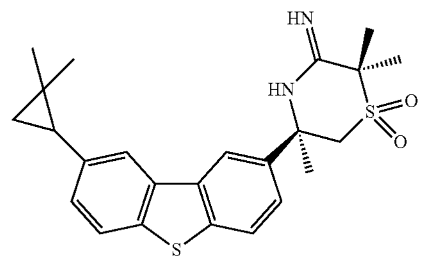 | (5R)-5-(8-(2,2-Dimethylcyclopropyl)dibenzo[b,d]thiophen-2-yl)-3-imino-2,2,5-trimethylthiomorpholine 1,1-dioxide |
| 177 | 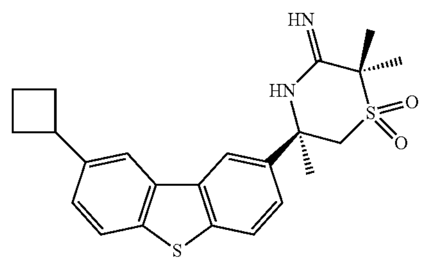 | (R)-5-(8-Cyclobutyldibenzo[b,d]thiophen-2-yl)-3-imino-2,2,5-trimethyl-thiomorpholine 1,1-dioxide |
| 178 | 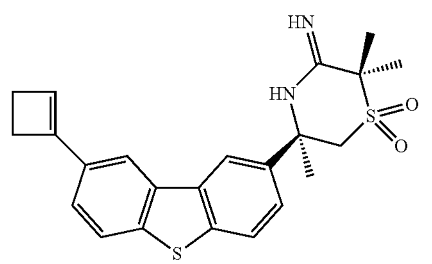 | (R)-5-(8-(Cyclobut-1-en-1-yl)dibenzo[b,d]thiophen-2-yl)-3-imino-2,2,5-trimethylthiomorpholine 1,1-dioxide |
| 179 | 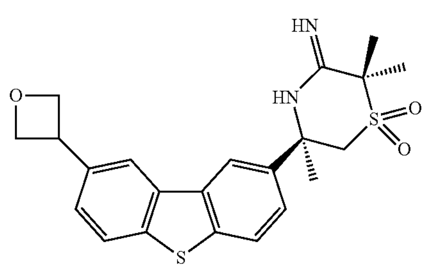 | (R)-3-imino-2,2,5-Trimethyl-5-(8-(oxetan-3-yl)dibenzo[b,d]thiophen-2-yl)thiomorpholine 1,1-dioxide |
| 180 | 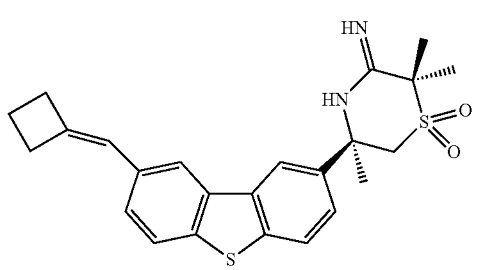 | (R)-5-(8-(Cyclobutylidenemethyl)dibenzo[b,d]thiophen-2-yl)-3-imino-2,2,5-trimethylthiomorpholine 1,1-dioxide |

-continued

| Example | Structure | Compound name |
|---|---|---|
| 181 | 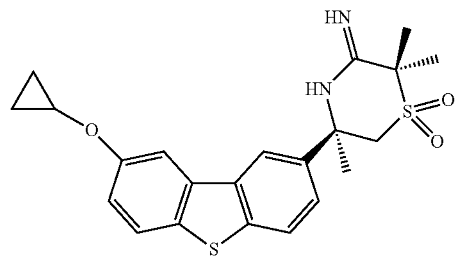 | (R)-5-(8-Cyclopropoxydibenzo[b,d]thiophen-2-yl)-3-imino-2,2,5-trimethyl-thiomorpholine 1,1-dioxide |
| 182 | 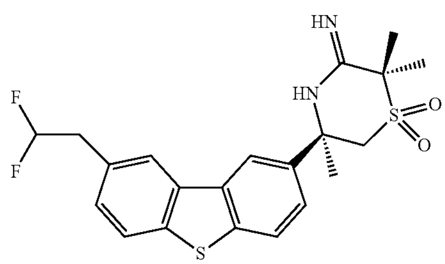 | (R)-5-(8-(2,2-Difluoroethyl)dibenzo[b,d]thiophen-2-yl)-3-imino-2,2,5-trimethylthiomorpholine 1,1-dioxide |
| 183 | 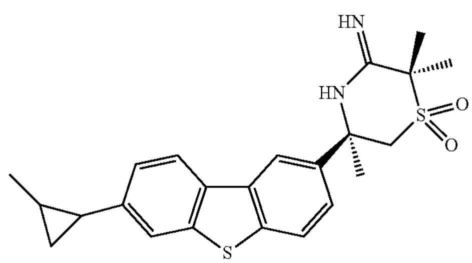 | (5R)-3-Imino-2,2,5-trimethyl-5-(7-(2-methylcyclopropyl)dibenzo[b,d]thiophen-2-yl)thiomorpholine 1,1-dioxide |
| 184 | 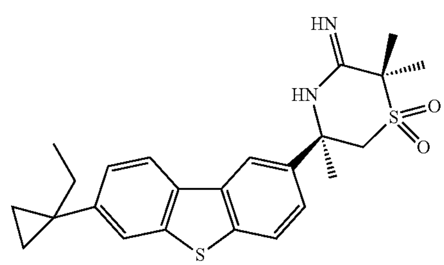 | (R)-5-(7-(1-Ethylcyclopropyl)dibenzo[b,d]thiophen-2-yl)-3-imino-2,2,5-trimethylthiomorpholine 1,1-dioxide |
| 185 | 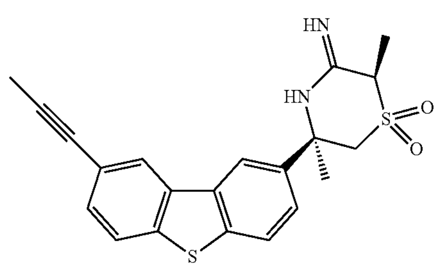 [SMILES: CC#Cc1ccc2sc3ccc([C@]4(C)CS(=O)(=O)[C@H](C)C(=N)N4)cc3c2c1] | (2R,5R)-3-Imino-2,5-dimethyl-5-(8-(prop-1-yn-1-yl)dibenzo[b,d]thiophen-2-yl)thiomorpholine 1,1-dioxide |
| 186 | 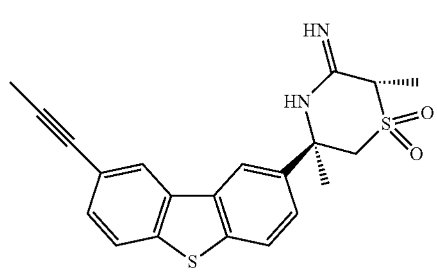 [SMILES: CC#Cc1ccc2sc3ccc([C@]4(C)CS(=O)(=O)[C@@H](C)C(=N)N4)cc3c2c1] | (2S,5R)-3-Imino-2,5-dimethyl-5-(8-(prop-1-yn-1-yl)dibenzo[b,d]thiophen-2-yl)thiomorpholine 1,1-dioxide |

| Example | Structure | Compound name |
|---|---|---|
| 187 | 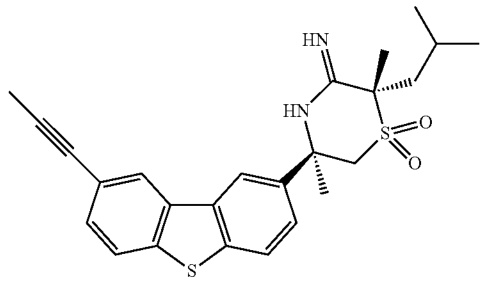 [SMILES: CC#Cc1ccc2sc3ccc([C@]4(C)CS(=O)(=O)[C@@](C)(CC(C)C)C(=N)N4)cc3c2c1] | (2S,5R)-3-Imino-2-isobutyl-2,5-dimethyl-5-(8-(prop-1-yn-1-yl)dibenzo[b,d]thiophen-2-yl)thiomorpholine 1,1-dioxide |
| 188 | 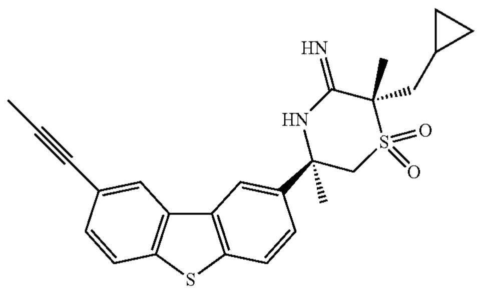 [SMILES: CC#Cc1ccc2sc3ccc([C@]4(C)CS(=O)(=O)[C@@](C)(CC5CC5)C(=N)N4)cc3c2c1] | (2S,5R)-2-(Cyclopropylmethyl)-3-imino-2,5-dimethyl-5-(8-(prop-1-yn-1-yl)dibenzo[b,d]thiophen-2-yl)thiomorpholine 1,1-dioxide |
| 189 | 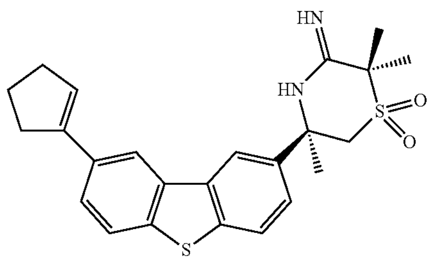 | (R)-5-(8-(Cyclopent-1-en-1-yl)dibenzo[b,d]thiophen-2-yl)-3-imino-2,2,5-trimethylthiomorpholine 1,1-dioxide |
| 190 | 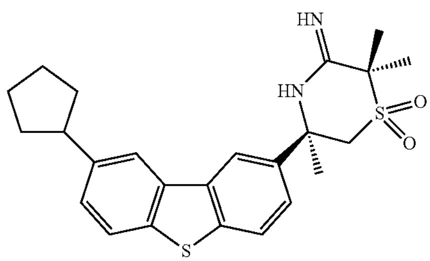 | (R)-5-(8-Cyclopentyldibenzo[b,d]thiophen-2-yl)-3-imino-2,2,5-trimethylthiomorpholine 1,1-dioxide |
| 191 | 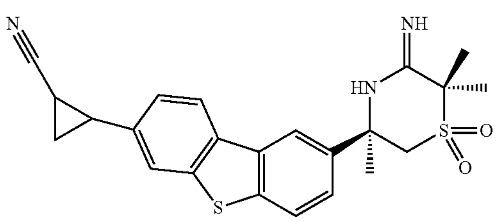 | 2-(8-((R)-5-Imino-3,6,6-trimethyl-1,1-dioxidothiomorpholin-3-yl)dibenzo[b,d]thiophen-3-yl)cyclopropanecarbonitrile |
| 192 | 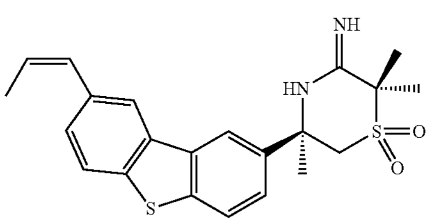 | (R,2)-3-Imino-2,2,5-trimethyl-5-(8-(prop-1-en-1-yl)dibenzo[b,d]thiophen-2-yl)thiomorpholine 1,1-dioxide |

-continued

| Example | Structure | Compound name |
|---|---|---|
| 193 | 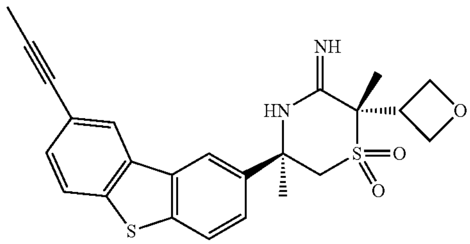 [SMILES: CC#Cc1ccc2sc3ccc([C@]4(C)CS(=O)(=O)[C@@](C)(C5COC5)C(=N)N4)cc3c2c1] | (2S,5R)-3-Imino-2,5-dimethyl-2-(oxetan-3-yl)-5-(8-(prop-1-yn-1-yl)dibenzo[b,d]thiophen-2-yl)thiomorpholine 1,1-dioxide |
| 194 | 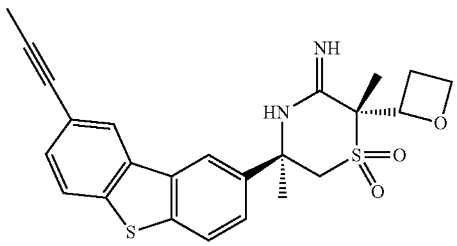 [SMILES: CC#Cc1ccc2sc3ccc([C@]4(C)CS(=O)(=O)[C@@](C)(C5CCO5)C(=N)N4)cc3c2c1] | (2R,5R)-3-Imino-2,5-dimethyl-2-((R)-oxetan-2-yl)-5-(8-(prop-1-yn-1-yl)dibenzo[b,d]thiophen-2-yl)thiomorpholine 1,1-dioxide |
| 195 | 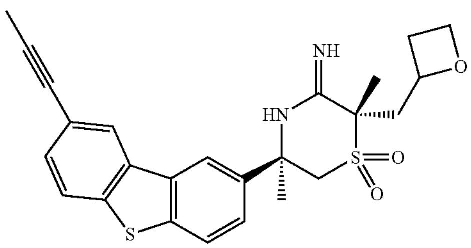 [SMILES: CC#Cc1ccc2sc3ccc([C@]4(C)CS(=O)(=O)[C@@](C)(CC5CCO5)C(=N)N4)cc3c2c1] | (2S,5R)-3-Imino-2,5-dimethyl-2-(oxetan-2-ylmethyl)-5-(8-(prop-1-yn-1-yl)dibenzo[b,d]thiophen-2-yl)thiomorpholine 1,1-dioxide |
| 196 | 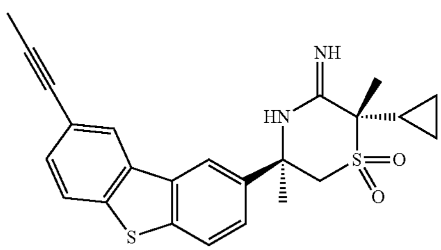 [SMILES: CC#Cc1ccc2sc3ccc([C@]4(C)CS(=O)(=O)[C@@](C)(C5CC5)C(=N)N4)cc3c2c1] | (2S,5R)-2-Cyclopropyl-3-imino-2,5-dimethyl-5-(8-(prop-1-yn-1-yl)dibenzo[b,d]thiophen-2-yl)thiomorpholine 1,1-dioxide |
| 197 | 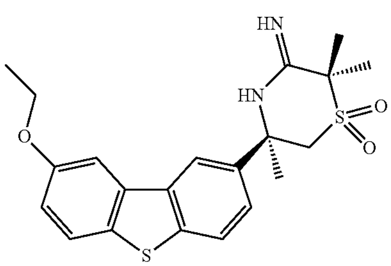 | (R)-5-(8-Ethoxydibenzo[b,d]thiophen-2-yl)-3-imino-2,2,5-trimethylthiomorpholine 1,1-dioxide |
| 198 | 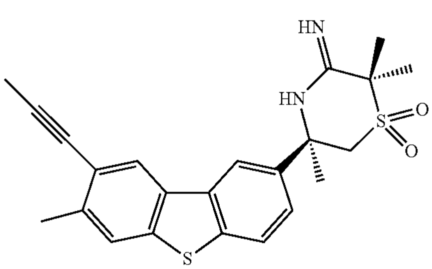 | (R)-3-Imino-2,2,5-trimethyl-5-(7-methyl-8-(prop-1-yn-1-yl)dibenzo[b,d]thiophen-2-yl)thiomorpholine 1,1-dioxide |

-continued

| Example | Structure | Compound name |
|---|---|---|
| 199 | 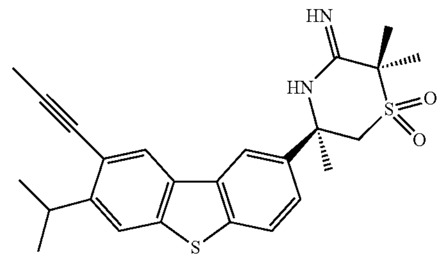 | (R)-3-Imino-5-(7-isopropyl-8-(prop-1-yn-1-yl)dibenzo[b,d]thiophen-2-yl)-2,2,5-trimethylthiomorpholine 1,1-dioxide |
| 200 | 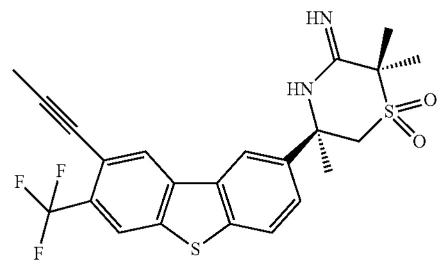 | (R)-3-Imino-2,2,5-trimethyl-5-(8-(prop-1-yn-1-yl)-7-(trifluoromethyl)dibenzo[b,d]thiophen-2-yl)thiomorpholine 1,1-dioxide |
| 201 | 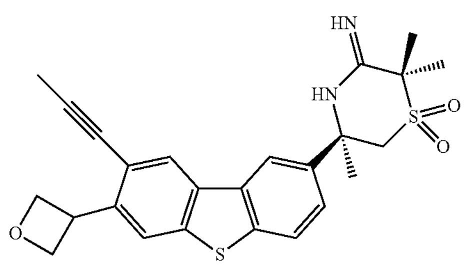 | (R)-3-Imino-2,2,5-trimethyl-5-(7-(oxetan-3-yl)-8-(prop-1-yn-1-yl)dibenzo[b,d]thiophen-2-yl)thiomorpholine 1,1-dioxide |
| 202 | 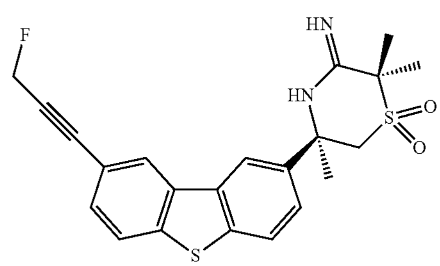 | (R)-5-(8-(3-Fluoroprop-1-yn-1-yl)dibenzo[b,d]thiophen-2-yl)-3-imino-2,2,5-trimethylthiomorpholine 1,1-dioxide |
| 203 | 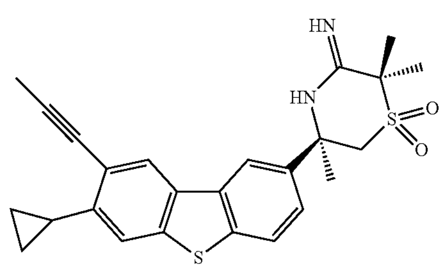 | (R)-5-(7-Cyclopropyl-8-(prop-1-yn-1-yl)dibenzo[b,d]thiophen-2-yl)-3-imino-2,2,5-trimethylthiomorpholine 1,1-dioxide |
| 204 | 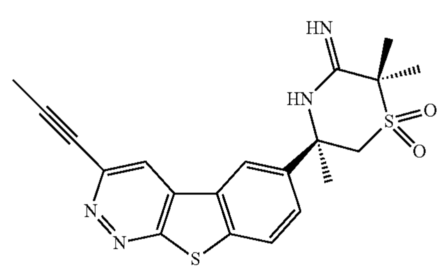 | (R)-3-Imino-2,2,5-trimethyl-5-(3-(prop-1-yn-1-yl)benzo[4,5]thieno[2,3-c]pyridazin-6-yl)thiomorpholine 1,1-dioxide |

| Example | Structure | Compound name |
|---|---|---|
| 205 | 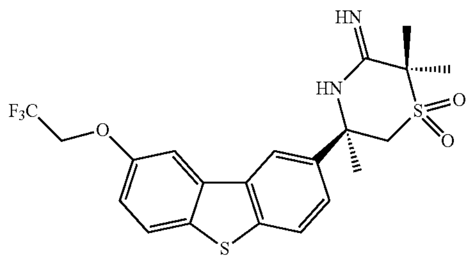 | (R)-3-Imino-2,2,5-trimethyl-5-(8-(2,2,2-trifluoroethoxy)dibenzo[b,d]thiophen-2-yl)thiomorpholine 1,1-dioxide |
| 206 | 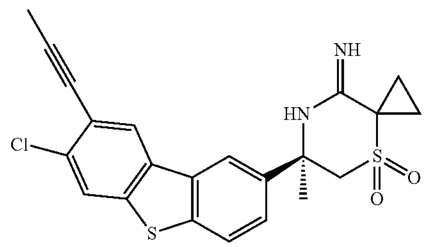 [SMILES: CC#Cc1cc2c(cc1Cl)sc1ccc([C@]3(C)CS(=O)(=O)C4(CC4)C(=N)N3)cc12] | (R)-6-(7-Chloro-8-(prop-1-yn-1-yl)dibenzo[b,d]thiophen-2-yl)-8-imino-6-methyl-4-thia-7-azaspiro[2.5]octane 4,4-dioxide |
| 207 | 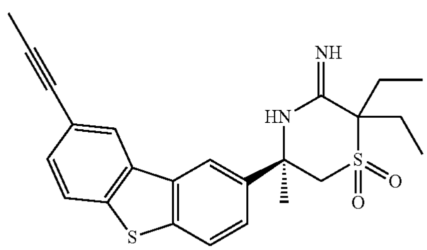 [SMILES: CC#Cc1ccc2sc3ccc([C@]4(C)CS(=O)(=O)C(CC)(CC)C(=N)N4)cc3c2c1] | (R)-2,2-Diethyl-3-imino-5-methyl-5-(8-(prop-1-yn-1-yl)dibenzo[b,d]thiophen-2-yl)thiomorpholine 1,1-dioxide |
| 208 | 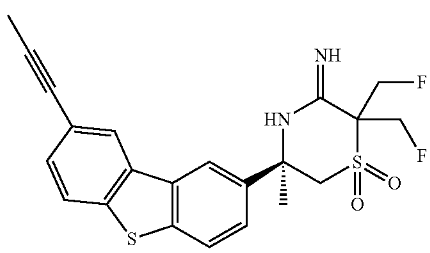 [SMILES: CC#Cc1ccc2sc3ccc([C@]4(C)CS(=O)(=O)C(CF)(CF)C(=N)N4)cc3c2c1] | (R)-2,2-Bis(fluoromethyl)-3-imino-5-methyl-5-(8-(prop-1-yn-1-yl)dibenzo[b,d]thiophen-2-yl)thiomorpholine 1,1-dioxide |
| 209 | 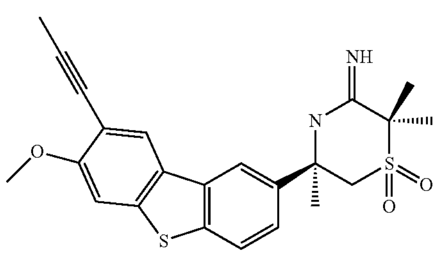 | (R)-3-Imino-5-(7-methoxy-8-(prop-1-yn-1-yl)dibenzo[b,d]thiophen-2-yl)-2,2,5-trimethylthiomorpholine 1,1-dioxide |
| 210 | 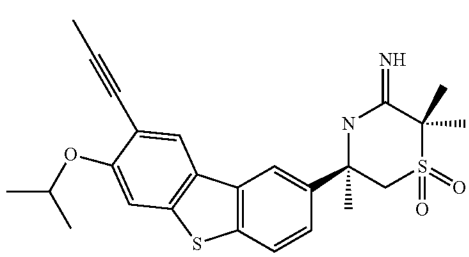 | (R)-3-Imino-5-(7-isopropoxy-8-(prop-1-yn-1-yl)dibenzo[b,d]thiophen-2-yl)-2,2,5-trimethylthiomorpholine 1,1-dioxide |

| Example | Structure | Compound name |
|---|---|---|
| 211 | 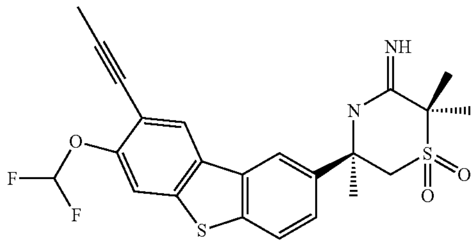 | (R)-5-(7-(Difluoromethoxy)-8-(prop-1-yn-1-yl)dibenzo[b,d]thiophen-2-yl)-3-imino-2,2,5-trimethylthiomorpholine 1,1-dioxide |
| 212 | 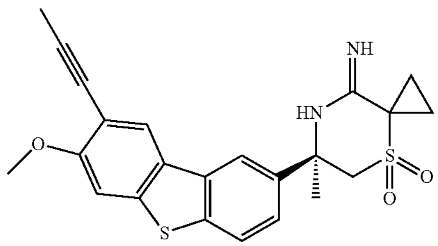 [SMILES: CC#Cc1cc2c(cc1OC)sc1ccc([C@]3(C)CS(=O)(=O)C4(CC4)C(=N)N3)cc12] | (R)-8-Imino-6-(7-methoxy-8-(prop-1-yn-1-yl)dibenzo[b,d]thiophen-2-yl)-6-methyl-4-thia-7-azaspiro[2.5]octane 4,4-dioxide |
| 213 | 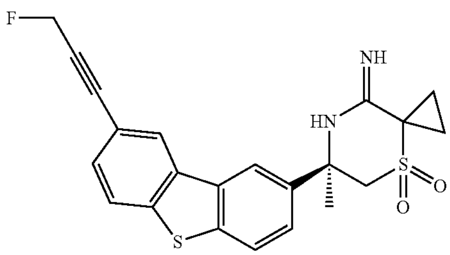 [SMILES: C[C@@]1(c2ccc3sc4ccc(C#CCF)cc4c3c2)CS(=O)(=O)C2(CC2)C(=N)N1] | (R)-6-(8-(3-Fluoroprop-1-yn-1-yl)dibenzo[b,d]thiophen-2-yl)-8-imino-6-methyl-4-thia-7-azaspiro[2.5]octane 4,4-dioxide |
| 214 | 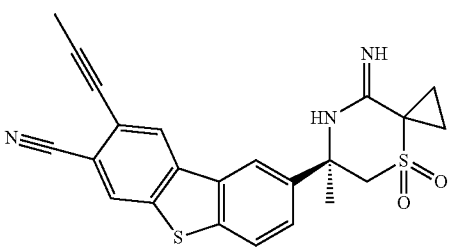 [SMILES: CC#Cc1cc2c(cc1C#N)sc1ccc([C@]3(C)CS(=O)(=O)C4(CC4)C(=N)N3)cc12] | (R)-8-(8-Imino-6-methyl-4,4-dioxido-4-thia-7-azaspiro[2.5]octan-6-yl)-2-(prop-1-yn-1-yl)dibenzo[b,d]thiophene-3-carbonitrile |
| 215 | 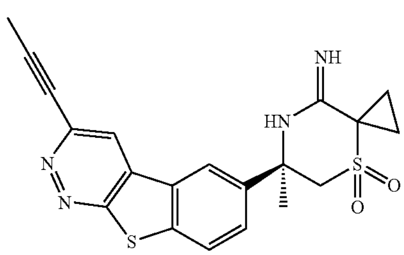 [SMILES: CC#Cc1cc2c(nn1)sc1ccc([C@]3(C)CS(=O)(=O)C4(CC4)C(=N)N3)cc12] | (R)-8-Imino-6-methyl-6-(3-(prop-1-yn-1-yl)benzo[4,5]thieno[2,3-c]pyridazin-6-yl)-4-thia-7-azaspiro[2.5]octane 4,4-dioxide |
| 216 | 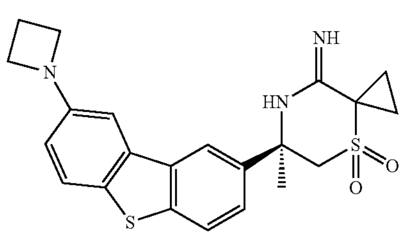 [SMILES: C[C@@]1(c2ccc3sc4ccc(N5CCC5)cc4c3c2)CS(=O)(=O)C2(CC2)C(=N)N1] | (R)-6-(8-(Azetidin-1-yl)dibenzo[b,d]thiophen-2-yl)-8-imino-6-methyl-4-thia-7-azaspiro[2.5]octane 4,4-dioxide |

| Example | Structure | Compound name |
|---|---|---|
| 217 | 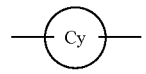 | (R)-6-(8-(1,3,4-Oxadiazol-2-yl) dibenzo[b,d]thiophen-2-yl)-8-imino-6-methyl-4-thia-7-azaspiro[2.5]octane 4,4-dioxide |
| 218 | 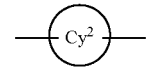 | (R)-5-(8-((1-Hydroxycydopropyl) ethynyl)dibenzo[b,d]thiophen-2-yl)-3-imino-2,2,5-trimethylthiomorpholine 1,1-dioxide |

Preferred compounds of formula (I) also include the structures of the following Formula:

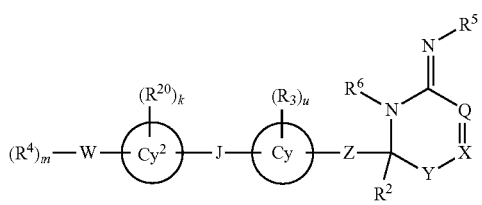

Formula (VII)

wherein

X is absent or present and when present selected from the group consisting of C(O), C(S), S(O)$_2$, (CR$^7$R$^8$)$_n$, O, N, NR$^1$, S and S(O);

Y is absent or present and when present is selected from the group consisting of (CR$^7$R$^8$)$_n$;

Z is absent or present and when present is selected from the group consisting of alkyl, haloalkyl, heteroalkyl, alkenyl, alkynyl, (CR$^{10}$R$^{11}$)$_o$NR$^9$(CR$^{12}$R$^{13}$)$_p$, (CR$^{10}$R$^{11}$)$_o$NR$^9$C(O) (CR$^{12}$R$^{13}$)$_p$, (CR$^{10}$R$^{11}$)$_o$C(O)NR$^9$(CR$^{12}$R$^{13}$)$_p$, (CR$^{10}$R$^{11}$)$_o$C(O)(CR$^{12}$R$^{13}$)$_p$, (CR$^{10}$R$^{11}$)$_o$C(O)O(CR$^{12}$R$^{13}$)$_p$, (CR$^{10}$R$^{11}$)$_o$OC(O)(CR$^{12}$R$^{13}$)$_p$, (CR$^{10}$R$^{11}$)$_o$OC(O)NR$^9$(CR$^{12}$R$^{13}$)$_p$, (CR$^{10}$R$^{11}$)$_o$NR$^9$C(O)O(CR$^{12}$R$^{13}$)$_p$, (CR$^{10}$R$^{11}$)$_o$NR$^9$C(O) NR$^9$(CR$^{12}$R$^{13}$)$_p$, (CR$^{10}$R$^{11}$)$_o$O(CR$^{12}$R$^{13}$)$_p$, (CR$^{10}$R$^{11}$)$_o$ S(O)$_n$(CR$^{12}$R$^{13}$)$_p$ and cycloalkyl;

J is absent or present and when present is selected from alkyl, haloalkyl, C(O)NR$^1$, NR$^1$C(O), NR$^7$, NR$^7$R$^8$, C(CR$^7$R$^8$)$_n$NR$^1$ or NR$^1$C(CR$^7$R$^8$)$_n$;

W is absent or present and when present is selected from the group consisting of alkyl, haloalkyl, heteroalkyl, alkenyl, alkynyl, OR$^9$, O, NR$^9$R$^{10}$, NR$^9$, CR$^9$, CR$^9$R$^{10}$, C(O)R$^9$, C(O)NR$^9$, NR$^9$C(O), C(O)NR$^9$R$^{10}$, NR$^9$R$^{10}$C(O), C(O) OR$^9$, OC(O)R$^9$ and heterocycloalkyl;

Q is absent or present and when present is selected from O, S, NR$^1$, CR$^1$, (CR$^{14}$R$^{15}$)$_t$ or C(O);

ring

—(Cy)— is selected from the group consisting of monocyclic aryl, multicyclic aryl, monocyclic heteroaryl, multicyclic heteroaryl, monocyclic carbocyclic, multicyclic carbocyclic, monocyclic heterocyclic, and multicyclic heterocyclic ring systems;

ring

—(Cy$^2$)— is selected from the group consisting of monocyclic aryl, multicyclic aryl, monocyclic heteroaryl, multicyclic heteroaryl, monocyclic carbocyclic, multicyclic carbocyclic, monocyclic heterocyclic, and multicyclic heterocyclic ring systems;

the bond between Q and X is a single or double bond;

R$^1$ is selected from hydrogen, alkyl, cycloalkyl, haloalkyl, heteroalkyl, heterohaloalkyl or heteroalkynyl;

R$^2$ is selected from hydrogen, deuterium, halogen, CN, alkyl, cycloalkyl, haloalkyl, heteroalkyl, aryl, heteroaryl, heterohaloalkyl or heteroalkynyl;

R$^3$ is independently selected from the group consisting of: hydrogen, deuterium, halogen, CN, alkyl, haloalkyl, heteroalkyl, alkenyl, alkynyl, aryl, arylalkyl, cycloalkyl, heteroaryl, heteroarylalkyl, heterocycloalkyl and C(O);

R$^4$ is independently selected from the group consisting of: hydrogen, deuterium, halogen, hydroxyl, CN, alkyl, haloalkyl, heteroalkyl, alkenyl, alkynyl, aryl, arylalkyl, arylalkenyl, arylalkynyl, cycloalkyl, heteroaryl, heteroarylalkyl, heteroarylalkenyl, heteroarylalkynyl and heterocycloalkyl;

R⁵ is selected from hydrogen, simple alkyl or a prodrug moiety. Said prodrug moiety may be selected from $C(O)R^{14}$ or $CR^{15}R^{16}OC(O)R^{14}$;

R⁶ is selected from hydrogen, simple alkyl or a prodrug moiety. Said prodrug moiety may be selected from $C(O)R^{17}$ or $CR^{18}R^{19}OC(O)R^{17}$;

R⁷ is independently selected from hydrogen, deuterium, halogen, simple alkyl or haloalkyl;

R⁸ is independently selected from hydrogen, deuterium, halogen, simple alkyl or haloalkyl;

R⁹ is independently selected from hydrogen, deuterium, halogen, simple alkyl or alkynyl;

R¹⁰ is independently selected from hydrogen, deuterium, halogen or simple alkyl;

R¹¹ is independently selected from hydrogen, deuterium, halogen or simple alkyl;

R¹² is independently selected from hydrogen, deuterium or simple alkyl;

R¹³ is independently selected from hydrogen, deuterium or simple alkyl;

R¹⁴ is a straight chain or branched alkyl group of 3 to 28 carbons, heterocycloalkyl, cycloalkyl, monocyclic aryl, multicyclic aryl, monocyclic heteroaryl, multicyclic heteroaryl, simple alkyl, haloalkyl or heteralkyl;

R¹⁵ is independently selected from hydrogen, deuterium, halogen or simple alkyl;

R¹⁶ is independently selected from hydrogen, deuterium, halogen or simple alkyl;

R¹⁷ is a straight chain or branched alkyl group of 3 to 28 carbons, heterocycloalkyl, cycloalkyl, monocyclic aryl, multicyclic aryl, monocyclic heteroaryl or multicyclic heteroaryl;

R¹⁸ is independently selected from hydrogen, deuterium, halogen or simple alkyl;

R¹⁹ is independently selected from hydrogen, deuterium, halogen or simple alkyl;

R²⁰ is independently selected from the group consisting of: hydrogen, deuterium, halogen, CN, C(O), alkyl, haloalkyl, heteroalkyl, alkenyl, alkynyl, aryl, arylalkyl, cycloalkyl, heteroaryl, heteroarylalkyl and heterocycloalkyl;

n is 0 or more;
m is 0 or more;
o is 0, 1, 2, or 3;
p is 0, 1, 2, or 3;
t is 0, 1, or 2;
u is 0, 1, or 2; and
k is 0, 1, or 2.

Preferred compounds of Formula (VII) include the following structures:

| Example | Structure | Compound name |
|---|---|---|
| 4 | 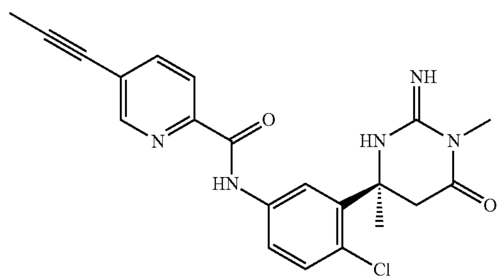 [SMILES: CC#Cc1ccc(C(=O)Nc2ccc(Cl)c([C@]3(C)CC(=O)N(C)C(=N)N3)c2)nc1] | (S)-N-(4-Chloro-3-(2-imino-1,4-dimethyl-6-oxohexahydropyrimidin-4-yl)phenyl)-5-(prop-1-yn-1-yl)picolinamide |
| 5 | 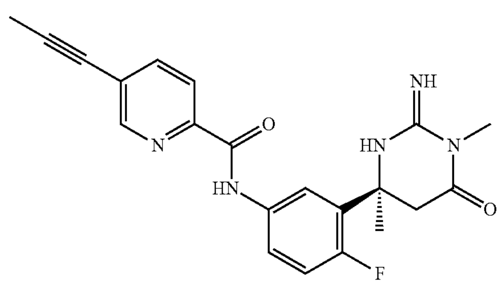 [SMILES: CC#Cc1ccc(C(=O)Nc2ccc(F)c([C@]3(C)CC(=O)N(C)C(=N)N3)c2)nc1] | (S)-N-(4-Fluoro-3-(2-imino-1,4-dimethyl-6-oxohexahydropyrimidin-4-yl)phenyl)-5-(prop-1-yn-1-yl)picolinamide |
| 219 | 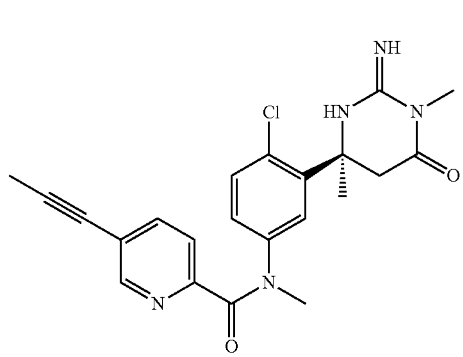 [SMILES: CC#Cc1ccc(C(=O)N(C)c2ccc(Cl)c([C@]3(C)CC(=O)N(C)C(=N)N3)c2)nc1] | (S)-N-(4-Chloro-3-(2-imino-1,4-dimethyl-6-oxohexahydropyrimidin-4-yl)phenyl)-N-methyl-5-(prop-1-yn-1-yl)picolinamide |

-continued

| Example | Structure | Compound name |
|---|---|---|
| 220 | 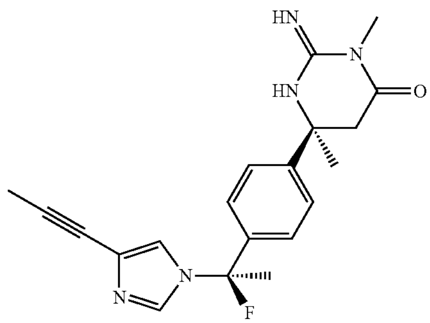 [SMILES: CC#Cc1cn([C@](C)(F)c2ccc([C@]3(C)CC(=O)N(C)C(=N)N3)cc2)cn1] | (S)-6-(4-((R)-1-Fluoro-1-(4-(prop-1-yn-1-yl)-1H-imidazol-1-yl)ethyl)phenyl)-2-imino-3,6-dimethyltetrahydropyrimidin-4(1H)-one |
| 221 | 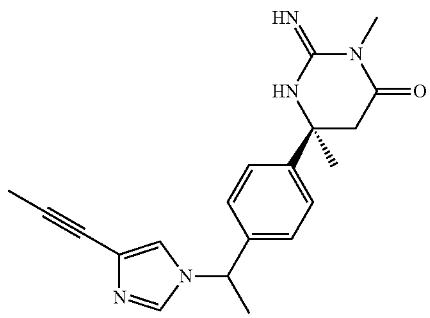 [SMILES: CC#Cc1cn(C(C)c2ccc([C@]3(C)CC(=O)N(C)C(=N)N3)cc2)cn1] | (6S)-2-Imino-3,6-dimethyl-6-(4-(1-(4-(prop-1-yn-1-yl)-1H-imidazol-1-yl)ethyl)phenyl)tetrahydropyrimidin-4(1H)-one |
| 222 | 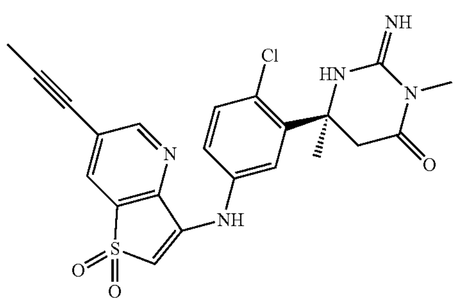 [SMILES: CC#Cc1cnc2c(c1)S(=O)(=O)C=C2Nc1ccc(Cl)c([C@]2(C)CC(=O)N(C)C(=N)N2)c1] | (S)-6-(2-Chloro-5-((1,1-dioxido-6-(prop-1-yn-1-yl)thieno[3,2-b]pyridin-3-yl)amino)phenyl)-2-imino-3,6-dimethyltetrahydropyrimidin-4(1H)-one |
| 223 | 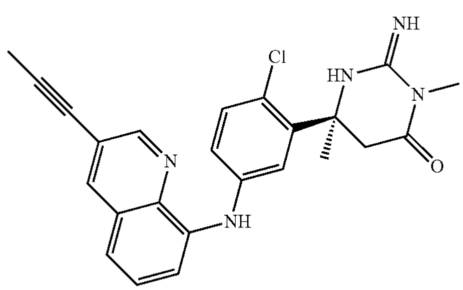 [SMILES: CC#Cc1cnc2c(Nc3ccc(Cl)c([C@]4(C)CC(=O)N(C)C(=N)N4)c3)cccc2c1] | (S)-6-(2-Chloro-5-((3-(prop-1-yn-1-yl)quinolin-8-yl)amino)phenyl)-2-imino-3,6-dimethyltetrahydropyrimidin-4(1H)-one |
| 224 | 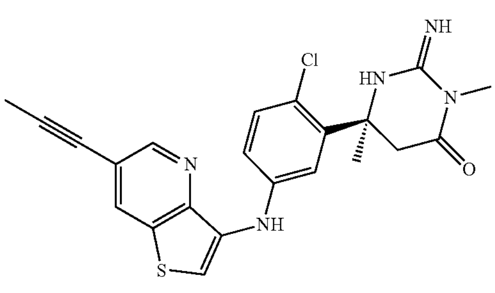 [SMILES: CC#Cc1cnc2c(Nc3ccc(Cl)c([C@]4(C)CC(=O)N(C)C(=N)N4)c3)csc2c1] | (S)-6-(2-Chloro-5-((6-prop-1-yn-1-yl)thieno[3,2-b]pyridin-3-yl)amino)phenyl)-2-imino-3,6-dimethyltetrahydropyrimidin-4(1H)-one |

-continued

| Example | Structure | Compound name |
|---|---|---|
| 225 | 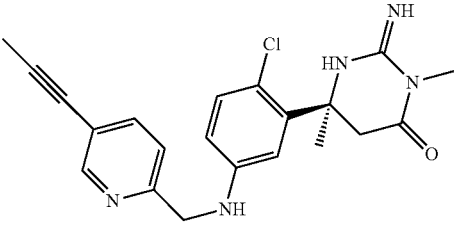 [SMILES: CC#Cc1ccc(CNc2ccc(Cl)c([C@]3(C)CC(=O)N(C)C(=N)N3)c2)nc1] | (S)-6-(2-Chloro-5-(((5-(prop-1-yn-1-yl)pyridin-2-yl)methyl)amino)phenyl)-2-imino-3,6-dimethyltetrahydropyrimidin-4(1H)-one |
| 226 | 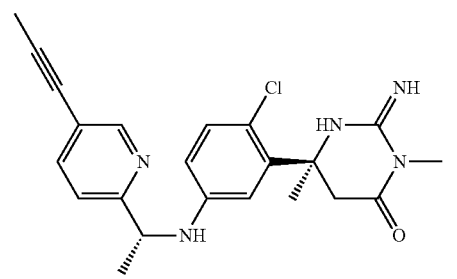 [SMILES: CC#Cc1ccc([C@@H](C)Nc2ccc(Cl)c([C@]3(C)CC(=O)N(C)C(=N)N3)c2)nc1] | (S)-6-(2-Chloro-5-(((R)-1-(5-prop-1-yn-1-yl)pyridin-2-yl)ethyl)amino)phenyl)-2-imino-3,6-dimethyltetrahydropyrimidin-4(1H)-one |
| 227 | 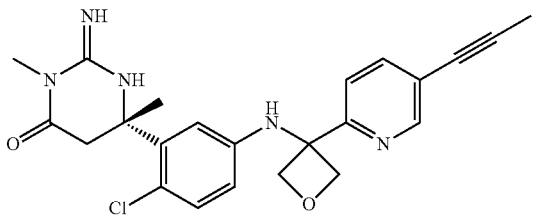 [SMILES: CC#Cc1ccc(C2(Nc3ccc(Cl)c([C@]4(C)CC(=O)N(C)C(=N)N4)c3)COC2)nc1] | (S)-6-(2-Chloro-5-((3-(5-(prop-1-yn-1-yl)pyridin-2-yl)oxetan-3-yl)amino)phenyl)-2-imino-3,6-dimethyltetrahydropyrimidin-4(1H)-one |
| 228 | 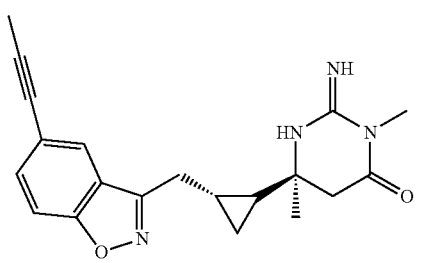 [SMILES: CC#Cc1ccc2onc(C[C@H]3CC3[C@]3(C)CC(=O)N(C)C(=N)N3)c2c1] | (S)-2-Imino-3,6-dimethyl-6-((1R,2R)-2-((5-(prop-1-yn-1-yl)benzo[d]isoxazol-3-yl)methyl)cyclopropyl)tetrahydropyrimidin-4(1H)-one |
| 229 | 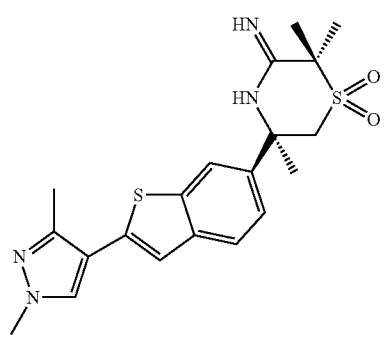 | (R)-5-(2-(1,3-Dimethyl-1H-pyrazol-4-yl)benzo[b]thiophen-6-yl)-3-imino-2,2,5-trimethylthiomorpholine 1,1-dioxide |

| Example | Structure | Compound name |
|---|---|---|
| 230 | 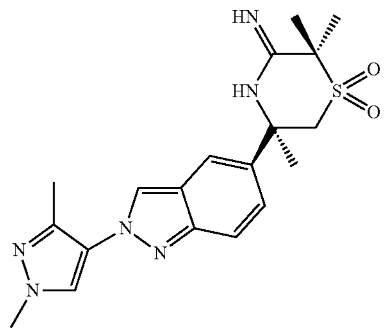 | (R)-5-(2-(1,3-Dimethyl-1H-pyrazol-4-yl)-2H-indazol-5-yl)-3-imino-2,2,5-trimethylthiomorpholine 1,1-dioxide |
| 231 | 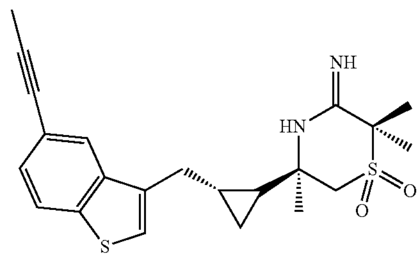 | R)-3-Imino-2,2,5-trimethyl-5-((1R,2R)-2-((5-(prop-1-yn-1-yl)benzo[b]thiophen-3-yl)methyl)cyclopropyl)thiomorpholine 1,1-dioxide |
| 232 | 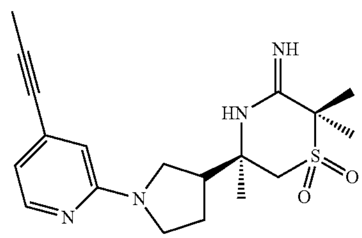 | (R)-3-Imino-2,2,5-trimethyl-5-((R)-1-(4-(prop-1-yn-1-yl)pyridin-2-yl)pyrrolidin-3-yl)thiomorpholine 1,1-dioxide |
| 233 | 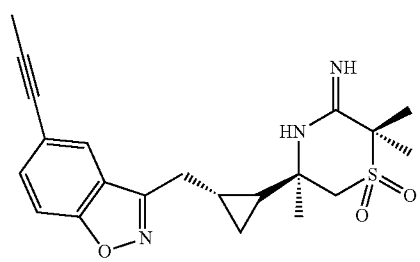 | (R)-3-Imino-2,2,5-trimethyl-5-((1R,2R)-2-((5-(prop-1-yn-1-yl)benzo[d]isoxazol-3-yl)methyl)cyclopropyl)thiomorpholine 1,1-dioxide |
| 234 | 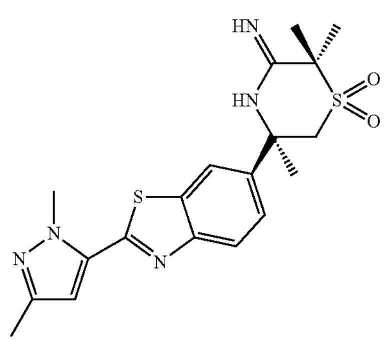 | (R)-5-(2-(1,3-Dimethyl-1H-pyrazol-5-yl)benzo[d]thiazol-6-yl)-3-imino-2,2,5-trimethylthiomorpholine 1,1-dioxide |

-continued

| Example | Structure | Compound name |
|---|---|---|
| 235 | 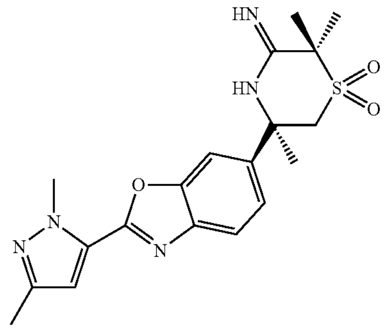 | (R)-5-(2-(1,3-Dimethyl-1H-pyrazol-5-yl)benzo[d]oxazol-6-yl)-3-imino-2,2,5-trimethylthiomorpholine 1,1-dioxide |
| 236 | 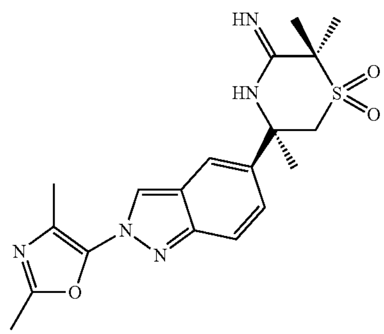 | (R)-5-(2-(2,4-Dimethyloxazol-5-yl)-2H-indazol-5-yl)-3-imino-2,2,5-trimethylthiomorpholine 1,1-dioxide |
| 237 | 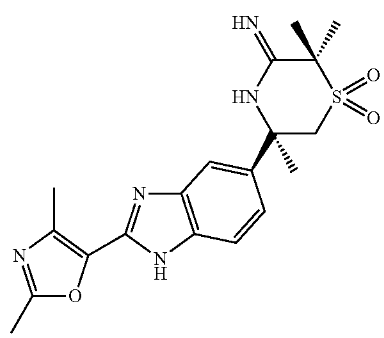 | (R)-5-(2-(2,4-Dimethyloxazol-5-yl)-1H-benzo[d]imidazol-5-yl)-3-imino-2,2,5-trimethylthiomorpholine 1,1-dioxide |
| 238 | 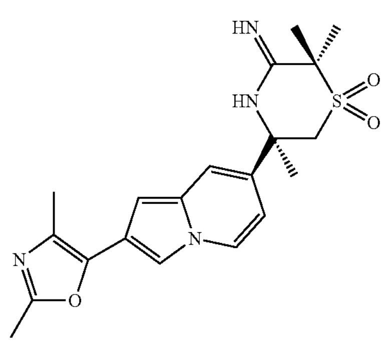 | (R)-5-(2-(2,4-Dimethyloxazol-5-yl)indolizin-7-yl)-3-imino-2,2,5-trimethylthiomorpholine 1,1-dioxide |

| Example | Structure | Compound name |
|---|---|---|
| 239 | 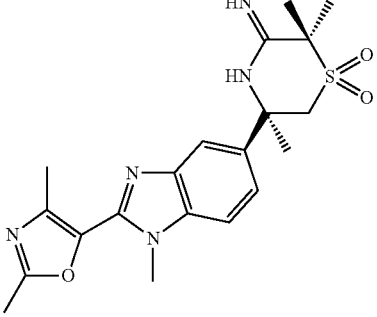 | (R)-5-(2(2,4-Dimethyloxazol-5-yl)-1-methyl-1H-benzo[d]imidazol-5-yl)-3-imino-2,2,5-trimethylthiomorpholine 1,1-dioxide |

The compounds of Formula (I) are useful as beta-secretase 1 (BACE1) inhibitors. As such compounds of Formula (I) will be useful for treating diseases related to aberrant activity of the BACE1 enzyme, for example Down's Syndrome; β-amyloid angiopathy; disorders associated with cognitive impairment; Alzheimer's disease; memory loss; attention deficit symptoms associated with Alzheimer's disease; neurodegenerative diseases; pre-senile dementia; senile dementia; dementia associated with Parkinson's disease, Alzheimer's disease and/or Down's syndrome; age-related macular degeneration (AMD); glaucoma; olfactory function impairment; traumatic brain injury; progressive muscle diseases; Type II diabetes mellitus and cardiovascular diseases (stroke).

In some embodiments, the present invention relates to the use of compounds of Formula (I) as hereinbefore defined as well as to the salts thereof. Salts for use in pharmaceutical compositions will be pharmaceutically acceptable salts, but other salts may be useful in the production of the compounds of Formula (I).

As used herein, "pharmaceutically acceptable salts" refer to derivatives of the disclosed compounds wherein the parent compound is modified by making acid or base salts thereof.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric acid.

In some embodiments, the present invention also includes pharmaceutical compositions which contain, as the active ingredient, one or more of the compounds of the invention herein together with at least one pharmaceutically acceptable carrier, diluent or excipient.

In some embodiments, compounds of the present invention may be administered by oral, parenteral, buccal, vaginal, rectal, inhalation, insufflation, sublingual, intramuscular, subcutaneous, topical, intranasal, intraperitoneal, intrathoracic, intravenous, epidural, intrathecal, and intracerebroventricular routes and by injection into the intraocular, intravitreal, and/or joints.

The dosage will depend on the route of administration, the severity of the disease, age and weight of the patient and other factors normally considered by the attending physician, when determining the individual regimen and dosage level as the most appropriate for a particular patient.

In some embodiments, for preparing pharmaceutical compositions from the compounds of this invention, inert, pharmaceutically acceptable carriers can be either solid or liquid. Solid form preparations include powders, tablets, dispersible granules, capsules, cachets, and suppositories.

The term composition is intended to include the formulation of the active component or a pharmaceutically acceptable salt with a pharmaceutically acceptable carrier. For example this invention may be formulated by means known in the art into the form of, for example, tablets, capsules, aqueous or oily solutions, suspensions, emulsions, creams, ointments, gels, nasal sprays, suppositories, finely divided powders or aerosols or nebulizers for inhalation, and for parenteral use (including intravenous, intramuscular or infusion) sterile aqueous or oily solutions or suspensions or sterile emulsions.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. Liquid pharmaceutically administrable compositions can, for example, be prepared by dissolving, dispersing, etc., an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art The compounds of Formula (I) are useful as BACE1 inhibitors and shown to inhibit beta secretase (including BACE) activity in vitro. Inhibitors of β-secretase have been shown to be useful in blocking formation or aggregation of Aβ peptide and be useful for treating diseases related to aberrant activity of the BACE1 enzyme, for example Down's Syndrome; β-amyloid angiopathy; disorders associated with cognitive impairment; Alzheimer's disease; memory loss; attention deficit symptoms associated with Alzheimer's disease; neurodegenerative diseases; pre-senile dementia; senile dementia; dementia associated with Parkinson's disease, Alzheimer's disease and/or Down's syndrome; age-related macular degeneration (AMD); glaucoma; olfactory function impairment; traumatic brain injury; progressive muscle diseases; Type II diabetes mellitus and cardiovascular diseases (stroke).

Methods of Preparation

The present invention also describes processes for preparing the compounds of Formula (I). The compounds of Formula (I) according to the invention can be prepared analogously to conventional methods as understood by the person skilled in the art of synthetic organic chemistry. The synthetic chemistry schemes set forth below, illustrate how the compounds of the invention can be made.

The following examples are for illustrative purposes only and are not intended as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names, intermediate and reagent names were generated with Chem Bio Draw Ultra version 12.0.

In the Examples below, the following abbreviations are used:
"AcOH" refers to acetic acid
"Boc" refers to tert-butoxycarbonyl
"CuI" refers to copper iodide
"DI PEA" refers to diisopropylethylamine "DMA" refers to dimethylacetamide
"DMAP" refers to dimethylamino pyridine
"DMF" refers to dimethylformamide
"EDCI" refers to 1-[3-(dimethylamino)propyl]-3-ethylcarbodiimide hydrochloride
"HATU" refers to (1-[Bis(dimethylamino)methylene]-1H-1,2,3-triazolo[4,5-b]pyridinium 3-oxid hexafluorophosphate)
"HBTU" refers to (1H-benzotriazol-1-yloxy)(dimethylamino)-N,N-dimethyl-methaniminium hexafluorophosphate
"HPLC" refers to high pressure liquid chromatography
"LDA" refers to lithium diisopropylamide
"i-PrOH" refers to isopropyl alcohol
"KOAc" refers to potassium acetate
"MeOH" refers to methanol
"MeI" refers to methyl Iodide
"NMP" refers to N-methylpyrrolidinone
"Pd(PPh$_3$)$_4$" refers to tetrakis(triphenylphosphine)palladium (0)
"Pd$_2$(dba)$_3$" refers to tris(dibenzylideneacetone)dipalladium (0)
"PdCl$_2$(PPh$_3$)$_2$" refers to dichlorobis(triphenylphosphine) palladium
"SnBu$_3$" refers to tributylstannane
"TBAF" refers to tetrabutylammonium fluoride
"THF" refers to tetrahydrofuran
"TMS" refers to tetramethylsilane In general, characterization of the compounds is performed according to the following methods; NMR spectra are recorded on 300 or 600 MHz NMR spectrometers and are acquired at room temperature. Chemical shifts are given in ppm referenced either to internal TMS or to the solvent signal.

Usually the compounds of the invention are purified by low to medium pressure silica gel chromatography.

Certain compounds were prepared as follows:

Example 1-1

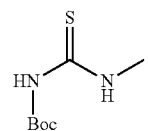

Example 1-1 t-Butyl N-[(methylamino)thioxomethyl]-carbamate (Example 1-1)

To a mixture of sodium hydride (60 wt % in mineral oil, 5.63 g, and 141.0 mmol) and anhydrous THF (300 ml), was added a solution of t-butyl carbamate (15.0 g, 128 mmol) and methyl isothiocyanate (7.38 ml, 109 mmol) in anhydrous THF (30 ml) dropwise at 0° C. Thereafter, the reaction mixture was slowly warmed to room temperature. The reaction mixture was then slowly quenched with water (10 ml) and the organic solvent was evaporated under reduced pressure and the residue was diluted with CH$_2$Cl$_2$. Then the reaction mixture was washed with saturated aqueous NaHCO$_3$ solution and extracted with CH$_2$Cl$_2$. The organic layer was washed with water, dried over anhydrous MgSO$_4$, concentrated in vacuo and purified by silica gel column chromatography to afford (Example 1-1) (15.0 g, 73%) as a white solid.

Example 1-2

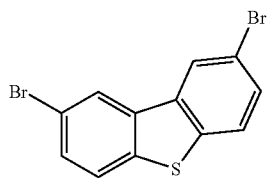 [SMILES: Brc1ccc2sc3ccc(Br)cc3c2c1]

Example 1-2

2,8-Dibromodibenzo[b,d]thiophene (Example 1-2)

To a mixture of dibenzo[b,d]thiophene (Example 1-1) (4 g, 21.73 mmol) and CH$_2$Cl$_2$ (100 mL) was added bromine (3.35 ml, 65.22 mmol) at 0° C. under nitrogen atmosphere. The reaction mixture was stirred at room temperature overnight. The organic layer was collected and concentrated in vacuo to yield a solid product. The product obtained was recrystallized using CH$_2$Cl$_2$ to afford the title compound (Example 1-2) as a white solid (6.34 g, 85.33%). $^1$H NMR (500 MHz, CDCl$_3$) δ 8.22 (d, J=2 Hz, 2H), 7.70 (d, J=8.5 Hz, 2H), 7.57 (dd, J=8.5, 2 Hz, 2H).

Example 1-3

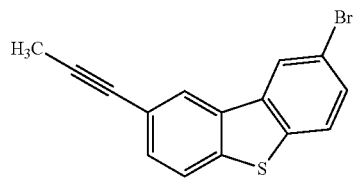 [SMILES: CC#Cc1ccc2sc3ccc(Br)cc3c2c1]

Example 1-3

2-Bromo-8-(prop-1-yn-1yl)dibenzo[b,d]thiophene (Example 1-3)

To a mixture of 2,8-dibromodibenzo[b,d]thiophene (Example 1-2) (4.00 g, 11.70 mmol), PPh$_3$ (0.03 g, 0.12 mmol), CuI (0.11 g, 0.58 mmol), PdCl$_2$(PPh$_3$)$_2$ (0.1 g, 0.12 mmol), and triethylamine (80 ml) was added to trimethyl(prop-1-yn-1-yl)silane (2 ml, 17.54 mmol) at room temperature. To the resultant mixture was added a solution of tetrabutylammonium fluoride (TBAF) (1M in THF, 26.5 ml) over 20 minutes. The mixture was stirred at 80° C. overnight. The reaction was quenched with water and extracted with CH$_2$Cl$_2$. The organic layer was collected and dried over anhydrous MgSO$_4$ and then concentrated in vacuo to yield the product as black oil. The product obtained was then purified by silica gel column chromatography (100% n-hexane Rf=0.45) to afford the title compound (Example 1-3) (1.27 g, 36.08%).

Example 1-4

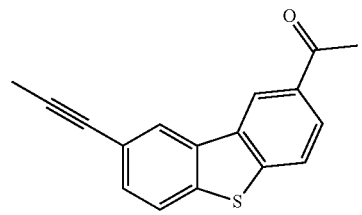 [SMILES: CC#Cc1ccc2sc3ccc(C(C)=O)cc3c2c1]

Example 1-4

1-(8-(Prop-1-yn-1yl)dibenzo[b,d]thiophen-2-yl)ethanone (Example 1-4)

To a mixture of 2-bromo-8-(prop-1-yn-1yl)dibenzo[b,d]thiophene (Example 1-3) (1.00 g, 3.32 mmol), Pd(PPh$_3$)$_4$ (0.38 g, 0.33 mmol) and N-methylpyrrolidinone (NMP) (4.00 ml) was added tributyl(1-ethoxyvinyl)tin (1.56 ml, 4.31 mmol) at room temperature. The mixture was stirred at 130° C. for 1 hour under nitrogen atmosphere. The reaction mixture was then quenched with 4N HCl (2.5 ml) and extracted with CH$_2$Cl$_2$. The organic layer was collected, dried over anhydrous MgSO$_4$ and concentrated in vacuo to get the product as black oil. The product obtained was then purified by silica gel column chromatography (ethyl acetate: n-hexane=1:15, Rf=0.3) to afford the title compound (Example 1-4) (0.71 g, 80.95%). $^1$H NMR (300 MHz, CDCl$_3$) δ 8.71 (s, 1H), 8.28 (s, 1H), 8.06 (d, J=8.4 Hz, 1H), 7.90 (d, J=8.4 Hz, 1H), 7.77 (d, J=8.1 Hz, 1H), 7.52 (d, J=8.4 Hz, 1H), 2.73 (d, J=2.1 Hz, 3H), 2.12 (d, J=2.4 Hz, 3H).

Example 1-5

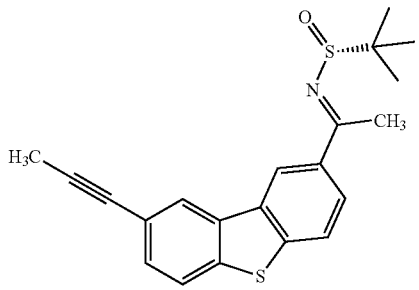 [SMILES: CC#Cc1ccc2sc3ccc(/C(C)=N/[S@](=O)C(C)(C)C)cc3c2c1]

Example 1-5

(R,E)-2-Methyl-N-(1-(8-(prop-1-yn-1-yl)dibenzo[b,d]thiophen-2-yl)ethylidene)pro pane-2-sulfinamide (Example 1-5)

A mixture of 1-(8(prop-1-yn-1yl)dibenzo[b,d]thiophen-2-yl)ethanone (Example 1-4) (2.6 g 9.85 mmol), (R)-2-methylpropane-2-sulfinamide (1.78 g, 14.77 mmol), Ti(OEt)$_4$ (4.5 ml, 19.70 mmol) and THF (80 ml) was refluxed overnight. The reaction was quenched with water and extracted with CH$_2$Cl$_2$. The precipitate was filtered off and the organic layer was collected, dried over anhydrous MgSO$_4$ and concentrated in vacuo to get the product as yellow oil. The yellow oil obtained was then purified by silica gel column chromatography (ethyl acetate: n-hexane=1:2, Rf=0.5) to afford the title compound (Example 1-5) (3.0 g, 83.10%). ¹H NMR (300 MHz, CDCl₃) δ 8.60 (d, J=1.5 Hz, 1H), 8.23 (d, J=1.5 Hz, 1H), 8.03 (dd, J=8.4, 1.8 Hz, 1H), 7.85 (dd, J=27.6, 8.1 Hz, 1H), 7.51 (dd, J=8.4, 1.5 Hz, 1H), 2.89 (s, 3H), 2.12 (s, 3H), 1.37 (s, 9H).

Example 1-6

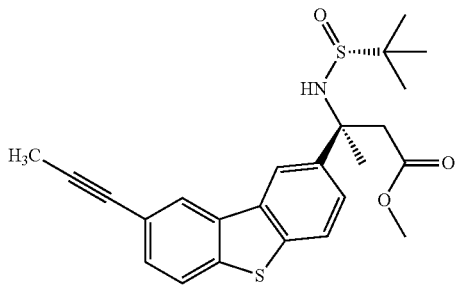 [SMILES: CC#Cc1ccc2sc3ccc([C@](C)(CC(=O)OC)N[S@](=O)C(C)(C)C)cc3c2c1]

Example 1-6

(S)-Methyl 3-((R)-1,1-dimethylethylsulfinamido)-3-(8-(prop-1-yn-1-yl) dibenzo[b,d]thiophen-2-yl)butanoate (Example 1-6)

To a solution of diisopropylamine (1.4 ml, 9.54 mmol) in THF (3 ml), cooled to −78° C. under an atmosphere of nitrogen was added n-BuLi (2.5 M in hexanes, 3.8 mL, 9.54 mmol). The mixture was stirred for 0.5 hour. After stirring, the solution was cooled to −78° C., and methyl acetate (0.8 ml, 9.34 mmol) was added. The resultant solution was further stirred at −78° C. for another 0.5 hour. To this solution was then added a solution of chlorotitanium triisopropoxide (4.95 g, 19.07 mmol) in THF (10 ml) and stirred for another 0.5 hour. The solution was then cooled to −78° C., and (R,E)-2-methyl-N-(1-(8-(prop-1-yn-1-yl)dibenzo[b,d]thiophen-2-yl)ethylidene)propane-2-sulfinamide (Example 1-5) (0.7 g, 1.91 mmol) in THF (3 ml) and the mixture was stirred for 1 hour. After 1 hour, the reaction was quenched with water and extracted with CH₂Cl₂. The precipitate was filtered off and the organic layer was collected, dried over anhydrous MgSO₄, concentrated in vacuo to yield yellow solid. The yellow product obtained was purified by silica gel column chromatography (ethyl acetate: n-hexane=1:2, Rf=0.25) to afford the title compound (Example 1-6) (0.45 g, 54.16%). ¹H NMR (500 MHz, CDCl₃) δ 8.14 (m, 2H), 7.77 (dd, J=22.5, 8.5 Hz, 2H), 7.54-7.46 (m, 2H), 5.60 (s, 1H), 3.62 (s, 3H), 3.18 (q, J=16.5 Hz, 2H), 2.11 (s, 3H), 1.85 (s, 3H), 1.34 (s, 9H).

Example 1-7

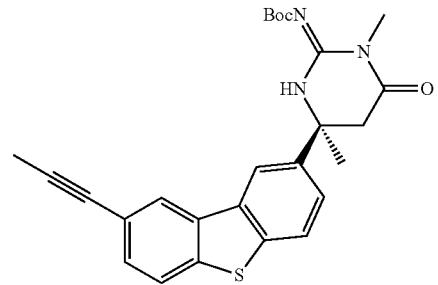

Example 1-7

(S)-Tert-butyl (1,4-dimethyl-6-oxo-4-(8-(prop-1-yn-1-yl)dibenzo[b,d]thiophen-2-yl)tetrahydropyrimidin-2(1H)-ylidene)carbamate (Example 1-7)

To mixture of (S)-methyl 3-((R)-1,1-dimethylethylsulfinamido)-3-(8-(prop-1-yn-1-yl) dibenzo[b,d]thiophen-2-yl) butanoate (Example 1-6) (1.3 g, 2.95 mmol) and MeOH (20 mL) was added hydrogen chloride (4N in dioxane, 1.47 mL, 5.9 mmol). The reaction mixture was stirred at room temperature for 1.5 hours and concentrated in vacuo to yield a colorless oil that was used directly in the next step.

To a solution of the above colorless oil in DMF (5 mL) was added diisopropylethylamine (DIPEA) (0.9 mL, 8.85 mmol), t-butyl-N-[(methylamino)thioxomethyl]carbamate (1.1 g, 5.9 mmol) and 1-[3-(dimethylamino)propyl]-3-ethylcarbodiimide HCl (0.91 g, 5.9 mmol). The resulting solution was stirred at 50° C. overnight. The reaction was quenched with water and extracted with CH₂Cl₂. The organic layer was collected and dried over anhydrous MgSO₄, concentrated in vacuo to yield a white solid. The white solid was purified by silica gel column chromatography (ethyl acetate: n-hexane=1:2, Rf=0.4) to afford the title compound (Example 1-7) (1.12 g, 82.35%). ¹H NMR (300 MHz, CDCl₃) δ 10.47 (s, 1H), 8.15 (d, J=1.5 Hz, 1H), 8.04 (d, J=2.1 Hz, 1H), 7.83 (d, J=8.7 Hz, 1H), 7.75 (d, J=8.4 Hz, 1H), 7.49-7.39 (m, 2H), 3.36 (d, J=16.2 Hz, 1H), 3.20 (s, 3H), 2.99 (d, J=16.2 Hz, 1H), 2.10 (s, 3H), 1.76 (s, 3H), 1.47 (s, 9H).

Example 1

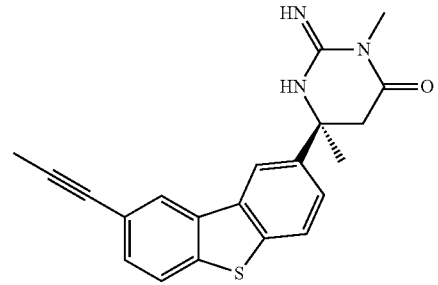 [SMILES: CC#Cc1ccc2sc3ccc([C@]4(C)CC(=O)N(C)C(=N)N4)cc3c2c1]

Example 1

(S)-2-Imino-3,6-dimethyl-6-(8-(prop-1-yn-1-yl)dibenzo[b,d]thiophen-2-yl)tetrahydropyrimidin-4(1H)-one (Example 1)

To a mixture of (S)-tert-Butyl (1,4-dimethyl-6-oxo-4-(8-(prop-1-yn-1-yl)dibenzo[b,d]thiophen-2-yl)tetrahydropyrimidin-2(1H)-ylidene)carbamate (Example 1-7) (0.8 g, 1.74 mmol) and $CH_2Cl_2$ (8 ml) was added trifluoroacetic acid (2 ml). The reaction mixture was stirred at room temperature for 2 hours, concentrated in vacuo and purified by silica gel column chromatography (MeOH: $CH_2Cl_2$=1:30, Rf=0.2) to afford the title compound (Example 1) TFA salt (0.55 g, 66.5%). $^1$H NMR (300 MHz, MeOD) δ ppm 8.25 (m, 2H), 7.93 (d, J=8.7 Hz, 1H), 7.81 (d, J=8.7 Hz, 1H), 7.55-7.44 (m, 2H), 3.64 (d, J=16.5 Hz, 1H), 3.22 (d, J=16.5 Hz, 1H), 3.16 (s, 3H), 2.07 (s, 3H), 1.80 (s, 3H). Analytical data mass m/z (ESI) 362.129 (M+H)$^+$.

Example 2-1

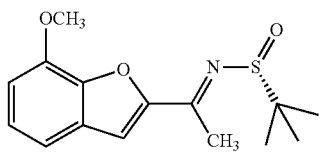 [SMILES: COc1cccc2cc(/C(C)=N/[S@](=O)C(C)(C)C)oc12]

Example 2-1

(R,E)-N-(1-(7-Methoxybenzofuran-2-yl)ethylidene)-2-methylpropane-2-sulfinamide (Example 2-1)

To a solution of 2-acetyl-7-methoxybenzofuran (2.0 g, 10.5 mmol) in anhydrous THF (20 ml) was added (R)-2-methylpropane-2-sulfinamide (1.34 g, 11.1 mmol) and titanium (IV) ethoxide (2.1 g, 11.5 mmol). The reaction mixture was heated to 50° C. for 17 hours. The reaction mixture was allowed to cool to room temperature and poured onto ice. The resultant mixture was filtered through a pad of celite and the filter pad was washed with $CH_2Cl_2$. The organic layer was separated and the aqueous layer was extracted with $CH_2Cl_2$ (2×). The combined organic layers were dried over $MgSO_4$, filtered and concentrated. The crude product was purified by silica gel column chromatography ($CH_2Cl_2$) to afford the title compound (1.55 g, 50% yield).

Example 2-2

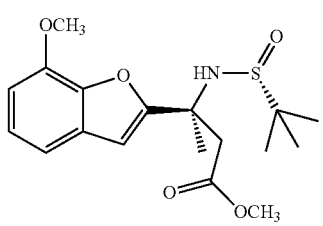 [SMILES: COC(=O)C[C@](C)(N[S@](=O)C(C)(C)C)c1cc2cccc(OC)c2o1]

Example 2-2

Methyl (S)-3-(((R)-tert-butylsulfinyl)amino)-3-(7-methoxybenzofuran-2-yl) butanoate (Example 2-2)

A solution of LDA (12 ml) in anhydrous THF (15 ml) under an atmosphere of nitrogen the solution was cooled to −78° C. To the cooled solution of LDA a solution of methyl acetate (1.8 g, 24.4 mmol) in THF (10 ml) was added slowly. The resulting solution was stirred at −78° C. for 45 minutes. The reaction mixture was then treated with a solution of chlorotitanium triisopropoxide (8.35 g, 41.4 mmol) in THF (10 ml) and the reaction mixture was stirred for 30 minutes. The reaction mixture was treated dropwise with a solution of (R,E)-N-(1-(7-methoxybenzofuran-2-yl)ethylidene)-2-methylpropane-2-sulfinamide (Example 2-1) (1.2 g, 4.1 mmol) in THF (10 ml). After stirring for 1 hour, saturated aqueous $NH_4Cl$ solution was added and the reaction mixture was warmed to room temperature. The solids were removed via filtration and the aqueous layer was extracted with ethyl acetate (3×). The combined organic extracts were washed with brine, dried over $MgSO_4$, filtered and concentrated. The crude product was purified by silica gel column chromatography (gradient elution 3:1 to 1:1 hexanes:ethyl acetate). The product containing eluent was concentrated to afford the title compound (1.02 g, 68%) as a light tan oil.

Example 2-3

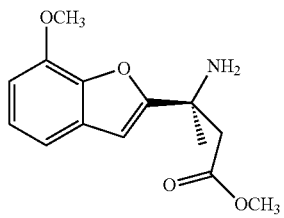 [SMILES: COC(=O)C[C@](C)(N)c1cc2cccc(OC)c2o1]

Example 2-3

Methyl (S)-3-amino-3-(7-methoxybenzofuran-2-yl)butanoate (Example 2-3)

A solution of methyl (S)-3-(((R)-tert-butylsulfinyl)amino)-3-(7-methoxybenzofuran-2-yl)butanoate (Example 2-2) (0.92 g, 25 mmol) in $CH_2Cl_2$ (15 mL) and MeOH (4 ml) was cooled to 0-10° C. The resulting solution was treated with hydrogen chloride (4N in dioxane, 3.13 mL). The resultant solution was stirred at 0-10° C. for 30 minutes and then concentration to dryness. The residue was treated with $CH_2Cl_2$ (20 ml) extracted twice with water. The combined aqueous extracts were adjusted to pH=7 and extracted with $CH_2Cl_2$ (2×). The combined organic extracts were dried over $MgSO_4$, filtered and concentrated to afford the title compound (0.62 g, 94% yield).

Example 2-4

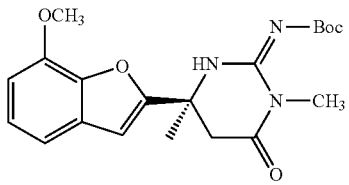 [SMILES: COc1cccc2cc([C@]3(C)CC(=O)N(C)/C(=N\C(=O)OC(C)(C)C)N3)oc12]

Example 2-4

Tert-butyl(S,Z)-(4-(7-methoxybenzofuran-2-yl)-1,4-dimethyl-6-oxotetrahydropyrimidin-2(1H)-ylidene)carbamate (Example 2-4)

Methyl (S)-3-amino-3-(7-methoxybenzofuran-2-yl)butanoate (Example 2-3) (0.6 g, 2.28 mmol) was dissolved in DMF (10 ml). To the resulting solution was added EDCI (0.66 g, 3.41 mmol), diisopropylethylamine (1.33 g, 10.3 mmol) and N-[(methylamino)thioxomethyl]-t-butylcarbamate (Example 1-1) (0.52 g, 2.73 mmol). The reaction mixture was stirred at room temperature for 17 hours. The reaction mixture was then treated with water (30 ml) and extracted with ethyl acetate (3×). The combined organic extracts were washed with water and brine, dried over MgSO$_4$, filtered and concentrated. The crude product was purified via silica gel column chromatography (gradient elution 6:1 to 2:1 hexane:ethyl acetate) to afford the title compound (Example 2-4) (0.81 g, 92% yield) as an off-white powdery solid.

Example 2

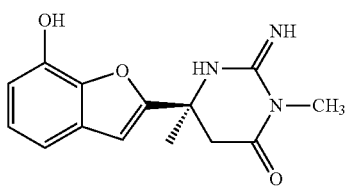 [SMILES: CN1C(=N)N[C@](C)(c2cc3cccc(O)c3o2)CC1=O]

Example 2

(S)-6-(7-Hydroxybenzofuran-2-yl)-2-imino-3,6-dimethyltetrahydropyrimidin-4(1H)-one (Example 2)

A solution of tert-butyl (S,Z)-(4-(7-methoxybenzofuran-2-yl)-1,4-dimethyl-6-oxotetrahydropyrimidin-2(1H)-ylidene)carbamate (Example 2-4) (0.43 g, 1.1 mmol) in CH$_2$Cl$_2$ (10 ml) was cooled to 0-10° C. The cooled solution was treated with BBr$_3$ (1.39 g, 5.55 mmol) slowly. The resulting solution was stirred at 0~10° C. for two hours and then treated with saturated aqueous NaHCO$_3$ solution and the mixture was warmed to room temperature. The aqueous layer was collected and extracted with CH$_2$Cl$_2$ (2×). The combined organic extracts were dried over MgSO$_4$, filtered and concentrated to afford the title compound (0.26 g, 86.0%) as a powdery off-white solid.

Example 3

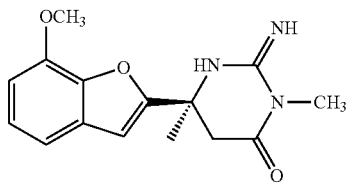 [SMILES: COc1cccc2cc([C@]3(C)CC(=O)N(C)C(=N)N3)oc12]

Example 3

(S)-2-Imino-6-(7-methoxybenzofuran-2-yl)-3,6-dimethyltetrahydropyrimidin-4(1H)-one (Example 3)

A solution of tert-butyl (S,Z)-(4-(7-methoxybenzofuran-2-yl)-1,4-dimethyl-6-oxotetrahydropyrimidin-2(1H)-ylidene)carbamate (Example 2-4) (60 mg, 0.15 mmol) in CH$_2$Cl$_2$ (2 ml) was cooled to 0-10° C. The cooled solution was treated slowly with BBr$_3$ (46.5 mg, 0.19 mmol). The resulting solution was stirred at 0~10° C. for 10 min and then treated with saturated aqueous NaHCO$_3$ solution. The reaction mixture was warmed to room temperature. The aqueous layer was collected and extracted with CH$_2$Cl$_2$ (2×). The combined organic extracts were dried over MgSO$_4$, filtered and concentrated to afford the title compound (example 3) as a powdery off white solid (40 mg, 90% yield).

Example 4-1

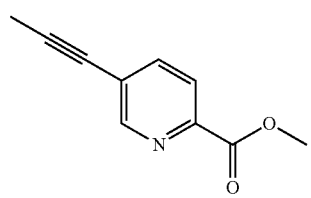

Example 4-1

Methyl 5-(prop-1-yn-1-yl)picolinate (Example 4-1)

To a mixture of methyl 5-bromopicolinate (0.5 g, 2.31 mmol), CuI (0.18 g, 0.69 mmol), Pd(PPh$_3$)$_4$(0.27 g, 0.23 mmol) and trimethylamine (10 ml) was added trimethyl(prop-1-yn-1-yl)silane (0.4 ml, 3.47 mmol) at room temperature. To the resultant mixture was added a solution of tetrabutylammonium fluoride (TBAF) (1M in THF, 4.29 ml) over 20 minutes. The mixture was stirred at room temperature overnight. The reaction was quenched with water and extracted with CH$_2$Cl$_2$. The organic layer was collected, dried over anhydrous MgSO$_4$ and concentrated in vacuo to yield product as black oil. The product obtained was purified by silica gel column chromatography (ethyl acetate:n-hexane=1:2, Rf=0.4) to give the title compound (Example 4-1) (0.31 g, 75.61%).

Example 4-2

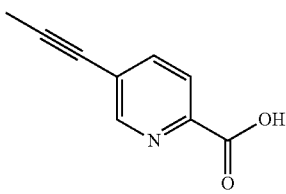

Example 4-2

5-(Prop-1-yn-1-yl)picolinic acid (Example 4-2)

A mixture of methyl 5-(prop-1-yn-1-yl)picolinate (Example 4-1) (1 g, 5.71 mmol), 4N LiOH (1.86 ml, 7.43 mmol) and dioxane (15 ml) was stirred for 3 hours at 40° C. The reaction was quenched with 4N HCl (3.8 ml, 14.86 mmol) and extracted with $CH_2Cl_2$. The organic layer was collected, dried over anhydrous $MgSO_4$ and concentrated in vacuo to yield the title compound (Example 4-2) as a colorless solid (0.45 g, 48.91%) that was used directly in the next step. $^1H$ NMR (300 MHz, MeOD) δ 8.59 (t, J=0.9 Hz, 1H), 8.07 (dd, J=8.1, 0.6 Hz, 1H), 7.91 (dd, J=8.1, 2.1 Hz, 1H), 2.09 (s, 3H).

Example 4-3

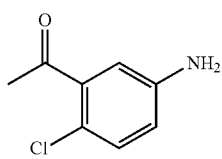

Example 4-3

1-(5-Amino-2-chlorophenyl)ethanone (Example 4-3)

A mixture of 1-(2-chloro-5-nitrophenyl)ethanone (0.5 g, 2.51 mmol), Fe powder (0.41 g, 7.53 mmol), $NH_4Cl$ (0.27 g, 5.02 mmol), iPrOH (20 ml) and $H_2O$ (5 ml) was refluxed for 3 hours. The insoluble precipitate was filtered off and the organic layer was extracted with $CH_2Cl_2$, dried over anhydrous $MgSO_4$ and concentrated in vacuo to yield the product as yellow oil. The yellow oil obtained was purified by silica gel column chromatography (ethyl acetate: n-hexane=1:2, Rf=0.3) to afford the title compound (Example 4-3) (0.35 g, 83.33%).

Example 4-4

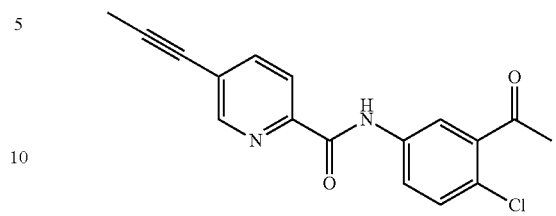

Example 4-4

N-(3-Acetyl-4-chlorophenyl)-5-(prop-1-yn-1-yl) picolinamide (Example 4-4)

To a mixture of 5-(prop-1-yn-1-yl)picolinic acid (Example 4-2) (0.4 g, 2.48 mmol), (1H-benzotriazol-1-yloxy)(dimethylamino)-N, N-dimethylmethaniminium hexafluorophosphate (HBTU) (1.88 g, 4.96 mmol), dimethyl amino pyridine (DMAP) (0.91 g, 7.44 mmol) and $CH_2Cl_2$ (15 ml) was added 1-(5-amino-2-chlorophenyl)ethanone (Example 4-3) (0.5 g, 2.98 mmol). The mixture was stirred at room temperature overnight. The reaction was quenched with water and extracted with $CH_2Cl_2$. The organic layer was collected, dried over anhydrous $MgSO_4$ and concentrated in vacuo to yield yellow solid as product. The yellow solid was then purified by silica gel column chromatography (ethyl acetate: n-hexane=1:2, Rf=0.65) to afford the title compound (Example 4-4) (0.67 g, 85.90%). $^1H$ NMR (500 MHz, $CDCl_3$) δ 10.00 (s, 1H), 8.57 (d, J=1.5 Hz, 1H), 8.18 (d, J=8 Hz, 1H), 7.92-7.84 (m, 3H), 7.41 (d, J=8.5 Hz, 1H), 2.66 (s, 3H), 2.11 (s, 3H).

Example 4-5

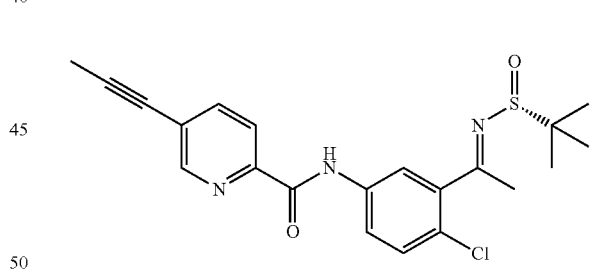

Example 4-5

(R,E)-N-(3-(1-((Tert-butylsulfinyl)imino)ethyl)-4-chlorophenyl)-5-(prop-1-yn-1-yl) picolinamide (Example 4-5)

A mixture of N-(3-acetyl-4-chlorophenyl)-5-(prop-1-yn-1-yl)picolinamide (Example 4-4) (0.62 g, 1.99 mmol), (R)-2-methylpropane-2-sulfinamide (0.48 g, 3.98 mmol), $Ti(OEt)_4$ (1.4 mL, 5.97 mmol) and THF (30 ml) was refluxed overnight. The reaction was quenched with water and extracted with $CH_2Cl_2$. The precipitate was filtered off and the organic layer was collected, dried over anhydrous $MgSO_4$ concentrated in vacuo to get product as yellow oil. The yellow oil obtained was purified by silica gel column

Example 4-6

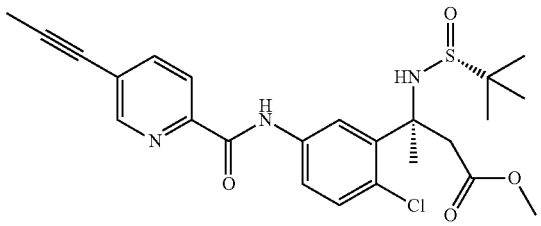 [SMILES: CC#Cc1ccc(C(=O)Nc2ccc(Cl)c([C@](C)(CC(=O)OC)N[S@](=O)C(C)(C)C)c2)nc1]

Example 4-6

Methyl (S)-3-(((R)-tert-butylsulfinyl)amino)-3-(2-chloro-5-(5-(prop-1-yn-1-yl)picolinamido)phenyl) butanoate (Example 4-6)

To a solution of diisopropylamine (0.95 mL, 9.40 mmol) in THF (5 ml) cooled to −78° C. under an atmosphere of nitrogen was added n-BuLi (2.5 M in hexanes, 3.8 ml, 9.54 mmol). The mixture was stirred for 0.5 hour. After stirring, the solution was cooled to −78° C., and methyl acetate (0.7 ml, 9.24 mmol) was added. The resultant solution was stirred at −78° C. for another 0.5 hour. To this solution was then added a solution of chlorotitanium triisopropoxide (4.88 g, 18.80 mmol) in THF (10 ml) and stirred for 0.5 hour. After stirring, the solution was cooled to −78° C., and (R,E)-N-(3-(1-((tert-butylsulfinyl)imino)ethyl)-4-chloro-phenyl)-5-(prop-1-yn-1-yl)picolinamide (Example 4-5) (0.65 g, 1.57 mmol) in THF (5 ml) and the mixture was stirred for 1 hour. The reaction was then quenched with water and extracted with CH$_2$Cl$_2$. The precipitate was filtered off and the organic layer was collected, dried over anhydrous MgSO$_4$ and concentrated in vacuo to yield a yellow solid. The yellow solid obtained was purified by silica gel column chromatography (ethyl acetate: n-hexane=1:1, Rf=0.25) to afford the title compound (Example 4-6) (0.4 g, 52.63%). $^1$H NMR (300 MHz, MeOD) δ 8.64 (t, J=1.2 Hz, 1H), 8.31 (t, J=2.1 Hz, 1H), 8.14 (m, 1H), 7.93 (dd, J=8.1, 2.1 Hz, 1H), 7.69-7.65 (m, 1H), 7.38 (d, J=8.7 Hz, 1H), 3.72 (dd, J=16.5, 2.1 Hz, 1H), 3.58 (s, 3H), 3.19 (d, J=16.5 Hz, 1H), 2.10 (s, 3H), 1.96 (s, 3H), 1.31 (d, J=0.9 Hz, 9H).

Example 4-7

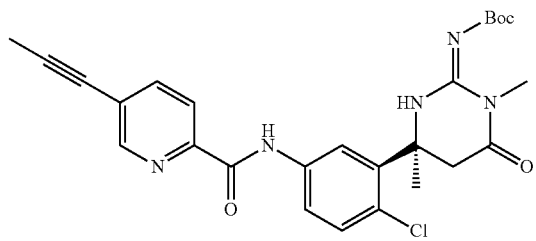

Example 4-7

(S,Z)-tert-Butyl (4-(2-chloro-5-(5-(prop-1-yn-1-yl) picolinamido)phenyl)-1,4-dimethyl-6-oxotetrahydropyrimidin-2(1H)-ylidene)carbamate (Example 4-7)

To a mixture of Methyl (S)-3-(((R)-tert-butylsulfinyl) amino)-3-(2-chloro-5-(5-(prop-1-yn-1-yl)picolinamido) phenyl)butanoate (Example 4-6) (0.35 g, 0.71 mmol) and MeOH (10 ml) was added hydrogen chloride (4N in dioxane, 0.4 ml, 1.43 mmol). The reaction mixture was stirred at room temperature for 1.5 hours and concentrated in vacuo to yield product as colorless oil that was used directly in the next step.

To a solution of the above material in DMF (5 ml) was added diisopropylethylamine (DIPEA) (0.21 ml, 2.13 mmol), t-butyl-N-[(methylamino)thioxomethyl]carbamate (Example 1-1) (0.2 g, 1.07 mmol) and 1-[3-(dimethylamino) propyl]-3-ethylcarbodiimide HCl (0.17 g, 1.07 mmol). The resulting solution was stirred at 50° C. overnight. The reaction was quenched with water and extracted with CH$_2$Cl$_2$. The organic layer was collected, dried over anhydrous MgSO$_4$ and concentrated in vacuo to yield yellow solid. The yellow product was purified by silica gel column chromatography (ethyl acetate: n-hexane=1:2, Rf=0.5) to afford the title compound (Example 4-7) (0.32 g, 88.89%).

Example 4

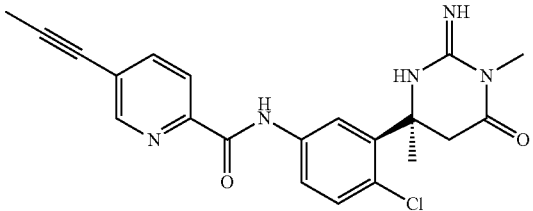

Example 4

(S)-N-(4-Chloro-3-(2-imino-1,4-dimethyl-6-oxotetrahydropyrimidin-4-yl)phenyl)-5-(prop-1-yn-1-yl) picolinamide (Example 4)

To a mixture of (S,Z)-tert-butyl (4-(2-chloro-5-(5-(prop-1-yn-1-yl)picolinamido)phenyl)-1,4-dimethyl-6-oxotetrahydropyrimidin-2(1H)-ylidene)carbamate (Example 4-7) (0.3 g, 0.59 mmol) and CH$_2$Cl$_2$ (4 ml) was added trifluoroacetic acid (TFA) (1 ml). The reaction mixture was stirred at room temperature for 2 hours, concentrated in vacuo and purified by silica gel column chromatography (MeOH: CH$_2$Cl$_2$=1:15, Rf=0.3) to afford the title compound (0.11 g, 45.83%). $^1$H NMR (300 MHz, MeOD) δ 8.64 (t, J=0.9 Hz, 1H), 8.14-8.11 (m, 2H), 7.94 (dd, J=8.1, 2.1 Hz, 1H), 7.70 (dd, J=8.7, 2.4 Hz, 1H), 7.48 (d, J=8.7 Hz, 1H), 3.91 (d, J=16.8 Hz, 2H), 3.19 (s, 3H), 2.10 (s, 3H), 1.90 (s, 3H).

Example 5-1

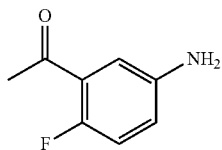

Example 5-1

1-(5-Amino-2-fluorophenyl) ethanone (Example 5-1)

A mixture of 1-(2-fluoro-5-nitrophenyl) ethanone (0.3 g, 1.64 mmol), Fe powder (0.27 g, 4.92 mmol), NH$_4$Cl (0.17 g, 3.28 mmol), iPrOH (12.8 ml) and H$_2$O (3.2 ml) was refluxed for 3 hours. The insoluble precipitate was filtered off and the organic layer was extracted with CH$_2$Cl$_2$, dried over anhydrous MgSO$_4$ and concentrated in vacuo to yield the product as yellow oil. The yellow oil obtained was purified by silica gel column chromatography (ethyl acetate: n-hexane=1:2, Rf=0.3) to afford the title compound (0.19 g, 76%).

Example 5-2

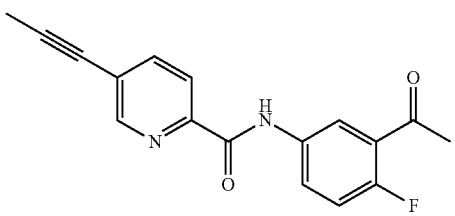 [SMILES: CC#Cc1ccc(C(=O)Nc2ccc(F)c(C(C)=O)c2)nc1]

Example 5-2

N-(3-Acetyl-4-fluorophenyl)-5-(prop-1-yn-1-yl)picolinamide (Example 5-2)

To a mixture of 5-(prop-1yn-1yl)picolinic acid (0.5 g, 3.11 mmol), HBTU (2.36 g, 6.22 mmol), dimethylamino pyridine (DMAP) (1.14 g, 9.33 mmol) and CH$_2$Cl$_2$ (15 ml) was added 1-(5-amino-2-fluorophenyl) ethanone (Example 5-1) (0.58 g, 3.73 mmol). The mixture was stirred at room temperature overnight. The reaction was quenched with water and extracted with CH$_2$Cl$_2$. The organic layer was collected, dried over anhydrous MgSO$_4$ and concentrated in vacuo to yield yellow solid as product. The yellow solid obtained was purified by silica gel column chromatography (ethyl acetate: n-hexane=1:2, Rf=0.65) to afford the title compound (Example 5-2) (0.77 g, 83.70%). $^1$H NMR (300 MHz, CDCl$_3$) δ 10.03 (s, 1H), 8.57 (t, J=1.2 Hz, 1H), 8.28-8.22 (m, 1H), 8.18 (dd, J=8.1, 0.9 Hz, 1H), 7.95 (dd, J=6, 3 Hz, 1H), 7.85 (dd, J=8.1, 2.1 Hz, 1H), 7.25-7.14 (m, 1H), 2.66 (d, J=4.8 Hz, 3H), 2.11 (s, 3H).

Example 5-3

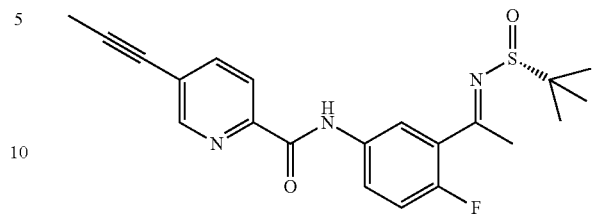

Example 5-3

(R,E)-N-(3-(1-((tert-butylsulfinyl)imino)ethyl)-4-fluorophenyl)-5-(prop-1-yn-1-yl)picolinamide (Example 5-3)

A mixture of N-(3-acetyl-4-fluorophenyl)-5-(prop-1-yn-1-yl)picolinamide (Example 5-2) (0.75 g, 2.53 mmol), (R)-2-methylpropane-2-sulfinamide (0.61 g, 5.06 mmol), Ti(OEt)$_4$ (1.73 ml, 7.59 mmol) and THF (40 ml) was refluxed overnight. The reaction was quenched with water and extracted with CH$_2$Cl$_2$. The precipitate was filtered off and the organic layer was collected, dried over anhydrous MgSO$_4$ and concentrated in vacuo to get yellow oil product. The product obtained was purified by silica gel column chromatography (ethyl acetate: n-hexane=1:2, Rf=0.5) to afford the title compound (Example 5-3) (0.82 g, 81.19%).

Example 5-4

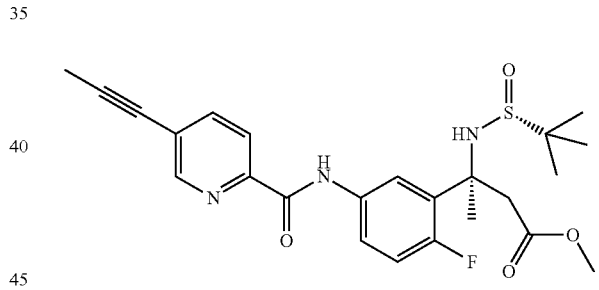

Example 5-4

Methyl (S)-3-(((R)-tert-butylsulfinyl)amino)-3-(2-fluoro-5-(5-(prop-1-yn-1-yl)picolinamido)phenyl)butanoate (Example 5-4)

To a solution of diisopropylamine (1.2 mL, 12.06 mmol) in THF (5 ml) cooled to −78° C. under an atmosphere of nitrogen was added n-BuLi (2.5 M in hexanes, 4.8 ml, 12.06 mmol). The mixture was stirred for 0.5 hour. After stirring, the solution was cooled to −78° C., and methyl acetate (0.9 ml, 11.83 mmol) was added. The resultant solution was further stirred at −78° C. for another 0.5 hour. To this solution was then added a solution of chlorotitanium triisopropoxide (6.26 g, 24.06 mmol) in THF (15 ml) and stirred for 0.5 hour. Then the solution was cooled to −78° C., and (R,E)-N-(3-(1-((tert-butylsulfinyl)imino)ethyl)-4-fluorophenyl)-5-(prop-1-yn-1-yl)picolinamide (Example 5-3) (0.8 g, 2.01 mmol) in THF (5 ml) and the mixture was stirred for 1 hour. The reaction was quenched with water and extracted with CH$_2$Cl$_2$. The precipitate was filtered off and the organic layer was collected, dried over anhydrous MgSO$_4$ and concentrated in vacuo to yield a yellow solid. The yellow solid obtained was purified by silica gel column chromatography (ethyl acetate: n-hexane=1:1, Rf=0.25) to afford the title compound (Example 5-4) (0.52 g, 54.74%).

Example 5-5

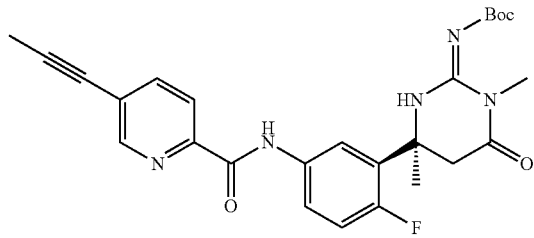

Example 5-5

(S,Z)-tert-Butyl (4-(2-fluoro-5-(5-(prop-1-yn-1-yl)picolinamido)phenyl)-1,4-dimethyl-6-oxotetrahydropyrimidin-2(1H)-ylidene)carbamate (Example 5-5)

To a mixture of Methyl (S)-3-(((R)-tert-butylsulfinyl)amino)-3-(2-fluoro-5-(5-(prop-1-yn-1-yl)picolinamido)phen yl)butanoate (Example 5-4) (0.5 g, 1.06 mmol) and MeOH (15 ml) was added hydrogen chloride (4N in dioxane, 0.53 ml, 2.12 mmol). The reaction mixture was stirred at room temperature for 1.5 hours then concentrated in vacuo to yield product as colorless oil that was used directly in the next step.

To a solution of the above material in DMF (5 ml) was added diisopropylethylamine (DIPEA) (0.32 ml, 3.18 mmol), t-butyl-N-[(methylamino)thioxomethyl]carbamate (Example 1-1) (0.4 g, 2.12 mmol) and 1-[3-(dimethylamino)propyl]-3-ethylcarbodiimide HCl (0.33 g, 2.12 mmol). The resulting solution was stirred at 50° C. overnight. The reaction was quenched with water and extracted with CH$_2$Cl$_2$. The organic layer was collected, dried over anhydrous MgSO$_4$ and concentrated in vacuo to yield a yellow solid. The yellow solid obtained was purified by silica gel chromatography (ethyl acetate: n-hexane=1:2, Rf=0.5) to afford the title compound (Example 5-5) (0.4 g, 76.92%).

Example 5

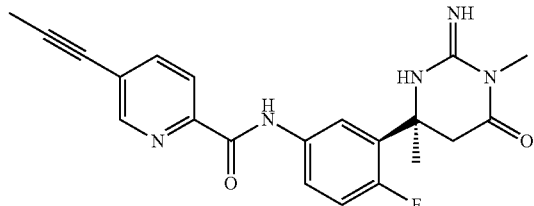

Example 5

(S)-N-(4-Fluoro-3-(2-imino-1,4-dimethyl-6-oxotetrahydropyrimidin-4-yl)phenyl)-5-(prop-1-yn-1-yl)picolinamide (Example 5)

To a mixture of (S,Z)-tert-butyl (4-(2-fluoro-5-(5-(prop-1-yn-1-yl)picolinamido)phenyl)-1,4-dimethyl-6-oxotetrahydropyrimidin-2(1H)-ylidene)carbamate (Example 5-5) (0.35 g, 0.71 mmol) and CH$_2$Cl$_2$ (4 ml) was added trifluoroacetic acid (TFA) (1 ml). The reaction mixture was stirred at room temperature for 2 hours, concentrated in vacuo and purified by silica gel column chromatography (MeOH: CH$_2$Cl$_2$=1:15, Rf=0.3) to afford the title compound (Example 5) (0.15 g, 53.57%). $^1$H NMR (300 MHz, MeOD) δ ppm 8.65 (t, J=1.2 Hz, 1H), 8.12 (dd, J=8.1, 0.9 Hz, 1H), 7.98-7.93 (m, 2H), 7.71-7.66 (m, 1H), 7.21 (dd, J=12, 9 Hz, 1H), 3.50 (d, J=16.5 Hz, 1H), 3.18 (m, 4H), 2.10 (s, 3H), 1.80 (s, 3H).

Example 14-1

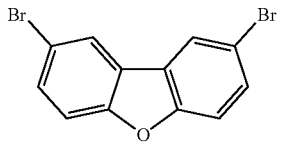 [SMILES: Brc1ccc2oc3ccc(Br)cc3c2c1]

Example 14-1

2,8-Dibenzo(b,d)furan (Example 14-1)

To a mixture of dibenzo(b,d)furan (4 g, 23.8 mmol) and CH$_2$Cl$_2$ (100 ml), was added bromine (3.66 ml, 71.4 mmol) at 00° C. under nitrogen atmosphere. The reaction mixture was stirred at room temperature overnight. The organic layer was collected and concentrated in vacuo to yield a solid product. The product obtained was recrystallized using CH$_2$Cl$_2$ to afford compound (Example 14-1) as a white solid (5.85 g, 75.7%).

Example 14-2

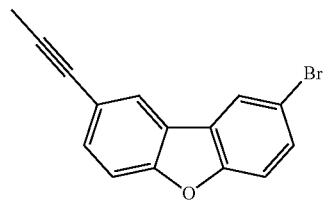 [SMILES: CC#Cc1ccc2oc3ccc(Br)cc3c2c1]

Example 14-2

2-Bromo-8-(prop-1-yn-1yl)dibenzo(b,d)furan (Example 14-2)

To a mixture of (Example 14-1) (4.00 g, 12.3 mmol), PPh$_3$(0.03 g, 0.12 mmol), CuI (0.47 g, 2.46 mmol), PdCl$_2$(PPh$_3$)$_2$ (0.1 g, 0.12 mmol), and triethylamine (80 ml was added trimethyl(prop-1-yn-1-yl)silane (2.1 ml, 18.5 mmol) at room temperature. To the resultant mixture was added a solution of tetrabutylammonium fluoride (TBAF) (1M in THF, 28.5 ml) over 20 minutes. The mixture was stirred at 80° C. overnight. The reaction was quenched with water and extracted with CH$_2$Cl$_2$. The organic layer was collected, dried over anhydrous MgSO$_4$ and concentrated in vacuo to yield the product as black oil. The product obtained was then purified by silica gel column chromatography (100% n-hexane Rf=0.45) to afford the title compound (Example 14-2) (1.05 g, 29.9%).

Example 14-3

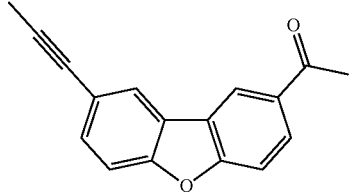 [SMILES: CC#Cc1ccc2oc3ccc(C(C)=O)cc3c2c1]

Example 14-3

1-(8(Prop-1-yn-1yl)dibenzo(b,d)furan-2-yl)ethanone (Example 14-3)

To a mixture of (Example 14-2) (1.00 g, 3.51 mmol), Pd (PPh$_3$)$_4$ (0.41 g, 0.35 mmol) and n-methylpyrrolidinone (NMP) (4.00 ml) was added tributyl (1-ethoxyvinyl) tin (1.52 mL, 4.21 mmol) at room temperature. The mixture was stirred at 130° C. for 1 hour under nitrogen atmosphere. The reaction mixture was then quenched with 4N HCl (2.50 ml) and extracted with CH$_2$Cl$_2$. The organic layer was collected, dried over anhydrous MgSO$_4$ and concentrated in vacuo to get the product as black oil. The product obtained was then purified by silica gel column chromatography (ethyl acetate: n-hexane=1:15, Rf=0.3) to afford the title compound (Example 14-3) (0.53 g, 60.92%).

Example 14-4

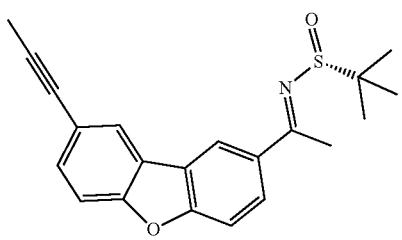 [SMILES: CC#Cc1ccc2oc3ccc(/C(C)=N/[S@](=O)C(C)(C)C)cc3c2c1]

Example 14-4

(R,E)-2-Methyl-N-(1-(8(prop-1-yn-1 yl)di benzo(b, d)furan-2-yl)ethylidene) propane-2-sulfonamide (Example 14-4)

A mixture of (Example 14-3) (0.75 g 3.02 mmol), (R)-2-methylpropane-2-sulfinamide (0.73 g, 6.04 mmol), Ti (OEt)$_4$ (2.1 ml, 9.06 mmol) and THF (80 ml) were refluxed overnight. The reaction was quenched with water and extracted with CH$_2$Cl$_2$. The precipitate was filtered off, the organic layer was collected, dried over anhydrous MgSO$_4$ and concentrated in vacuo to get the product as yellow oil. The product obtained was then purified by silica gel column chromatography (ethyl acetate: n-hexane=1:2, Rf=0.5) to afford the title compound (Example 14-4) (0.62 g, 58.5%).

Example 14-5

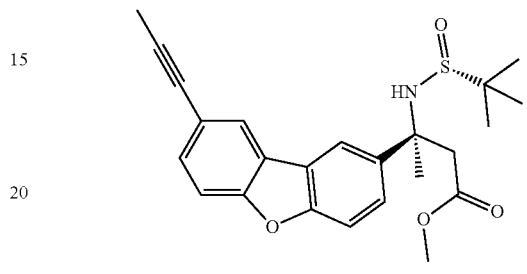

Example 14-5

(S)-Methyl 3-((R)-1,1-dimethylethylsulfinamido)-3-(8-(prop-1-yn-1-yl) dibenzo(b,d)furan-2-yl)butanoate (Example 14-5)

To a solution of diisopropylamine (1.5 mL, 13.7 mmol) in THF (3 ml), under nitrogen atmosphere at −78° C. was added n-BuLi (2.5 M in hexanes, 5.48 ml, 13.7 mmol). The mixture was stirred for 0.5 hour. After stirring, the solution was cooled to −78° C., and methyl acetate (1.1 ml, 13.7 mmol) was added. The resultant solution was further stirred at −78° C. for another 0.5 hour. To this solution was then added a solution of chlorotitanium triisopropoxide (4.74 g, 18.2 mmol) in THF (10 ml) and stirred for another 0.5 hour. The solution was then cooled to −78° C., and (Example 14-4) (0.8 g, 2.28 mmol) in THF (3 ml) was added and the mixture was stirred for 1 hour. After 1 hour, the reaction was quenched with water and extracted with CH$_2$Cl$_2$. The precipitate was filtered off, the organic layer was collected, dried over anhydrous MgSO$_4$ and concentrated in vacuo to yield yellow solid. The yellow product obtained was purified by silica gel column chromatography (ethyl acetate: n-hexane=1:2, Rf=0.25) to afford the title compound (Example 14-5) (0.45 g, 49.5%). $^1$H NMR (500 MHz, CDCl$_3$) δ 7.96 (s, 2H), 7.52-7.47 (m, 4H), 5.65 (s, 1H), 3.61 (s, 3H), 2.09 (s, 3H), 2.04 (s, 2H), 1.84 (s, 3H), 1.34 (s, 9H).

Example 14-6

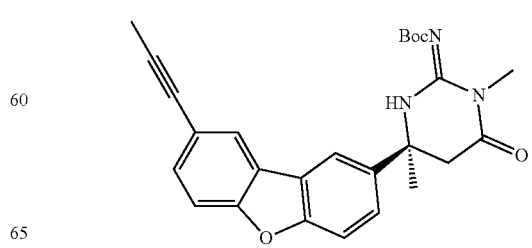

Example 14-6

(S)-tert-Butyl(1,4-dimethyl-6-oxo-4-(8-(prop-1-yn-1-yl)dibenzo[b,d]furan-2-yl) tetrahydropyrimidin-2(1H)-ylidene) carbamate (Example 14-6)

To a mixture of (Example 14-5) 0.5 g, 1.17 mmol) and MeOH (20.0 ml) was added hydrogen chloride (4N in dioxane, 0.6 ml, 2.35 mmol). The reaction mixture was stirred at room temperature for 1.5 hours and concentrated in vacuo to yield product as colorless oil that was used directly in the next step.

To a solution of the above material in DMF (5 ml) was added diisopropylethylamine (DIPEA) (0.4 ml, 3.51 mmol), t-butyl-N-[(methylamino) thioxomethyl]carbamate (Example 1-1) (0.45 g, 2.35 mmol) and 1-[3-(dimethylamino)propyl]-3-ethylcarbodiimide HCl (EDCI) (0.36 g, 2.35 mmol). The resulting solution was stirred at 50° C. overnight. The reaction was quenched with water and extracted with CH$_2$Cl$_2$. The organic layer was collected, dried over anhydrous MgSO$_4$ and concentrated in vacuo to yield the product as white solid. The obtained product was purified by silica gel column chromatography (ethyl acetate: n-hexane=1:2, Rf=0.4) to afford the title compound (Example 14-6) (0.27 g, 51.92%). $^1$H NMR (300 MHz, CDCl$_3$) δ 8.01 (s, 1H), 7.87 (d, J=2.1 Hz, 1H), 7.59-7.42 (m, 4H), 3.36 (d, J=15.5 Hz, 1H), 3.25 (s, 3H), 3.00 (d, J=16.2 Hz, 1H), 2.13 (s, 3H), 1.80 (s, 3H), 1.62 (s, 9H).

Example 14

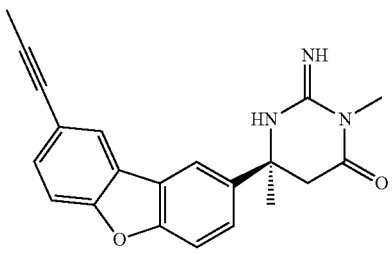 [SMILES: CC#Cc1ccc2oc3ccc([C@]4(C)CC(=O)N(C)C(=N)N4)cc3c2c1]

Example 14

(S)-2-Imino-3,6-dimethyl-6-(8-(prop-1-yn-1-yl)dibenzo[b,d]furan-2-yl)tetrahydropyrimidin-4(1H)-one (Example 14)

To a mixture of (Example 14-6) (0.45 g, 1.01 mmol) and CH$_2$Cl$_2$ (8 ml) was added trifluroacetic acid (TFA) (2 ml). The reaction mixture was stirred at room temperature for 2 hours, concentrated in vacuo and purified by silica gel column chromatography (MeOH:CH$_2$Cl$_2$=1:30, Rf=0.2) to afford (Example 14) (0.22 g, 66.7%). $^1$H NMR (300 MHz, MeOD) δ ppm 8.13 (d, J=1.8 Hz, 1H), 8.11 (d, J=8.1 Hz, 1H), 7.68-7.51 (m, 4H), 3.63 (d, J=16.5 Hz, 1H), 3.23 (d, J=16.2 Hz, 1H), 3.21 (s, 3H), 2.09 (s, 3H), 1.83 (s, 3H). ESI MS: m/z 346.15 (M+H)$^+$; HPLC: 99.1%.

Example 24-1

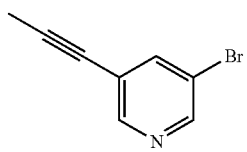

Example 24-1

3-Bromo-5-(prop-1-yn-1yl)pyridine (Example 24-1)

To a mixture of 3,5-dibromopyridine (0.5 g, 2.12 mmol), PPh$_3$ (0.03 g, 0.11 mmol), CuI (0.02 g, 0.11 mmol), PdCl$_2$(PPh$_3$)$_2$(0.7 g, 0.11 mmol) and triethylamine (15 ml) was added trimethyl(prop-1-yn-1-yl)silane (0.24 ml, 2.12 mmol) at room temperature. To the resultant mixture was added a solution of TBAF (1M in tetrahydrofuran, 2.7 ml) over 20 minutes. The mixture was stirred at room temperature for 3 hours. The reaction was quenched with water and extracted with CH$_2$Cl$_2$. The organic layer was collected, dried over anhydrous MgSO$_4$ and concentrated in vacuo to yield the product as black oil. The black oil obtained was purified by silica gel column chromatography (ethyl acetate: n-hexane=1:15, Rf=0.6) to afford the title compound (Example 24-1) (0.35 g, 84.6%). $^1$H NMR (500 MHz, CDCl$_3$) δ 8.53 (s, 1H), 8.50 (s, 1H), 7.79 (t, J=1.5 Hz, 1H), 2.06 (s, 3H).

Example 24-2

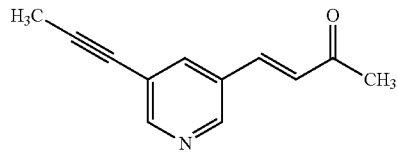

Example 24-2

(E)-4-(5-(Prop-1-yn-1yl)pyridine-3yl)but-3-en-2-one (Example 24-2)

To a mixture of 3-bromo-5-(prop-1-yn-1yl)pyridine (Example 24-1) (0.3 g, 1.53 mmol), Pd$_2$(dba)$_3$ (0.15 g, 0.16 mmol), tri-tert-butylphosphine tetrafluoroborate (0.02 g, 0.08 mmol), triethylamine (0.5 ml, 4.74 mmol), NaHCO$_3$ (0.4 g, 4.74 mmol) and dimethylformamide (5 ml) was added methyl vinyl ketone (0.25 ml, 3.16 mmol). The reaction mixture was stirred at 100° C. for 3 hours. The reaction was then quenched with water and extracted with CH$_2$Cl$_2$. The organic layer was collected, dried over anhydrous MgSO$_4$ and concentrated in vacuo to get the product as black oil. The product obtained was purified by silica gel column chromatography (ethyl acetate: n-hexane=1:2, Rf=0.2) to afford the title compound (Example 24-2) (0.15 g, 53.57%). $^1$H NMR (500 MHz, CDCl$_3$) δ 8.63 (s, 1H), 8.59 (s, 1H), 7.89 (s, 1H), 7.44 (d, J=16.5 Hz, 1H), 6.78 (d, J=16 Hz, 1H), 2.39 (s, 3H), 2.09 (s, 3H).

Example 24-3

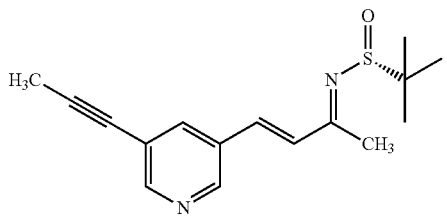 [SMILES: CC#Cc1cncc(/C=C/C(C)=N/[S@](=O)C(C)(C)C)c1]

Example 24-3

(R)-2-Methyl-N-((2E,3E)-4-(5-(prop-1-yn-1-yl)pyridin-3-yl)but-3-en-2-ylidene)propane-2-sulfinamide (Example 24-3)

A mixture of (E)-4-(5-(prop-1-yn-1yl)pyridine-3yl)but-3-en-2-one (Example 24-2) (1.7 g 9.19 mmol), (R)-2-methylpropane-2-sulfinamide (1.3 g, 18.38 mmol), Ti(OEt)$_4$ (3.5 ml, 27.57 mmol) and tetrahydrofuran (50 ml) was refluxed overnight. The reaction was quenched with water and extracted with CH$_2$Cl$_2$. The precipitate was filtered off and the organic layer was collected, dried over anhydrous MgSO$_4$ and concentrated in vacuo to yield the product as yellow oil. The product obtained was purified by silica gel column chromatography (ethyl acetate: n-hexane=1:2, Rf=0.5) to afford the title compound (Example 24-3) (2.33 g, 87.92%).

Example 24-4

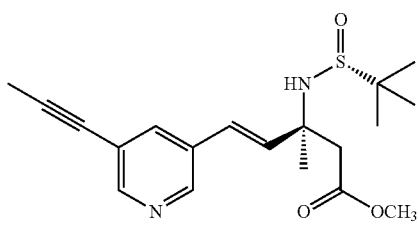 [SMILES: CC#Cc1cncc(/C=C/[C@](C)(CC(=O)OC)N[S@](=O)C(C)(C)C)c1]

Example 24-4

Methyl(S,E)-3-(((R)-tert-butylsulfinyl)amino)-3-methyl-5-(5-(prop-1-yn-1-yl)pyridin-3-yl)pent-4-enoate (Example 24-4)

To a solution of diisopropylamine (0.42 ml, 4.14 mmol) in THF (2 ml) cooled to −78° C. under an atmosphere of nitrogen was added n-BuLi (2.5 M in hexanes, 1.6 ml, 4.14 mmol). The mixture was stirred for 0.5 hour. After stirring, the solution was cooled to −78° C., and methyl acetate (0.3 ml, 4.10 mmol) was added. The resultant solution was stirred further at −78° C. for 0.5 hour. To this solution was then added a solution of chlorotitanium triisopropoxide (1.8 g, 6.9 mmol) in THF (10 ml) and stirred for 0.5 hour. The resulting solution was cooled to −78° C., and (R)-2-methyl-N-((2E,3E)-4-(5-(prop-1-yn-1-yl)pyridin-3-yl)but-3-en-2-ylidene)propane-2-sulfinamide (Example 24-3) (0.2 g, 0.69 mmol) in THF (2 mL) and the mixture was stirred for 1 hour. The reaction was then quenched with water and extracted with CH$_2$Cl$_2$. The precipitate was filtered off and the organic layer was collected, dried over anhydrous MgSO$_4$ and concentrated in vacuo to yield a yellow solid. The solid obtained was purified by silica gel column chromatography (ethyl acetate: n-hexane=1:2, Rf=0.25) to afford the title compound (Example 24-4) (0.12 g, 48%). $^1$H NMR (300 MHz, MeOD) δ 8.47 (d, J=1.8 Hz, 1H), 8.39 (d, J=1.8 Hz, 1H), 7.88 (d, J=1.8 Hz, 1H), 6.65 (d, J=16.2 Hz, 1H), 6.53 (d, J=16.2 Hz, 1H), 3.68 (s, 3H), 2.81 (s, 2H), 2.08 (s, 3H), 1.65 (s, 3H), 1.27 (s, 9H).

Example 24-5

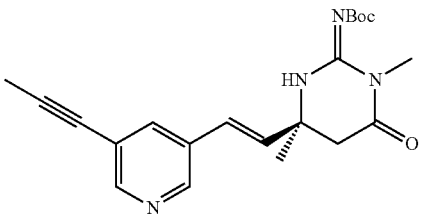

Example 24-5 tert-Butyl (S)-(1,4-dimethyl-6-oxo-4-((E)-2-(5-(prop-1-yn-1-yl)pyridine-3-yl)vinyl) tetrahydropyrimidin-2(1H)-ylidene)carbamate (Example 24-5)

To a mixture of (S,E)-3-(((R)-tert-butylsulfinyl)amino)-3-methyl-5-(5-(prop-1-yn-1-yl)pyridin-3-yl)pent-4-enoate (Example 24-4) (0.5 g, 1.38 mmol) and MeOH (15 ml) was added hydrogen chloride (4N in dioxane, 0.7 ml, 2.76 mmol). The reaction mixture was stirred at room temperature for 1.5 hours and concentrated in vacuo to get the product as colorless oil that was used directly in the next step.

To a solution of the above material in DMF (5 ml) was added DIPEA (0.42 mL, 4.14 mmol), t-butyl-N-[(methylamino)thioxomethyl]carbamate (Example 1-1) (0.31 g, 1.66 mmol) and 1-[3-(dimethylamino)propyl]-3-ethylcarbodiimide HCl (0.26 g, 1.66 mmol). The resulting solution was stirred at 50° C. overnight. The reaction was quenched with water and extracted with CH$_2$Cl$_2$. The organic layer was collected, dried over anhydrous MgSO$_4$ and concentrated in vacuo to yield a yellow solid. The yellow solid obtained was purified by silica gel column chromatography (ethyl acetate: n-hexane=2:1, Rf=0.35) to afford the title compound (Example 24-5) (0.44 g, 83.02%). $^1$H NMR (500 MHz, CDCl$_3$) δ 10.05 (s, 1H), 8.48 (d, J=2 Hz, 1H), 8.41 (d, J=2 Hz, 1H), 7.64 (s, 1H), 6.42 (d, J=16 Hz, 1H), 6.17 (d, J=16 Hz, 1H), 3.27 (s, 3H), 2.86 (d, J=16 Hz, 1H), 2.76 (d, J=16 Hz, 1H), 2.06 (s, 3H), 1.53 (s, 12H).

Example 24

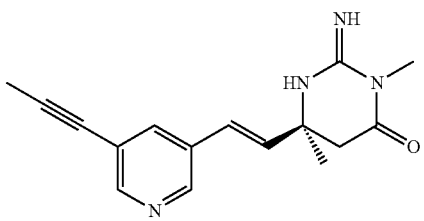 [SMILES: CC#Cc1cncc(/C=C/[C@]2(C)CC(=O)N(C)C(=N)N2)c1]

Example 24

(S,E)-2-Imino-3,6-dimethyl-6-(2-(5-(prop-1-yn-1-yl)pyridin-3-yl)vinyl)tetrahydropyrimidin-4(1H)-one (Example 24)

To a mixture of tert-butyl(S)-(1,4-dimethyl-6-oxo-4-((E)-2-(5-(prop-1-yn-1-yl)pyridine-3-yl)vinyl)tetrahydropyrimidin-2(1H)-ylidene)carbamate (Example 23-5) (0.25 g, 0.65 mmol) and CH$_2$Cl$_2$ (4 ml) was added trifluoroacetic acid (TFA) (1 ml). The reaction mixture was stirred at room temperature for 2 hours, concentrated in vacuo and purified by silica gel column chromatography (ethyl acetate: n-hexane=2:1, Rf=0.2) to afford the title compound (Example 24) (0.12 g, 66.67%). $^1$H NMR (300 MHz, MeOD) δ 8.42 (d, J=19.2 Hz, 2H), 7.89 (t, J=1.8 Hz, 1H), 6.57 (d, J=16.2 Hz, 1H), 6.47 (d, J=16.2 Hz, 1H), 3.26 (s, 3H), 3.04 (q, J=16.5 Hz, 2H), 2.05 (s, 3H), 1.57 (s, 3H).

Example 50

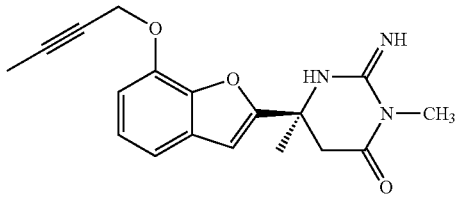 [SMILES: CC#CCOc1cccc2cc([C@]3(C)CC(=O)N(C)C(=N)N3)oc12]

Example 50

(S)-6-(7-(But-2-yn-1-yloxy)benzofuran-2-yl)-2-imino-3,6-dimethyltetrahydropyrimidin-4(1H)-one (Example 50)

To a solution of (S)-6-(7-hydroxybenzofuran-2-yl)-2-imino-3,6-dimethyltetrahydropyrimidin-4(1H)-one (Example 2) (260 mg, 0.95 mmol) in anhydrous CH$_2$Cl$_2$ (5 ml) was added triethylamine (288 mg, 2.85 mmol). The solution was cooled to 0~10° C. and treated slowly with 1-bromo-2-butyne (190 mg, 1.43 mmol). The resulting solution was stirred at 0~10° C. for 10 minutes. The reaction mixture was warmed to room temperature and then stirred 17 hours. The reaction mixture was diluted with water and extracted with ethyl acetate (3×). The combined organic extracts were washed with water and brine, dried over MgSO$_4$, filtered and concentrated. The crude product was purified by silica gel chromatography (gradient elution 15:1 to 9:1 CH$_2$Cl$_2$: MeOH) to afford the title compound (Example 50) (65 mg, 21% yield) as a powdery pale-yellow solid.

Example 71-1

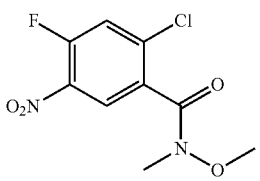

Example 71-1

2-Chloro-4-fluoro-N-methoxy-N-methyl-5-nitrobenzamide (Example 71-1)

To a solution of 2-chloro-4-fluoro-5-nitrobenzoic acid (20.0 g, 91.3 mmol) in CH$_2$Cl$_2$ (500 ml) was added DIPEA (22.6 ml, 137.0 mmol), N,O-Dimethylhydroxylamine hydrochloride (10.7 g, 109.6 mmol) and HATU (52.1 g, 137.0 mmol). The reaction mixture was stirred at room temperature overnight. Then the mixture was diluted with H$_2$O (500 ml) and the organic layer was separated. The aqueous layer was extracted with CH$_2$Cl$_2$ (150 ml×2), and the combined organic layers were washed with brine, then dried over anhydrous Na$_2$SO$_4$ and concentrated. The residue was purified through silica gel (petroleum ether/ethyl acetate=30/1-10/1) to give the title compound (Example 71-1) as a yellow solid (20.0 g, 83.3%).

Example 71-2

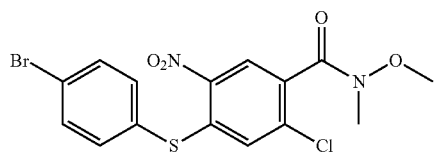 [SMILES: CON(C)C(=O)c1cc([N+](=O)[O-])c(Sc2ccc(Br)cc2)cc1Cl]

Example 71-2

4-((4-Bromophenyl)thio)-2-chloro-N-methoxy-N-methyl-5-nitrobenzamide (Example 71-2)

To a solution of 4-bromobenzenethiol (14.5 g, 76.7 mmol) in MeOH (500 ml) was added NaH (4.6 g, 115.1 mmol, 60% oil dispersion) at −78° C. under argon atmosphere and the mixture was stirred 30 minutes, then the solution of 2-chloro-4-fluoro-N-methoxy-N-methyl-5-nitrobenzamide (Example 71-1) (20.0 g, 76.3 mmol) in MeOH (100 ml) was added dropwise. After addition, the resulting mixture was stirred at −78° C. for 3 hours under argon atmosphere. Then the reaction mixture was quenched with H$_2$O (500 ml) and extracted with ethyl acetate (300 ml×3). The combined organic layer was washed with brine and dried over anhydrous Na$_2$SO$_4$ and concentrated to give the title compound (Example 71-2) as a yellow solid (30.0 g, 90.9%). LCMS: [M+1]: 431.0.

Example 71-3

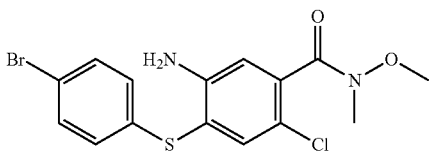 [SMILES: CON(C)C(=O)c1cc(N)c(Sc2ccc(Br)cc2)cc1Cl]

Example 71-3

5-Amino-4-((4-bromophenyl)thio)-2-chloro-N-methoxy-N-methylbenzamide (Example 71-3)

To a solution of 4-((4-bromophenyl)thio)-2-chloro-N-methoxy-N-methyl-5-nitrobenzamide (Example 71-2) (30.0 g, 69.5 mmol) in AcOH (1000 ml) was added Zn dust (22.6 g, 347.5 mmol) and the mixture was stirred at room temperature overnight. Then the resulting mixture was diluted with H$_2$O (1500 ml), extracted with EA (500 ml×3). The combined organic layer were washed with brine, dried over anhydrous Na$_2$SO$_4$ and concentrated. The residue was purified through silica gel (petroleum ether/ethyl acetate=5/1-3/1, containing 0.5% NH$_4$OH, v/v) to give title compound (Example 71-3) (20.0 g, 71.6%) as light brown flocculent solid. LCMS: [M+1]: 401.0.

Example 71-4

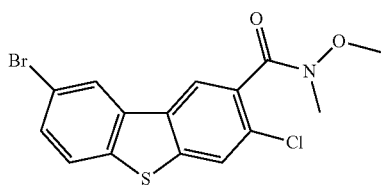 [SMILES: CON(C)C(=O)c1cc2c(cc1Cl)sc1ccc(Br)cc12]

Example 71-4

8-Bromo-3-chloro-N-methoxy-N-methyldibenzo[b,d]thiophene-2-carboxamide (Example 71-4)

5-Amino-4-((4-bromophenyl)thio)-2-chloro-N-methoxy-N-methylbenzamide (Example 71-3) (20.0 g, 49.8 mmol) was dissolved in HCl (6 M, 400 ml). The reaction mixture was cooled below 5° C. To this reaction mixture, sodium nitrite (5.2 g, 74.7 mmol) was added slowly with maintaining temperature below 5° C. After addition, the reaction mixture was stirred for 30 minutes below 5° C. Then sodium terafluoroborate (10.9 g, 99.6 mmol) was added to it and stirred for another 30 minutes below 5° C. The above mentioned diazotized solution was added to the stirred solution of copper (I) oxide (14.2 g, 99.6 mmol) in sulfuric acid (0.1 M, 800 ml) at 35-40° C. The reaction mixture was stirred for 50 minutes. Ethyl acetate was added to the reaction mixture and filtered to remove inorganic compound. The filtrate was then extracted by ethyl acetate (400 ml×3). The organic layers was washed with water followed by brine, then concentrated under vacuum to give a brown colored solid, which was purified through silica gel (petroleum ether/ethyl acetate=5/1) to give the title compound (Example 71-4) as light yellow solid (1.1 g, 5.7%). LCMS: [M+1]: 384.0.

Example 71-5

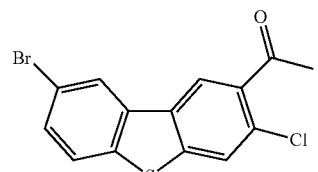

Example 71-5

1-(8-Bromo-3-chlorodibenzo[b,d]thiophen-2-yl)ethanone (Example 71-5)

To a solution of 8-bromo-3-chloro-N-methoxy-N-methyldibenzo[b,d]thiophene-2-carboxamide (Example 71-4) (1.1 g, 2.86 mmol) in THF (60 ml) was added MeMgBr (1.1 ml, 3.43 mmol, 3 M in THF) dropwise at 0° C. After addition, the mixture was stirred at room temperature for 4 hours. Then the reaction mixture was quenched with saturated aqueous NH$_4$Cl (200 ml) solution and extracted with ethyl acetate (150 ml×2). The combined organic layers were washed with brine, then dried over anhydrous Na$_2$SO$_4$ and concentrated to give the title compound (Example 71-5) as an earth yellow solid (900 mg, 92.8%).

Example 71-6

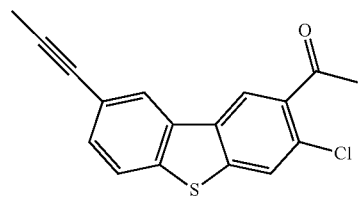 [SMILES: CC#Cc1ccc2sc3cc(Cl)c(C(C)=O)cc3c2c1]

Example 71-6

1-(3-Chloro-8-(prop-1-yn-1-yl)dibenzo[b,d]thiophen-2-yl)ethanone (Example 71-6)

To a mixture of 1-(8-bromo-3-chlorodibenzo[b,d]thiophen-2-yl)ethanone (Example 71-5) (760 mg, 2.249 mmol) and Pd(PPh$_3$)$_4$ (260 mg, 0.2249 mmol) in dioxane (20 ml) was added tributyl(prop-1-ynyl)stannane (891 mg, 2.698 mmol) at room temperature. The mixture was stirred at 110° C. overnight under N$_2$. The reaction was quenched with water and extracted with CH$_2$Cl$_2$ (30 ml×2). The organic layers were collected and dried over anhydrous MgSO$_4$ and then concentrated in vacuo to yield the product as black oil, which was purified by silica gel column chromatography (100% n-hexane, Rf=0.45) to afford the title compound (Example 71-6) (520 mg, 77.6%).

Example 71-7

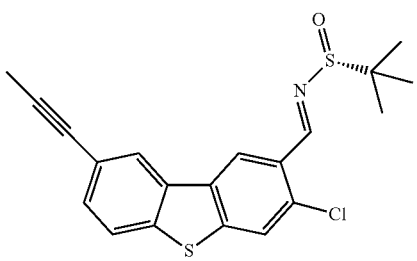 [SMILES: CC#Cc1ccc2sc3cc(Cl)c(/C=N/[S@](=O)C(C)(C)C)cc3c2c1]

Example 71-7

(R,E)-N-(1-(3-chloro-8-(prop-1-yn-1-yl)dibenzo[b,d]thiophen-2-yl)ethylidene)-2-m ethylpropane-2-sulfinamide (Example 71-7)

The mixture of 1-(3-chloro-8-(prop-1-yn-1-yl)dibenzo[b,d]thiophen-2-yl)ethanone (Example 71-6) (520 mg, 1.745 mmol), (R)-2-methylpropane-2-sulfinamide (317 mg, 2.617 mmol), Ti(OEt)$_4$ (796 mg, 3.49 mmol) and THF (5 ml) was refluxed overnight. The reaction mixture was quenched with water and extracted with CH$_2$Cl$_2$ (20 ml×3). The precipitate was filtered off and the organic layers were collected, dried over anhydrous MgSO$_4$ and concentrated in vacuo to give the crude as yellow oil, which was purified by silica gel column chromatography (ethyl acetate: n-hexane=1:2, Rf=0.5) to afford the title compound (Example 71-7) (480 mg, 68.6%).

Example 71-8

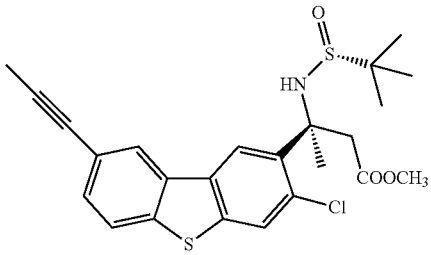 [SMILES: CC#Cc1ccc2sc3cc(Cl)c([C@](C)(CC(=O)OC)N[S@](=O)C(C)(C)C)cc3c2c1]

Example 71-8

Methyl (S)-3-(((R)-tert-butylsulfinyl)amino)-3-(3-chloro-8-(prop-1-yn-1-yl)dibenzo[b,d]thiophen-2-yl)butanoate (Example 71-8)

To a solution of LDA (6 ml, 12 mmol, 2 M) in THF (6 ml) was added methyl acetate (888 mg, 12 mmol) at −78° C. under nitrogen atmosphere. The resultant solution was further stirred at −78° C. for another 0.5 hour. To this reaction mixture was added chlorotitanium triisopropoxide (12 ml, 12 mmol, 1M in THF) and stirred for another 0.5 hour. The resulting mixture was then cooled to −78° C., and (R,E)-N-(1-(3-chloro-8-(prop-1-yn-1-yl)dibenzo[b,d]thiophen-2-yl)ethylidene)-2-methyl propane-2-sulfinamide (Example 71-7) (480 mg, 1.197 mmol) in THF (4 ml) was added and the mixture was stirred for 1 hour. The reaction mixture was quenched with saturated NH$_4$Cl solution and extracted with CH$_2$Cl$_2$. The precipitate was filtered off and the organic layer was collected, dried over anhydrous MgSO$_4$, concentrated in vacuo to give a yellow solid, which was purified by prep-TLC (ethyl acetate: n-hexane=1:2, Rf=0.25) to afford the title compound (Example 71-8) (310 mg, 54.5%).

Example 71-9

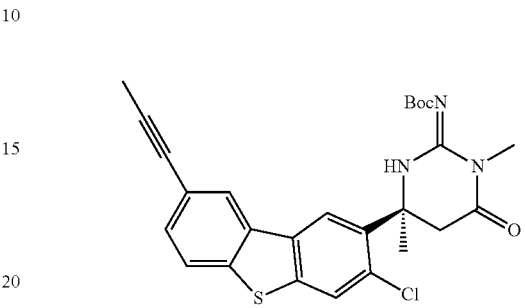

Example 71-9

(S)-tert-Butyl (4-(3-chloro-8-(prop-1-yn-1-yl)dibenzo[b,d]thiophen-2-yl)-1,4-dimethyl-6-oxo-1,4,5,6-tetrahydropyrimidin-2-yl)carbamate (Example 71-9)

To a mixture of methyl (S)-3-(((R)-tert-butylsulfinyl)amino)-3-(3-chloro-8-(prop-1-yn-1-yl)dibenzo[b,d]thiophen-2-yl)butanoate (Example 71-8) (310 mg, 0.653 mmol) and acetonitrile (4 ml) was added hydrogen chloride (4N in dioxane, 2 ml, 4 mmol). The reaction mixture was stirred at room temperature for 1 hours and concentrated in vacuo to yield the intermediate (methyl (S)-3-amino-3-(3-chloro-8-(prop-1-ynyl)dibenzo[b,d]thiophen-2-yl)butanoate hydrochloride) as colorless oil, which was used directly in the next step. To a solution of the above mentioned intermediate in DMF (4 ml) was added DIPEA (253 mg, 1.958 mmol), t-butyl-N-[(methylamino)thioxomethyl]carbamate (Example 1-1) (248 mg, 1.305 mmol) and EDCI HCl(251 mg, 1.305 mmol). The resulting solution was stirred at 50° C. overnight. The reaction mixture was quenched with water (10 ml) and extracted with CH$_2$Cl$_2$ (20 ml×3). The organic layers were collected and dried over anhydrous MgSO$_4$, concentrated in vacuo to yield a crude white solid, which was purified by prep-TLC (ethyl acetate: n-hexane=1:3, Rf=0.4) to afford the title compound (Example 71-9) (290 mg, 89.7%).

Example 71

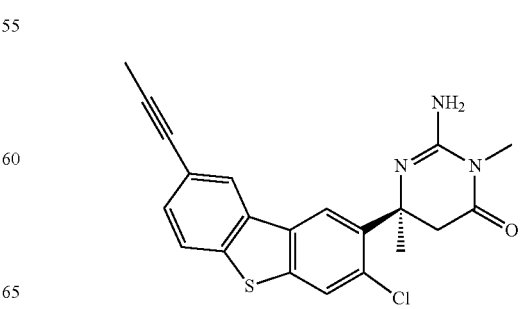

Example 71

(S)-2-Amino-6-(3-chloro-8-(prop-1-yn-1-yl)dibenzo[b,d]thiophen-2-yl)-3,6-dimethyl-5,6-dihydropyrimidin-4(3H)-one (Example 71)

To a mixture of (S)-tert-butyl (4-(3-chloro-8-(prop-1-yn-1-yl)dibenzo[b,d]thiophen-2-yl)-1,4-dimethyl-6-oxo-1,4,5,6-tetrahydropyrimidin-2-yl)carbamate (Example 71-9) (290 mg, 0.586 mmol) and Acetonitrile (4 ml) was added HCl/dioxane (2 ml, 4M). The reaction mixture was stirred at room temperature for 4 hours. The mixture was concentrated and purified by prep-HPLC to afford the title compound (Example 71) (142 mg, 61%).1H NMR (400 MHz, CDCl$_3$) δ ppm 8.32 (s, 1H), 8.07 (s, 1H), 7.77 (s, 1H), 7.65 (d, J=8.4 Hz, 1H), 7.39 (d, J=9.2 Hz, 1H), 3.48 (d, J=18.2 Hz, 1H), 3.10 (s, 3H), 3.03 (d, J=19.1 Hz, 1H), 2.03 (s, 3H), 1.73 (s, 3H).

Example 79

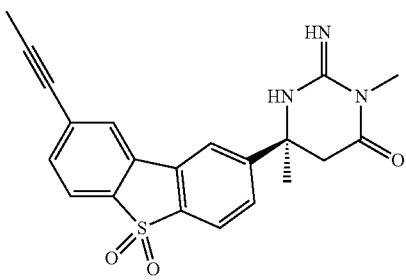 [SMILES: CC#Cc1ccc2c(c1)-c1cc([C@]3(C)CC(=O)N(C)C(=N)N3)ccc1S2(=O)=O]

Example 79

(S)-2-Amino-6-(5,5-dioxido-8-(prop-1-yn-1-yl)dibenzo[b,d]thiophen-2-yl)-3,6-dimethyl-5,6-dihydropyrimidin-4(3H)-one (Example 79)

To a stirred solution of (S)-2-Imino-3,6-dimethyl-6-(8-(prop-1-yn-1-yl)dibenzo[b,d]thiophen-2-yl)tetrahydropyrimidin-4(1H)-one (example 1) (20 mg, 0.0554 mmol) in acetonitrile (3 ml) was added the solution of m-CPBA (28.7 mg, 0.1662 mmol) in CH$_2$Cl$_2$ (5.0 ml). The mixture was kept stirring at room temperature overnight (16 hours). The resulting mixture was evaporated via reduced pressure and the solid residual was purified via prep-HPLC to give the title compound (Example 79) as a white solid (10 mg, yield=46%). LCMS: [M+1]: 394.1. 1H NMR (400 MHz, DMSO): δ 8.37-8.31 (m, 2H), 7.95-7.93 (m, 2H), 7.80 (m, 1H), 7.623-7.603 (m, 1H), 3.04 (s, 3H), 2.943-2.932 (m, 2H), 2.15 (s, 3H), 1.43 (s, 3H).

Example 80

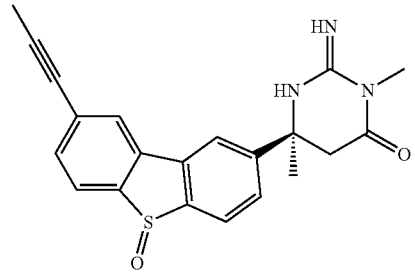 [SMILES: CC#Cc1ccc2c(c1)-c1cc([C@]3(C)CC(=O)N(C)C(=N)N3)ccc1S2=O]

Example 80

(6S)-2-Amino-3,6-dimethyl-6-(5-oxido-8-(prop-1-yn-1-yl)dibenzo[b,d]thiophen-2-yl)-5,6-dihydropyrimidin-4(3H)-one (Example 80)

To a stirred solution of (S)-2-Imino-3,6-dimethyl-6-(8-(prop-1-yn-1-yl)dibenzo[b,d]thiophen-2-yl)tetrahydropyrimidin-4(1H)-one (example 1) (20 mg, 0.0554 mmol) in acetonitrile (3 ml) was added the solution of m-CPBA(28.7 mg, 0.1662 mmol) in CH$_2$Cl$_2$ (5.0 ml). The mixture was kept stirring at room temperature for 2 hours. The reaction was quenched with 2 ml of saturated Na$_2$SO$_3$, The resulting mixture was diluted with CH$_2$Cl$_2$(20 mL), washed with brine (10 ml×3), the organic phase was dried over anhydrous sodium sulfate, then evaporated via reduced pressure. The solid residual was purified via prep-HPLC to give the title compound (Example 80) as a white solid (7 mg, yield=33%). LCMS: [M+1]: 378.1. 1H NMR (400 MHz, CDCl$_3$): δ 7.92-7.76 (m, 4H), 7.56-7.47 (m, 2H), 3.16 (s, 3H), 2.97-2.83 (m, 2H), 2.11-2.10 (m, 3H), 1.54 (s, 3H).

Example 86-1

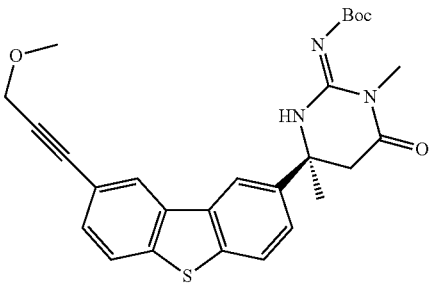 [SMILES: COCC#Cc1ccc2sc3ccc([C@]4(C)CC(=O)N(C)/C(=N\C(=O)OC(C)(C)C)N4)cc3c2c1]

Example 86-1

(S)-tert-Butyl (4-(8-(3-methoxyprop-1-yn-1-yl)dibenzo[b,d]thiophen-2-yl)-1,4-dimethyl-6-oxo-1,4,5,6-tetrahydropyrimidin-2-yl)carbamate (Example 86-1)

A mixture of ((S)-tert-butyl (4-(8-bromodibenzo[b,d]thiophen-2-yl)-1,4-dimethyl-6-oxo-1,4,5,6-tetrahydropyrimidin-2-yl)carbamate) (1 g, 2 mmol), 3-methyoxyprop-1-yne (550 mg, 10 mmol), Pd (OAc)$_2$ (224 mg, 0.2 mmol), PPh$_3$ (500 mg, 0.2 mmol), CuI (380 mg, 0.2 mmol), triethylamine (2 g, 20 mmol) in DMF (5 ml) was stirred at 90° C. for 2 hours under microwave. ethyl acetate (50 ml) was added and washed with water (20 ml×2). The organic layer was concentrated and the residue was purified by combiflash (petroleum ether:ethyl acetate=2:1, normal phase silica, UV 254) to give the title compound (Example 86-1) (60 mg, 6%) as a white solid. LC-MS [M-55]+=436.

Example 86

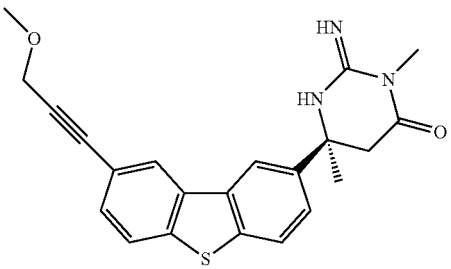 [SMILES: COCC#Cc1ccc2sc3ccc([C@]4(C)CC(=O)N(C)C(=N)N4)cc3c2c1]

Example 86

(S)-2-Amino-6-(8-(3-methoxyprop-1-yn-1-yl) dibenzo[b,d]thiophen-2-yl)-3,6-dimethyl-5,6-dihydropyrimidin-4(3H)-one (Example 86)

((S)-tert-butyl (4-(8-(3-methoxyprop-1-yn-1-yl)dibenzo[b,d]thiophen-2-yl)-1,4-dimethyl-6-oxo-1,4,5,6-tetrahydropyrimidin-2-yl)carbamate) (Example 86-1) (50 mg, 0.1 mmol) was added to a mixture of CH$_2$Cl$_2$ (3 ml) and 4M HCl in dioxane (3 ml). The resulting mixture was stirred for 1 hour. Concentrated and residue was purified by prep-HPLC to give the title compound (Example 86) (15 mg, 38%) as a white solid. LC-MS: [M+H]$^+$=392. $^1$H NMR (400 MHz, CDCl$_3$): δ ppm 8.52 (s, 1H), 8.50 (s, 1H), 8.05-8.03 (d, J=8 Hz, 1H), 7.97-7.95 (d, J=8 Hz, 1H), 7.68-7.66 (d, J=8 Hz, 1H), 7.56-7.57 (m, 1H), 6.00 (br, 1H), 4.39 (s, 2H), 3.39 (s, 3H), 3.00 (s, 3H), 3.01-3.00 (m, 1H), 2.50-2.49 (m, 1H), 1.46 (s, 3H).

Example 87-1

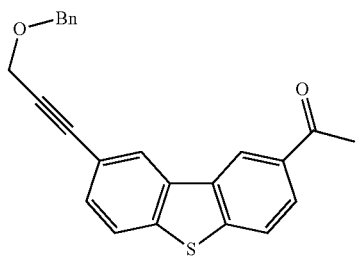 [SMILES: CC(=O)c1ccc2sc3ccc(C#CCOCc4ccccc4)cc3c2c1]

Example 87-1

1-(8-(3-(Benzyloxy)prop-1-yn-1-yl)dibenzo[b,d] thiophen-2-yl)ethanone (Example 87-1)

A mixture of 1-(8-bromodibenzo[b,d]thiophen-2-yl)ethanone (800 mg, 2.61 mmol), ((prop-2-ynyloxy)methyl)benzene (1.6 g, 10.9 mmol), Pd(PPh$_3$)Cl$_2$ (420 mg, 0.59 mmol), CuI (200 mg, 1.04 mmol) in triethylamine (50 ml) was stirred at 100° C. for 16 hours. Ethyl acetate (100 ml) was added and the organic layer was washed with water (50 ml×2), dried and concentrated. The residue was purified by combiflash (petroleum ether:ethyl acetate=10:1, normal phase silica, UV 254) to give the title compound (Example 87-1) (600 mg, 62%) as a white solid. LC-MS: [M+H]$^+$=371.

Example 87-2

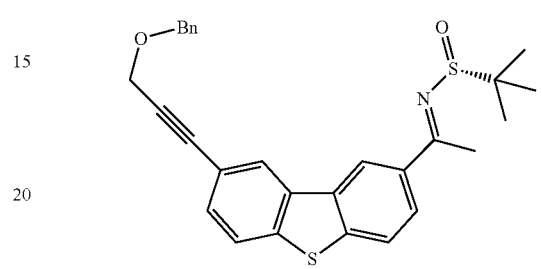

Example 87-2

(R,E)-N-(1-(8-(3-(benzyloxy)prop-1-yn-1-yl) dibenzo[b,d]thiophen-2-yl)ethylidene)-2-methylpropane-2-sulfinamide (Example 87-2)

A mixture of 1-(8-(3-(benzyloxy)prop-1-yn-1-yl)dibenzo[b,d]thiophen-2-yl)ethan-1-one (Example 87-1) (400 mg, 1.08 mmol), (R)-2-methylpropane-2-sulfinamide (400 mg, 3.3 mmol), Ti(OEt)$_4$ (1.2 g, 5.2 mmol) in THF (25 ml) was stirred at reflux for 16 hours.

Water (25 ml) was added, extracted with ethyl acetate (50 ml×2). The organic layer was dried and concentrated. Residue was purified by combiflash (petroleum ether:ethyl acetate=5:1, normal phase silica, UV 254) to give the title compound (Example 87-2) (260 mg, 50.8%) as a white solid. LC-MS: [M+H]$^+$=474.

Example 87-3

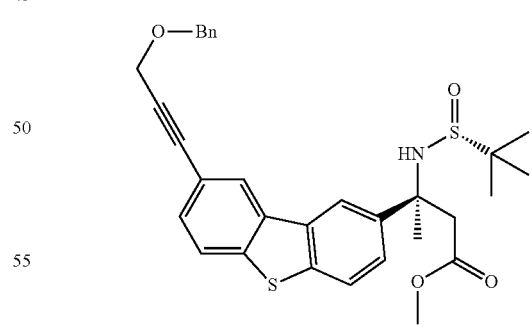

Example 87-3

Methyl (S)-3-(8-(3-(benzyloxy)prop-1-yn-1-yl)di benzo[b,d]thiophen-2-yl)-3-(((R)-tert-butylsulfinyl) amino)butanoate (Example 87-3)

To a solution of LDA (2.75 ml, 5.5 mmol, 2 M) in THF (5 ml) was added methyl acetate (407 mg, 5.5 mmol) at −78°

C. under nitrogen atmosphere. The resultant solution was further stirred at −78° C. for another 0.5 hour. To this reaction mixture was added chlorotitanium triisopropoxide (5.5 ml, 5.5 mmol, 1M in THF) and stirred for another 0.5 hour. The resulting mixture was then cooled to −78° C., and (R,E)-N-(1-(8-(3-(benzyloxy)prop-1-yn-1-yl)dibenzo[b,d]thiophen-2-yl)ethylidene)-2-m ethylpropane-2-sulfinamide (Example 87-2) (260 mg, 0.55 mmol) in THF (4 ml) was added and the mixture was stirred for 1 hour. The reaction mixture was quenched with saturated NH$_4$Cl solution and extracted with CH$_2$Cl$_2$. The precipitate was filtered off and the organic layer was collected, dried over anhydrous MgSO$_4$, concentrated in vacuo to give a yellow solid, which was purified by prep-TLC (ethyl acetate: n-hexane=1:2) to afford the title compound (Example 87-3) (230 mg, 76%). LC-MS: [M+Na]$^+$=570.

Example 87-4

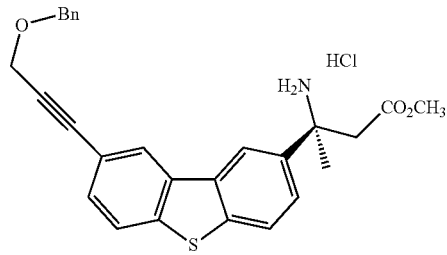 [SMILES: COC(=O)C[C@](C)(N)c1ccc2sc3ccc(C#CCOCc4ccccc4)cc3c2c1 ; Cl]

Example 87-4

(S)-Methyl 3-amino-3-(8-(3-(benzyloxy)prop-1-yn-1-yl)dibenzo[b,d]thiophen-2-yl)butanoate hydrochloride (Example 87-4)

To a mixture of methyl (S)-3-(8-(3-(benzyloxy)prop-1-yn-1-yl)dibenzo[b,d]thiophen-2-yl)-3-(((R)-tert-butylsulfinyl)amino)butanoate (Example 87-3) (230 mg, 0.42 mmol) and Acetonitrile (4 ml) was added hydrogen chloride (4N in dioxane, 2 ml, 4 mmol). The reaction mixture was stirred at room temperature for 1 hour and concentrated in vacuo to give the title compound (Example 87-4) as a yellow solid, which was used directly in the next step.

Example 87-5

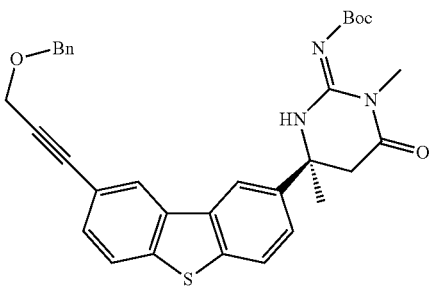 [SMILES: CN1C(=O)C[C@@](C)(c2ccc3sc4ccc(C#CCOCc5ccccc5)cc4c3c2)N/C1=N/C(=O)OC(C)(C)C]

Example 87-5

(S)-tert-Butyl (4-(8-(3-(benzyloxy)prop-1-yn-1-yl)dibenzo[b,d]thiophen-2-yl)-1,4-dimethyl-6-ox o-1,4,5,6-tetrahydropyrimidin-2-yl)carbamate (Example 87-5)

To a solution of (S)-methyl 3-amino-3-(8-(3-(benzyloxy)prop-1-yn-1-yl)dibenzo[b,d]thiophen-2-yl)butanoate hydrochloride (Example 87-4) (201 mg, 0.42 mmol) in DMF (4 ml) was added DIPEA (280 mg, 2.10 mmol), t-butyl-N-[(methylamino)thioxomethyl]carbamate (160 mg, 0.84 mmol) and EDCI HCl(161 mg, 0.84 mmol). The resulting solution was stirred at 50° C. overnight. The reaction mixture was quenched with water (10 ml) and extracted with CH$_2$Cl$_2$ (20 ml×3). The organic layers were collected and dried over anhydrous MgSO$_4$, concentrated in vacuo to yield a crude white solid, which was purified by prep-TLC (ethyl acetate: n-hexane=1:3) to afford the title compound (Example 87-5) (130 mg, 55%).

Example 87

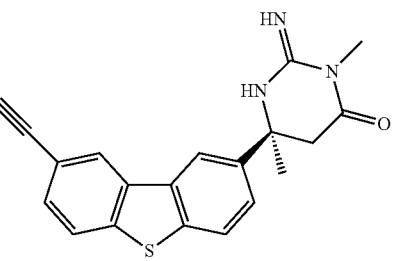

Example 87

(S)-2-Amino-6-(8-(3-hydroxyprop-1-yn-1-yl)dibenzo[b,d]thiophen-2-yl)-3,6-dimethyl-5,6-dihydropyrimidin-4(3H)-one (Example 87)

BBr$_3$ (0.2 ml) was added to a solution of (S)-tert-butyl (4-(8-(3-(benzyloxy)prop-1-yn-1-yl)dibenzo[b,d]thiophen-2-yl)-1,4-dimethyl-6-oxo-1,4,5,6-tetrahydropyrimidin-2-yl)carbamate (Example 87-5) (110 mg, 0.194 mmol) in CH$_2$Cl$_2$ (15 ml) at −78° C. and stirred for 30 minutes. Quenched with NaHCO$_3$ solution, extracted with ethyl acetate (50 ml×2). The organic layer was concentrated and residue was purified by prep-HPLC to give the title compound (Example 87) (10 mg, 13.9%). LC-MS: [M+H]$^+$=378. 1H NMR (400 MHz, CDCl$_3$): δ ppm 8.24 (s, 1H), 7.85 (s, 1H), 7.71-7.74 (d, 1H), 7.61-7.63 (d, 1H), 7.47-7.49 (t, 1H), 7.32-7.35 (m, 1H), 4.54 (s, 2H), 3.24-3.21 (d, 1H), 3.20 (s, 3H), 2.87-2.91 (d, 1H) 1.62 (s, 3H).

Example 94-1

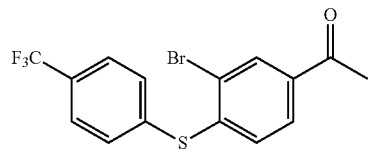 [SMILES: CC(=O)c1ccc(Sc2ccc(C(F)(F)F)cc2)c(Br)c1]

Example 94-1

1-(3-Bromo-4-((4-(trifluoromethyl)phenyl)thio)phenyl)ethan-1-one (Example 94-1)

To the solution of 4-(trifluoromethyl)benzenethiol (750 mg, 4.209 mmol), 1-(3-bromo-4-fluorophenyl)ethanone (913 mg, 4.209 mmol) in DMF (10 ml) was added $K_2CO_3$ (697 mg, 5.051 mmol). The mixture was kept stirring at 90° C. for 16 hours under a nitrogen atmosphere. The resulting mixture was diluted with diethyl ether (20 ml), washed (water, brine), dried ($MgSO_4$), and concentrated in vacuum. Purification via silica gel column chromatography eluted with petroleum ether:ethyl acetate=10:1 afforded the title compound (Example 94-1) (324 mg, yield=20.5%) as a yellow solid. LCMS: [M+1]: 377.0.

Example 94-2

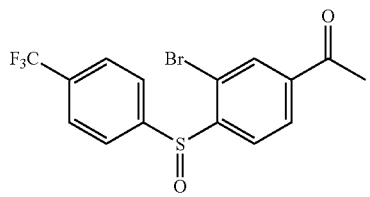 [SMILES: CC(=O)c1ccc(S(=O)c2ccc(C(F)(F)F)cc2)c(Br)c1]

Example 94-2

1-(3-Bromo-4-((4-(trifluoromethyl)phenyl)sulfinyl)phenyl)ethan-1-one (Example 94-2)

To a stirred solution of 1-(3-bromo-4-((4-(trifluoromethyl)phenyl)thio)phenyl)ethan-1-one (Example 94-1) (546 mg, 1.455 mmol) in $CH_2Cl_2$ (27 ml) was added solution of m-CPBA (295 mg, 85%, 1.455 mmol) in $CH_2Cl_2$ (55 ml) in dropwise at 0° C. The mixture was kept stirring at 0° C. for 1 hour. The resulting mixture was washed with solution of sodium bicarbonate and solution of sodium sulfite. The organic phase was dried over anhydrous sodium sulfate, evaporated and purified with column chromatography with eluent (petroleum ether:ethyl acetate=8:1) to afford the title compound (Example 94-2) (469 mg, yield=81%) as light yellow oil. LCMS: [M+1]: 392.0.

Example 94-3

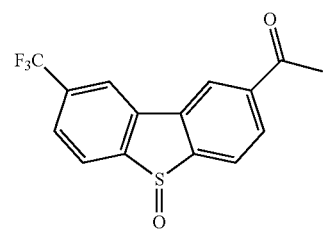 [SMILES: CC(=O)c1ccc2c(c1)-c1cc(C(F)(F)F)ccc1S2=O]

Example 94-3

1-(5-Oxido-8-(trifluoromethyl)dibenzo[b,d]thiophen-2-yl)ethan-1-one (Example 94-3)

$Pd(OAc)_2$ (8 mg, 0.036 mmol) and KOAc (235 mg, 2.4 mmol) were suspended in the solution of 1-(3-bromo-4-((4-(trifluoromethyl)phenyl)sulfinyl)phenyl)ethan-1-one (Example 94-2) (459 mg, 1.2 mmol) in DMA (12 ml). The mixture was kept stirring at 130° C. for 5 hours. The resulting mixture was cooled to room temperature and diluted with $CH_2Cl_2$ (50 ml), then filtered over celite. The filtrate was washed with brine, dried over $MgSO_4$ and concentrated in vacuum. The solid residual was purified via column chromatography with eluent (petroleum ether:ethyl acetate=3:1) to afford the title compound (Example 94-3) (396 mg, yield=100%) as a white solid. LCMS: [M+1]: 311.1.

Example 94-4

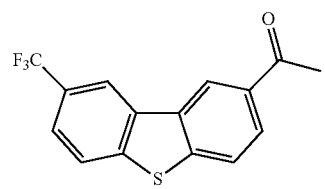 [SMILES: CC(=O)c1ccc2sc3ccc(C(F)(F)F)cc3c2c1]

Example 94-4

1-(8-(Trifluoromethyl)dibenzo[b,d]thiophen-2-yl)ethan-1-one (Example 94-4)

To a stirred solution of 1-(5-oxido-8-(trifluoromethyl)dibenzo[b,d]thiophen-2-yl)ethan-1-one (Example 94-3) (380 mg, 1.226 mmol), KI (610 mg, 3.667 mmol) in $CH_2Cl_2$ (5 ml) was added HCl/1,4-dioxane (4 M, 1.5 ml, 6.0 mmol) solution of m-CPBA (295 mg, 85%, 1.455 mmol) in $CH_2Cl_2$ (55 ml) in dropwise at 0° C. The mixture was kept stirring at 0° C. for 30 minutes. The resulting mixture was diluted with $CH_2Cl_2$, washed with solution of sodium bicarbonate and solution of sodium sulfite. The organic phase was dried over anhydrous sodium sulfate, evaporated to afford the title compound (Example 94-4) (360 mg, yield=100%) as a light yellow solid. LCMS: [M+1]: 295.1.

Example 94-5

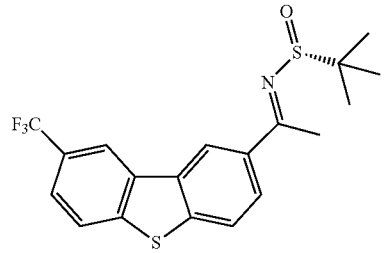 [SMILES: C/C(=N\[S@](=O)C(C)(C)C)c1ccc2sc3ccc(C(F)(F)F)cc3c2c1]

Example 94-5

(R,E)-2-Methyl-N-(1-(8-(trifluoromethyl)dibenzo[b,d]thiophen-2-yl)ethylidene)propane-2-sulfinamide (Example 94-5)

To a stirred solution of 1-(8-(trifluoromethyl)dibenzo[b,d]thiophen-2-yl)ethan-1-one (Example 94-4) (360 mg, 1.226 mmol), (R)-2-methylpropane-2-sulfinamide (223 mg, 1.839 mmol) in THF (10 ml) was added Ti(OEt)$_4$ (0.77 ml, 839 mg, 3.678 mmol). The mixture was kept stirring and refluxing under a nitrogen atmosphere for 8 hours. The resulting mixture was cooled to room temperature, quenched with water and filtered over celite. The filtrate was dried over MgSO$_4$ and evaporated. The solid residual was purified via silica gel column chromatography with eluent (petroleum ether:ethyl acetate=1:1) to give the title compound (Example 94-5) (347 mg, yield=70%) as a light yellow solid. LCMS: [M+1]: 398.1.

Example 94-6

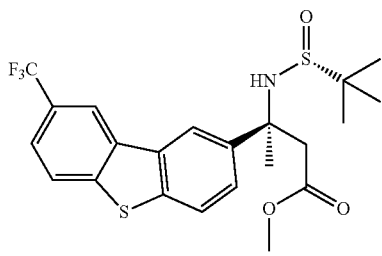 [SMILES: COC(=O)C[C@](C)(N[S@](=O)C(C)(C)C)c1ccc2sc3ccc(C(F)(F)F)cc3c2c1]

Example 94-6

(S)-Methyl 3-((R)-1,1-dimethylethylsulfinamido)-3-(8-(trifluoromethyl)dibenzo[b,d]thiophen-2-yl)butanoate (Example 94-6)

To a solution of anhydrous methyl acetate (0.5 ml, 435 mg, 5.876 mmol) in anhydrous THF (1.2 ml) in a three-neck-flask under Argon atmosphere was added LDA (2.9 ml, 2 M, 5.876 mmol) at −78° C. The mixture was kept stirring at −78° C. for 30 minutes, then ClTi(OiPr)$_3$ (1 M, 5.9 ml, 5.0503 mmol) was added, the resulting mixture was kept stirring at −78° C. for 30 minutes. Then the solution of (R,E)-2-methyl-N-(1-(8-(trifluoromethyl)dibenzo[b,d]thiophen-2-yl)ethylidene)propane-2-sulfinamide (Example 94-5) (200 mg, 0.5876 mmol) in THF (1.2 ml) was added. The mixture was kept stirring at −78° C. for 1 hour. The resulting mixture was quenched with water at −78° C., then filtered off, the filtrate was dried over anhydrous magnesium sulfate and evaporated via reduced pressure. The solid residual was purified via silica gel column chromatography with eluent (petroleum ether:ethyl acetate=1:1) to get the title compound (Example 94-6) (193 mg, yield=81%) as a white foamy solid. LCMS: [M+1]: 472.1.

Example 94-7

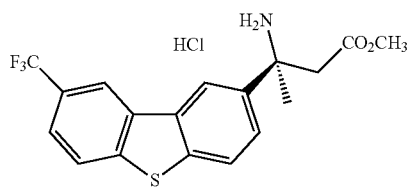 [SMILES: COC(=O)C[C@](C)(N)c1ccc2sc3ccc(C(F)(F)F)cc3c2c1 ; Cl]

Example 94-7

(S)-Methyl 3-amino-3-(8-(trifluoromethyl)dibenzo[b,d]thiophen-2-yl)butanoate (Example 94-7)

To a stirred solution of (S)-methyl 3-((R)-1,1-dimethylethylsulfinamido)-3-(8-(trifluoromethyl)dibenzo[b,d]thiophen-2-yl)butanoate (Example 94-6) (50 mg, 0.1060 mmol) in CH$_2$Cl$_2$ (6 ml) was added HCl/1,4-dioxane (4 M, 4 ml, 16.0 mmol). The mixture was kept stirring at room temperature for 1 hour. The resulting mixture was evaporated to afford the title compound (Example 94-7) (39 mg, yield=100%) as a white solid. LCMS: [M-NH$_2$]: 351.1.

Example 94-8

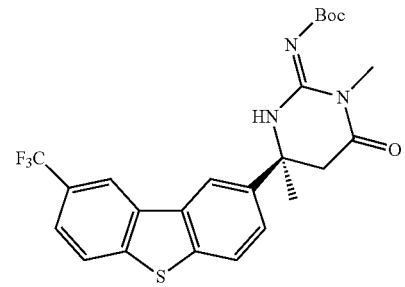 [SMILES: CN1C(=O)C[C@@](C)(c2ccc3sc4ccc(C(F)(F)F)cc4c3c2)N/C1=N/C(=O)OC(C)(C)C]

Example 94-8

(S)-tert-Butyl (1,4-dimethyl-6-oxo-4-(8-(trifluoromethyl)dibenzo[b,d]thiophen-2-yl)-1,4,5,6-tetrahydropyrimidin-2-yl)carbamate (Example 94-8)

To a stirred solution of (S)-methyl 3-amino-3-(8-(trifluoromethyl)dibenzo[b,d]thiophen-2-yl)butanoate (Example 94-7) (39 mg, 0.1060 mmol), tert-butyl N-(methyl carbomothioyl) carbomate (40 mg, 0.2120 mmol), EDCI (40 mg, 0.2120 mmol) in DMF (5.0 ml) was DIPEA (68 mg, 0.530 mmol). The mixture was kept stirring at 50° C. for 16 hours. The resulting mixture was diluted with ethyl acetate, washed with (water, brine). The organic phase was dried over anhydrous magnesium sulfate and evaporated. The solid residual was purified via silica gel column chromatography eluted with petroleum ether:ethyl acetate=4:1) to get the title compound (Example 94-8) (40 mg, yield=77%) as a light yellow solid. LCMS: [M+1]: 492.2.

Example 94

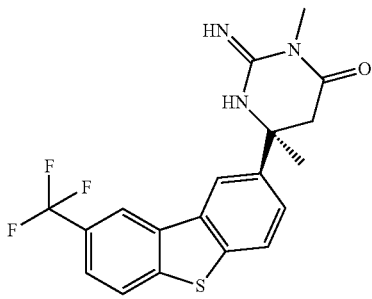

Example 94

(S)-2-Amino-3,6-dimethyl-6-(8-(trifluoromethyl)
dibenzo[b,d]thiophen-2-yl)-5,6-di hydropyrimidin-4
(3H)-one (Example 94)

To a stirred solution of (S)-tert-butyl (1,4-dimethyl-6-oxo-4-(8-(trifluoromethyl)dibenzo[b,d]thiophen-2-yl)-1,4,5,6-tetrahydropyrimidin-2-yl)carbamate (Example 94-8) (40 mg, 0.0815 mmol) in $CH_2Cl_2$ (3 ml) was added HCl/1,4-dioxane (4 M, 3 ml, 12.0 mmol). The mixture was kept stirring at room temperature for 16 hours. The resulting mixture was evaporated and purified via prep-RP-HPLC to afford the title compound (Example 94) (10.9 mg, yield=34%) as a white solid.

LCMS: [M+1]: 392.1, 1H NMR (400 MHz, $CDCl_3$): δ 8.69 (s, 1H), 8.44 (s, 1H), 8.27 (s, 1H), 7.97-7.88 (dd, J1=8.4 Hz, J2=8.4 Hz, 2H), 7.72 (d, J=8.4 Hz, 1H), 7.58-7.55 (dd, J1=1.6 Hz, J2=2.0 Hz, 1H), 3.58 (d, J=16.4 Hz, 1H), 3.08 (d, J=16.4 Hz, 1H), 1.83 (s, 3H), 3.27 (s, 3H).

Example 100-1

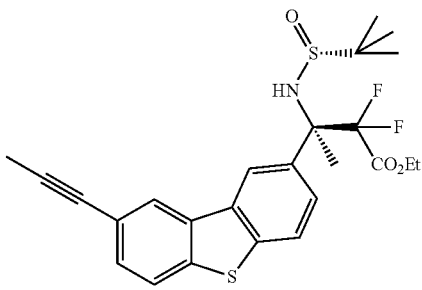 [SMILES: CC#Cc1ccc2sc3ccc([C@@](C)(N[S@](=O)C(C)(C)C)C(F)(F)C(=O)OCC)cc3c2c1]

Example 100-1

(R)-Ethyl 3-((R)-1,1-dimethylethylsulfinamido)-2,2-difluoro-3-(8-(prop-1-yn-1-yl) dibenzo[b,d]thiophen-2-yl)butanoate (Example 100-1)

To a mixture of zinc (0.20 g, 3.27 mmol) and copper (I) chloride (0.10 g, 1.09 mmol) in water (3.00 ml) was added 2N HCl (1.00 ml) then removed aqueous phase and washed with acetone three times. The mixture was treated with THF (10.0 ml) and ethyl bromodifluoroacetate (0.60 ml, 2.72 mmol), heated by heat gun for 3 minutes and treated with (R,E)-2-Methyl-N-(1-(8(prop-1-yn-1yl)dibenzo(b,d)thiophene-2-yl) ethylidene)propane-2-sulfonamide (Example 1-5) (0.20 g, 0.52 mmol) in THF (5.00 ml). The resulting reaction mixture was stirred at room temperature for 1.5 hours. The mixture was filtered through celite and the organic layer was concentrated in vacuo and purified by column chromatography (ethyl acetate/hexane=1:2) to afford the title compound (Example 100-1) (0.12 g, 46.9%) 1H NMR (300 MHz, $CDCl_3$) δ 8.31 (d, J=1.5 Hz, 1H), 8.17 (d, J=1.2 Hz, 1H), 7.89 (d, J=13.2 Hz, 1H), 7.82 (d, J=7.8 Hz, 1H), 7.68 (dd, J=0.9, 8.4 Hz, 1H), 7.55 (dd, J=1.5, 8.4 Hz, 1H), 4.68 (s, 1H), 4.30-4.19 (m, 2H), 2.15 (s, 6H), 1.37 (s, 9H), 1.21 (t, J=7.2 Hz, 3H).

Example 100-2

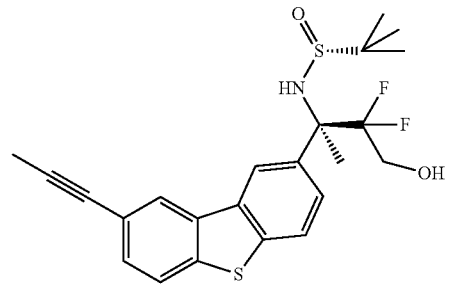 [SMILES: CC#Cc1ccc2sc3ccc([C@@](C)(N[S@](=O)C(C)(C)C)C(F)(F)CO)cc3c2c1]

Example 100-2

(R)-N-((R)-3,3-difluoro-4-hydroxy-2-(8-(prop-1-yn-1-yl)dibenzo[b,d]thiophen-2-yl) butan-2-yl)-2-methylpropane-2-sulfinamide (Example 100-2)

To a solution of (R)-Ethyl 3-((R)-1,1-dimethylethylsulfinamido)-2,2-difluoro-3-(8-(prop-1-yn-1-yl) dibenzo[b,d]thiophen-2-yl)butanoate (Example 100-1) (1 g, 2.03 mmol) in anhydrous THF (15 ml) was added 1M $LiBH_4$ in THF (4 ml, 4.06 mmol) dropwise. The reaction mixture was stirred at 0° C. for 1.5 hours. The reaction was quenched with water and extracted with ethyl acetate (3×200 ml). The organic layer was dried over anhydrous $MgSO_4$, filtered and concentrated. The residue was purified by column chromatography (ethyl acetate/hexane=1:2) to afford the title compound (Example 100-2) (0.73 g, 77.66%). $^1$H NMR (300 MHz, $CD_3OD$) δ 8.42 (s, 1H), 8.19 (d, J=1.2 Hz, 1H), 7.91 (d, J=8.7, 21.9 Hz, 1H), 7.84 (d, J=8.4 Hz, 1H), 7.75 (d, J=9.0 Hz, 1H), 7.48 (dd, J=1.5, 8.4 Hz, 1H), 4.02-3.69 (m, 2H), 2.10 (s, 3H), 2.07 (s, 3H), 1.31 (s, 9H)

Example 100-3

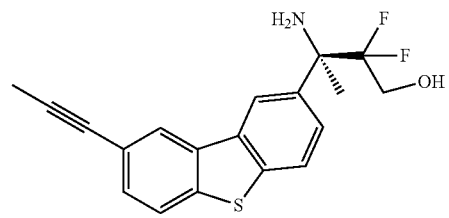 [SMILES: CC#Cc1ccc2sc3ccc([C@@](C)(N)C(F)(F)CO)cc3c2c1]

Example 100-3

(R)-3-Amino-2,2-difluoro-3-(8-(prop-1-yn-1-yl)
dibenzo[b,d]thiophen-2-yl)butanoic Acid (Example
100-3)

To a solution of (R)-N-((R)-3,3-difluoro-4-hydroxy-2-(8-(prop-1-yn-1-yl)dibenzo[b,d]thiophen-2-yl)buta n-2-yl)-2-methylpropane-2-sulfinamide (Example 100-2) (0.50 g, 1.08 mmol) in MeOH (15.0 ml) was added HCl (4N in dioxane, 0.50 ml). The reaction mixture was stirred at room temperature for 1.5 hours and concentrated in vacuo to give the title compound (Example 100-3) (0.30 g, 78.9%). 1H NMR (300 MHz, CD$_3$OD) δ 8.57 (d, J=1.5 Hz, 1H), 8.39 (d, J=1.2 Hz, 1H), 8.11 (d, J=8.7 Hz, 1H), 7.92 (d, J=8.7 Hz, 1H), 7.78 (dd, J=1.5, 8.4 Hz, 1H), 7.57 (dd, J=1.8, 8.4 Hz, 1H), 3.90 (s, 2H), 2.12 (s, 6H).

Example 100

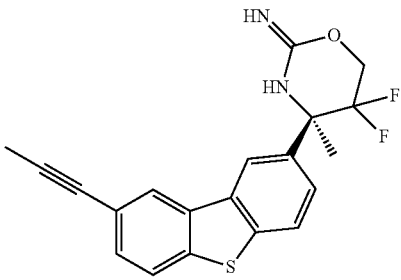 [SMILES: CC#Cc1ccc2sc3ccc([C@@]4(C)NC(=N)OCC4(F)F)cc3c2c1]

Example 100

(R)-5,5-Difluoro-4-methyl-4-(8-(prop-1-yn-1-yl)
dibenzo[b,d]thiophen-2-yl)-1,3-oxazinan-2-imine
(Example 100)

To a solution of (R)-3-Amino-2,2-difluoro-3-(8-(prop-1-yn-1-yl)dibenzo[b,d]thiophen-2-yl)butanoic acid (Example 100-3) (0.30 g, 0.84 mmol) in ethanol (10.0 ml) was added cyanogen bromide (0.17 g, 1.68 mmol) and stirred at 80° C. overnight. The mixture was concentrated under reduced pressure. The residue was extracted with ethyl acetate and water. The organic layer was dried over anhydrous MgSO$_4$, filtered and concentrated. The residue was purified by column chromatography (ethyl acetate/hexane=2:1) to afford the title compound (Example 100) (0.11 g, 35.5%).1H NMR (300 MHz, CD$_3$OD) δ 8.42 (s, 1H), 8.29 (s, 1H), 8.19 (d, J=0.6 Hz, 1H), 7.85 (d, J=5.1 Hz, 1H), 7.78 (d, J=4.8 Hz, 1H), 7.63 (d, J=4.8 Hz, 1H), 7.43 (dd, J=0.9, 4.8 Hz, 1H), 4.29-4.23 (m, 1H), 4.05-3.98 (m, 1H), 2.01 (s, 3H), 1.75 (d, J=1.2 Hz, 3H). ESI MS: m/z 371 (M+H)+; HPLC: 98.3%.

Example 103-1

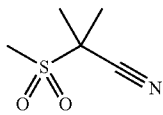

Example 103-1

2-Methyl-2-(methylsulfonyl)propanenitrile
(Example 103-1)

To a stirred solution of the 2-(methylsulfonyl)-acetonitrile (1 g, 8.4 mmol) in THF (25 mL) was added NaH (0.7 g, 60% in mineral oil, 16.8 mmol) slowly at 0° C. After 20 minutes, MeI (2.4 g, 16.8 mmol) was added. The mixture was allowed to warm overnight (16 hours). It was quenched with H$_2$O (10 ml), and the THF was evaporated. The aqueous solution was extracted with ethyl acetate (25 ml×3). The combined organic extracts were washed with brine (50 ml), and concentrated. Trituration of the residue with hexanes/ether gave the title compound (Example 103-1) (600 mg, 48%).

Example 103-2

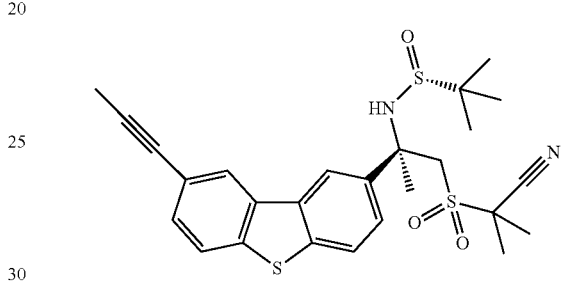

Example 103-2

(R)-N-((R)-1-((2-cyanopropan-2-yl)sulfonyl)-2-(8-(prop-1-yn-1-yl)di benzo[b,d]thio phen-2-yl)propan-2-yl)-2-methylpropane-2-sulfinamide (Example 103-2)

To a stirred solution of 2-methyl-2-(methylsulfonyl)-propanenitrile (Example 103-1) (765 mg, 5.20 mmol) in tetrahydrofuran (10 ml) was added n-butyllithium (2.5 M in hexanes, 2.6 ml, 6.42 mmol) at −78° C. After 30 minutes, a solution of (R,E)-2-methyl-N-(1-(8-(prop-1-yn-1-yl) dibenzo[b,d]thiophen-2-yl)ethylidene)propane-2-sulfinamide (Example 1-5) (800 mg, 2.17 mmol) in THF (10 ml) was added. The mixture was stirred at −78° C. for an additional 2 hours, quenched with saturated aqueous NH$_4$Cl (25 ml) and water (30 ml). It was extracted with ethyl acetate (100 ml×2). The combined organic extracts were concentrated. The residue was purified by flash chromatography (0 to 70% ethyl acetate in hexanes) to give the title compound (Example 103-2) as a white solid (350 mg, 31%).

Example 103-3

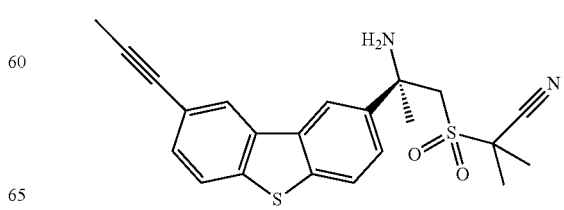

Example 103-3

(R)-2-((2-Amino-2-(8-(prop-1-yn-1-yl)dibenzo[b,d]thiophen-2-yl)propyl)sulfonyl)-2-methylpropanenitrile (Example 103-3)

A solution of (R)-N-((R)-1-((2-cyanopropan-2-yl)sulfonyl)-2-(8-(prop-1-yn-1-yl)dibenzo[b,d]thiophen-2-yl)propan-2-yl)-2-methylpropane-2-sulfinamide (Example 103-2) (300 mg, 0.58 mmol) in MeOH (20 ml) and HCl solution in dioxane (4 M, 2.5 ml) was stirred at room temperature for 1 hour. The mixture was concentrated, and the residue was triturated with ether to give a white solid. Ethyl acetate (50 ml) was added, washed with Na$_2$CO$_3$ solution, and the organic layer was dried and concentrated to give the title compound (Example 103-3) as a white solid (240 mg, 95%).

Example 103

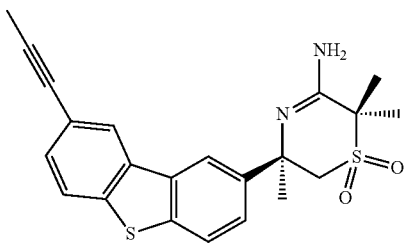

Example 103

(R)-5-Amino-3,6,6-trimethyl-3-(8-(prop-1-yn-1-yl)dibenzo[b,d]thiophen-2-yl)-3,6-dihydro-2H-1,4-thiazine 1,1-dioxide A mixture of compound (Example 103-3) (240 mg, 0.59 mmol), CuCl (87 mg, 0.88 mol) in ethanol (20 ml) was heated at reflux for 4 hours. The reaction mixture was filtered and concentrated. The residue was purified by combiflash (CH$_2$Cl$_2$:CH$_3$OH=15:1, normal phase silica, UV254) to give the title compound (Example 103) as a white solid (70 mg, 29%). LCMS: [M+1]: 411. 1H NMR (400 MHz, DMSO): δ 8.52 (S, 1H), 8.40 (s, 1H), 7.99-7.92 (m, 2H), 7.70-7.68 (d, J=8.4 Hz, 1H), 7.49-7.47 (d, J=8.0 Hz, 1H), 6.06 (br, 2H), 3.90-3.87 (d, J=14.4 Hz, 1H), 3.62-3.59 (d, J=14.4 Hz, 1H), 2.10-2.08 (d, J=11.2 Hz, 3H), 1.65 (s, 1H), 1.58 (s, 1H), 1.47 (s, 3H).

Example 109-1

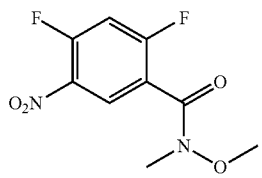 [SMILES: CON(C)C(=O)c1cc([N+](=O)[O-])c(F)cc1F]

2,4-Difluoro-N-methoxy-N-methyl-5-nitrobenzamide (Example 109-1)

To a solution of 2,4-difluoro-5-nitrobenzoic acid (11.0 g, 54.2 mmol) in CH$_2$Cl$_2$ (350 ml) was added DIPEA (13.4 ml, 81.3 mmol), N,O-Dimethylhydroxylamine hydrochloride (6.3 g, 65.0 mmol) and HATU (30.9 g, 81.3 mmol). The mixture was stirred at room temperature overnight, then the mixture was diluted with H$_2$O (500 ml) and the organic layer was separated. The aqueous layer was extracted with CH$_2$Cl$_2$ (150 ml), and the combined organic layer was washed with brine, dried over anhydrous Na$_2$SO$_4$ and concentrated. The residue was purified through silica gel (petroleum ether/ethyl acetate=30/1-15/1) to give the title compound (Example 109-1) as yellow oil (12.0 g, 90.2%). LCMS: [M+1]=247.1.

Example 109-2

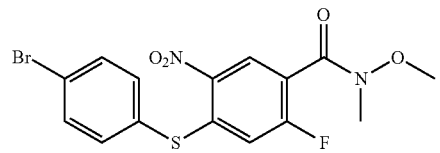

Example 109-2

4-((4-Bromophenyl)thio)-2-fluoro-N-methoxy-N-methyl-5-nitrobenzamide (Example 109-2)

To a solution of 4-bromobenzenethiol (7.7 g, 40.7 mmol) in MeOH (200 ml) was added NaH (2.4 g, 61.0 mmol, 60% oil dispersion) at −78° C. under argon atmosphere. The mixture was stirred for 30 minutes, then the solution of 2,4-difluoro-N-methoxy-N-methyl-5-nitrobenzamide (Example 109-1) (10.0 g, 40.7 mmol) in MeOH (50 ml) was added dropwise. After addition, the resulting mixture was stirred at −78° C. for 3 hours under argon atmosphere. Then the reaction solution was quenched with H$_2$O (300 ml) and extracted with ethyl acetate (300 ml×2). The combined organic layer was washed with brine and dried over anhydrous Na$_2$SO$_4$ and concentrated to give the title compound (Example 109-2) as a yellow solid (15.0 g, 88.7%). LCMS: [M+1]=415.0.

Example 109-3

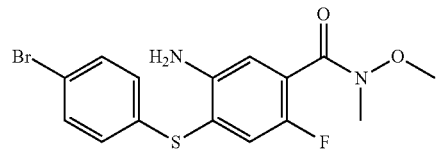 [SMILES: CON(C)C(=O)c1cc([N+](=O)[O-])c(Sc2ccc(Br)cc2)cc1F]

Example 109-3

5-Amino-4-((4-bromophenyl)thio)-2-fluoro-N-methoxy-N-methylbenzamide (Example 109-3)

To a solution of 4-((4-bromophenyl)thio)-2-fluoro-N-methoxy-N-methyl-5-nitrobenzamide (Example 109-2) (10.0 g, 24.1 mmol) in AcOH (200 ml) was added Zn dust (7.8 g, 120.5 mmol). The mixture was stirred at room temperature overnight. Then the mixture was diluted with H$_2$O (300 ml) and extracted with ethyl acetate (150 ml×3), the combined organic layer was washed with brine, dried over anhydrous Na$_2$SO$_4$ and concentrated to give 7.0 g crude title compound (Example 109-3) as light brown oil. LCMS: [M+1]=385.0.

Example 109-4

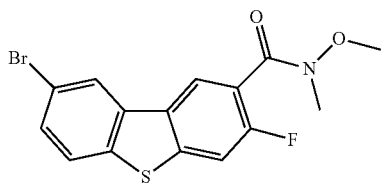 [SMILES: CON(C)C(=O)c1cc2c(cc1F)sc1ccc(Br)cc12]

Example 109-4

8-Bromo-3-fluoro-N-methoxy-N-methyldibenzo[b,d]thiophene-2-carboxamide (Example 109-4)

5-Amino-4-((4-bromophenyl)thio)-2-fluoro-N-methoxy-N-methylbenzamide (Example 109-3) (7.0 g, 18.2 mmol) was dissolved in HCl (v/v=1:1, 140 ml). The resulting mixture was cooled below 5° C. To this reaction mixture, sodium nitrite (1.9 g, 27.3 mmol) was added slowly with maintaining temperature below 5° C. after addition, reaction was stirred below 5° C. for 30 minutes. Then sodium fluoroborate (4.0 g, 36.4 mmol) was added to the above mentioned mixture and stirred below 5° C. for another 30 minutes. The above diazotized solution was then added to the stirred solution of copper (I) oxide (5.2 g, 36.4 mmol) in 0.1 N sulfuric acid (500 ml) at 35~400° C. The reaction mixture was stirred for 50 minutes. Ethyl acetate was added to the reaction mixture and filtered to remove inorganic compound. Filtrate was then extracted by ethyl acetate (150 ml×3). Organic volume was washed with water followed by brine and then concentrated under vacuum. The brown colored solid was purified through silica gel (petroleum ether/ethyl acetate=5/1) to give the title compound (Example 109-4) as a white-off solid (850 mg, two step yield: 9.6%). LCMS: [M+1]=368.0.

Example 109-5

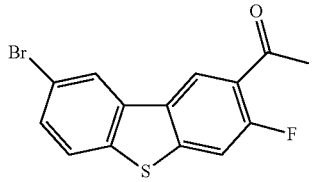

Example 109-5

1-(8-Bromo-3-fluorodibenzo[b,d]thiophen-2-yl)ethanone (Example 109-5)

To a solution of 8-bromo-3-fluoro-N-methoxy-N-methyl-dibenzo[b,d]thiophene-2-carboxamide (Example 109-4) (850 mg, 2.3 mmol) in THF (60 ml) was added MeMgBr (3.8 ml, 11.5 mmol, 3M in THF) dropwise at 0° C. After addition, the mixture was stirred at room temperature for 4 hours, then the reaction mixture was quenched with saturated aqueous NH$_4$Cl (100 ml) and extracted with ethyl acetate (100 ml×2). The combined organic layer was washed with brine, dried over anhydrous Na$_2$SO$_4$ and concentrated to give the title compound (Example 109-5) as a white-off solid (700 g, 93.8%).

Example 109-6

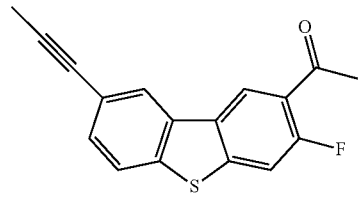 [SMILES: CC#Cc1ccc2sc3cc(F)c(C(C)=O)cc3c2c1]

Example 109-6

1-(3-Fluoro-8-(prop-1-yn-1-yl)dibenzo[b,d]thiophen-2-yl)ethanone (Example 109-6)

The mixture of 1-(8-bromo-3-fluorodibenzo[b,d]thiophen-2-yl)ethanone (Example 109-5) (1.5 g, 4.6 mmol), tributyl(prop-1-ynyl)stannane (2.3 g, 6.9 mmol), Pd(PPh$_3$)$_4$ (500 mg, 0.46 mmol) in dioxane (100 ml) was stirred at 100° C. for 16 hours. The reaction mixture was concentrated and residue was purified by combiflash (petroleum ether:ethyl acetate=5:1, normal phase silica, UV 254) to give the title compound (Example 109-6) (800 mg, 61%) as a white solid. LC-MS: [M+H]$^+$=283.

Example 109-7

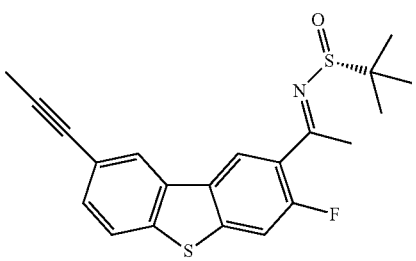 [SMILES: CC#Cc1ccc2sc3cc(F)c(/C(C)=N/[S@](=O)C(C)(C)C)cc3c2c1]

Example 109-7

(R,E)-N-(1-(3-fluoro-8-(prop-1-yn-1-yl)dibenzo[b,d]thiophen-2-yl)ethylidene)-2-m ethylpropane-2-sulfinamide (Example 109-7)

A mixture of 1-(3-fluoro-8-(prop-1-yn-1-yl)dibenzo[b,d]thiophen-2-yl)ethanone (Example 109-6) (650 mg, 2.3 mmol), (R)-2-methylpropane-2-sulfinamide (836 mg, 6.9 mmol), Ti(OEt)₄ (2.6 g, 11.5 mmol) in THF (25 ml) was stirred at reflux for 16 hours. Water (25 ml) was added and extracted with ethyl acetate (50 ml×2). The organic layer was dried and concentrated. Residue was purified by combiflash (petroleum ether:ethyl acetate=5:1, normal phase silica, UV 254) to give the title compound (Example 109-7) (800 mg, 90%) as a white solid. LC-MS: [M+H]⁺=386.

Example 109-8

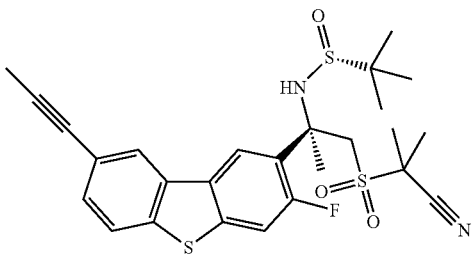 [SMILES: CC#Cc1ccc2sc3cc(F)c([C@](C)(CS(=O)(=O)C(C)(C)C#N)N[S@](=O)C(C)(C)C)cc3c2c1]

Example 109-8

(R)-N-((R)-1-((2-cyanopropan-2-yl)sulfonyl)-2-(3-fluoro-8-(prop-1-yn-1-yl)dibenzo[b,d]thiophen-2-yl)propan-2-yl)-2-methylpropane-2-sulfinamide (Example 109-8)

To a stirred solution of 2-methyl-2-(methylsulfonyl)-propanenitrile (Example 103-1) (228 mg, 1.56 mmol) in tetrahydrofuran (10 ml) was added n-butyllithium (2.5 M in hebxanes, 0.6 ml, 1.56 mmol) at −78° C. After 30 minutes, a solution of (R,E)-N-(1-(3-fluoro-8-(prop-1-yn-1-yl)dibenzo[b,d]thiophen-2-yl)ethylidene)-2-methyl propane-2-sulfinamide (Example 109-7) (300 mg, 0.78 mmol) in THF (10 ml) was added. The mixture was stirred at −78° C. for an additional 2 hours, then quenched with saturated aqueous NH₄Cl (25 ml) and water (30 ml). The resulting mixture was extracted with ethyl acetate (100 ml×2). The combined organic extracts were concentrated. The residue was purified by flash chromatography (0 to 70% ethyl acetate in hexanes) to give the title compound (Example 109-8) as a white solid (300 mg, 73%). LC-MS: [M+H]⁺=533.

Example 109-9

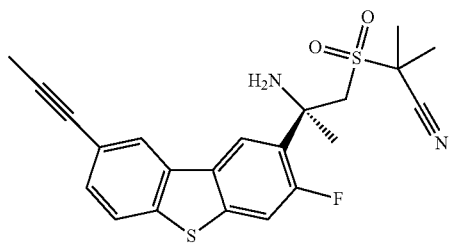 [SMILES: CC#Cc1ccc2sc3cc(F)c([C@@](C)(N)CS(=O)(=O)C(C)(C)C#N)cc3c2c1]

Example 109-9

(R)-2-((2-Amino-2-(3-fluoro-8-(prop-1-yn-1-yl)dibenzo[b,d]thiophen-2-yl)propyl)sulfonyl)-2-methylpropanenitrile (Example 109-9)

To a mixture of (R)-N-((R)-1-((2-cyanopropan-2-yl)sulfonyl)-2-(3-fluoro-8-(prop-1-yn-1-yl)dibenzo[b,d]thiophen-2-yl)propan-2-yl)-2-methylpropane-2-sulfinamide (Example 109-8) (300 mg, 0.56 mmol) and Acetonitrile (4 ml) was added hydrogen chloride (4N in dioxane, 2 ml, 4 mmol). The reaction mixture was stirred at room temperature for 1 hour and concentrated in vacuo to give the title compound (Example 109-9) as a yellow solid, which was used directly in the next step.

Example 109

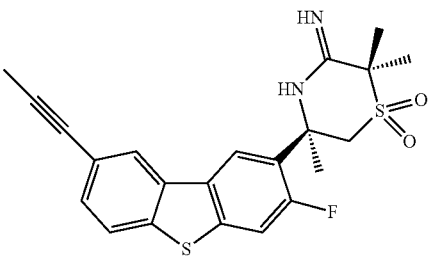

Example 109

((R)-5-Amino-3-(3-fluoro-8-(prop-1-yn-1-yl)dibenzo[b,d]thiophen-2-yl)-3,6,6-trim ethyl-3,6-dihydro-2H-1,4-thiazine 1,1-dioxide) (Example 109)

A mixture of (R)-2-((2-amino-2-(3-fluoro-8-(prop-1-yn-1-yl)dibenzo[b,d]thiophen-2-yl)propyl)sulfonyl)-2-methylpropanenitrile (Example 109-9) (220 mg, 0.51 mmol), CuCl (51 mg, 0.51 mmol) in ethanol (20 ml) was stirred at reflux for 4 hours. The reaction mixture was filtered and concentrated. The residue was purified by prep-HPLC to give the title compound (Example 109) as a white solid (102 mg, 49%). LC-MS: [M+H]⁺=429. 1H NMR (400 MHz, CDCl₃) δ ppm 8.19-8.17 (d, J=8.0 Hz, 1H), 8.13 (s, 1H), 7.73-7.71 (d, J=8.0 Hz, 1H), 7.56-7.53 (d, J=12.0 Hz, 1H), 7.47-7.45 (d, J=8.0 Hz, 1H), 3.81-3.69 (m, 2H), 2.09 (s, 3H), 1.98 (s, 3H), 1.81 (s, 3H), 1.72 (s, 3H).

Example 131-1

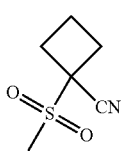

Example 131-1

1-(Methylsulfonyl)cyclobutanecarbonitrile (Example 131-1)

To a mixture of 2-(methylsulfonyl)-acetonitrile (2.00 g, 16.8 mmol), benzenetriethylammonium chloride (0.19 g, 0.84 mmol), and potassium carbanate (5.88 g, 42.0 mmol) in DMF (40.0 ml) was added 1,3 dibromopropane (0.17 ml, 16.8 mmol) dropwise at 10° C. The reaction mixture was warmed to room temperature with continuous stirring for 3 hours and quenched with water. The organic layer was extracted by ethyl acetate, washed with water, dried over anhydrous MgSO$_4$ and concentrated in vacuo to get the product as yellow oil. The product obtained was then purified by silica gel column chromatography (10% ethyl acetate in hexane) to afford the title compound (Example 131-1) (1.65 g, 62.0%).

Example 131-2

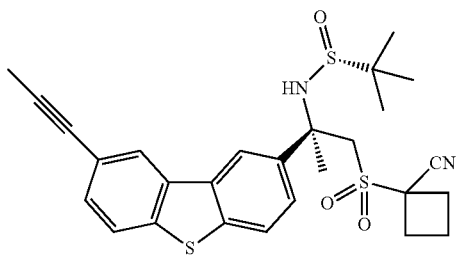 [SMILES: CC#Cc1ccc2sc3ccc([C@](C)(CS(=O)(=O)C4(C#N)CCC4)N[S@](=O)C(C)(C)C)cc3c2c1]

Example 131-2

(R)-N-((R)-1-((1-Cyanocyclobutyl)sulfonyl)-2-(8-(prop-1-yn-1-yl)dibenzo[b,d]thiophen-2-yl)propan-2-yl)-2-methylpropane-2-sulfinamide (Example 131-2)

To a stirred solution of 1-(Methylsulfonyl)cyclobutanecarbonitrile (Example 131-1) (1.16 g, 7.35 mmol) in tetrahydrofuran (40.0 ml) was added n-butyl lithium (2.5 M in hexanes, 3.00 ml, 7.50 mmol) at −78° C. After 30 minutes, a solution of the compound (Example 1-5) (0.99 g, 2.69 mmol) in THF was added. The mixture was stirred at −78° C. for additional 2 hours, quenched with saturated NH$_4$Cl solution and extracted with ethyl acetate. The organic layer was collected, dried over anhydrous MgSO$_4$ and concentrated in vacuo to get the product as yellow oil. The product obtained was then purified by silica gel column chromatography (40% ethyl acetate in hexane) to afford the title compound (Example 131-2) (0.39 g, 28.0%).

Example 131-3

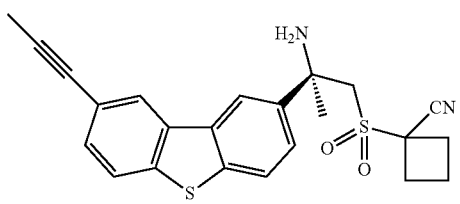 [SMILES: CC#Cc1ccc2sc3ccc([C@@](C)(N)CS(=O)(=O)C4(C#N)CCC4)cc3c2c1]

Example 131-3

(R)-1-((2-Amino-2-(8-(prop-1-yn-1-yl)dibenzo[b,d]thiophen-2-yl) propyl)sulfonyl)cyclobutanecarbonitrile (Example 131-3)

To a mixture of (Example 131-2) (0.30 g, 0.57 mmol) and THF (20.0 ml) was added hydrogen chloride (4N in dioxane, 0.90 ml, 3.60 mmol). The reaction mixture was stirred at room temperature for 1.5 hours and concentrated in vacuo to yield the title compound (Example 131-3) as colorless oil that was used directly in the next step.

Example 131

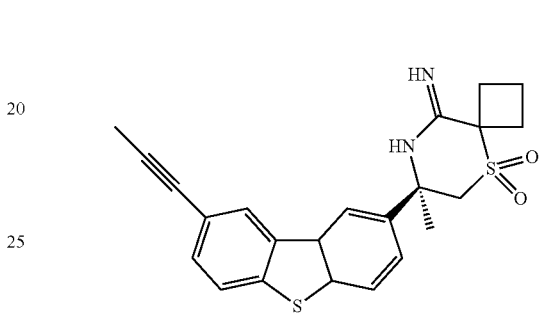

Example 131

(R)-9-Imino-7-methyl-7-(8-(prop-1-yn-1-yl)-4a,9b-dihydrodibenzo[b,d]thiophen-2-yl)-5-thia-8-azaspiro[3.5]nonane 5,5-dioxide (Example 131)

A mixture of compound (Example 131-3) (0.23 g, 0.54 mmol), CuCl (0.09 g, 0.90 mmol) in ethanol (30.0 ml) was heated at reflux for 4 hours. The reaction mixture was filtered through zeolite and the filtrate was concentrated. The concentrate was redissolved using dichloromethane and washed with excess of water and brine. The organic layer was collected, dried over anhydrous MgSO$_4$ and concentrated in vacuo to get the product as solid. The product obtained was then purified by silica gel column chromatography (2% methanol in dichloromethane) to give the title compound (Example 131) as an off white solid (0.07 g, 30%). $^1$H NMR (300 MHz, CH$_3$OD): δ 8.27 (S, 1H), 8.21 (s, 1H), 7.83-7.75 (m, 2H), 7.53 (d, J=9.0 Hz, 1H), 7.41 (d, J=9.0 Hz, 1H), 3.67-3.54 (m, 2H), 2.83-2.61 (m, 4H), 2.55-2.12 (m, 2H), 2.07 (s, 3H), 1.81 (s, 3H), Analytical data: ESI-MS; m/z 423.1194 [M+H]+, molecular Formula; C$_{23}$H$_{22}$N$_2$O$_2$S$_2$ and HPLC; 99.5%.

Example 205-1

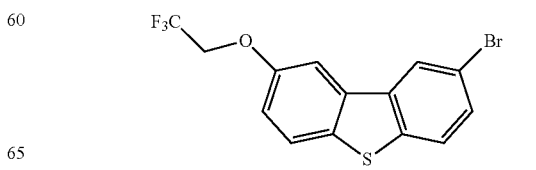

Example 205-1

2-Bromo-8-(2,2,2-trifluroethoxy)dibenzo[b,d]thiophene (Example 205-1)

Sodium (0.53 g, 23 mmol) was dissolved in trifluroethanol (14.1 mL, 176 mmol) at room temperature. The reaction mixture was then homogenized by adding 30 ml of NMP. Subsequently (Example 1-2) (6.00 g, 17.6 mmol and copper I bromide (0.25 g, 1.76 mmol) were added. The reaction mixture was refluxed at 250° C. for four hours. The reaction mixture was then quenched with 4N HCl (15.0 ml) and extracted with CH$_2$Cl$_2$. The organic layer was collected, dried over anhydrous MgSO$_4$ and concentrated in vacuo to get the product as yellow oil. The product obtained was then purified by silica gel column chromatography (2% ethyl acetate in hexane) to afford the title compound (Example 205-1) (3.88 g, 61.0%). $^1$H NMR (300 MHz, CDCl$_3$) δ 8.10 (d, J=3.0 Hz, 1H), 7.68 (d, J=9.0 Hz, 1H), 7.61 (d, J=6.0 Hz, 1H), 7.50 (m, 2H), 7.10 (dd, J=3.0, 9.0 Hz, 1H), 4.47-4.39 (m, 2H),

Example 205-2

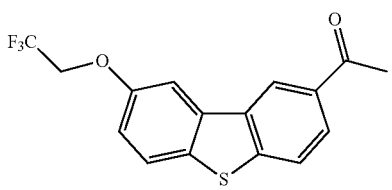 [SMILES: CC(=O)c1ccc2sc3ccc(OCC(F)(F)F)cc3c2c1]

Example 205-2

1-(8-(2,2,2-Trifluoroethoxy)dibenzo[b,d]thiophen-2-yl)ethanone (Example 205-2)

To a mixture of (Example 205-1) (3.80 g, 10.5 mmol), Pd(PPh$_3$)$_4$(1.22 g, 1.05 mmol) and n-methylpyrrolidinone (NMP) (30.0 ml) was added tributyl (1-ethoxyvinyl)tin (5.69 g 15.8 mmol) at room temperature. The mixture was stirred at 130° C. for 3 hour under nitrogen atmosphere. The reaction mixture was then quenched with 4N HCl and extracted with CH$_2$Cl$_2$. The organic layer was collected, dried over anhydrous MgSO$_4$ and concentrated in vacuo to get the product as black oil. The product obtained was then purified by silica gel column chromatography (10% ethyl acetate in hexane) to afford the title compound (Example 205-2) (2.20 g, 65.0%). $^1$H NMR (300 MHz, CDCl$_3$) δ 8.69 (d, J=3.0 Hz, 1H), 8.06 (d, J=9.0 Hz, 1H), 7.91 (d, J=9.0 Hz, 1H), 7.87-7.74 (m, 2H), 7.20 (dd, J=3.0, 9.0 Hz, 1H), 4.57-4.49 (m, 2H), 2.75 (s, 3H).

Example 205-3

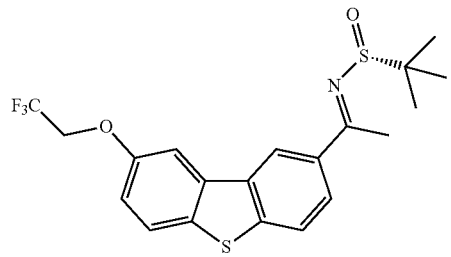 [SMILES: C/C(=N\[S@](=O)C(C)(C)C)c1ccc2sc3ccc(OCC(F)(F)F)cc3c2c1]

Example 205-3

(R,E)-N-(1-(8-(2,2,2-Trifluoroethoxy)dibenzo[b,d]thiophen-2-yl)ethylidene)propane-2-sulfinamide (Example 205-3)

A mixture of (Example 205-2) (1.00 g 3.10 mmol), (R)-2-methylpropane-2-sulfinamide (1.27 g, 9.30 mmol), Ti(OEt)$_4$ (4.25 g, 18.6 mmol) and THF (30.0 ml) was refluxed overnight. The reaction was quenched with water and extracted with CH$_2$Cl$_2$. The precipitate was filtered off, the organic layer was collected, dried over anhydrous MgSO$_4$ and concentrated in vacuo to get the product as yellow oil. The product was then purified by silica gel column chromatography (25% ethyl acetate in hexane) to afford the title compound (Example 205-3) (1.08 g, 82.0%). $^1$H NMR (300 MHz, CDCl$_3$) δ 8.56 (d, J=3.0 Hz, 1H), 8.04 (d, J=9.0 Hz, 1H), 7.86 (d, J=9.0 Hz, 1H), 7.77 (d, J=9.0 Hz, 1H), 7.71 (d, J=3.0 Hz, 1H), 7.17 (dd, J=3.0, 9.0 Hz, 1H), 4.57-4.49 (m, 2H), 2.90 (s, 3H), 1.39 (s, 9H).

Example 205-4

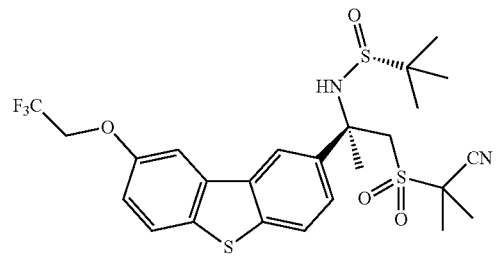 [SMILES: CC(C)(C)[S@@](=O)N[C@@](C)(CS(=O)(=O)C(C)(C)C#N)c1ccc2sc3ccc(OCC(F)(F)F)cc3c2c1]

Example 205-4

(R)-N-((R)-1-((2-Cyanopropan-2-yl)sulfonyl)-2-(8-(2,2,2-trifluoroethoxy) dibenzo[b,d]thiophen-2-yl) propan-2-yl)-2-methylpropane-2-sulfinamide (Example 205-4)

To a stirred solution of 2-methyl-2-(methylsulfonyl)-propanenitrile (0.77 g, 5.25 mmol) in tetrahydrofuran (25 ml) was added n-butyllithium (2.5 M in hexanes, 2.10 ml, 5.25 mmol) at −78° C. After 30 minutes, a solution of the compound (Example 205-3) (0.90 g, 2.10 mmol) in THF was added. The mixture was stirred at −78° C. for an additional 2 hours, quenched with water and extracted with ethyl acetate. The organic layer was collected, dried over anhydrous MgSO₄ and concentrated in vacuo to get the product as yellow oil. The product obtained was then purified by silica gel column chromatography (40% ethyl acetate in hexane) to afford the title compound (Example 205-4) (0.58 g, 48%). ¹H NMR (300 MHz, CDCl₃): δ 8.23 (s, 1H), 7.85 (d, J=9.0 Hz, 1H), 7.75 (d, J=9.0 Hz, 1H), 7.64-7.57 (m, 2H), 7.13 (dd, J=3.0, 9.0 Hz, 1H), 4.52-4.09 (m, 2H), 4.15-4.04 (m, 2H), 2.12 (s, 3H), 1.80 (s, 3H), 1.68 (s, 3H), 1.34 (s, 9H).

Example 205-5

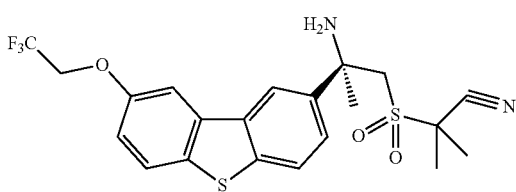 [SMILES: CC(C)(C#N)S(=O)(=O)C[C@](C)(N)c1ccc2sc3ccc(OCC(F)(F)F)cc3c2c1]

(Example 205-5

(R)-2-((2-Amino-2-(8-(2,2,2-trifluoroethoxy)dibenzo[b,d]thiophen-2-yl)propyl) sulfonyl)-2-methylpropanenitrile (Example 205-5)

To a mixture of (Example 205-4) 0.55 g, 0.96 mmol) and THF (25.0 mL) was added hydrogen chloride (4N in dioxane, 1.50 mL, 5.74 mmol). The reaction mixture was stirred at room temperature for 1.5 hours and concentrated in vacuo to yield (Example 205-5) as colorless oil that was used directly in the next step.

Example 205

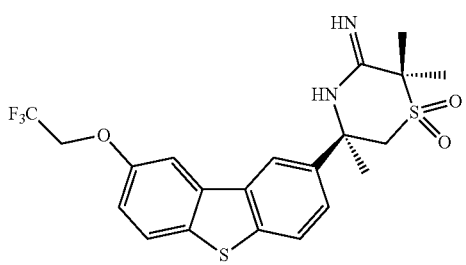

Example 205

(5R)-3-Imino-2,2,5-trimethyl-5-(8-(2,22-trifluoroethoxy)-4a,9b-dihydrodibenzo[b,d]thiophen-2-yl)thiomorpholine 1,1-dioxide (Example 205)

A mixture of compound (Example 205-5) (0.45 g, 0.96 mmol), CuCl (0.14 g, 1.44 mmol) in ethanol (30 ml) was heated at reflux for 4 hours. The reaction mixture was filtered through zeolite and the filtrate was concentrated. The concentrate was redissolved using dichloromethane and washed with excess of water and brine. The organic layer was collected, dried over anhydrous MgSO₄ and concentrated in vacuo to get the product as solid. The product obtained was then purified by silica gel column chromatography (2% methanol in dichloromethane) to give (Example 205) as a off white solid (70 mg, 15%). ¹H NMR (300 MHz, CH₃OD): δ 8.34 (s, 1H), 7.95 (s, 1H), 7.88-7.81 (m, 2H), 7.59 (dd J=3.0; 9.0 Hz, 1H), 7.24-7.21 (m, 1H), 4.76-4.68 (m, 2H), 3.77 (d, J=15 Hz, 1H), 3.63 (d, J=15 Hz, 1H), 1.89 (s, 3H), 1.74 (s, 3H), 1.68 (s, 3H). Analytical data: ESI-MS; m/z 471.004 [M+H]+, molecular Formula; C₂₁H₂₁F₃N₂O₃S₂ and HPLC; 100%

Assays

I. Potency Assays a. Beta-Secretase Activity Assay

The generation of amyloid β peptide that aggregates in the brain of patients with Alzheimer's disease (AD) depends on two sequential cleavages of the amyloid precursor protein (APP). Extracellular cleavage of APP by β-secretase (β-site amyloid precursor protein cleaving enzyme 1 (BACE1)) generates a soluble fragment, and a cell-associated C-terminal fragment which is subsequently released by γ-secretase. It is known that a BACE1 inhibitor can enter the brain sufficiently to lower amyloid β peptide levels. Therefore, inhibition of BACE1 has emerged as a key target for anti-amyloid therapy for the treatment of AD. In vitro assays have been developed to detect β-secretase activity using IC₅₀ value which is defined as the concentration of BACE1 inhibitors that is required to inhibit 50% of BACE1 activity.

A BACE1 activity assay kit from AnaSpec (Fremont, Calif.) was used to determine the potency of the selected BACE1 inhibitors by AnaSpec BACE1 fluorescent assay. The recombinant β-secretase enzyme was diluted 1:200 in 1× assay buffer (1 part of 1× assay buffer and 1 part of TBS containing 0.1% Tween 20). The enzyme was added in a volume of 40 μl to each well of a black 96-well micro plate.

The BACE1 inhibitors were serially diluted into DMSO from their 10 mM stock concentrations in DMSO. The serially diluted inhibitors were diluted 1:100 into 1× assay buffer in a 96-well polypropylene plate (assay dilution plate). The final concentration of the BACE1 inhibitor tested was 300 nM, 100 nM, 30 nM, 10 nM, 3 nM, 1 nM 0.3 nM, and 0.00 nM. Dose responses for inhibitors were run in duplicate.

A volume of 10 μl of the inhibitor from the assay dilution plate, a control inhibitor LY2886721 or inhibitor vehicle was then added to each well of the black 96-well micro plate containing BACE1.

To each well of the black 96-well micro plate, 50 μl of the β-secretase substrate (Hylite Fluor 488) diluted 1:100 using assay buffer was added. The reagents were mixed gently and the assay plate was placed into a POLARstar fluorescent plate reader with excitation wavelength set at 485 nm and the emission wavelength set at 520 nm. The plate reader was set to take readings every 5 minutes for up to 30 minutes or a 30 minute endpoint reading was used.

An appropriate integrated first-order rate equation was used to fit the data accumulated over a 30-40 minute collection period. The selected BACE1 inhibitor IC₅₀ values in accordance with examples of the invention were then determined for their IC₅₀ values and illustrated in Table 1 below. FIG. 1 shows an exemplary dose response curve evaluating the inhibition of amyloid β peptide secretion by the treatment of the selected compound (example 1) wherein the IC₅₀ value of example 1 is 30.25±3.98 nM.

TABLE 1

Beta-Secretase Activity of Selected Compounds

| Examples | BACE1 IC$_{50}$ (nM) | BACE2 IC$_{50}$ (nM) | Cell Abeta$_{40}$ IC50 (nM) |
|---|---|---|---|
| 1 | 26 | | |
| 38 | 44 | 24 | |
| 72 | 21 | | |
| 79 | 87 | | |
| 80 | 48 | | |
| 81 | >300 | | |
| 82 | >300 | | |
| 85 | >300 | | |
| 86 | 218 | | |
| 87 | 17 | | |
| 88 | >300 | | |
| 89 | >300 | | |
| 90 | 78 | | |
| 91 | >300 | | |
| 92 | >300 | | |
| 94 | 81 | | |
| 99 | >300 | | |
| 100 | 202 | | |
| 103 | 39 | 12 | 13 |
| 104 | >300 | | |
| 105 | >300 | | |
| 106 | >300 | | |
| 109 | 25 | 16 | 5 |
| 115 | >300 | | |

A BACE2 activity assay kit from AnaSpec (Fremont, Calif.) was used to determine the potency of the selected compounds by AnaSpec BACE2 fluorescent assay. To each well of a black 96-well micro plate, 50 µl of the β-secretase substrate (Hylite Fluor 488) diluted 1:100 using assay buffer was first added.

The compounds were serially diluted (1:2) into DMSO from their 10 mM stock concentrations in DMSO. The serially diluted inhibitors were diluted 1:100 into 1× assay buffer in a 96-well polypropylene plate (assay dilution plate). The final concentration of these compounds tested was 300 nM, 150 nM, 75 nM, 37.5 nM, 18.75 nM, 9.375 nM, 4.688 nM, 2.344 nM, 1.172 nM, 0.586 nM, and 0.293 nM.

A volume of 10 µl of the inhibitor from the assay dilution plate, a control inhibitor LY2886721 or inhibitor vehicle was then added to each well of the black 96-well micro plate.

The recombinant BACE2 was diluted in an assay buffer and the final BACE2 was 10.6 nM. The enzyme was added in a volume of 40 µl to each well of a black 96-well micro plate.

The reagents were mixed gently and the assay plate was placed into a POLARstar fluorescent plate reader with excitation wavelength set at 485 nm and the emission wavelength set at 520 nm. The plate reader was set to take readings every 5 minutes for up to 30 minutes or a 30 minute endpoint reading was used.

An appropriate integrated first-order rate equation was used to fit the data accumulated over a 30-40 minute collection period. Dose responses for inhibitors were run in duplicate.

Figure 2:
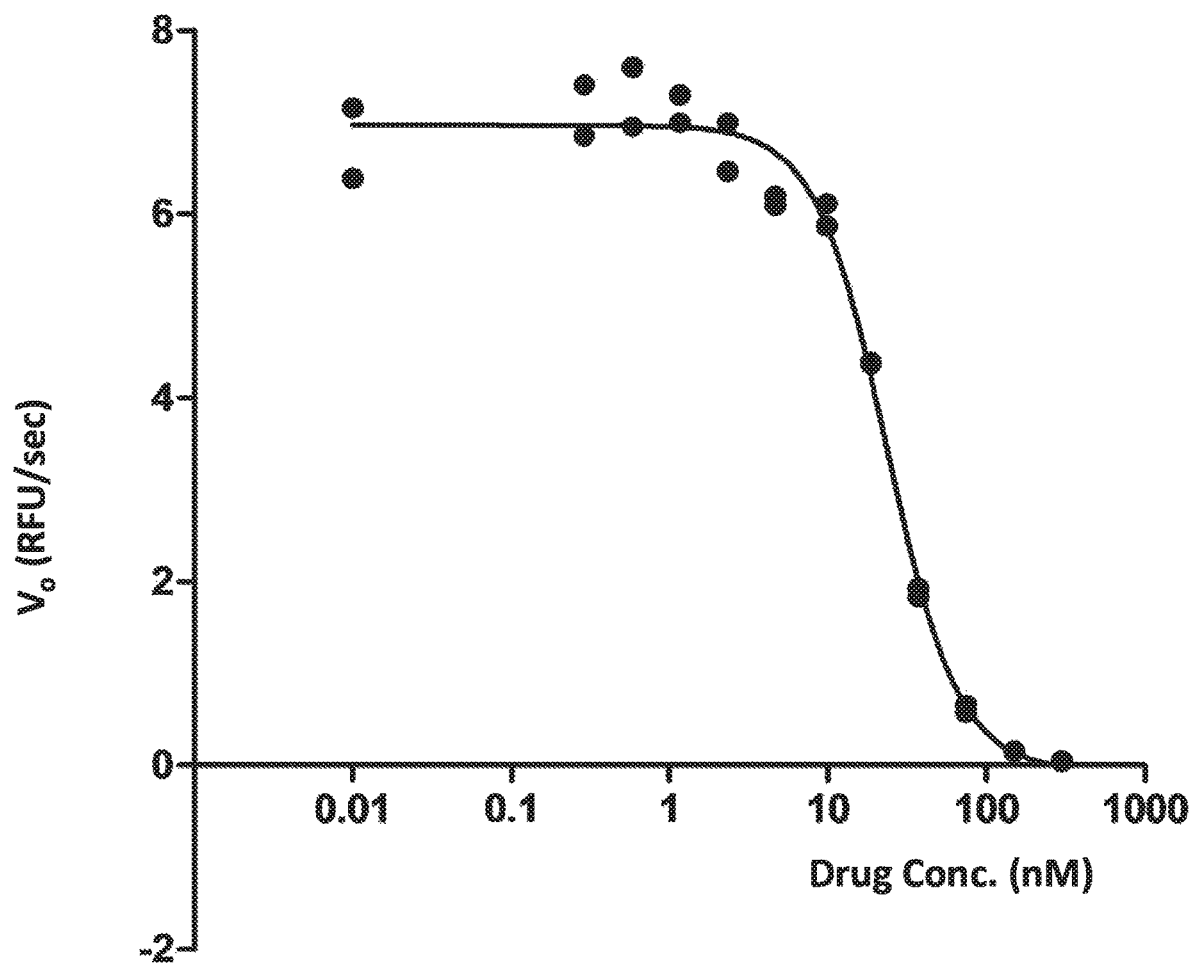
FIG. 2 shows an exemplary dose response curve evaluating the inhibition of amyloid β peptide secretion by the treatment of a selected BACE1 inhibitor using the AnaSpec BACE2 fluorescent assay.

The selected BACE2 inhibitor IC$_{50}$ values, in accordance with examples of the invention, were then determined for their IC$_{50}$ values and illustrated in Table 1 below and FIG. 2. FIG. 2 shows an exemplary dose response curve evaluating the inhibition of amyloid β peptide secretion by the treatment of the selected compound (example 71) wherein BACE2 IC$_{50}$ value of example 71 is 23.76±1.52 nM.

b. Cell Amyloid-Beta Production Assay

Amyloid-β (Aβ) is a 33-42-amino acid post-proteolytic peptide generated as the result of the sequential cleavage of amyloid precursor protein (APP) by BACE1 and γ-secretase. Substantial evidence points to aggregation and deposition of certain isoforms of amyloid β peptide in the brain being causal to neurodegeneration and dementia typical of AD. There are two major isoforms of Aβ which are monitored as a biomarker to gain early read on Aβ aggregation: Aβ340 and Aβ342. Increased extracellular accumulation of amyloid β peptide results in the formation of amyloid β peptide oligomers, cerebral amyloid plaques, neurodegeneration, and ultimately brain atrophy, all of which play a pivotal role in AD neuropathological hallmarks.

The reagents for the cell amyloid beta production assay were prepared as follows.

7PA2 CHO cells (licensed from Dr. Dennis Selkoe's laboratory) were plated into 96-well plates at a density of 50,000 cells per 0.1 µL complete medium (DMEM medium containing 10% fetal bovine serum, L-glutamine, penicillin/streptomycin and 200 µg/ml of G418). Cells were incubated for 16-18 hours in complete medium and the culture medium was aspirated and discarded. Fresh complete medium containing test articles or positive control, LY2886721, within drug concentration range from 0.01 to 100 nM or complete medium only (controls) was added for 12 hours, and the cell culture medium was assayed directly or following a dilution with complete cell culture medium and frozen at −80° C. until it could be assayed for Aβ38, Aβ40 and Aβ42 content using an MSD multiplex electrochemiluminescence immunoassay.

In the Meso Scale Discovery electrochemiluminescence immunoassay, on a block plate, add 150 µL of Diluent 35 to each well, seal the plate with an adhesive plate seal and incubate with shaking for 1 hour at room temperature. Wash and then add detection antibody solution and samples. Wash the plate 3 times with at least 150 µL/well of wash buffer. Add 25 µL of detection antibody solution to each well. Then, add 25 µL of diluted sample, calibrator, or control per well. Seal the plate with an adhesive plate seal and incubate with shaking for 2 hours at room temperature. After the incubation, wash the plate 3 times with at least 150 µL/well of wash buffer. Add 150 µL of 2× Read Buffer T to each well. Read the plate on the MSD imager. No incubation in read buffer is required before reading the plate.

Figure 3:
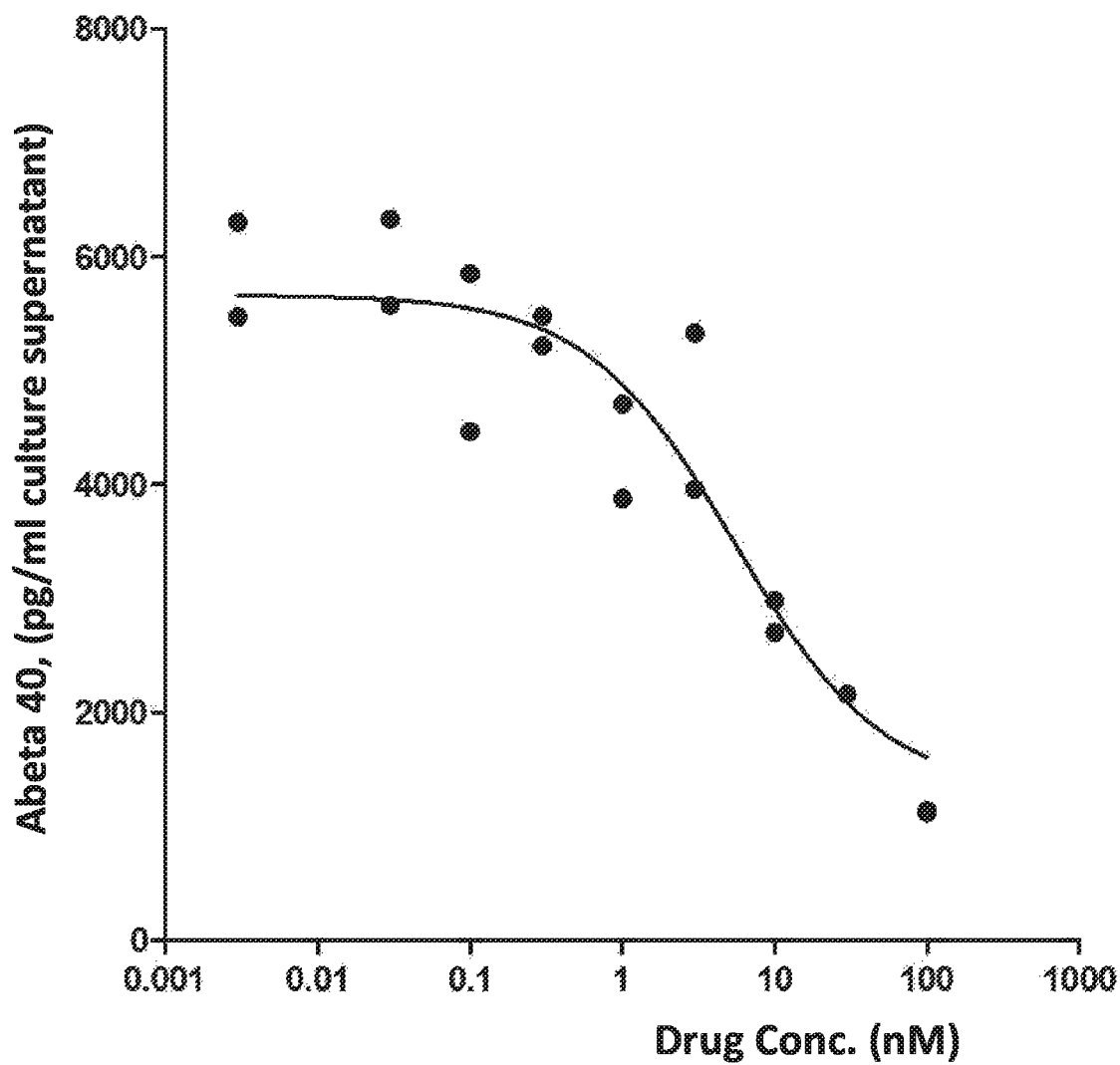
FIG. 3 shows the effect of a selected BACE1 inhibitor on the cellular production of amyloid β peptides.

The BACE1 inhibitors of the present invention were screened for their effects on cellular production of amyloid β peptide by incubating with cells for a period of time (Table 1). Through this in vitro assay, the compounds of the invention were expected to reduce cellular production of some isoforms of amyloid β peptide significantly. FIG. 3 shows the effect of a selected BACE1 inhibitor (example 109) on cellular production of amyloid β peptides wherein cell Aβ40 IC$_{50}$ (nM) of example 109 is 5.50±1.95 nM.

II. Selectivity Assays a. Cathepsin D Activity Assay

Cathepsin D (Cat D) is a major intercellular member of the mammalian aspartic proteinase family and is thought to be in the normal degradation of intracellular and extracellular proteins. Thus inhibition of CatD may lead to unwanted pathophysiological conditions. CatD plays a role in the generation of biologically active peptides, the processing of exogenous antigens and to a smaller extent the beta-amyloid precursor protein. The development of a CatD activity assay is used to determine any potential cross reactivity for compounds selected from the β-secretase activity assay and to determine the selectivity to BACE1 inhibition. The CatD activity is reported for assessing target selectivity ratio (CatD $IC_{50}$/BACE1 $IC_{50}$).

The reagents for the cathepsin D assay were prepared as follows.

Human recombinant cathepsin D stored frozen in 2.0 µl aliquots was thawed and 42 µl of enzyme buffer (0.1M NaOAC, 0.2 M NaCl, pH 3.5) was added and incubated at 37° C. for 30 minutes. After 30 minutes the enzyme was further diluted to a final volume of 4.4 ml in enzyme buffer containing 5.0 mM DTT for immediate use in the cathepsin D assay.

The 7-methoxycoumarin-labeled peptide substrate (ES010) for cathepsin D was supplied as a 6.2 mM stock in DMSO. For use in the cathepsin D assay, the 6.2 mM stock was diluted to a 1.55 mM stock with DMSO. The 1.55 mM peptide stock in DMSO was further diluted 1:100 in reaction buffer (0.1M NaOAC, 0.2M NaCl, 0.1% Tween 20, 5.0 mM DTT, pH3.5) to create a 15.5 µM stock for use in the assay.

The selected BACE1 active compounds were weighed and brought up in DMSO at a concentration of 30 mM. Serial 1:2 dilutions in DMSO were made for the selected BACE1 active compounds to create concentrations of 15, 7.5, 3.75, 1.875, 0.938, 0.469, 0.234, 0.117, 0.059, 0.029 mM in DMSO that serve as 1,000× stocks for use in the cathepsin D assay. DMSO without compound served as a DMSO vehicle control for the cathepsin D assay. For each test compound, 30 µl of each dilution was pipetted into a separate well of a 96-well polypropylene plate. This polypropylene plate was labeled as the DMSO dilution plate and a plate map of test compound locations was made.

Test compounds from the DMSO dilution plate require a 1:100 dilution into reaction buffer before they can be added to the cathepsin D assay plate. To accomplish the 1:100 dilution of test compounds, 2.0 µl of each test compound at each concentration was pipetted from the DMSO dilution plate (using a multi-channel pipette calibrated to accurately dispense a 2.0 µl volume) into a new 96-well polypropylene plate using the plate map created for the DMSO dilution plate. This 96-well plate served as the inhibitor dilution plate. Next, 198 µl of reaction buffer was pipetted into each well of the inhibitor dilution plate (using a multi-channel pipette calibrated for accurate delivery of a 198 µl volume) and the pipetted test compound mixed by gentle up and down pipetting.

A 1.0 mM stock of pepstatin A was made in DMSO and aliquotted into 5.0 µl samples for freezing and storage at −20° C. Upon thawing, 45 µl of DMSO (1:10 dilution) was added to create a 100 µM stock of pepstatin A in DMSO. The 100 µM Pepstatin A stock was further diluted 1:10 with DMSO to create a 10 µM stock in DMSO. The 10 µM stock was serially diluted 1:2 with DMSO to create stocks of 5, 2.5, 1.25, 0.625, 0.313, 0.156, 0.078, 0.039, 0.0195, 0.0098 µM in DMSO. The pepstatin A stocks in DMSO are added to a DMSO dilution plate and a mapping location for Pepstatin A added to the inhibitor dilution plate. Pepstatin A from the DMSO dilution plate is pipetted into the inhibitor dilution plate and diluted 1:100 with reaction buffer as described above for test inhibitors.

The cathepsin D inhibition assay was conducted with the following steps.

A volume of 10 µl of each inhibitor at each concentration to be tested (BACE1 active compound) and pepstatin A (inhibitor control agent) diluted 1:100 in reaction buffer (see above) was pipetted from the inhibitor dilution plate into a solid black 96-well assay plate.

Next, a 50 µl volume of 15.5 µM peptide substrate (ES010) was added to each well of the cathepsin D assay plate and mixed with the test inhibitor by up and down pipetting using a multi-channel pipette.

The reaction was started by the addition of 40 µl of recombinant human cathepsin D (see above) to the assay plate and the plate was immediately centrifuged at 1,500 rpm (450×g) for 1 minute to remove any air bubbles that could potentially interfere with the fluorescent measurement of cathepsin D activity.

The assay plate was placed into a fluorescent plate reader with the excitation wavelength set at 320 nm and the emission wavelength set at 405 nm. Readings were collected every minute over a 30 minute collection period.

Time-course data that is linear was fitted using linear regression analysis and the calculated slope used as an initial velocity. For time course data that is not linear an integrated first-order rate equation was used to fit the data accumulated over a 30-40 minute collection period.

Figure 4:
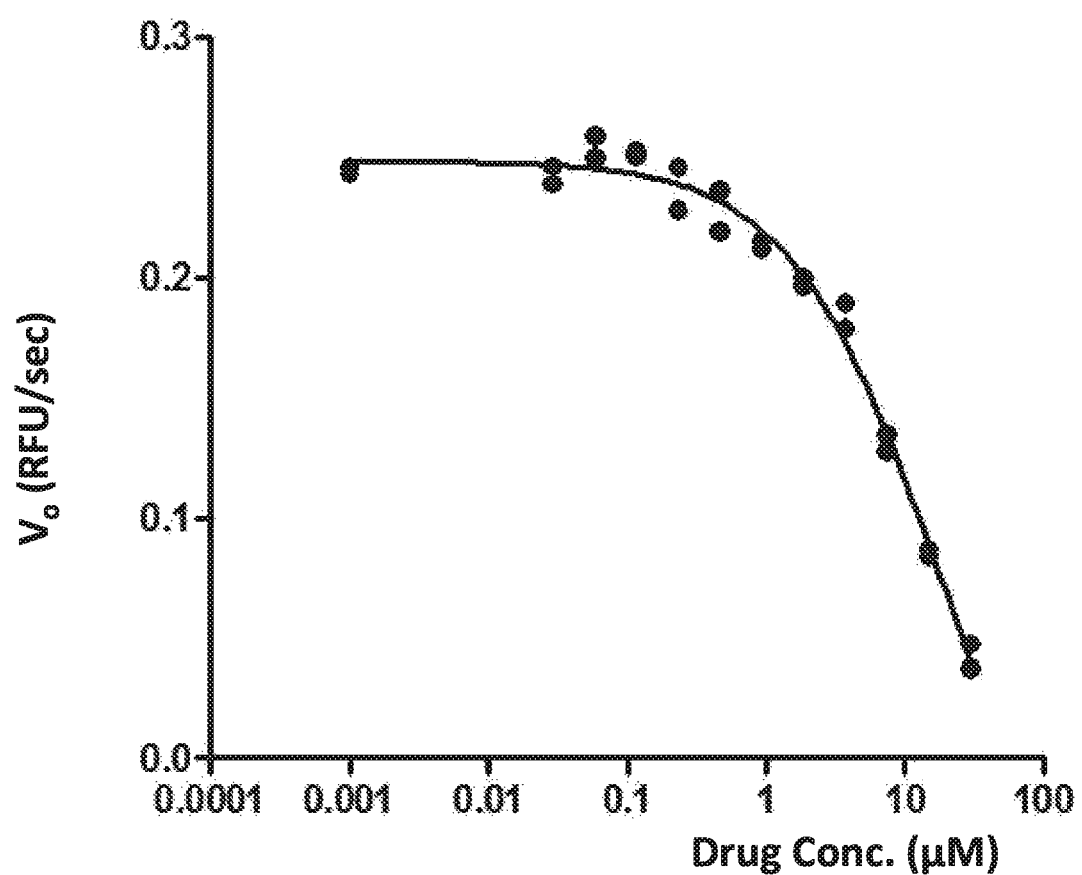
FIG. 4 shows the cross reactivity of a selected BACE1 inhibitor to cathepsin D using the Cathepsin D activity assay.

The selected BACE1 inhibitors in accordance with examples of the invention were then determined for CatD activity and target selectivity ratio (CatD $IC_{50}$/BACE1 $IC_{50}$). The values are illustrated in Table 2 below and FIG. 4. FIG. 4 shows the cross reactivity of a selected BACE1 inhibitor (example 103) by a Cathepsin D activity assay.

TABLE 2

Cathepsin D Activity of Selected Compounds

| Examples | BACE1 $IC_{50}$ (nM) | CatD $IC_{50}$ (µM) | CatD/BACE1 selectivity ratio |
|---|---|---|---|
| 1 | 26 | 12.3 | 471 |
| 71 | 44 | 3.9 | 89 |
| 103 | 39 | 17.2 | 441 |
| 109 | 25 | 10.8 | 432 | b. Pepsin Activity Assay

Most of the aspartic proteases belong to a pepsin structural superfamily, having homologous primary and tertiary structures and nearly identical catalytic apparatus. These proteases are synthesized as a single chain proenzyme, such as pepsinogen in the case of pepsin. The prosegment is then cleaved off during the activation and the protease part may also be processed into two or more chains as in cathepsin D. Pepsin is one of the major enzymes in the stomach which are involved in the normal degradation of intracellular and extracellular proteins. Thus, the inhibition of pepsin may also lead to unwanted pathophysiological conditions.

30 mM stocks of the experimental inhibitor compounds were prepared in DMSO. A 10 mM concentration of the inhibitor was prepared by diluting the 30 mM stock 3-fold in DMSO (30 µl of the [30 mM]:60 µl DMSO). 10-fold serial dilutions of 10 mM and 30 mM stocks were made on a dilution plate..

The pepstatin A inhibitor was received from Tocris Bioscience as 10 mg of lyophilized powder. DMSO was used to reconstitute the powder to a 10 mM concentration, which was aliquoted and stored at −20° C. A 40 µl volume of the 10 mM stock was thawed before use. 10-fold serial dilutions of 10 mM and 3 mM stocks were made in DMSO on a dilution plate.

Using a multichannel pipette, take a 2 µl volume of the diluted samples from the dilution plate into a new polypropylene 96-well plate. Add 198 µl of assay buffer (100-fold dilution) to each well containing compound and mix well.

The recombinant human pepsinogen A (20 µg) was activated prior to use in the assay by diluting a volume of concentrate (0.88 mg/ml) 10-fold into activation buffer (50 mM sodium citrate pH 2.5) and the pepsinogen incubated at room temperature for 15 minutes. Following the 15 minute incubation, the activated enzyme was diluted 500-fold into assay buffer (50 mM sodium citrate, 0.5 M sodium chloride pH 4.0) to achieve an enzyme concentration of 0.176 µg/ml.

The substrate was prepared by diluting the 2 mM stock of ES002 substrate 100-fold into assay buffer (60 µl of substrate: 5940 µl assay buffer) to a concentration of 20 µM. The substrate was stored protected from light at room temperature until it was used in the assay.

Using a multichannel pipette, 10 µl of each compound was transferred from the assay buffer dilution plate to corresponding rows in a black 96 well plate. Following the addition of compounds, 40 µl of recombinant human pepstatin A was added to each well containing inhibitor.

After the enzyme addition, the substrate was added to each well in 50 µl volumes. The reaction mix per well (100 µl) contains 0.088 µg/ml of enzyme, 10 µM of substrate and the test compound. The plate was immediately sealed and placed on a shaker set to 350 rpm for approximately 30 sec prior to reading in the Polar Star plate reader at room temperature with the excitation wavelength set at 320 nm, the emission wavelength set at 405 nm. Readings were taken every 41 seconds for approximately 25 minutes.

Figure 5:
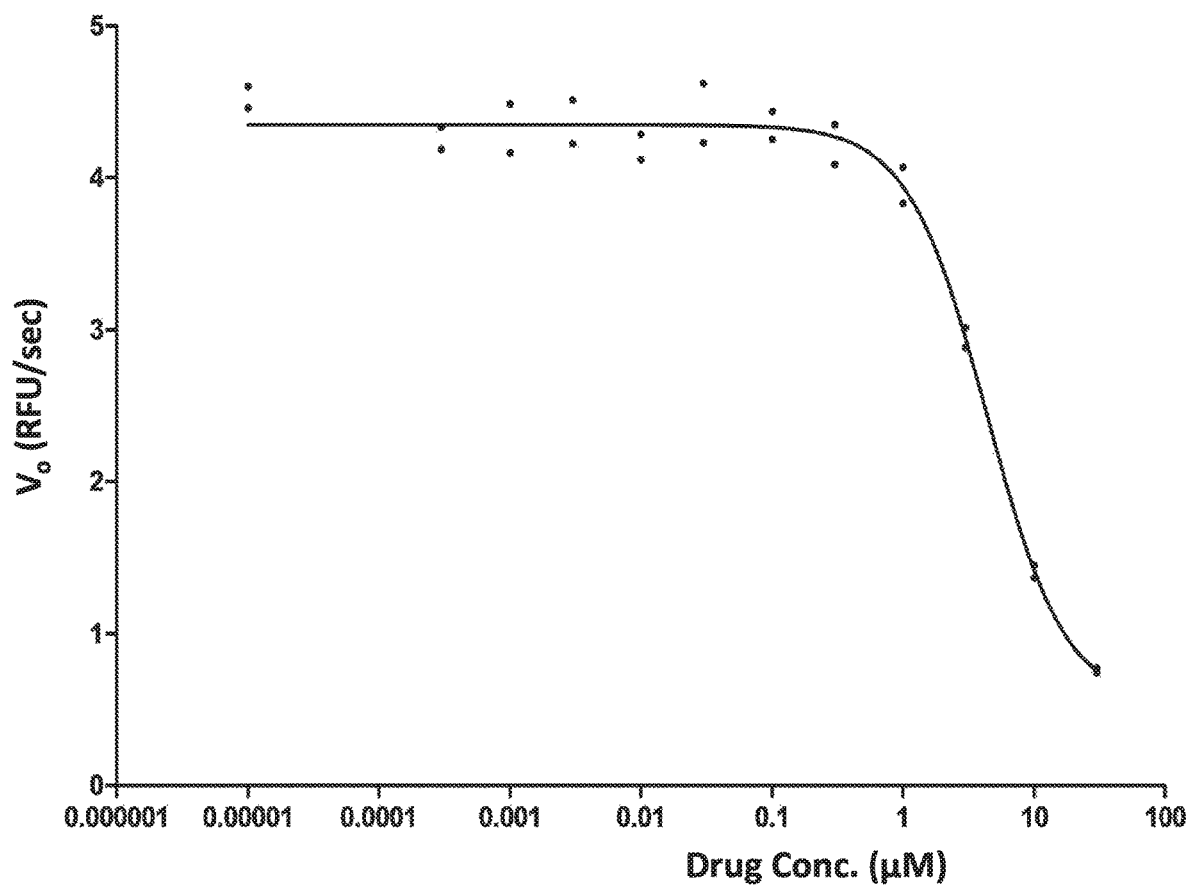
FIG. 5 shows the effect of a selected BACE1 inhibitor on pepsin by a pepsin assay.

The selected BACE1 inhibitors in accordance with examples of the invention were then determined for Pepsin activity and target selectivity ratio (Pepsin $IC_{50}$/BACE1 $IC_{50}$). The values are illustrated in Table 3 below and FIG. 5. FIG. 5 shows the cross reactivity of a selected BACE1 inhibitor (example 109) by a pepsin activity assay.

TABLE 3

Pepsin IC50 of Selected Compounds

| Examples | BACE1 $IC_{50}$ (nM) | Pepsin $IC_{50}$ (µM) | Pepsin/BACE1 selectivity ratio |
|---|---|---|---|
| 103 | 39 | 3.14 | 81 |
| 109 | 25 | 4.38 | 175 |

III. Other In Vitro Assays a. Potassium Channel hERG Assay

The human ether-á-go-go related gene (hERG) encodes the inward rectifying voltage gated potassium channel on mammalian heart which is involved in repolarization and relaxation of cardiac muscle. Blockage of the hERG current causes QT interval prolongation resulting in potential lethal ventricular tachyarrhythmia, also known as Torsade de Pointes (TdP). The cardiotoxic effects of numerous withdrawn drugs were manifested by prolonged QT intervals. This assay determines the possible interaction of the investigational drug with the potassium channel to determine cardiotoxic risk.

The [$^3$H] astemizole binding assay was conducted as follows:

All binding assays were performed in a total volume of 111.1 µL consisting of 100 µL of buffer (10 mM HEPES, pH 7.4, 130 mM NaCl, 5 mM KCl, 0.8 mM $MgCl_2$, 1 mM NaEGTA, 10 mM glucose 0.1% BSA, 10 µg membrane suspension), 1.1 µL of test compound or vehicle, 10 µL of [$^3$H] astemizole with a final concentration of 1.5 nM and incubated at 25° C. and 60 minutes.

Binding was terminated by rapid filtration onto GF/B glass fiber filter mats, presoaked in 0.3% polyethyleneimine and washing filter mats 4 times with ice-cold washing buffer (25 mM Tris-HCl, pH 7.4, 130 mM NaCl, 5 mM KCl, 0.8 mM $MgCl_2$, 0.05 mM $CaCl_2$, 0.1% BSA).

As to a non-specific binding assay, it was defined by 10 µM astemizole. Non-specific binding means excess (i.e. 200~1000 folds or higher) unlabeled ligand will be used. In the assay, it is estimated in the presence of 10 µM astemizole or test compound. Channel proteins are incubated at 25° C. for 60 minutes, filtered and washed. The filters are then counted to determine [$^3$H] astemizole specifically bound. When screening the compounds, its concentration is 10 µM and is carried each time on the non-specific binding assay.

The radioactivity in both assays was counted by a liquid scintillation counter.

The selected BACE1 inhibitors in accordance with examples of the invention were then determined for the activity of the selected compounds by the radioligand binding assays. The values are illustrated in Table 4 below.

TABLE 4 hERG Binding Activity of Selected Compounds

| Examples | % hERG binding at 10 µM |
|---|---|
| 1 | 50 |
| 71 | 53 |
| 103 | 64 |
| 109 | 43 | b. In Vitro Permeability Study Using MDCK-hMDR1 Monolayer

Madin-Darby canine kidney (MDCK) cells transfected with human MDR1 gene (MDCK-MDR1) establishing for the characterization of human P-glycoprotein (Pgp) substrates and inhibitors are widely used for transport studies to identify drug candidates as substrates of this efflux protein. The cellular transport model (in MDR1-MDCK cells) is to realize a mechanism of drug efflux, and highlights early potential issues with drug permeability by one of the major efflux transporter in the blood brain barrier (BBB), Pgp. Pgp efflux ratio is a net flux across the monolayer. If efflux ratio larger than 2, a compound is typically considered as a possible Pgp substrate, which limits brain penetration of the compound, not ideal for CNS treatment.

The measurements for permeability and efflux ratio are as follows: MDCK-hMDR1 cells (100,000 cells/well) were seeded onto Corning 12-well transwell plates. The volumes of medium in the apical side (A-side) and the basolateral side (B-side) were 0.5 ml and 1.5 ml, respectively. Cells were cultured in the growth medium for approximately 5 days to allow the formation of cell monolayer on the filter. At this time, cells were fully matured and P-glycoprotein was expressed with increased trans-epithelial electrical resistance. Medium was changed every 48 hours and on the day before the experiment the medium was changed. The trans-epithelial electrical resistance (TEER) was measured to ensure the quality of cell monolayer before the study, and the minimum resistance was 200 Ω·cm2. MDCK-hMDR1 cells were washed three times with pre-warmed HBSS buffer, and the MDCK-hMDR1 monolayer was pre-incubated in the HBSS buffer (the volumes in A-side and B-side are 0.5 ml and 1.5 ml, respectively) for 30 min at 37° C. prior to the addition of test compounds. The trans-epithelial electrical resistance (TEER) was measured again and the minimum resistance was 200 Ω·cm2.

To assess A→B permeability assessment, the HBSS buffer from A-side chamber was aspirated and 0.5 ml of test compounds or positive control dissolved in HBSS buffer were subsequently added to it. All experiments were performed in triplicate (n=3) for each compound. Cells were incubated for 2 hours at 37° C. and samples were collected from the donor (A-side) and the receiver (B-side) chambers after incubation. Drug concentrations in the medium were analyzed using LC-MS/MS.

To assess B→A permeability assessment, the cell culture was prepared in the same method described above. The HBSS buffer from B-side chamber was aspirated and 1.5 ml of test compounds or positive control dissolved in HBSS were subsequently added to it. In this case, A-side is the receiver side. Cells were incubated for 2 hours at 37° C. and samples were collected.

The efflux ratio was calculated as the rate of permeation of test compounds through the MDCK-hMDR1 monolayer is used to determine the permeability coefficient (Papp), which can be used to predict the in vivo absorption of test compounds. After obtaining values of Papp(A→B) and Papp(B→A), the efflux ratio can then be calculated using the following equation: Efflux Ratio (ER)=Papp(B→A)/Papp(A→B).

The selected BACE1 inhibitors in accordance with examples of the invention were then determined for the absorption of the selected compounds using MDCK-hMDR1 monolayer (Table 5).

TABLE 5

MDCK Efflux Ratio of Selected Compounds

| Examples | MDCK Efflux Ratio |
|---|---|
| 1 | 8.1 |
| 71 | 2.2 |
| 72 | 1.6 |
| 78 | 3.0 |
| 79 | 46.2 |
| 80 | 59.0 |
| 87 | 44.0 |
| 89 | >38.1 |
| 103 | 1.6 |
| 105 | 8.3 |
| 106 | 10.3 |
| 109 | 1.6 |
| 127 | 1.0 |
| 128 | 0.8 |
| 132 | 1.2 |
| 136 | 2.3 |
| 159 | 2.0 |
| 162 | 1.1 | c. Caco-2 Permeability Assay

Differentiated polarized Caco-2 cells (a human colon carcinoma cell line) express a wide range of transporter proteins on its cell membranes mimicking the intestinal endothelium cells. A bi-directional Caco-2 permeability assay is considered to be the industry reference standard for in vitro prediction of in vivo human intestinal permeability of orally administered drugs. This assay is performed where the transport of the compound is measured in the apical to basolateral direction as well as the basolateral to apical direction. The result is typically reported as an efflux ratio i.e. $Pa_{pp}(B→A)/P_{app}(A→B)$ where $P_{app}$ is apparent permeability. If the efflux ratio is greater than two then this indicates drug efflux is occurring.

IV. Efficacy Study in Mammals

Certain isoforms of amyloid β peptide (AR), such as Aβ338, Aβ340 and Aβ342 have been established as relevant biomarkers that reflect BACE1 activity and have been exploited to establish translational relationships between different cellular assays and animal models. In this efficacy study, mammals were used to assess amyloid β reduction with BACE1 inhibitors. In a clinical setting, plasma and cerebrospinal fluid (CSF) are the accessible compartments to measure soluble amyloid β levels to determine target profile. It is important to analyze plasma and CSF levels which relate to changes in brain amyloid β levels. The concentration of BACE1 inhibitors and their time-dependent reduction of plasma, CSF and brain amyloid β levels were investigated following intravenous and oral administrations of BACE1 inhibitors.

a. Formulations Used in Mice, Rat and Monkey Studies:

The procedures and instruction to prepare the vehicle and test article solutions for animal studies are as follows:

a (i). Formulation for IV administration: 10% (v/v) dimethylacetamide (DMA), 5% (v/v) solutol and 85% (v/v) saline: The test article solutions were prepared by dissolving the compound in DMA and solutol followed by the addition of the aqueous solution to the final volume.

a (ii). Formulation for PO administration: 5% (v/v) PEG400+95% (v/v) of 1% (w/v) methyl cellulose in water (the viscosity of methyl cellulose is 20 g/L, 20° C., cPa·s: 350.0-550.0). The test article solutions were prepared by dissolving the compound in PEG400 followed by the addition of the aqueous solution to the final volume.

a (iii). Formulation for PO administration: 5% (v/v) PEG400+0.1% (v/v) Tween 80+20% (w/v) hydroxypropyl-β-cyclodextrin (HP-β-CD): the test article solutions by dissolving the compound in PEG400 and Tween 80 followed by adding the aqueous solution to the final volume.

a (iv) Formulation for PO administration: 10% (v/v) PEG400+0.2% (v/v) Tween 80+10% (w/v) hydroxypropyl-β-cyclodextrin (HP-β-CD): the test article solutions were prepared by dissolving the compound in PEG400 and Tween 80 followed by adding the aqueous HP-β-CD solution to the final volume.

The details preparation procedures for efficacy studies were listed as following:

For the oral formulation of a BACE1 inhibitor in the monkey efficacy study (at the dose of 20 mg/kg with the concentration of 2 mg/ml)

1) Weighed 101.39 mg of the selected BACE1 inhibitors into a clean vial;
2) Added 2.826 mL of PEG400 into the tube containing the compound. Then vortexed for 5 min and sonicated for 45 min;
3) Added 53.688 mL of 1% MC in water into the tube containing the compound. Then vortexed for 4 min and sonicated for 4 min; and
4) Adjusted the pH to the physiological value by using 1N NaOH.

For oral formulation of a BACE1 inhibitor in the rat efficacy study (at the dose of 20 mg/kg with the concentration of 4 mg/ml), the preparation procedure was similar to that in monkey studies.

b) Efficacy Studies in Monkeys

Several studies have shown that drug transport into the CNS may be more similar between humans and primates. Hence, non-human primates give an indication of the expected distribution to CSF of AG compounds in humans. To explore the mechanism of BACE1 compounds, the compounds were tested using this in vivo study. The selected BACE1 compounds demonstrated significant Aβ reduction in CSF compared to the baseline level in CSF over a prolonged period. The monkey Aβ reduction study usually takes 3 weeks.

The time-course profiles of neurodegeneration biomarkers were determined following single oral administration of the selected BACE1 inhibitors to male cynomolgus monkeys. Blood samples were collected from all animals via the saphenous vein or cephalic vein at 0 (pre-dose), 0.5, 1, 3, 6, 8, 12 and 24 hr post-dose into test tubes containing potassium ethylenediaminotetraacetic acid ($K_2EDTA$). CSF samples were collected via a pre-implanted cannula at the foramina occipital magnum site at 0 (pre-dose), 3, 6, 12 and 24 hr post-dose.

Plasma was separated from the blood by centrifugation at 4° C. and stored at −80° C. until analyzing. The biomarkers of Aβ38, Aβ40 and Aβ42 in CSF were quantified using Meso Scale Discovery (MSD) multiplex electrochemiluminescence immunoassay according to the manufacturer's instructions. The plates were first blocked with 150 μL of Diluent 35 for 1 hour at room temperature with constant shaking at 600 rpm. After washing three times with 200 μL washing buffer, 25 μL of 1× detection antibody solution, plus Aβ40 blocker, 25 μL of seven standards, zero standard and four-fold diluted samples were added to the assay plate. The plate was incubated for 2 hours at room temperature, with constant shaking at 600 rpm. Upon finishing, the plate was washed three times with washing buffer and read in a Sector Imager 6000 (MSD) immediately after addition of 150 μL of 2× Read Buffer T. Aβ concentrations were calculated with reference to the standard curves of each individual peptide and expressed as pg/mL using SoftMax Pro GXP 5.4.4.

Figure 6:
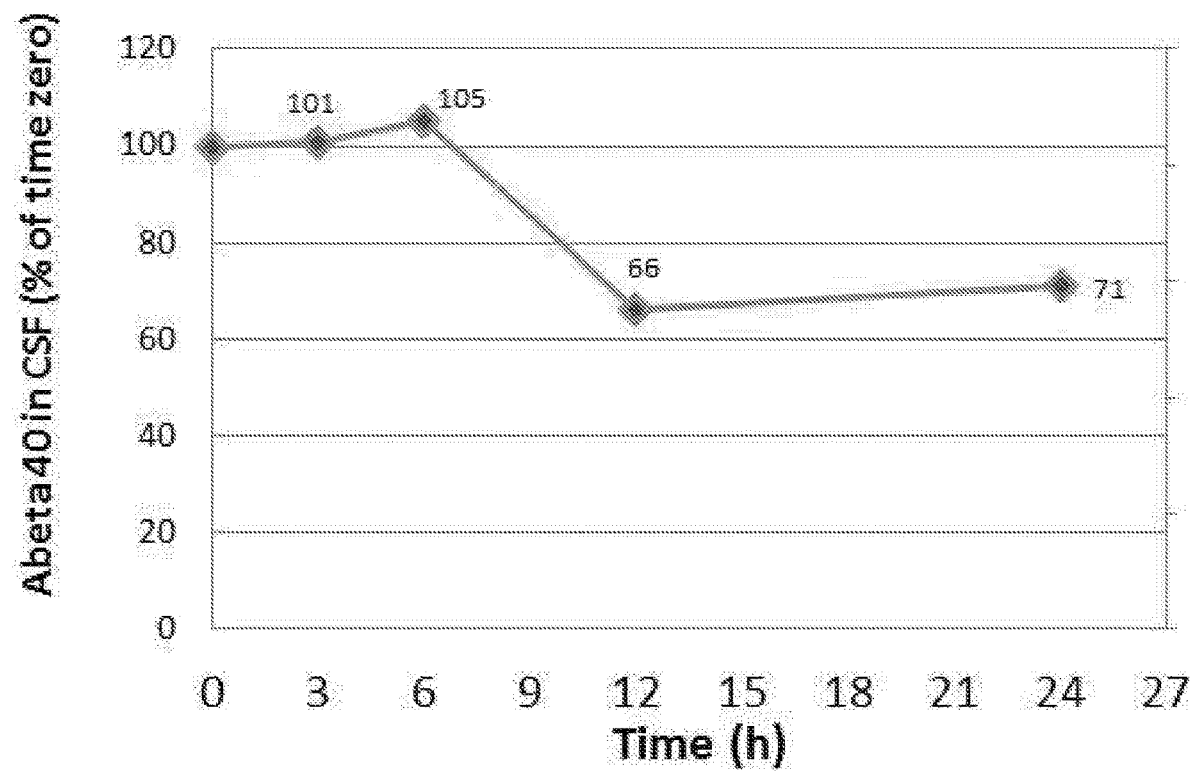
FIG. 6 shows the amount of neurodegenerative biomarker Aβ40 in cerebrospinal fluid (CSF) of a monkey after a selected BACE1 inhibitor was orally administered.

The CSF level of three neurodegeneration biomarkers, Aβ38, Aβ40 and Aβ42, were shown to be significantly inhibited by the selected BACE1 inhibitors. FIG. 6 shows a neurodegenerative biomarker Aβ40 in CSF of a monkey after a single oral administration of a selected compound (example 72) at a dose of 20 mg/kg. The Aβ40 inhibition results in the Monkey after oral administration of selected compounds were shown in the Table 6 below.

TABLE 6

Aβ$_{40}$ inhibition of selected compounds in Monkey

| Examples | % of maximum Aβ$_{40}$ inhibition over 24 hours |
|---|---|
| 72 | 33.7 |
| 103 | 45.9 |
| 109 | 37.3 |
| 128 | 49.1 |
| 136 | 44.5 | c) Efficacy Studies in Rats

Similar time-course profile of neurodegeneration biomarkers were determined following single oral administration of the selected BACE1 inhibitors to Sprague Dawley rats.

Figure 7:
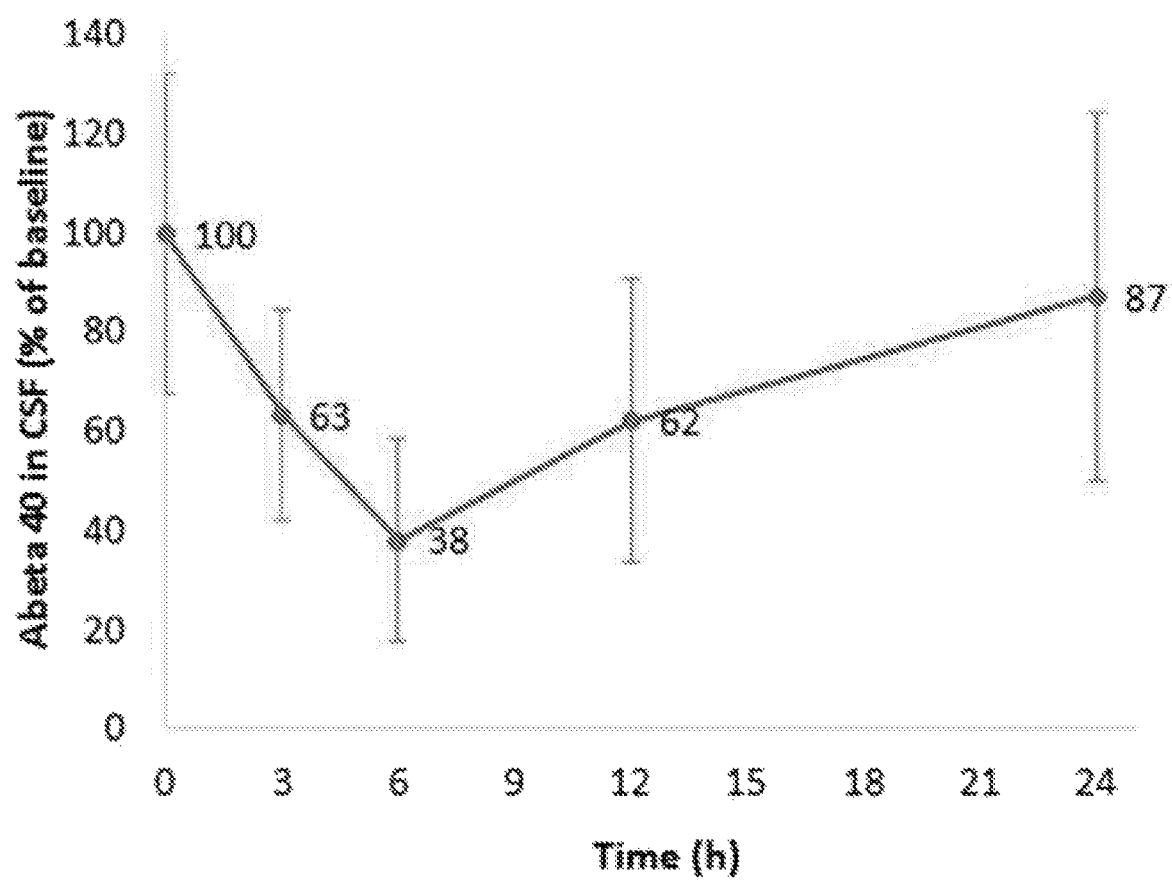
FIG. 7 shows the amount of neurodegenerative biomarker Aβ40 in cerebrospinal fluid (CSF) of three rats after a selected BACE1 inhibitor was orally administered.

The CSF level of three neurodegeneration biomarkers, Aβ38, Aβ40 and Aβ42, were shown to be significantly inhibited by the selected BACE1 inhibitors. FIG. 7 shows a neurodegenerative biomarker Aβ40 in the CSF of three rats after a single oral administration of a selected compound (example 109) at a dose of 20 mg/kg.

d) Efficacy Study in Transgenic AD Animal

To investigate the relationship among the formation of Aβ toxicity, and AD-related phenotypes, one of the most extensively studied AD models is analyzed, the transgenic Tg2576 (APP K670N/M671L) mouse that is characterized by the overproduction and deposition of Aβ protein. APP mutations in Swedish familial AD (SFAD) are distal to the amino terminus of the Aβ peptide and result in two amino acid substitution: K670N and M671L. These mutations increase the rate of proteolysis of APP by BACE. Transgenic AD mice overproducing mutant APP develop pathology that is similar within the human brain. In addition, the triple-transgenic mouse model, APP/PS/Tau (3×TgAPP, APP (swe)/PS1(M 146V)/MAPT(P301L)) mice, which exhibits both Aβ and tau pathology, mimic human AD. These models are genetically modified to produce more Aβ in the brain. The accumulation of Aβ is correlated with memory deficits. The efficacy is determined using the memory function assessment assays, including the Morris water maze, radial arm maze and radial arm water maze, etc.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The invention claimed is:

1. A compound according to Formula (VI):

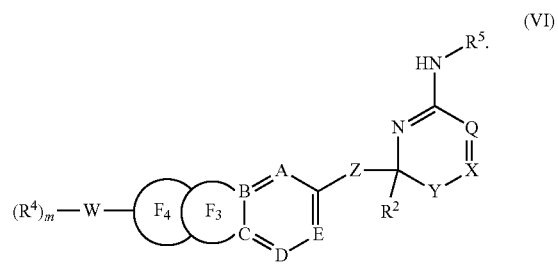

(VI)

Wherein

X is selected from the group consisting of C(O), S(O)$_2$, CR$^7$R$^8$, O, NR$^1$, and S(O);

Y is (CR$^7$R$^8$)$_n$;

X and Y are optionally taken together to form a ring structure

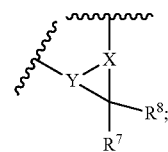

Z is absent;

W is absent or present and when present is selected from the group consisting of alkyl, haloalkyl, heteroalkyl, alkenyl, alkynyl, $OR^9$, O, $NR^9R^{10}$, $NR^9$, $C(O)R^9$, $C(O)NR^9$, $NR^9C(O)$, $C(O)OR^9$, $OC(O)R^9$ and heterocycloalkyl;
Q is selected from O, S, $NR^1$, $(CR^{14}R^{15})_p$, C(O);
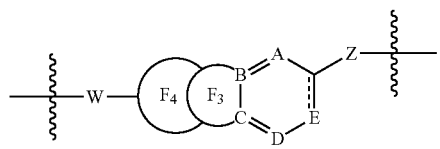
is selected from
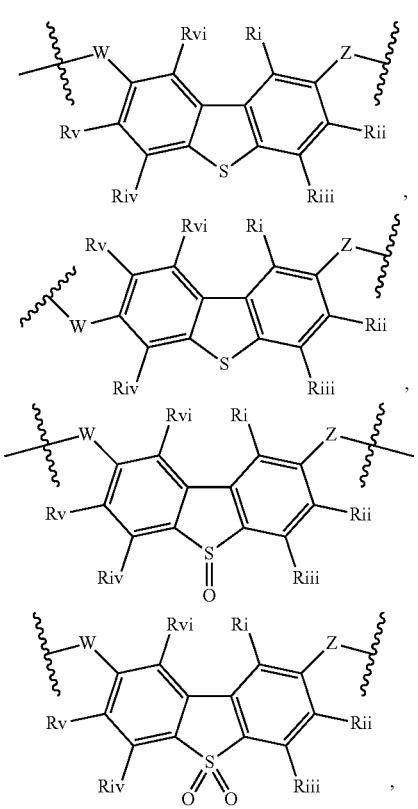
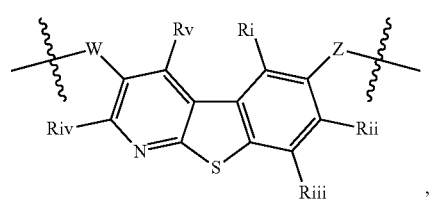
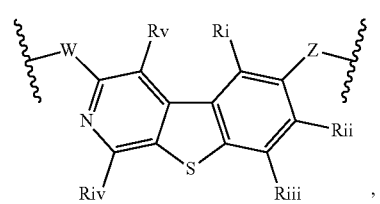
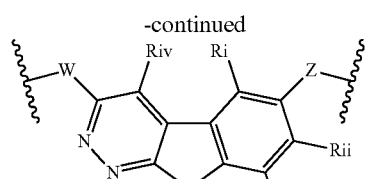
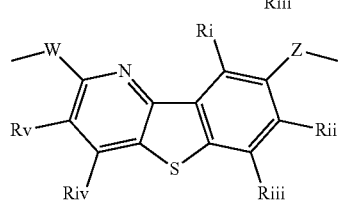
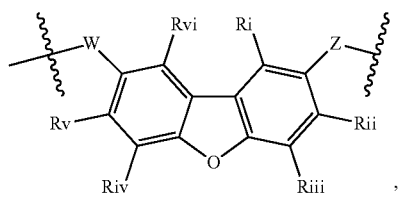
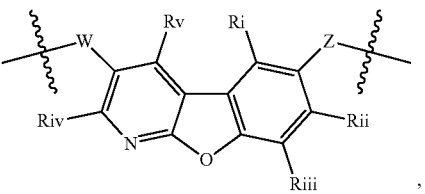
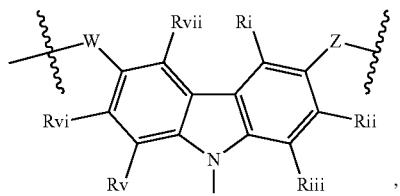
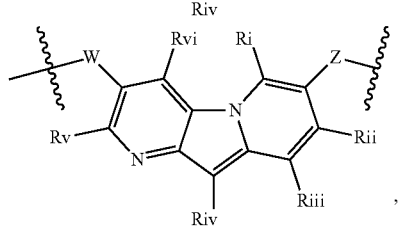
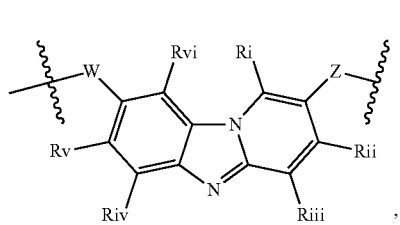
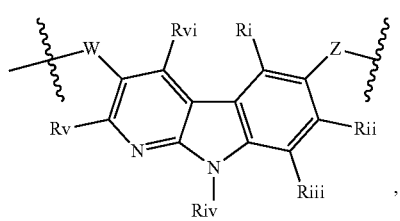

-continued

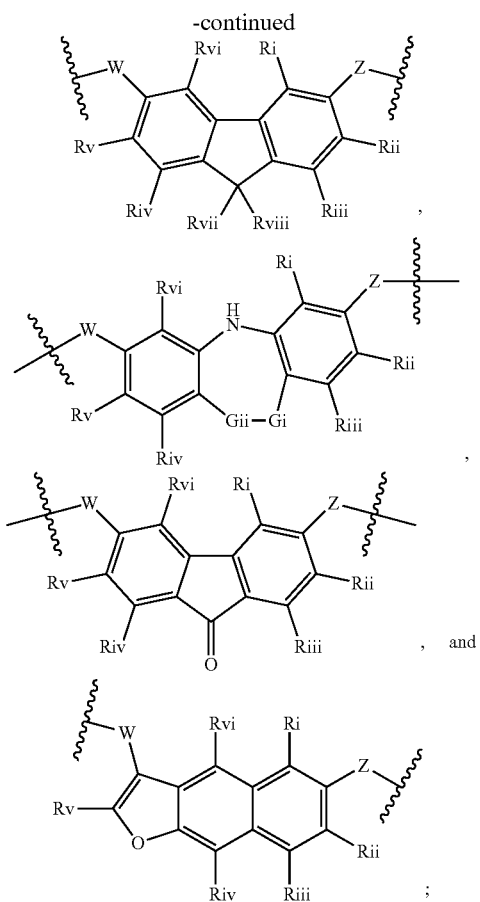

wherein each of Ri, Rii, Riii, Riv, Rv, Rvi, Rvii, and Rviii, independently, is hydrogen, halogen, cyano group, amino group, amido group, $C_{1-6}$ alkyl, $C_{1-6}$ alkoxyl, $C_{2-6}$ alkenyl, or $C_{2-6}$ alkynyl, or is a moiety selected from $C_{3-10}$ cycloalkyl, $C_{1-10}$ heterocycloalkyl, aryl, and heteroaryl, each of which is optionally mono-, di-, or tri-substituted with halogen, nitro group, cyano group, amino group, amido group, $C_{1-6}$ alkyl, $C_{1-6}$ alkoxyl, $C_{2-6}$ alkenyl, $C_{2-6}$ alkynyl, aryl, or heteroaryl, or optionally fused with $C_{3-10}$ cycloalkyl, $C_{1-10}$ heterocycloalkyl, aryl, or heteroaryl;

Gi is selected from $CH_2$, O, and $SO_2$;
Gii is selected from $CH_2$ and O;
the bond between Gi and Gii is a single bond;
$R^1$ is selected from hydrogen, alkyl, cycloalkyl, haloalkyl, heteroalkyl, heterohaloalkyl and heteroalkynyl;
$R^2$ is selected from CN, alkyl, cycloalkyl, and aryl;
$R^4$ is independently selected from the group consisting of: hydrogen, deuterium, halogen, hydroxyl, CN, alkyl, haloalkyl, heteroalkyl, alkenyl, alkynyl, aryl, arylalkyl, arylalkenyl, arylalkynyl, cycloalkyl, heteroaryl, heteroarylalkyl, heteroarylalkenyl, heteroarylalkynyl and heterocycloalkyl;
$R^5$ is selected from hydrogen, $C_{1-5}$ alkyl, $C(O)R^{14}$ and $CR^{17}R^{16}OC(O)R^{18}$;
a $R^7$ is independently selected from hydrogen, fluorine, and trifluoromethyl;
$R^8$ is independently selected from hydrogen, fluorine, and trifluoromethyl;
$R^9$ is independently selected from hydrogen, deuterium, halogen, $C_{1-5}$ alkyl and alkynyl;

$R^{10}$ is independently selected from hydrogen, deuterium, halogen and $C_{1-5}$ alkyl;
$R^{14}$ is a straight chain or branched alkyl group of 1 to 28 carbons, heterocycloalkyl and cycloalkyl, monocyclic aryl, multicyclic aryl, monocyclic heteroaryl, multicyclic heteroaryl, haloalkyl or heteroalkyl;
$R^{15}$ is independently selected from hydrogen, deuterium, halogen and $C_{1-5}$ alkyl; or
$R^{14}$ and $R^{15}$ are optionally taken together with the carbon atom they are attached to form a cycloalkyl or heterocycloalkyl ring structure;
$R^{16}$ is independently selected from hydrogen, deuterium, halogen and $C_{1-5}$ alkyl;
$R^{17}$ is independently selected from hydrogen, deuterium, halogen and C1-5 alkyl;
$R^{18}$ is a straight chain or branched alkyl group of 1 to 28 carbons, heterocycloalkyl and cycloalkyl, monocyclic aryl, multicyclic aryl, monocyclic heteroaryl, multicyclic heteroaryl, haloalkyl or heteroalkyl;
n is 1 or 2;
m is 0 or more;
t is 1;
or a stereoisomer, tautomer, prodrug, pharmaceutically acceptable salt, solvate, or solvate of a salt thereof.

2. A compound according to Formula (VI):

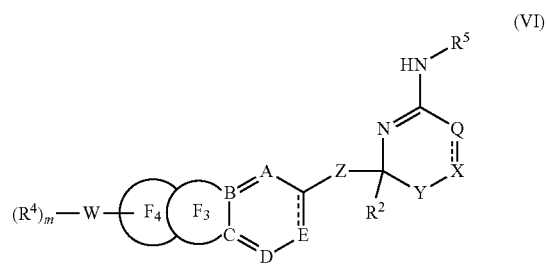

Wherein
X is selected from the group consisting of C(O) and $S(O)_2$;
Y is $(CR^7R^8)_n$;
Z is absent;
W is absent or present and when present is selected from the group consisting of alkyl, haloalkyl, heteroalkyl, alkenyl, alkynyl, $OR^9$, O, $NR^9R^{10}$, $NR^9$, $C(O)R^9$, $C(O)NR^9$, $NR^9C(O)$, $C(O)OR^9$, $OC(O)R^9$ and heterocycloalkyl;
Q is selected from $NR^1$, $(CR^{14}R^{15})_t$;

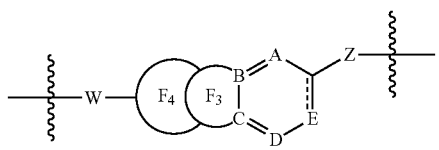

is selected from
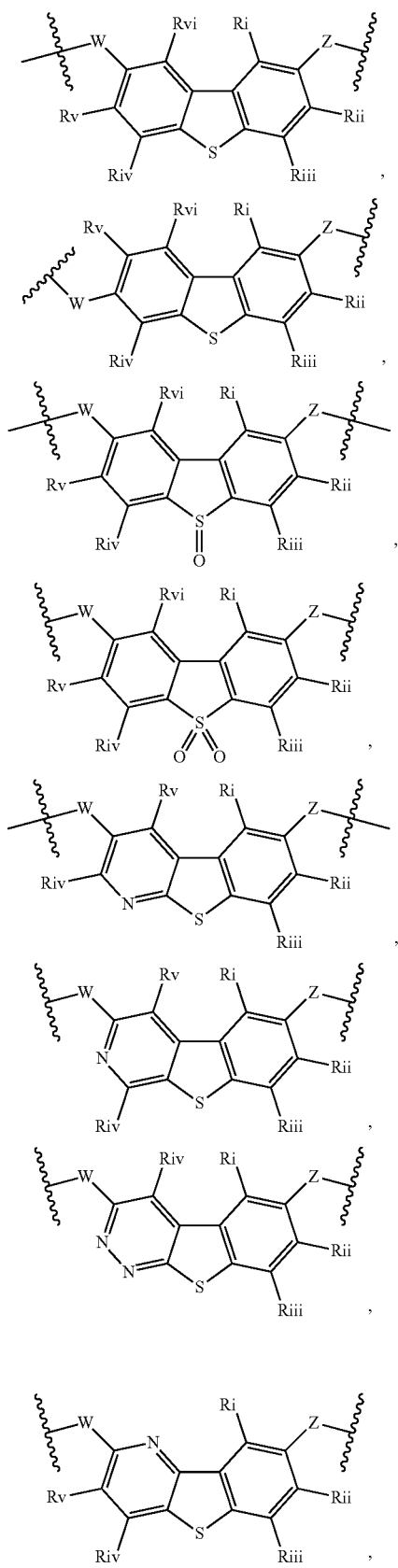
-continued
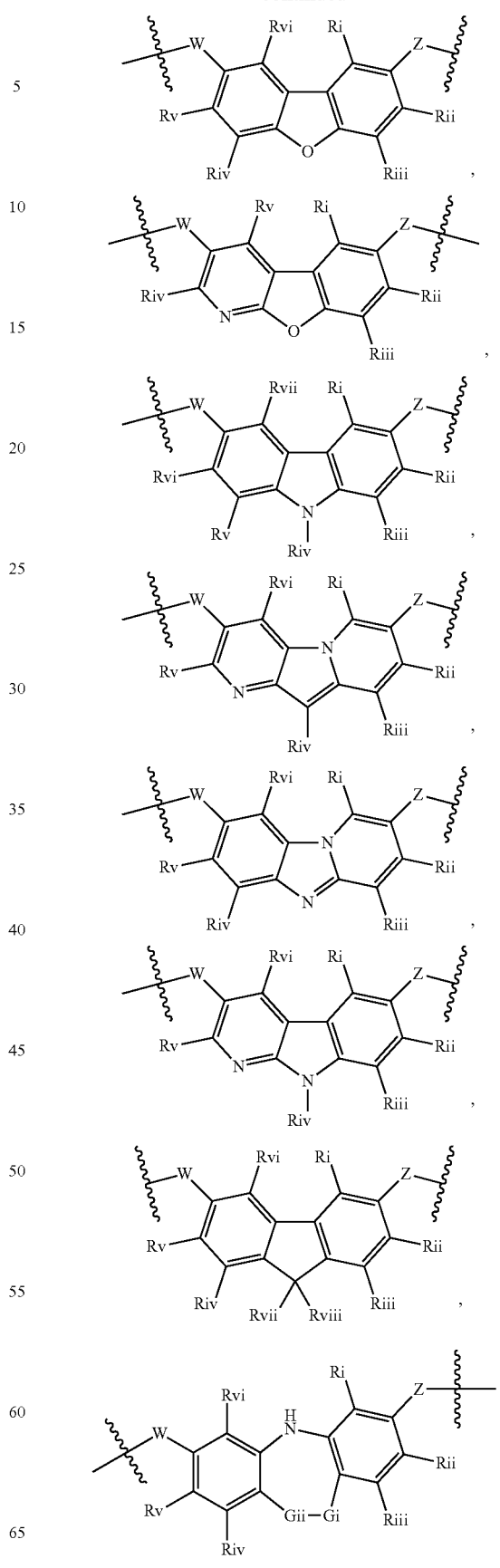

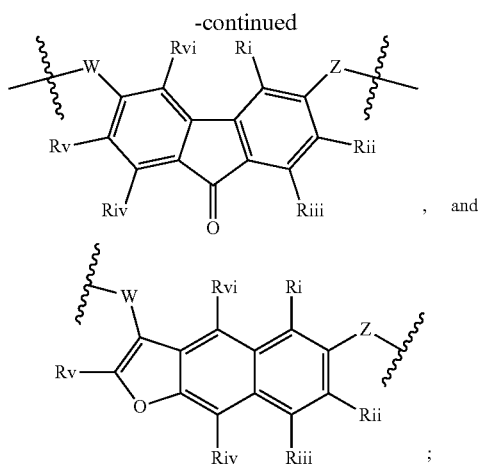
, and wherein each of Ri, Rii, Riii, Riv, Rv, Rvi, Rvii, and Rviii, independently, is hydrogen, halogen, cyano group, amino group, amido group, $C_{1-6}$ alkyl, $C_{1-6}$ alkoxyl, $C_{2-6}$ alkenyl, or $C_{2-6}$ alkynyl, or is a moiety selected from $C_{3-10}$ cycloalkyl, $C_{1-10}$ heterocycloalkyl, aryl, and heteroaryl, each of which is optionally mono-, di-, or tri-substituted with halogen, nitro group, cyano group, amino group, amido group, $C_{1-6}$ alkyl, $C_{1-6}$ alkoxyl, $C_{2-6}$ alkenyl, $C_{2-6}$ alkynyl, aryl, or heteroaryl, or optionally fused with $C_{3-10}$ cycloalkyl, $C_{1-10}$ heterocycloalkyl, aryl, or heteroaryl;

Gi is selected from $CH_2$, O, and $SO_2$;
Gii is selected from $CH_2$ and O;
the bond between Gi and Gii is a single bond;
$R^1$ is selected from hydrogen, alkyl, cycloalkyl, haloalkyl, heteroalkyl, heterohaloalkyl and heteroalkynyl;
$R^2$ is selected from CN, alkyl, cycloalkyl, and aryl;
$R^4$ is independently selected from the group consisting of: hydrogen, deuterium, halogen, hydroxyl, CN, alkyl, haloalkyl, heteroalkyl, alkenyl, alkynyl, aryl, arylalkyl, arylalkenyl, arylalkynyl, cycloalkyl, heteroaryl, heteroarylalkyl, heteroarylalkenyl, heteroarylalkynyl and heterocycloalkyl;
$R^5$ is selected from hydrogen, $C_{1-5}$ alkyl, $C(O)R^{14}$ and $CR^{17}R^{16}OC(O)R^{18}$;
$R^7$ is independently selected from hydrogen, fluorine, and trifluoromethyl;
$R^8$ is independently selected from hydrogen, fluorine, and trifluoromethyl;
$R^9$ is independently selected from hydrogen, deuterium, halogen, $C_{1-5}$ alkyl or alkynyl;
$R^{10}$ is independently selected from hydrogen, deuterium, halogen and $C_{1-5}$ alkyl;
$R^{14}$ is a straight chain or branched alkyl group of 1 to 28 carbons, heterocycloalkyl, cycloalkyl, monocyclic aryl, multicyclic aryl, monocyclic heteroaryl, multicyclic heteroaryl, haloalkyl or heteroalkyl;
$R^{15}$ is independently selected from hydrogen, deuterium, halogen and $C_{1-5}$ alkyl; or
$R^{14}$ and $R^{15}$ are optionally taken together with the carbon atom they are attached to form a cycloalkyl or heterocycloalkyl ring structure;
$R^{16}$ is independently selected from hydrogen, deuterium, halogen and $C_{1-5}$ alkyl;
$R^{17}$ is independently selected from hydrogen, deuterium, halogen and $C_{1-5}$ alkyl;
$R^{18}$ is a straight chain or branched alkyl group of 1 to 28 carbons, heterocycloalkyl and cycloalkyl, monocyclic aryl, multicyclic aryl, monocyclic heteroaryl, multicyclic heteroaryl, haloalkyl or heteroalkyl;

n is 1 or 2;
m is 0 or more;
t is 1;
or a stereoisomer, tautomer, prodrug, pharmaceutically acceptable salt, solvate, or solvate of a salt thereof.

3. A compound according to Formula (VI):

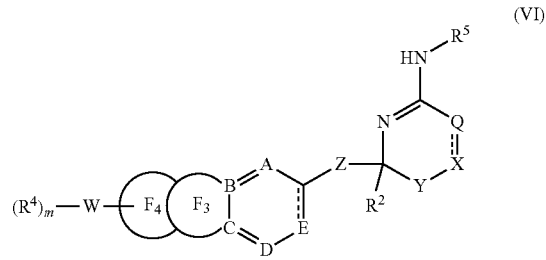

(VI)

wherein
X is selected from the group consisting of C(O) and $S(O)_2$;
Y is $CH_2$;
Z is absent;
W is absent or present and when present is selected from the group consisting of alkyl, haloalkyl, heteroalkyl, alkenyl, alkynyl, $OR^9$, O, $NR^9R^{10}$, $NR^9$, $C(O)R^9$, $C(O)NR^9$, $NR^9C(O)$, $C(O)OR^9$, $OC(O)R^9$ and heterocycloalkyl;
Q is selected from $NR^1$, or $(CR^{14}R^{15})_t$;

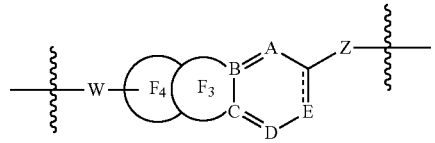

is selected from

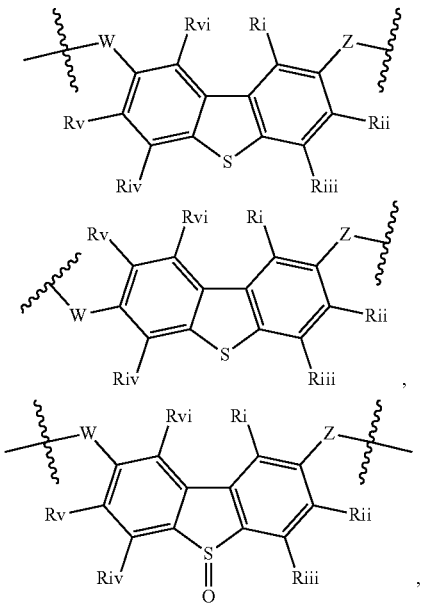

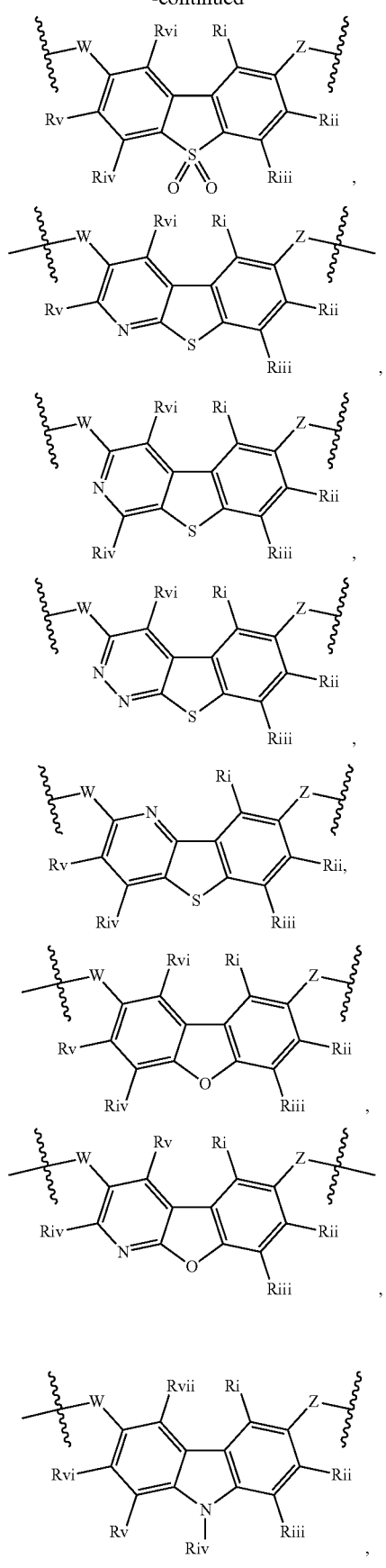
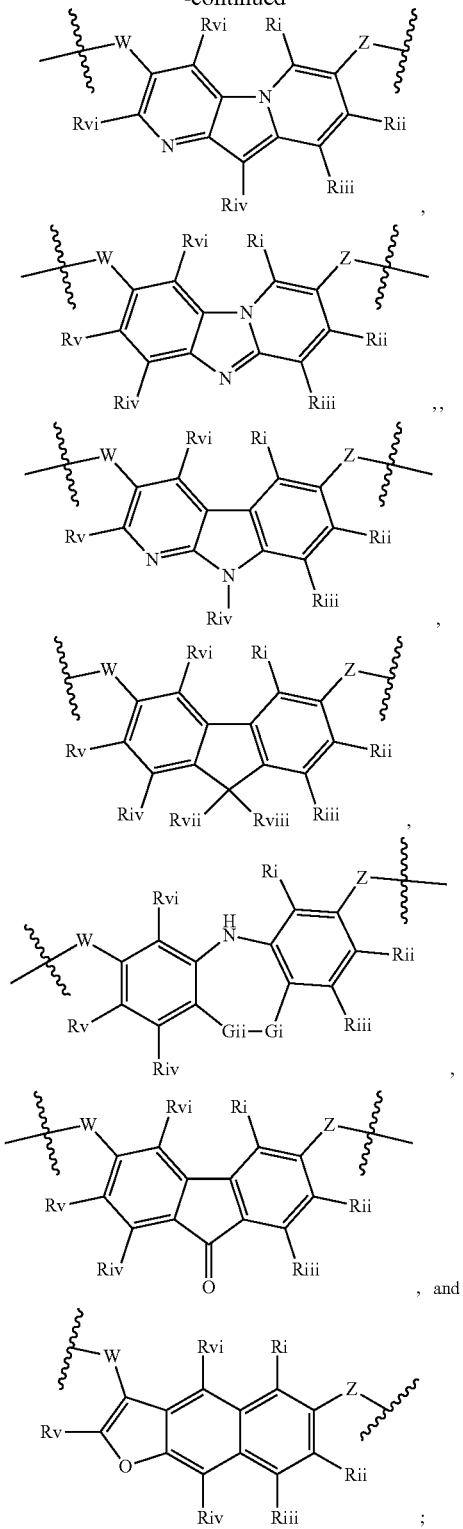
wherein each of Ri, Rii, Riii, Riv, Rv, Rvi, Rvii, and Rviii, independently, is hydrogen, halogen, cyano group, amino group, amido group, $C_{1-6}$ alkyl, $C_{1-6}$ alkoxyl, $C_{2-6}$ alkenyl, or $C_{2-6}$ alkynyl, or is a moiety selected from $C_{3-10}$ cycloalkyl, $C_{1-10}$ heterocycloalkyl, aryl, and heteroaryl, each of which is optionally mono-, di-, or tri-substituted with halogen, nitro group, cyano group, amino group, amido group, $C_{1-6}$ alkyl, $C_{1-6}$ alkoxyl, $C_{2-6}$ alkenyl, $C_{2-6}$ alkynyl, aryl, or heteroaryl, or optionally fused with $C_{3-10}$ cycloalkyl, $C_{1-10}$ heterocycloalkyl, aryl, or heteroaryl;

Gi is selected from $CH_2$, O, and $SO_2$;

Gii is selected from $CH_2$ and O;

the bond between Gi and Gii is a single bond;

$R^1$ is selected from hydrogen, alkyl, cycloalkyl, haloalkyl, heteroalkyl, heterohaloalkyl and heteroalkynyl;

$R^2$ is alkyl;

$R^4$ is independently selected from the group consisting of: hydrogen, deuterium, halogen, hydroxyl, CN, alkyl, haloalkyl, heteroalkyl, alkenyl, alkynyl, aryl, arylalkyl, arylalkenyl, arylalkynyl, cycloalkyl, heteroaryl, heteroarylalkyl, heteroarylalkenyl, heteroarylalkynyl and heterocycloalkyl;

$R^5$ is selected from hydrogen, $C_{1-5}$ alkyl, $C(O)R^{14}$ and $CR^{17}R^{16}OC(O)R^{18}$;

$R^9$ is independently selected from hydrogen, deuterium, halogen, $C_{1-5}$ alkyl and alkynyl;

$R^{10}$ is independently selected from hydrogen, deuterium, halogen and $C_{1-5}$ alkyl;

$R^{14}$ is a straight chain or branched alkyl group of 3 to 28 carbons, heterocycloalkyl, or cycloalkyl;

$R^{15}$ is independently selected from hydrogen, deuterium, halogen and $C_{1-5}$ alkyl; or $R^{14}$ and $R^{15}$ are optionally taken together with the carbon atom they are attached to form a cycloalkyl or heterocycloalkyl ring structure;

$R^{16}$ is independently selected from hydrogen, deuterium, halogen and $C_{1-5}$ alkyl;

$R^{17}$ is independently selected from hydrogen and $C_{1-5}$ alkyl;

$R^{18}$ is a straight chain or branched alkyl group of 3 to 28 carbons, heterocycloalkyl or cycloalkyl;

m is 0 or more;

t is 1;

or a stereoisomer, tautomer, prodrug, pharmaceutically acceptable salt, solvate, or solvate of a salt thereof.

4. The compound according to claim 1, wherein the compound is selected from:

(S)-2-Imino-3,6-dimethyl-6-(8-(prop-1-yn-1-yl)dibenzo[b,d]thiophen-2-yl)tetrahydropyrimidin-4(1H)-one;

(S,Z)-N-(1,4-Dimethyl-6-oxo-4-(8-(prop-1-yn-1-yl)dibenzo[b,d]thiophen-2-yl)tetrahydropyrimidin-2(1H)-ylidene)benzamide;

(S)-1-Benzoyl-2-imino-3,6-dimethyl-6-(8-(prop-1-yn-1-yl)dibenzo[b,d]thiophen-2-yl)tetrahydropyrimidin-4(1H)-one;

(S,Z)-((1,4-Dimethyl-6-oxo-4-(8-(prop-1-yn-1-yl)dibenzo[b,d]thiophen-2-yl)tetrahydropyrimidin-2(1H)-ylidene)amino)methyl benzoate;

(S,Z)-N-(1,4-Dimethyl-6-oxo-4-(8-(prop-1-yn-1-yl)dibenzo[b,d]thiophen-2-yl)tetrahydropyrimidin-2(1H)-ylidene)palmitamide;

(S,Z)-((1,4-Dimethyl-6-oxo-4-(8-(prop-1-yn-1-yl)dibenzo[b,d]thiophen-2-yl)tetrahydropyrimidin-2(1H)-ylidene)amino)methyl dodecanoate;

(S)-2-Imino-3,6-dimethyl-6-(8-(prop-1-yn-1-yl)dibenzo[b,d]furan-2-yl)tetrahydropyrimidin-4(1H)-one;

(R)-3-Imino-2,2,5-trimethyl-5-(7-methyl-10,11-dihydro-5H-dibenzo[b,f]azepin-3-yl)thiomorpholine 1,1-dioxide;

(R)-5-(7-Fluoro-10,11-dihydro-5H-dibenzo[b,f]azepin-3-yl)-3-imino-2,2,5-trimethylthiomorpholine 1,1-dioxide;

(R)-3-Imino-2,2,5-trimethyl-5-(7-methyl-5,11-dihydrodibenzo[b,e][1,4]oxazepin-3-yl)thiomorpholine 1,1-dioxide;

(R)-3-Imino-2,2,5-trimethyl-5-(3-methyl-5,11-dihydrodibenzo[b,e][1,4]oxazepin-7-yl)thiomorpholine 1,1-dioxide;

(R)-7-(5-Imino-3,6,6-trimethyl-1,1-dioxidothiomorpholin-3-yl)-3-methyl-5,11-dihydrodibenzo[b,e][1,4]thiazepine 10,10-dioxide;

(S)-6-(3-chloro-8-(prop-1-yn-1-yl)dibenzo[b,d]thiophen-2-yl)-2-imino-3,6-dimethyltetrahydropyrimidin-4(1H)-one;

(S)-6-(3-fluoro-8-(prop-1-yn-1-yl)dibenzo[b,d]thiophen-2-yl)-2-imino-3,6-dimethyltetrahydropyrimidin-4(1N)-one;

(S)-6-(9-fluoro-8-(prop-1-yn-1-yl)dibenzo[b,d]thiophen-2-yl)-2-imino-3,6-dimethyltetrahydropyrimidin-4(1N)-one;

(S)-6-(5,5-di oxido-8-(prop-1-yn-1-yl)dibenzo[b,d]thiophen-2-yl)-2-imino-3,6-dimethyltetrahydropyrimidin-4(1H)-one;

(6S)-2-imino-3,6-dimethyl-6-(5-oxido-8-(prop-1-yn-1-yl)dibenzo[b,d]thiophen-2-yl)tetrahydropyrimidin-4(1H)-one;

(S)-6-(9,9-Dimethyl-6-(prop-1-yn-1-yl)-9H-fluoren-3-yl)-2-imino-3,6-dimethyltetrahydropyrimidin-4(1H)-one;

(S)-6-(9,9-Difluoro-6-(prop-1-yn-1-yl)-9H-fluoren-3-yl)-2-imino-3,6-dimethyltetrahydropyrimidin-4(1H)-one;

(S)-8-(2-Imino-1,4-dimethyl-6-oxohexahydropyrimidin-4-yl)dibenzo[b,d]thiophene-2-carbonitrile;

(S)-2-imino-6-(8-(3-methoxyprop-1-yn-1-yl)dibenzo[b,d]thiophen-2-yl)-3,6-dimethyltetrahydropyrimidin-4(1H)-one;

(S)-6-(8-(3-hydroxyprop-1-yn-1-yl)dibenzo[b,d]thiophen-2-yl)-2-imino-3,6-dimethyltetrahydropyrimidin-4(1H)-one;

(S)-6-(8-Bromodibenzo[b,d]thiophen-2-yl)-2-imino-3,6-dimethyltetrahydropyrimidin-4(1H)-one, (S)-6-(8-cyclopropyldibenzo[b,d]thiophen-2-yl)-2-imino-3,6-dimethyltetrahydropyrimidin-4(1N)-one;

(S)-8-(2-Imino-1,4-dimethyl-6-oxohexahydropyrimidin-4-yl)dibenzo[b,d]thiophene-2-carboxamide;

(S)-6-(8-(Diethylamino)dibenzo[b,d]thiophen-2-yl)-2-imino-3,6-dimethyltetrahydropyrimidin-4(1N)-one;

(S)-2-Imino-3,6-dimethyl-6-(8-(trifluoromethyl)dibenzo[b,d]thiophen-2-yl)tetrahydropyrimidin-4(1N)-one;

(R)-6-Cyclopropyl-2-imino-3-methyl-6-(8-(prop-1-yn-1-yl)dibenzo[b,d]thiophen-2-yl)tetrahydropyrimidin-4(1N)-one;

(R)-5,5-difluoro-4-methyl-4-(8-(prop-1-yn-1-yl)dibenzo[b,d]thiophen-2-yl)-1,3-oxazinan-2-imine;

(R)-3-imino-2,2,5-trimethyl-5-(8-(prop-1-yn-1-yl)dibenzo[b,d]thiophen-2-yl)thiomorpholine 1,1-dioxide;

(R)-3-Imino-2,5-dimethyl-5-(8-(prop-1-yn-1-yl)dibenzo[b,d]thiophen-2-yl)-1,2,4-thiadiazinane 1,1-dioxide;

(S)-3-(2,2-Difluoroethyl)-2-imino-6-methyl-6-(8-(prop-1-yn-1-yl)dibenzo[b,d]thiophen-2-yl)tetrahydropyrimidin-4(1H)-one;

(S)-2-Imino-3-(2-methoxyethyl)-6-methyl-6-(8-(prop-1-yn-1-yl)dibenzo[b,d]thiophen-2-yl)tetrahydropyrimidin-4(1H)-one;

(R)-5-(3-fluoro-8-(prop-1-yn-1-yl)dibenzo[b,d]thiophen-2-yl)-3-imino-2,2,5-trimethylthiomorpholine 1,1-dioxide;

(R)-3-Imino-1,5-dimethyl-5-(8-(prop-1-yn-1-yl)dibenzo[b,d]thiophen-2-yl)piperazin-2-one;

(R)-5-(4-Fluoro-8-(prop-1-yn-1-yl)dibenzo[b,d]thiophen-2-yl)-3-imino-2,2,5-trimethylthiomorpholine 1,1-dioxide;

(R)-5-(7-fluoro-8-(prop-1-yn-1-yl)dibenzo[b,d]thiophen-2-yl)-3-imino-2,2,5-trimethylthiomorpholine 1,1-dioxide;

(R)-10-Imino-8-methyl-8-(8-(prop-1-yn-1-yl)dibenzo[b,d]thiophen-2-yl)-6-thia-9-azaspiro[4.5]decane 6,6-dioxide;

(R)-8-Imino-6-methyl-6-(8-(prop-1-yn-1-yl)dibenzo[b,d]thiophen-2-yl)-4-thia-7-azaspiro[2.5]octane 4,4-dioxide;

(R,E)-3-Imino-2,2,5-trimethyl-5-(8-(prop-1-en-1-yl)dibenzo[b,d]thiophen-2-yl)thiomorpholine 1,1-dioxide;

(R)-6-(7-Fluoro-8-(prop-1-yn-1-yl)dibenzo[b,d]thiophen-2-yl)-8-imino-6-methyl-4-thia-7-azaspiro[2.5]octane 4,4-dioxide; and (S)-2-Imino-3,6-dimethyl-6-(8-propyldibenzo[b,d]thiophen-2-yl)tetrahydropyrimidin-4(1H)-one; as a stereoisomer, tautomer, or a prodrug or free base, or a pharmaceutically acceptable salt, solvate or solvate of a salt thereof.

5. A pharmaceutical composition comprising the compound according to claim 1 a pharmaceutically acceptable excipient.

6. A method of treating Alzheimer's disease in a patient, comprising administering to said patient an effective amount of the compound according to claim 1.

7. A pharmaceutical composition comprising the compound according to claim 2 a pharmaceutically acceptable excipient.

8. A pharmaceutical composition comprising the compound according to claim 3 a pharmaceutically acceptable excipient.

9. A pharmaceutical composition comprising the compound according to claim 4 a pharmaceutically acceptable excipient.

10. A method of treating Alzheimer's disease in a patient, comprising administering to said patient an effective amount of the compound according to claim 2.

11. A method of treating Alzheimer's disease in a patient, comprising administering to said patient an effective amount of the compound according to claim 3.

12. A method of treating Alzheimer's disease in a patient, comprising administering to said patient an effective amount of the compound according to claim 4.

* * * * *